US011091756B2

(12) United States Patent
Baltes

(10) Patent No.: US 11,091,756 B2
(45) **Date of Patent: *Aug. 17, 2021**

(54) METHODS FOR TARGETED INSERTION OF DNA IN GENES

(71) Applicant: BLUEALLELE CORPORATION, Oakdale, MN (US)

(72) Inventor: Nicholas J. Baltes, Maple Grove, MN (US)

(73) Assignee: BLUEALLELE CORPORATION, Oakdale, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/800,444

(22) Filed: Feb. 25, 2020

(65) Prior Publication Data

US 2020/0190504 A1 Jun. 18, 2020

Related U.S. Application Data

(63) Continuation of application No. 16/601,144, filed on Oct. 14, 2019, now abandoned.

(60) Provisional application No. 62/864,432, filed on Jun. 20, 2019, provisional application No. 62/830,654, filed on Apr. 8, 2019, provisional application No. 62/746,497, filed on Oct. 16, 2018.

(51) Int. Cl.
*C12N 15/10* (2006.01)
*C12N 15/90* (2006.01)

(52) U.S. Cl.
CPC ......... *C12N 15/102* (2013.01); *C12N 15/907* (2013.01); *C12N 2310/20* (2017.05); *C12N 2800/80* (2013.01)

(58) Field of Classification Search
CPC .................................................... C12N 15/102
See application file for complete search history.

(56) References Cited

U.S. PATENT DOCUMENTS 6,228,639 B1 5/2001 Gaitanaris
6,740,503 B1 * 5/2004 Harrington ........ C12N 15/1096 435/320.1
7,005,299 B1 2/2006 Smith et al.
9,255,250 B2 2/2016 Gregory et al.
9,677,070 B2 6/2017 Allison et al.
9,765,404 B2 9/2017 Sastry-Dent et al.
10,240,145 B2 3/2019 Tang et al.
2004/0106566 A1 6/2004 Lin et al.
2005/0064474 A1 * 3/2005 Urnov .................... A61K 35/12 435/6.18
2005/0208489 A1 * 9/2005 Carroll ..................... C12N 9/22 435/6.16
2013/0280222 A1 10/2013 Kay et al.
2014/0130205 A1 * 5/2014 Bhyri ................. C12N 15/8222 800/278
2016/0040155 A1 2/2016 Maizels et al.
2016/0102322 A1 4/2016 Ravinder et al.
2016/0281111 A1 9/2016 Cotta-Ramusino et al.
2017/0073664 A1 3/2017 McCafferty et al.
2018/0023075 A1 1/2018 Liang et al.
2018/0110877 A1 4/2018 Wilson et al.
2018/0112213 A1 4/2018 Welstead et al.
2018/0119123 A1 5/2018 Gori et al.
2018/0273932 A1 9/2018 Bothmer et al.
2018/0296603 A1 10/2018 Gori et al.
2018/0362590 A1 12/2018 Monds et al.
2019/0032089 A1 1/2019 Townes et al.
2019/0032092 A1 1/2019 Gong et al.
2019/0032156 A1 1/2019 Gong et al.
2019/0093114 A1 3/2019 Bower et al.
2019/0134221 A1 5/2019 Bumcrot et al.
2019/0136210 A1 5/2019 Cotta-Ramusino et al.
2019/0276850 A1 9/2019 Brinkmann et al.
2019/0330603 A1 10/2019 Ahlfors et al.
2019/0390189 A1 12/2019 Lee et al.
2020/0040362 A1 * 2/2020 Carlo ..................... C12N 15/11

FOREIGN PATENT DOCUMENTS

BR 102014027448 A2 9/2015
CA 2906747 A1 9/2014
EP 2893025 B1 7/2015
EP 3114227 A1 1/2017
EP 3122880 A2 2/2017
EP 3344771 A1 7/2018
EP 3375877 A1 9/2018
EP 3426784 A1 1/2019
EP 3556858 A2 10/2019
EP 3592140 A1 1/2020
ES 2653212 T3 2/2018
ES 2699848 T3 2/2019
ES 2730378 T3 11/2019
WO 2013075008 A1 5/2013
(Continued)

OTHER PUBLICATIONS

Kaiser Science, 317, 580 (Year: 2007).*
Frank et al N. Engl. J Med. Jul 9;361 (2):161-9 (Year: 2009).*
Edelstein Journal Gene Med., 597-602 (Year: 2004).*
High Nature, 435, 577-579 (Year: 2005).*
Ramirez Nature Methods, 5(5): 374-375 (Year: 2008).*
. Li Nature, Jul. 14,, 475, 7355, 217-221 (Year: 2011).*
Christian Genetics, 757-761 (Year: 2010).*
Hauschild PNAS, 108(29), 12013-12017 (Year: 2011).*
Hsu et al Nat Biotechnology. Sep. 31(9):827-32 (Year: 2013).*
Lee et al., (Drug Discovery Today: Disease Models, vol. 20, 13-20 (Year: 2016).*
(Continued)

*Primary Examiner* — Scott Long
(74) *Attorney, Agent, or Firm* — Arrigo, Lee, Guttman & Mouta-Bellum LLP

(57) ABSTRACT

Methods and compositions for modifying the coding sequence of endogenous genes using rare-cutting endonucleases and transposases. The methods and compositions described herein can be used to modify the coding sequence of endogenous genes.

10 Claims, 8 Drawing Sheets

Specification includes a Sequence Listing.

(56) References Cited

FOREIGN PATENT DOCUMENTS

| | | | | | |
|---|---|---|---|---|---|
| WO | 2013169802 | A1 | 11/2013 | | |
| WO | 2015017866 | A1 | 2/2015 | | |
| WO | 2015089351 | A1 | 6/2015 | | |
| WO | WO-2015089351 | A1 * | 6/2015 | ........... | C12Y 301/00 |
| WO | 2015153780 | A1 | 10/2015 | | |
| WO | 2015173436 | A1 | 11/2015 | | |
| WO | 2016073990 | A2 | 5/2016 | | |
| WO | 2016109840 | A2 | 7/2016 | | |
| WO | 2016161380 | A1 | 10/2016 | | |
| WO | 2016172727 | A1 | 10/2016 | | |
| WO | 2016182959 | A8 | 11/2016 | | |
| WO | 2017048995 | A1 | 3/2017 | | |
| WO | 2017155408 | A1 | 9/2017 | | |
| WO | 2018009534 | A1 | 1/2018 | | |
| WO | 2018009562 | A1 | 1/2018 | | |
| WO | WO-2018009534 | A1 * | 1/2018 | ........... | C12N 15/102 |
| WO | 2018195555 | A1 | 10/2018 | | |
| WO | 2018197020 | A1 | 11/2018 | | |
| WO | 2019005851 | A1 | 1/2019 | | |
| WO | 2019092505 | A1 | 5/2019 | | |
| WO | 2019113149 | A1 | 6/2019 | | |
| WO | 2019118875 | A1 | 6/2019 | | |
| WO | 2019157326 | A1 | 8/2019 | | |
| WO | 2019178225 | A2 | 9/2019 | | |
| WO | 2019183123 | A1 | 9/2019 | | |
| WO | 2019210216 | A2 | 10/2019 | | |
| WO | 2020082041 | A1 | 4/2020 | | |
| WO | 2020082042 | A2 | 4/2020 | | |
| WO | 2020082046 | A2 | 4/2020 | | |
| WO | 2020082047 | A1 | 4/2020 | | |

OTHER PUBLICATIONS

Kosicki et al Nature Biotechnology, 36, 765-771 (Year: 2018).*

Robert et al Curr Genetics, 64(2):389-391 (Year: 2018).*

Cox et al , Nature Medicine 21(2), 121-13 (Year: 2015).*

Kuscu et al Nature biotechnology, 32(7), 677 (Year: 2014).*

Kleinstiver Nature, 523, 481-485 (Year: 2015).*

Sheng et al Canadian Journal of Microbiology, 445-454 (Year: 2014).*

Ryu et al Plant Molecular Biology 54: 489-502 (Year: 2004).*

Senis et al Nucleic acid Res. , 45(1), e3 (Year: 2016).*

Robert, Francois, "Bidirectional terminators: an underestimated aspect of gene regulation", Curr Genet, vol. 64, pp. 389-391, 2018.

Ouyang et al., "CRISPR/Cas9-Targeted Deletion of Polyglutamine in Spinocerebellar Ataxia Type 3-Derived Induced Pluripotent Stem Cells", vol. 27, No. 11, pp. 756-770, 2018.

Blueallele, LLC in connection with PCTUS2019/056083 filed Oct. 14, 2019, "The International Search Report and the Written Opinion of the International Searching Authority, or the Declaration", 21 pages, dated Dec. 19, 2019.

Friedel et al., "Gene targeting using a promoterless gene trap vector ("targeted trapping") is an efficient method to mutate a large fraction of genes", PNAS, vol. 102, No. 37, pp. 13188-13193, Sep. 13, 2005.

Gilles et al., "Efficient CRISPR-mediated gene targeting and transgene replacement in the beetle Tribolium castaneum", The Company of Biologists, vol. 142, pp. 2832-2839, Jun. 29, 2015.

Hahm et al., "Construction of retroviral vectors with enhanced efficiency of transgene expression", Journal of Virological Methods, vol. 121, pp. 127-136, May 27, 2004.

Hildinger et al., "Design of 5' Untranslated Sequences in Retroviral Vectors Developed for Medical Use", Journal of Virology, vol. 73, No. 5, pp. 4083-4089, May 1999.

Intellia Therapeutics, "Q3 2018 Earnings and Corporate Development", Powerpoint, 23 pages, presented Oct. 31, 2018.

Ruan et al., "Highly efficient CRISPR/Cas9-mediated transgene knockin at the H11 locus in pigs", Scientific Reports, 10 pages, Sep. 18, 2015.

Suzuki et al., "In vivo genome editing via CRISPR/Cas9 mediated homology-independent targeted integration", Nature, vol. 540, 24 pages, Dec. 1, 2016.

Uno et al., "CRISPR/Cas9-induced transgene insertion and telomere-associated truncation of a single human chromosome for chromosome engineering in CHO and A9 cells", Scientific Reports, 10 pages, Oct. 6, 2017.

Yao et al., "Homology-mediated end joining-based targeted integration using CRISPR/Cas9", Cell Research, vol. 27, pp. 801-814, Apr. 6, 2017.

Blueallelle, LLC in connection with PCT/US2019/058857 filed Oct. 30, 2019, "The International Search Report and the Written Opinion of the International Searching Authority, or the Declaration", 19 pages, dated Jun. 23, 2020.

* cited by examiner pBA1012-D1 (SEQ ID NO: 10); pBA1135 (SEQ ID NO:17)

SEQUENCE LISTING

<160> NUMBER OF SEQ ID NOS: 51

<210> SEQ ID NO 1
<211> LENGTH: 3527
<212> TYPE: DNA
<213> ORGANISM: Artificial Sequence
<220> FEATURE:
<223> OTHER INFORMATION: Construct

<400> SEQUENCE: 1

```
gtgcggctgc aagtgacccc aggctgggct cggccgggag gcggggagga gagaagggga     60
taccccatcc aacagccact ctaggcaaag gtccccggat cccggctgtg accacctccc    120
atcctgcccc caagccaccg gggtgcccgg cggccggagc ggacacggat ccccaccaca    180
ccagctgcct atgctgtccc cccagccccc ttgcccaccc gccgcccct ccccgccgcc     240
cgcagctgct tgctcctcgg ttgtggatca tatttgagtt ctgggccgtg ccgcccgacc    300
tttcactttc ctttaacccg gcttctgttt ttgtttcaat tatgatttct gtcctctgga    360
cgcctgtgag taatttttga aacttctgct atttttaacc ccgaaactta caaaactcca    420
tttctcattt ctcttttcac tttgttgtgt tggttttcga ctcctcccct ccctgtctca    480
ctccccctcc tcccctccct cctccctgtg gctgttgctt ttttccattc aatgtcctgt    540
gtcccccctc tcctcctcct cctcctcctc cccctccccc tcctccctct cctcccggcc    600
cctctccctt cgctcccctc tcttcctccc aatcccgtgt ctcctttgat tttgttgtat    660
cttttttttt gatttccttt gtttcaattt tcgtgtaggg cagtagttcc gtaagtggaa    720
gcccagcccc ctcaacatct ggtaccagca ctccgcggcg gggccgccgc cagctccccc    780
agacccccctc cacccccccgg ccacacgtgt cctattcccc tgtgatccgt aaggccggcg  840
gctcggggcc cccgcagcag cagcagcagc agcagcagca gcagcagcag caggcggtgg    900
ccaggccggg ccgggcggcc accagcggcc ctcggaggta cccaggcccc acggccgagc    960
ctctggccgg agatcggccg cccacggggg gccacagcag cggccgctcg cccaggatgg   1020
agaggcgggt cccaggcccg gcccggagcg agtcccccag ggcctgtcga cacggcgggg   1080
cccggtggcc ggcatctggc ccgcacgtgt ccgaggggcc cccgggtccc cggcaccatg   1140
gctactaccg gggctccgac tacgacgagg ccgatggccc gggcagcggg ggcggcgagg   1200
aggccatggc cggggcctac gacgcgccac cccccgtacg acacgcgtcc tcgggcgcca   1260
ccgggcgctc gcccaggact ccccgggcct cgggcccggc ctgcgcctcg ccttctcggc   1320
acggccggcg actccccaac ggctactacc cggcgcacgg actggccagg ccccgcgggc   1380
cgggctccag gaagggcctg cacgaaccct acagcgagag tgacgatgat tggtgctaaa   1440
acttgtttat tgcagcttat aatggttaca aataaagcaa tagcatcaca aatttcacaa   1500
ataaagcatt tttttcactg cattctagtt gtggtttgtc caaactcatc aatgtatctt   1560
atcatgtctg gatctcccca gcatgcctgc tattctcttc ccaatcctcc cccttgctgt   1620
cctgccccac cccacccccc agaatagaat gacacctact cagacaatgc gatgcaattt   1680
cctcatttta ttaggaaagg acagtgggag tggcaccttc cagggtcaag gaaggcacgg   1740
gggaggggca aacaacagat ggctggcaac tagaaggcac agtcagcacc agtcgtcgtc   1800
ggattcgctg tagggttcat ggagaccctt ccgagaccca ggtcctcttg gccgggccaa   1860
gccgtgtgca gggtaatatc cattggggag cctccggcca tgccgagaag gtgaagcgca   1920
cgctggtcct gacgcccggg gggtgcgagg agacctccct gtcgccccgg aagacgcatg   1980
cctaacggga ggcggagcat cataagcacc agccatcgct tcctcgccac caccactgcc   2040
```

```
gggcccgtca gcttcgtcat agtcagaacc ccgataatat ccgtgatggc gaggccctgg   2100

aggtccttcg ctaacgtgtg gcccagaagc aggccaccgc gcacctccat ggcgacatgc   2160

tctaggactc tcgcttcttg caggtccagg aacccgccgc tccattcgcg ggcttcgccc   2220

actactgtgt ccacctgtcg gagggcggtc tccggcaagg ggttcagcgg ttgggcctgg   2280

atagcgccgc ggaccggagg tagcagcccg accgggtcgt gctaccgctt gctgttgctg   2340

ttgttgctgt tgctgctgtt gttgttgggg tggcccgcta cctcccgctt ttctaataac   2400

tggtgaataa ctcacatgtg ggcgcggagt ggatggtgtc tgagggagtt gccttctccc   2460

tcggcggggt gtagacgtac cagatgttga aggcgccggg ctcccgctta ctgaactact   2520

gtaaatgaat gagaaaaccg gtttagaaag tgcacagctg tcagggaagt caacacttca   2580

gtgagcatgt gaccatgtgg agtcagcttc ctgtttcgtg ctgcaatcgc ccgggcgagg   2640

tggcgcccgc ccggcccccc acgcacccca cgcacacacc ccacccgagg agccgcgcag   2700

aggccgcggg ggcccagcac agagggcccg ggagagggcc agccgggaga ccccagactc   2760

tggagaggcc agggctgggc cacaagggtg tcccgcagag accctcggcc aaaagagacc   2820

ctcctgggca gccacggcgc cccccaacca gccccgatcc ccccacccac gacaggggct   2880

ctcgggtggg aggcagggag cagacaaacc acacagccaa gggatttgaa ttaactcagc   2940

catttttgga gaactttggg gaacatgaaa aaaaaaaaaa aaaaaaaaaa aaaaaacatt   3000

tttaaaagaa aaaacgggga gaaaaaaata gcttctattg atgagtttta tcatctcaat   3060

tgaatctttc ctttccctga tgaagacagc tggtggccga gtgcggcaaa gaagccagaa   3120

ggaaccagaa tcccagtgcc ctacacccac caccagacac actcacaccc acacacgttc   3180

tcagacacac acaagagtgc ttgccggtta taccaaaccc tactattact gcctgcagaa   3240

atcaatttaa aaaaataata ataacaataa acaattttaa aaaggacaaa aaaattaatg   3300

attgagaaaa gaggcatttt tttctgacat ttggtcctgc ttgaaacaac aaaagaagaa   3360

gaaaaaccca ccatcaccac cgattccttt gcttcttttt tcctttttttc ctaccttgtt   3420

tgaaaaccgt gggcttggga ctgtgaatta ttgcatgaca ttcaaaaaga aaaaaaaaat   3480

aaaaaaaagt tgaatcaaat ttctgtcctc tggacgcctg tgagtaa                 3527


<210> SEQ ID NO 2
<211> LENGTH: 703
<212> TYPE: DNA
<213> ORGANISM: Artificial Sequence
<220> FEATURE:
<223> OTHER INFORMATION: Construct

<400> SEQUENCE: 2

gtgcggctgc aagtgacccc aggctgggct cggccgggag gcggggagga gagaagggga     60

taccccatcc aacagccact ctaggcaaag gtccccggat cccggctgtg accacctccc    120

atcctgcccc caagccaccg gggtgcccgg cggccggagc ggacacggat ccccaccaca    180

ccagctgcct atgctgtccc cccagccccc ttgcccaccc gccgccccct ccccgccgcc    240

cgcagctgct tgctcctcgg ttgtggatca tatttgagtt ctgggccgtg ccgcccgacc    300

tttcactttc ctttaacccg gcttctgttt ttgtttcaat tatgatttct gtcctctgga    360

cgcctgtgag taatttttga aacttctgct atttttaacc ccgaaactta caaaactcca    420

tttctcattt ctcttttcac tttgttgtgt tggttttcga ctcctcccct ccctgtctca    480

ctccccctcc tcccctccct cctccctgtg gctgttgctt ttttccattc aatgtcctgt    540
```

```
gtccccccctc tcctcctcct cctcctcctc cccctccccc tcctccctct cctcccggcc    600

cctctccctt cgctcccctc tcttcctccc aatcccgtgt ctcctttgat tttgttgtat    660

cttttttttt gatttccttt gtttcaattt tcgtgtaggg cag                      703


<210> SEQ ID NO 3
<211> LENGTH: 736
<212> TYPE: DNA
<213> ORGANISM: Artificial Sequence
<220> FEATURE:
<223> OTHER INFORMATION: Construct

<400> SEQUENCE: 3

tagttccgta agtggaagcc cagccccctc aacatctggt accagcactc cgcggcgggg     60

ccgccgccag ctcccccaga ccccctccac cccccggcca cacgtgtcct attcccctgt    120

gatccgtaag gccggcggct cggggccccc gcagcagcag cagcagcagc agcagcagca    180

gcagcagcag gcggtggcca ggccgggccg ggcggccacc agcggccctc ggaggtaccc    240

aggccccacg gccgagcctc tggccggaga tcggccgccc acggggggcc acagcagcgg    300

ccgctcgccc aggatggaga ggcgggtccc aggcccggcc cggagcgagt cccccagggc    360

ctgtcgacac ggcggggccc ggtggccggc atctggcccg cacgtgtccg aggggccccc    420

gggtccccgg caccatggct actaccgggg ctccgactac gacgaggccg atggcccggg    480

cagcgggggc ggcgaggagg ccatggccgg ggcctacgac gcgccacccc ccgtacgaca    540

cgcgtcctcg ggcgccaccg ggcgctcgcc caggactccc cgggcctcgg gcccggcctg    600

cgcctcgcct tctcggcacg gccggcgact ccccaacggc tactacccgg cgcacggact    660

ggccaggccc cgcgggccgg gctccaggaa gggcctgcac gaaccctaca gcgagagtga    720

cgatgattgg tgctaa                                                    736


<210> SEQ ID NO 4
<211> LENGTH: 135
<212> TYPE: DNA
<213> ORGANISM: Artificial Sequence
<220> FEATURE:
<223> OTHER INFORMATION: Construct

<400> SEQUENCE: 4

aacttgttta ttgcagctta taatggttac aaataaagca atagcatcac aaatttcaca     60

aataaagcat ttttttcact gcattctagt tgtggtttgt ccaaactcat caatgtatct    120

tatcatgtct ggatc                                                     135


<210> SEQ ID NO 5
<211> LENGTH: 208
<212> TYPE: DNA
<213> ORGANISM: Artificial Sequence
<220> FEATURE:
<223> OTHER INFORMATION: Construct

<400> SEQUENCE: 5

tccccagcat gcctgctatt ctcttcccaa tcctcccccct tgctgtcctg ccccacccca     60

ccccccagaa tagaatgaca cctactcaga caatgcgatg caatttcctc attttattag    120

gaaaggacag tgggagtggc accttccagg gtcaaggaag gcacgggggga ggggcaaaca    180

acagatggct ggcaactaga aggcacag                                       208


<210> SEQ ID NO 6
<211> LENGTH: 736
```

<212> TYPE: DNA
<213> ORGANISM: Artificial Sequence
<220> FEATURE:
<223> OTHER INFORMATION: Construct

<400> SEQUENCE: 6

```
tcagcaccag tcgtcgtcgg attcgctgta gggttcatgg agacccttcc gagacccagg     60
tcctcttggc cgggccaagc cgtgtgcagg gtaatatcca ttggggagcc tccggccatg    120
ccgagaaggt gaagcgcacg ctggtcctga cgcccggggg gtgcgaggag acctccctgt    180
cgccccggaa gacgcatgcc taacgggagg cggagcatca taagcaccag ccatcgcttc    240
ctcgccacca ccactgccgg gcccgtcagc ttcgtcatag tcagaacccc gataatatcc    300
gtgatggcga ggccctggag gtccttcgct aacgtgtggc ccagaagcag gccaccgcgc    360
acctccatgg cgacatgctc taggactctc gcttcttgca ggtccaggaa cccgccgctc    420
cattcgcggg cttcgcccac tactgtgtcc acctgtcgga gggcggtctc cggcaagggg    480
ttcagcggtt gggcctggat agcgccgcgg accggaggta gcagcccgac cgggtcgtgc    540
taccgcttgc tgttgctgtt gttgctgttg ctgctgttgt tgttggggtg gcccgctacc    600
tcccgctttt ctaataactg gtgaataact cacatgtggg cgcggagtgg atggtgtctg    660
agggagttgc cttctccctc ggcggggtgt agacgtacca gatgttgaag gcgccgggct    720
cccgcttact gaacta                                                    736
```

<210> SEQ ID NO 7
<211> LENGTH: 110
<212> TYPE: DNA
<213> ORGANISM: Artificial Sequence
<220> FEATURE:
<223> OTHER INFORMATION: Construct

<400> SEQUENCE: 7

```
ctgtaaatga atgagaaaac cggtttagaa agtgcacagc tgtcagggaa gtcaacactt     60
cagtgagcat gtgaccatgt ggagtcagct tcctgtttcg tgctgcaatc               110
```

<210> SEQ ID NO 8
<211> LENGTH: 446
<212> TYPE: DNA
<213> ORGANISM: Artificial Sequence
<220> FEATURE:
<223> OTHER INFORMATION: Construct

<400> SEQUENCE: 8

```
gcccgggcga ggtggcgccc gcccggcccc ccacgcaccc cacgcacaca ccccacccga     60
ggagccgcgc agaggccgcg ggggcccagc acagagggcc cgggagaggg ccagccggga    120
gaccccagac tctggagagg ccagggctgg gccacaaggg tgtcccgcag agaccctcgg    180
ccaaaagaga ccctcctggg cagccacggc gccccccaac cagccccgat ccccccaccc    240
acgacagggg ctctcgggtg ggaggcaggg agcagacaaa ccacacagcc aagggatttg    300
aattaactca gccatttttg gagaactttg gggaacatga aaaaaaaaaa aaaaaaaaaa    360
aaaaaaaaca tttttaaaag aaaaaacggg gagaaaaaaa tagcttctat tgatgagttt    420
tatcatctca attgaatctt tccttt                                         446
```

<210> SEQ ID NO 9
<211> LENGTH: 24
<212> TYPE: DNA
<213> ORGANISM: Artificial Sequence
<220> FEATURE:

<223> OTHER INFORMATION: Target site

<400> SEQUENCE: 9
tttctgtcct ctggacgcct gtga 24

<210> SEQ ID NO 10
<211> LENGTH: 2288
<212> TYPE: DNA
<213> ORGANISM: Artificial Sequence
<220> FEATURE:
<223> OTHER INFORMATION: Construct

<400> SEQUENCE: 10
atttcattta tcaggtgttc agtgaatgct tactatgtaa cagcacagtt atcagcactg 60
gggaaataga tgagtaagat aagatttgca ctttcattag cttacatgcc ataaagaggg 120
aaataaagag aacaccagat gatgataagt ttatgctgag aattaaaatg aagtgatgaa 180
ataatgggaa tgtcaggtgg ctacttttgg tgggatggtc aggaaaggca tctctgggga 240
gataaatttt aagctcagac ctgagtgaaa agaatgagcc agccatggaa acattatgtt 300
aactcacatg gtagtttgaa atgctttatc tgatcaaagg tacttatttt tggtgacttt 360
caacaatatt aagggtctat aaaccaacac tcatttgcat aagaataact accagtgaat 420
ctttttgtat gataggtttt ttgtttgttg ttttttgag acagagtctc gctctgtcgc 480
ccaggctgga gtgcagtggc gcgatcttgg ctcactgcaa cctctacctc cccggttcaa 540
gtgattctcc tgcctcagcc tcccaaagta gctgggatta caggtgcctg ccaccacgcc 600
tggctaattt ttgtattttt agtagagatg gggtttcacc gtgttgtcca ggctcgtgtc 660
aaacttctga cctcaagcca tccacccgcc tcggcctccc aaagtgctgg gattacaggt 720
gtgagccacc actcctggcc atgataggtt attttgtgat gaaaatacct acctcttaat 780
ttgtctgata aatttaaatt ttatgtctag atttcctaag atcagcactt ccatatttta 840
aagtaatctg tatcagacta actgctcttg cattctttta ataccagtga ctactttgat 900
tcgtgaaaca atgtattttc cttatgaata gtttttctca tggtgtattt attcttttaa 960
gttttgtttt ttaaatatac ttcacttttg aatgtttcag acagcagcaa aagcagcaac 1020
agcagcagca gcagcagcag caggggggacc tatcaggaca gagttcacat ccatgtgaaa 1080
ggccagccac cagttcagga gcacttggga gtgatctagg tgatgctatg agtgaagaag 1140
acatgcttca ggcagctgtg accatgtctt tagaaactgt cagaaatgat ttgaaaacag 1200
aaggaaaaaa ataaaacttg tttattgcag cttataatgg ttacaaataa agcaatagca 1260
tcacaaattt cacaaataaa gcattttttt cactgcattc tagttgtggt ttgtccaaac 1320
tcatcaatgt atcttatcat gtctggatct ccccagcatg cctgctattc tcttcccaat 1380 cctcccccttt gctgtcctgc cccaccccac cccccagaat agaatgacac ctactcagac 1440
aatgcgatgc aatttcctca ttttattagg aaaggacagt gggagtggca ccttccaggg 1500
tcaaggaagg cacgggggag gggcaaacaa cagatggctg gcaactagaa ggcacagcta 1560
cttcttgccc tcggtcttca ggtcgttgcg cacggtctcc aggctcatgg tcacggcggc 1620
ctgcagcatg tcctcctcgc tcatggcgtc gcccaggtcg ctgcccaggg cgccgctgct 1680
ggtggcgggg cgctcgcagg ggtggctgct ctggccgctc aggtcgccct gctgctgctg 1740
ctgctgctgc tgctgctgct tctgctgctg tctgtaaatg aatgagaaaa ccggtttaga 1800
aagtgcacag ctgtcaggga agtcaacact tcagtgagca tgtgaccatg tggagtcagc 1860
ttcctgtttc gtgctgcaat cgtaaggcct gctcaccatt catcatgttc gctaccttca 1920

```
cactttatct gacatacgag ctccatgtga tttttgcttt acattattct tcattccctc   1980

tttaatcata ttaagaatct taagtaaatt tgtaatctac taaatttccc tggattaagg   2040

agcagttacc aaaagaaaaa aaaaaaaaaa agctagatgt ggtggctcac atctgtaatc   2100

ccagcacttt gggaaaccaa ggcaggagag gattgctaga acatttaatg aatactttaa   2160

cataataatt taaacttcac agtaatttgt acagtctcca aaaattcctt agacatcatg   2220

gatattttc ttttttgag atggagtctt gctctgtcac tttgagacag agtctcgctc   2280

tgtcgccc                                                             2288


<210> SEQ ID NO 11
<211> LENGTH: 24
<212> TYPE: DNA
<213> ORGANISM: Artificial Sequence
<220> FEATURE:
<223> OTHER INFORMATION: Target site

<400> SEQUENCE: 11

tttgagacag agtctcgctc tgtc                                            24


<210> SEQ ID NO 12
<211> LENGTH: 60
<212> TYPE: DNA
<213> ORGANISM: Artificial Sequence
<220> FEATURE:
<223> OTHER INFORMATION: gRNA
<220> FEATURE:
<221> NAME/KEY: misc_feature
<222> LOCATION: (9)..(40)
<223> OTHER INFORMATION: n is a, c, g, or t

<400> SEQUENCE: 12

ctgataacnn nnnnnnnnnn nnnnnnnnnn nnnnnnnnnn gtgaactgcc gagtaggtag     60


<210> SEQ ID NO 13
<211> LENGTH: 47
<212> TYPE: DNA
<213> ORGANISM: Vibrio cholerae

<400> SEQUENCE: 13

aattatcaat ttatgggtgt aattatcatt ttatggttgt atcaaca                   47


<210> SEQ ID NO 14
<211> LENGTH: 258
<212> TYPE: DNA
<213> ORGANISM: Artificial Sequence
<220> FEATURE:
<223> OTHER INFORMATION: gRNA
<220> FEATURE:
<221> NAME/KEY: misc_feature
<222> LOCATION: (236)..(258)
<223> OTHER INFORMATION: n is a, c, g, or t

<400> SEQUENCE: 14

tattaatagc gccgcaattc atgctgcttg cagcctctga attttgttaa atgagggtta     60

gtttgactgt ataaatacag tcttgctttc tgaccctggt agctgctcac cctgatgctg    120

ctgtcaatag acaggatagg tgcgctccca gcaataaggg cgcggatgta ctgctgtagt    180

ggctactgaa tcacccccga tcaaggggga accctccaaa aggtgggttg aaagtnnnnn    240

nnnnnnnnnn nnnnnnnn                                                  258


<210> SEQ ID NO 15
```

<211> LENGTH: 20
<212> TYPE: DNA
<213> ORGANISM: Artificial Sequence
<220> FEATURE:
<223> OTHER INFORMATION: Target site

<400> SEQUENCE: 15
ccgcccgacc tttcactttc 20

<210> SEQ ID NO 16
<211> LENGTH: 20
<212> TYPE: DNA
<213> ORGANISM: Artificial Sequence
<220> FEATURE:
<223> OTHER INFORMATION: Target site

<400> SEQUENCE: 16
cccggatccc ggctgtgacc 20

<210> SEQ ID NO 17
<211> LENGTH: 2391
<212> TYPE: DNA
<213> ORGANISM: Artificial Sequence
<220> FEATURE:
<223> OTHER INFORMATION: Construct

<400> SEQUENCE: 17
atttcattta tcaggtgttc agtgaatgct tactatgtaa cagcacagtt atcagcactg 60
gggaaataga tgagtaagat aagatttgca ctttcattag cttacatgcc ataaagaggg 120
aaataaagag aacaccagat gatgataagt ttatgctgag aattaaaatg aagtgatgaa 180
ataatgggaa tgtcaggtgg ctacttttgg tgggatggtc aggaaaggca tctctgggga 240
gataaatttt aagctcagac ctgagtgaaa agaatgagcc agccatggaa acattatgtt 300
aactcacatg gtagtttgaa atgctttatc tgatcaaagg tacttatttt tggtgacttt 360
caacaatatt aagggtctat aaaccaacac tcatttgcat aagaataact accagtgaat 420
ctttttgtat gataggtttt ttgtttgttg ttttttgag acagagtctc gctctgtcgc 480
ccaggctgga gtgcagtggc gcgatcttgg ctcactgcaa cctctacctc cccggttcaa 540
gtgattctcc tgcctcagcc tcccaaagta gctgggatta caggtgcctg ccaccacgcc 600
tggctaattt ttgtattttt agtagagatg gggtttcacc gtgttgtcca ggctcgtgtc 660
aaacttctga cctcaagcca tccacccgcc tcggcctccc aaagtgctgg gattacaggt 720
gtgagccacc actcctggcc atgataggtt attttgtgat gaaaatacct acctcttaat 780
ttgtctgata aatttaaatt ttatgtctag atttcctaag atcagcactt ccatatttta 840
aagtaatctg tatcagacta actgctcttg cattctttta ataccagtga ctactttgat 900
tcgtgaaaca atgtattttc cttatgaata gtttttctca tggtgtattt attcttttaa 960
gttttgtttt ttaaatatac ttcacttttg aatgtttcag acagcagcaa aagcagcaac 1020
agcagcagca gcagcagcag caggggggacc tatcaggaca gagttcacat ccatgtgaaa 1080
ggccagccac cagttcagga gcacttggga gtgatctagg tgatgctatg agtgaagaag 1140
acatgcttca ggcagctgtg accatgtctt tagaaactgt cagaaatgat ttgaaaacag 1200
aaggaaaaaa ataaaacttg tttattgcag cttataatgg ttacaaataa agcaatagca 1260
tcacaaattt cacaaataaa gcattttttt cactgcattc tagttgtggt ttgtccaaac 1320
tcatcaatgt atcttatcat gtctggatct ccccagcatg cctgctattc tcttcccaat 1380
cctccccctt gctgtcctgc cccaccccac cccccagaat agaatgacac ctactcagac 1440
aatgcgatgc aatttcctca ttttattagg aaaggacagt gggagtggca ccttccaggg 1500
tcaaggaagg cacgggggag gggcaaacaa cagatggctg gcaactagaa ggcacagcta 1560
cttcttgccc tcggtcttca ggtcgttgcg cacggtctcc aggctcatgg tcacggcggc 1620
ctgcagcatg tcctcctcgc tcatggcgtc gcccaggtcg ctgcccaggg cgccgctgct 1680
ggtggcgggg cgctcgcagg ggtggctgct ctggccgctc aggtcgccct gctgctgctg 1740
ctgctgctgc tgctgctgct tctgctgctg tctgtaaatg aatgagaaaa ccggtttaga 1800
aagtgcacag ctgtcaggga agtcaacact tcagtgagca tgtgaccatg tggagtcagc 1860
ttcctgtttc gtgctgcaat cgtaaggcct gctcaccatt catcatgttc gctaccttca 1920
cactttatct gacatacgag ctccatgtga tttttgcttt acattattct tcattccctc 1980
tttaatcata ttaagaatct taagtaaatt tgtaatctac taaatttccc tggattaagg 2040
agcagttacc aaaagaaaaa aaaaaaaaaa agctagatgt ggtggctcac atctgtaatc 2100
ccagcacttt gggaaaccaa ggcaggagag gattgctaga acatttaatg aatactttaa 2160
cataataatt taaacttcac agtaatttgt acagtctcca aaaattcctt agacatcatg 2220
gatatttttc tttttttgag atggagtctt gctcttttaa gctcagacct gagtgaaaag 2280
aatttgagac agagtctcgc tctgtcgcct ttcctaagat cagcacttcc atatttggtg 2340
actttcaaca atattaaggg tctataaacc aacactcatt tgcataagaa t 2391

<210> SEQ ID NO 18
<211> LENGTH: 20
<212> TYPE: DNA
<213> ORGANISM: Artificial Sequence
<220> FEATURE:
<223> OTHER INFORMATION: Target site

<400> SEQUENCE: 18
aatatggaag tgctgatctt 20

<210> SEQ ID NO 19
<211> LENGTH: 1205
<212> TYPE: DNA
<213> ORGANISM: Artificial Sequence
<220> FEATURE:
<223> OTHER INFORMATION: Construct

<400> SEQUENCE: 19
tttaagctca gacctgagtg aaaagaattt gagacagagt ctcgctctgt cgcctttcct 60
aagatcagca cttccatatt ttaaagtaat ctgtatcaga ctaactgctc ttgcattctt 120
ttaataccag tgactacttt gattcgtgaa acaatgtatt ttccttatga atagtttttc 180
tcatggtgta tttattcttt taagttttgt tttttaaata tacttcactt ttgaatgttt 240
cagacagcag caaaagcagc aacagcagca gcagcagcag cagcaggggg acctatcagg 300
acagagttca catccatgtg aaaggccagc caccagttca ggagcacttg ggagtgatct 360
aggtgatgct atgagtgaag aagacatgct tcaggcagct gtgaccatgt ctttagaaac 420
tgtcagaaat gatttgaaaa cagaaggaaa aaaataaaac ttgtttattg cagcttataa 480
tggttacaaa taaagcaata gcatcacaaa tttcacaaat aaagcatttt tttcactgca 540
ttctagttgt ggtttgtcca aactcatcaa tgtatcttat catgtctgga tctccccagc 600
atgcctgcta ttctcttccc aatcctcccc cttgctgtcc tgccccaccc cacccccag 660 aatagaatga cacctactca gacaatgcga tgcaatttcc tcattttatt aggaaaggac 720
agtgggagtg gcaccttcca gggtcaagga aggcacgggg gaggggcaaa caacagatgg 780
ctggcaacta gaaggcacag ctacttcttg ccctcggtct tcaggtcgtt gcgcacggtc 840
tccaggctca tggtcacggc ggcctgcagc atgtcctcct cgctcatggc gtcgcccagg 900
tcgctgccca gggcgccgct gctggtggcg gggcgctcgc aggggtggct gctctggccg 960
ctcaggtcgc cctgctgctg ctgctgctgc tgctgctgct gcttctgctg ctgtctgtaa 1020
atgaatgaga aaaccggttt agaaagtgca cagctgtcag ggaagtcaac acttcagtga 1080
gcatgtgacc atgtggagtc agcttcctgt ttcgtgctgc aatctttaag ctcagacctg 1140
agtgaaaaga atttgagaca gagtctcgct ctgtcgcctt tcctaagatc agcacttcca 1200
tattt 1205

<210> SEQ ID NO 20
<211> LENGTH: 1723
<212> TYPE: DNA
<213> ORGANISM: Artificial Sequence
<220> FEATURE:
<223> OTHER INFORMATION: Construct

<400> SEQUENCE: 20
atttcattta tcaggtgttc agtgaatgct tactatgtaa cagcacagtt atcagcactg 60
gggaaataga tgagtaagat aagatttgca ctttcattag cttacatgcc ataaagaggg 120
aaataaagag aacaccagat gatgataagt ttatgctgag aattaaaatg aagtgatgaa 180
ataatgggaa tgtcaggtgg ctacttttgg tgggatggtc aggaaaggca tctctgggga 240
gataaatttt aagctcagac ctgagtgaaa agaatgagcc agccatggaa acattatgtt 300
aactcacatg gtagtttgaa atgctttatc tgatcaaagg tacttatttt tggtgacttt 360
caacaatatt aagggtctat aaaccaacac tcatttgcat aagaataact accagtgaat 420
ctttttgtat gataggtttt ttgtttgttg ttttttgag acagagtctc gctctgtcgc 480
ccaggctgga gtgcagtggc gcgatcttgg ctcactgcaa cctctacctc cccggttcaa 540
gtgattctcc tgcctcagcc tcccaaagta gctgggatta caggtgcctg ccaccacgcc 600
tggctaattt ttgtattttt agtagagatg gggtttcacc gtgttgtcca ggctcgtgtc 660
aaacttctga cctcaagcca tccacccgcc tcggcctccc aaagtgctgg gattacaggt 720
gtgagccacc actcctggcc atgataggtt attttgtgat gaaaatacct acctcttaat 780
ttgtctgata aatttaaatt ttatgtctag aaatcctaag atcagcactt ccatatttta 840
aagtaatctg tatcagacta actgctcttg cattctttta ataccagtga ctactttgat 900
tcgtgaaaca atgtattttc cttatgaata gtttttctca tggtgtattt attcttttaa 960
gttttgtttt ttaaatatac ttcacttttg aatgtttcag acagcagcaa aagcagcaac 1020
agcagcagca gcagcagcag caggggggacc tatcaggaca gagttcacat ccatgtgaaa 1080
ggccagccac cagttcagga gcacttggga gtgatctagg tgatgctatg agtgaagaag 1140
acatgcttca ggcagctgtg accatgtctt tagaaactgt cagaaatgat ttgaaaacag 1200
aaggaaaaaa ataaaacttg tttattgcag cttataatgg ttacaaataa agcaatagca 1260
tcacaaattt cacaaataaa gcattttttt cactgcattc tagttgtggt ttgtccaaac 1320
tcatcaatgt atcttatcat gtctggatcg taaggcctgc tcaccattca tcatgttcgc 1380
taccttcaca ctttatctga catacgagct ccatgtgatt tttgctttac attattcttc 1440
attccctctt taatcatatt aagaatctta agtaaatttg taatctacta aatttccctg 1500
gattaaggag cagttaccaa aagaaaaaaa aaaaaaaaag ctagatgtgg tggctcacat 1560

```
ctgtaatccc agcactttgg gaaaccaagg caggagagga ttgctagaac atttaatgaa   1620

tactttaaca taataattta aacttcacag taatttgtac agtctccaaa aattccttag   1680

acatcatgga tatttttctt tttttgagat ggagtcttgc tct                     1723


<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21

caaaggtgcc cttgaggtt                                                  19


<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22

aggagaagtc tgccgttact                                                 20


<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23

ggacaaacca caactagaat gc                                              22


<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24

taggaaagga cagtgggagt                                                 20


<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25

ccattatgtc tcagttgttc agtg                                            24


<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26

ccagaccatc tcagacacc                                                  19
```

<210> SEQ ID NO 27
<211> LENGTH: 18
<212> TYPE: DNA
<213> ORGANISM: Artificial Sequence
<220> FEATURE:
<223> OTHER INFORMATION: Primer

<400> SEQUENCE: 27
ggctgggctt ccacttac 18

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
gtggtttgtc caaactcatc aa 22

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
agtaactctg cacttcccat tg 22

<210> SEQ ID NO 30
<211> LENGTH: 639
<212> TYPE: PRT
<213> ORGANISM: Scytonema hoffmanni

<400> SEQUENCE: 30

```
Met Ser Gln Ile Thr Ile Gln Ala Arg Leu Ile Ser Phe Glu Ser Asn
1               5                   10                  15

Arg Gln Gln Leu Trp Lys Leu Met Ala Asp Leu Asn Thr Pro Leu Ile
            20                  25                  30

Asn Glu Leu Leu Cys Gln Leu Gly Gln His Pro Asp Phe Glu Lys Trp
        35                  40                  45

Gln Gln Lys Gly Lys Leu Pro Ser Thr Val Val Ser Gln Leu Cys Gln
    50                  55                  60

Pro Leu Lys Thr Asp Pro Arg Phe Ala Gly Gln Pro Ser Arg Leu Tyr
65                  70                  75                  80

Met Ser Ala Ile His Ile Val Asp Tyr Ile Tyr Lys Ser Trp Leu Ala
                85                  90                  95

Ile Gln Lys Arg Leu Gln Gln Gln Leu Asp Gly Lys Thr Arg Trp Leu
            100                 105                 110

Glu Met Leu Asn Ser Asp Ala Glu Leu Val Glu Leu Ser Gly Asp Thr
        115                 120                 125

Leu Glu Ala Ile Arg Val Lys Ala Ala Glu Ile Leu Ala Ile Ala Met
    130                 135                 140

Pro Ala Ser Glu Ser Asp Ser Ala Ser Pro Lys Gly Lys Lys Gly Lys
145                 150                 155                 160

Lys Glu Lys Lys Pro Ser Ser Ser Ser Pro Lys Arg Ser Leu Ser Lys
                165                 170                 175

Thr Leu Phe Asp Ala Tyr Gln Glu Thr Glu Asp Ile Lys Ser Arg Ser
            180                 185                 190
```

-continued

```
Ala Ile Ser Tyr Leu Leu Lys Asn Gly Cys Lys Leu Thr Asp Lys Glu
        195                 200                 205

Glu Asp Ser Glu Lys Phe Ala Lys Arg Arg Arg Gln Val Glu Ile Gln
    210                 215                 220

Ile Gln Arg Leu Thr Glu Lys Leu Ile Ser Arg Met Pro Lys Gly Arg
225                 230                 235                 240

Asp Leu Thr Asn Ala Lys Trp Leu Glu Thr Leu Leu Thr Ala Thr Thr
                245                 250                 255

Thr Val Ala Glu Asp Asn Ala Gln Ala Lys Arg Trp Gln Asp Ile Leu
            260                 265                 270

Leu Thr Arg Ser Ser Ser Leu Pro Phe Pro Leu Val Phe Glu Thr Asn
        275                 280                 285

Glu Asp Met Val Trp Ser Lys Asn Gln Lys Gly Arg Leu Cys Val His
    290                 295                 300

Phe Asn Gly Leu Ser Asp Leu Ile Phe Glu Val Tyr Cys Gly Asn Arg
305                 310                 315                 320

Gln Leu His Trp Phe Gln Arg Phe Leu Glu Asp Gln Gln Thr Lys Arg
                325                 330                 335

Lys Ser Lys Asn Gln His Ser Ser Gly Leu Phe Thr Leu Arg Asn Gly
            340                 345                 350

His Leu Val Trp Leu Glu Gly Glu Gly Lys Gly Glu Pro Trp Asn Leu
        355                 360                 365

His His Leu Thr Leu Tyr Cys Cys Val Asp Asn Arg Leu Trp Thr Glu
    370                 375                 380

Glu Gly Thr Glu Ile Val Arg Gln Glu Lys Ala Asp Glu Ile Thr Lys
385                 390                 395                 400

Phe Ile Thr Asn Met Lys Lys Lys Ser Asp Leu Ser Asp Thr Gln Gln
                405                 410                 415

Ala Leu Ile Gln Arg Lys Gln Ser Thr Leu Thr Arg Ile Asn Asn Ser
            420                 425                 430

Phe Glu Arg Pro Ser Gln Pro Leu Tyr Gln Gly Gln Ser His Ile Leu
        435                 440                 445

Val Gly Val Ser Leu Gly Leu Glu Lys Pro Ala Thr Val Ala Val Val
    450                 455                 460

Asp Ala Ile Ala Asn Lys Val Leu Ala Tyr Arg Ser Ile Lys Gln Leu
465                 470                 475                 480

Leu Gly Asp Asn Tyr Glu Leu Leu Asn Arg Gln Arg Arg Gln Gln Gln
                485                 490                 495

Tyr Leu Ser His Glu Arg His Lys Ala Gln Lys Asn Phe Ser Pro Asn
            500                 505                 510

Gln Phe Gly Ala Ser Glu Leu Gly Gln His Ile Asp Arg Leu Leu Ala
        515                 520                 525

Lys Ala Ile Val Ala Leu Ala Arg Thr Tyr Lys Ala Gly Ser Ile Val
    530                 535                 540

Leu Pro Lys Leu Gly Asp Met Arg Glu Val Val Gln Ser Glu Ile Gln
545                 550                 555                 560

Ala Ile Ala Glu Gln Lys Phe Pro Gly Tyr Ile Glu Gly Gln Gln Lys
                565                 570                 575

Tyr Ala Lys Gln Tyr Arg Val Asn Val His Arg Trp Ser Tyr Gly Arg
            580                 585                 590

Leu Ile Gln Ser Ile Gln Ser Lys Ala Ala Gln Thr Gly Ile Val Ile
        595                 600                 605
```

```
Glu Glu Gly Lys Gln Pro Ile Arg Gly Ser Pro His Asp Lys Ala Lys
    610                 615                 620

Glu Leu Ala Leu Ser Ala Tyr Asn Leu Arg Leu Thr Arg Arg Ser
625                 630                 635


<210> SEQ ID NO 31
<211> LENGTH: 642
<212> TYPE: PRT
<213> ORGANISM: Anabaena cylindrica

<400> SEQUENCE: 31

Met Ser Val Ile Thr Ile Gln Cys Arg Leu Val Ala Glu Glu Asp Ser
1               5                   10                  15

Leu Arg Gln Leu Trp Glu Leu Met Ser Glu Lys Asn Thr Pro Phe Ile
            20                  25                  30

Asn Glu Ile Leu Leu Gln Ile Gly Lys His Pro Glu Phe Glu Thr Trp
        35                  40                  45

Leu Glu Lys Gly Arg Ile Pro Ala Glu Leu Leu Lys Thr Leu Gly Asn
    50                  55                  60

Ser Leu Lys Thr Gln Glu Pro Phe Thr Gly Gln Pro Gly Arg Phe Tyr
65                  70                  75                  80

Thr Ser Ala Ile Thr Leu Val Asp Tyr Leu Tyr Lys Ser Trp Phe Ala
                85                  90                  95

Leu Gln Lys Arg Arg Lys Gln Gln Ile Glu Gly Lys Gln Arg Trp Leu
            100                 105                 110

Lys Met Leu Lys Ser Asp Gln Glu Leu Glu Gln Glu Ser Gln Ser Ser
        115                 120                 125

Leu Glu Val Ile Arg Asn Lys Ala Thr Glu Leu Phe Ser Lys Phe Thr
    130                 135                 140

Pro Gln Ser Asp Ser Glu Ala Leu Arg Arg Asn Gln Asn Asp Lys Gln
145                 150                 155                 160

Lys Lys Val Lys Lys Thr Lys Lys Ser Thr Lys Pro Lys Thr Ser Ser
                165                 170                 175

Ile Phe Lys Ile Phe Leu Ser Thr Tyr Glu Glu Ala Glu Glu Pro Leu
            180                 185                 190

Thr Arg Cys Ala Leu Ala Tyr Leu Leu Lys Asn Asn Cys Gln Ile Ser
        195                 200                 205

Glu Leu Asp Glu Asn Pro Glu Glu Phe Thr Arg Asn Lys Arg Arg Lys
    210                 215                 220

Glu Ile Glu Ile Glu Arg Leu Lys Asp Gln Leu Gln Ser Arg Ile Pro
225                 230                 235                 240

Lys Gly Arg Asp Leu Thr Gly Glu Glu Trp Leu Glu Thr Leu Glu Ile
                245                 250                 255

Ala Thr Phe Asn Val Pro Gln Asn Glu Asn Glu Ala Lys Ala Trp Gln
            260                 265                 270

Ala Ala Leu Leu Arg Lys Thr Ala Asn Val Pro Phe Pro Val Ala Tyr
        275                 280                 285

Glu Ser Asn Glu Asp Met Thr Trp Leu Lys Asn Asp Lys Asn Arg Leu
    290                 295                 300

Phe Val Arg Phe Asn Gly Leu Gly Lys Leu Thr Phe Glu Ile Tyr Cys
305                 310                 315                 320

Asp Lys Arg His Leu His Tyr Phe Gln Arg Phe Leu Glu Asp Gln Glu
                325                 330                 335

Ile Leu Arg Asn Ser Lys Arg Gln His Ser Ser Ser Leu Phe Thr Leu
            340                 345                 350
```

-continued

```
Arg Ser Gly Arg Ile Ala Trp Leu Pro Gly Glu Glu Lys Gly Glu His
        355                 360                 365

Trp Lys Val Asn Gln Leu Asn Phe Tyr Cys Ser Leu Asp Thr Arg Met
    370                 375                 380

Leu Thr Thr Glu Gly Thr Gln Gln Val Val Glu Glu Lys Val Thr Ala
385                 390                 395                 400

Ile Thr Glu Ile Leu Asn Lys Thr Lys Gln Lys Asp Asp Leu Asn Asp
                405                 410                 415

Lys Gln Gln Ala Phe Ile Thr Arg Gln Gln Ser Thr Leu Ala Arg Ile
            420                 425                 430

Asn Asn Pro Phe Pro Arg Pro Ser Lys Pro Asn Tyr Gln Gly Lys Ser
        435                 440                 445

Ser Ile Leu Ile Gly Val Ser Phe Gly Leu Glu Lys Pro Val Thr Val
    450                 455                 460

Ala Val Val Asp Val Val Lys Asn Lys Val Ile Ala Tyr Arg Ser Val
465                 470                 475                 480

Lys Gln Leu Leu Gly Glu Asn Tyr Asn Leu Leu Asn Arg Gln Arg Gln
                485                 490                 495

Gln Gln Gln Arg Leu Ser His Glu Arg His Lys Ala Gln Lys Gln Asn
            500                 505                 510

Ala Pro Asn Ser Phe Gly Glu Ser Glu Leu Gly Gln Tyr Val Asp Arg
        515                 520                 525

Leu Leu Ala Asp Ala Ile Ile Ala Ile Ala Lys Lys Tyr Gln Ala Gly
    530                 535                 540

Ser Ile Val Leu Pro Lys Leu Arg Asp Met Arg Glu Gln Ile Ser Ser
545                 550                 555                 560

Glu Ile Gln Ser Arg Ala Glu Asn Gln Cys Pro Gly Tyr Lys Glu Gly
                565                 570                 575

Gln Gln Lys Tyr Ala Lys Glu Tyr Arg Ile Asn Val His Arg Trp Ser
            580                 585                 590

Tyr Gly Arg Leu Ile Glu Ser Ile Lys Ser Gln Ala Ala Gln Ala Gly
        595                 600                 605

Ile Ala Ile Glu Thr Gly Lys Gln Ser Ile Arg Gly Ser Pro Gln Glu
    610                 615                 620

Lys Ala Arg Asp Leu Ala Val Phe Thr Tyr Gln Glu Arg Gln Ala Ala
625                 630                 635                 640

Leu Ile
```

<210> SEQ ID NO 32
<211> LENGTH: 208
<212> TYPE: DNA
<213> ORGANISM: Artificial Sequence
<220> FEATURE:
<223> OTHER INFORMATION: Transposon left end

<400> SEQUENCE: 32

```
tacagtgaca aattatctgt cgtcggtgac agattaatgt cattgtgact atttaattgt     60

cgtcgtgacc catcagcgtt gcttaattaa ttgatgacaa attaaatgtc atcaatataa    120

tatgctctgc aattattata caaagcaatt aaaacaagcg gataaaagga cttgctttca    180

acccacccct aagtttaata gttactga                                       208
```

<210> SEQ ID NO 33
<211> LENGTH: 219
<212> TYPE: DNA

```
<213> ORGANISM: Artificial Sequence
<220> FEATURE:
<223> OTHER INFORMATION: Transposon right end

<400> SEQUENCE: 33

cgacagtcaa tttgtcatta tgaaaataca caaaagcttt ttcctatctt gcaaagcgac     60

agctaatttg tcacaatcac ggacaacgac atctattttg tcactgcaaa gaggttatgc    120

taaaactgcc aaagcgctat aatctatact gtataaggat tttactgatg acaataattt    180

gtcacaacga catataatta gtcactgtac acgtagaga                            219


<210> SEQ ID NO 34
<211> LENGTH: 394
<212> TYPE: PRT
<213> ORGANISM: Vibrio cholerae

<400> SEQUENCE: 34

Met Phe Leu Gln Arg Pro Lys Pro Tyr Ser Asp Glu Ser Leu Glu Ser
1               5                   10                  15

Phe Phe Ile Arg Val Ala Asn Lys Asn Gly Tyr Gly Asp Val His Arg
            20                  25                  30

Phe Leu Glu Ala Thr Lys Arg Phe Leu Gln Asp Ile Asp His Asn Gly
        35                  40                  45

Tyr Gln Thr Phe Pro Thr Asp Ile Thr Arg Ile Asn Pro Tyr Ser Ala
    50                  55                  60

Lys Asn Ser Ser Ser Ala Arg Thr Ala Ser Phe Leu Lys Leu Ala Gln
65                  70                  75                  80

Leu Thr Phe Asn Glu Pro Pro Glu Leu Leu Gly Leu Ala Ile Asn Arg
                85                  90                  95

Thr Asn Met Lys Tyr Ser Pro Ser Thr Ser Ala Val Val Arg Gly Ala
            100                 105                 110

Glu Val Phe Pro Arg Ser Leu Leu Arg Thr His Ser Ile Pro Cys Cys
        115                 120                 125

Pro Leu Cys Leu Arg Glu Asn Gly Tyr Ala Ser Tyr Leu Trp His Phe
    130                 135                 140

Gln Gly Tyr Glu Tyr Cys His Ser His Asn Val Pro Leu Ile Thr Thr
145                 150                 155                 160

Cys Ser Cys Gly Lys Glu Phe Asp Tyr Arg Val Ser Gly Leu Lys Gly
                165                 170                 175

Ile Cys Cys Lys Cys Lys Glu Pro Ile Thr Leu Thr Ser Arg Glu Asn
            180                 185                 190

Gly His Glu Ala Ala Cys Thr Val Ser Asn Trp Leu Ala Gly His Glu
        195                 200                 205

Ser Lys Pro Leu Pro Asn Leu Pro Lys Ser Tyr Arg Trp Gly Leu Val
    210                 215                 220

His Trp Trp Met Gly Ile Lys Asp Ser Glu Phe Asp His Phe Ser Phe
225                 230                 235                 240

Val Gln Phe Phe Ser Asn Trp Pro Arg Ser Phe His Ser Ile Ile Glu
                245                 250                 255

Asp Glu Val Glu Phe Asn Leu Glu His Ala Val Val Ser Thr Ser Glu
            260                 265                 270

Leu Arg Leu Lys Asp Leu Leu Gly Arg Leu Phe Phe Gly Ser Ile Arg
        275                 280                 285

Leu Pro Glu Arg Asn Leu Gln His Asn Ile Ile Leu Gly Glu Leu Leu
    290                 295                 300
```

```
Cys Tyr Leu Glu Asn Arg Leu Trp Gln Asp Lys Gly Leu Ile Ala Asn
305                 310                 315                 320

Leu Lys Met Asn Ala Leu Glu Ala Thr Val Met Leu Asn Cys Ser Leu
                325                 330                 335

Asp Gln Ile Ala Ser Met Val Glu Gln Arg Ile Leu Lys Pro Asn Arg
            340                 345                 350

Lys Ser Lys Pro Asn Ser Pro Leu Asp Val Thr Asp Tyr Leu Phe His
        355                 360                 365

Phe Gly Asp Ile Phe Cys Leu Trp Leu Ala Glu Phe Gln Ser Asp Glu
    370                 375                 380

Phe Asn Arg Ser Phe Tyr Val Ser Arg Trp
385                 390


<210> SEQ ID NO 35
<211> LENGTH: 640
<212> TYPE: PRT
<213> ORGANISM: Vibrio cholerae

<400> SEQUENCE: 35

Met Gln Thr Leu Lys Glu Leu Ile Ala Ser Asn Pro Asp Asp Leu Thr
1               5                   10                  15

Thr Glu Leu Lys Arg Ala Phe Arg Pro Leu Thr Pro His Ile Ala Ile
            20                  25                  30

Asp Gly Asn Glu Leu Asp Ala Leu Thr Ile Leu Val Asn Leu Thr Asp
        35                  40                  45

Lys Thr Asp Asp Gln Lys Asp Leu Leu Asp Arg Ala Lys Cys Lys Gln
    50                  55                  60

Lys Leu Arg Asp Glu Lys Trp Trp Ala Ser Cys Ile Asn Cys Val Asn
65                  70                  75                  80

Tyr Arg Gln Ser His Asn Pro Lys Phe Pro Asp Ile Arg Ser Glu Gly
                85                  90                  95

Val Ile Arg Thr Gln Ala Leu Gly Glu Leu Pro Ser Phe Leu Leu Ser
            100                 105                 110

Ser Ser Lys Ile Pro Pro Tyr His Trp Ser Tyr Ser His Asp Ser Lys
        115                 120                 125

Tyr Val Asn Lys Ser Ala Phe Leu Thr Asn Glu Phe Cys Trp Asp Gly
    130                 135                 140

Glu Ile Ser Cys Leu Gly Glu Leu Leu Lys Asp Ala Asp His Pro Leu
145                 150                 155                 160

Trp Asn Thr Leu Lys Lys Leu Gly Cys Ser Gln Lys Thr Cys Lys Ala
                165                 170                 175

Met Ala Lys Gln Leu Ala Asp Ile Thr Leu Thr Thr Ile Asn Val Thr
            180                 185                 190

Leu Ala Pro Asn Tyr Leu Thr Gln Ile Ser Leu Pro Asp Ser Asp Thr
        195                 200                 205

Ser Tyr Ile Ser Leu Ser Pro Val Ala Ser Leu Ser Met Gln Ser His
    210                 215                 220

Phe His Gln Arg Leu Gln Asp Glu Asn Arg His Ser Ala Ile Thr Arg
225                 230                 235                 240

Phe Ser Arg Thr Thr Asn Met Gly Val Thr Ala Met Thr Cys Gly Gly
                245                 250                 255

Ala Phe Arg Met Leu Lys Ser Gly Ala Lys Phe Ser Ser Pro Pro His
            260                 265                 270

His Arg Leu Asn Ser Lys Arg Ser Trp Leu Thr Ser Glu His Val Gln
        275                 280                 285
```

```
Ser Leu Lys Gln Tyr Gln Arg Leu Asn Lys Ser Leu Ile Pro Glu Asn
    290                 295                 300

Ser Arg Ile Ala Leu Arg Arg Lys Tyr Lys Ile Glu Leu Gln Asn Met
305                 310                 315                 320

Val Arg Ser Trp Phe Ala Met Gln Asp His Thr Leu Asp Ser Asn Ile
                325                 330                 335

Leu Ile Gln His Leu Asn His Asp Leu Ser Tyr Leu Gly Ala Thr Lys
            340                 345                 350

Arg Phe Ala Tyr Asp Pro Ala Met Thr Lys Leu Phe Thr Glu Leu Leu
        355                 360                 365

Lys Arg Glu Leu Ser Asn Ser Ile Asn Asn Gly Glu Gln His Thr Asn
    370                 375                 380

Gly Ser Phe Leu Val Leu Pro Asn Ile Arg Val Cys Gly Ala Thr Ala
385                 390                 395                 400

Leu Ser Ser Pro Val Thr Val Gly Ile Pro Ser Leu Thr Ala Phe Phe
                405                 410                 415

Gly Phe Val His Ala Phe Glu Arg Asn Ile Asn Arg Thr Thr Ser Ser
            420                 425                 430

Phe Arg Val Glu Ser Phe Ala Ile Cys Val His Gln Leu His Val Glu
        435                 440                 445

Lys Arg Gly Leu Thr Ala Glu Phe Val Glu Lys Gly Asp Gly Thr Ile
    450                 455                 460

Ser Ala Pro Ala Thr Arg Asp Asp Trp Gln Cys Asp Val Val Phe Ser
465                 470                 475                 480

Leu Ile Leu Asn Thr Asn Phe Ala Gln His Ile Asp Gln Asp Thr Leu
                485                 490                 495

Val Thr Ser Leu Pro Lys Arg Leu Ala Arg Gly Ser Ala Lys Ile Ala
            500                 505                 510

Ile Asp Asp Phe Lys His Ile Asn Ser Phe Ser Thr Leu Glu Thr Ala
        515                 520                 525

Ile Glu Ser Leu Pro Ile Glu Ala Gly Arg Trp Leu Ser Leu Tyr Ala
    530                 535                 540

Gln Ser Asn Asn Asn Leu Ser Asp Leu Leu Ala Ala Met Thr Glu Asp
545                 550                 555                 560

His Gln Leu Met Ala Ser Cys Val Gly Tyr His Leu Leu Glu Glu Pro
                565                 570                 575

Lys Asp Lys Pro Asn Ser Leu Arg Gly Tyr Lys His Ala Ile Ala Glu
            580                 585                 590

Cys Ile Ile Gly Leu Ile Asn Ser Ile Thr Phe Ser Ser Glu Thr Asp
        595                 600                 605

Pro Asn Thr Ile Phe Trp Ser Leu Lys Asn Tyr Gln Asn Tyr Leu Val
    610                 615                 620

Val Gln Pro Arg Ser Ile Asn Asp Glu Thr Thr Asp Lys Ser Ser Leu
625                 630                 635                 640
```

<210> SEQ ID NO 36
<211> LENGTH: 352
<212> TYPE: PRT
<213> ORGANISM: Vibrio cholerae

<400> SEQUENCE: 36

```
Met Lys Leu Pro Thr Asn Leu Ala Tyr Glu Arg Ser Ile Asp Pro Ser
1               5                   10                  15

Asp Val Cys Phe Phe Val Val Trp Pro Asp Asp Arg Lys Thr Pro Leu
```

```
            20                  25                  30

Thr Tyr Asn Ser Arg Thr Leu Leu Gly Gln Met Glu Ala Ala Ser Leu
        35                  40                  45

Ala Tyr Asp Val Ser Gly Gln Pro Ile Lys Ser Ala Thr Ala Glu Ala
    50                  55                  60

Leu Ala Gln Gly Asn Pro His Gln Val Asp Phe Cys His Val Pro Tyr
65                  70                  75                  80

Gly Ala Ser His Ile Glu Cys Ser Phe Ser Val Ser Phe Ser Ser Glu
                85                  90                  95

Leu Arg Gln Pro Tyr Lys Cys Asn Ser Ser Lys Val Lys Gln Thr Leu
            100                 105                 110

Val Gln Leu Val Glu Leu Tyr Glu Thr Lys Ile Gly Trp Thr Glu Leu
        115                 120                 125

Ala Thr Arg Tyr Leu Met Asn Ile Cys Asn Gly Lys Trp Leu Trp Lys
    130                 135                 140

Asn Thr Arg Lys Ala Tyr Cys Trp Asn Ile Val Leu Thr Pro Trp Pro
145                 150                 155                 160

Trp Asn Gly Glu Lys Val Gly Phe Glu Asp Ile Arg Thr Asn Tyr Thr
                165                 170                 175

Ser Arg Gln Asp Phe Lys Asn Asn Lys Asn Trp Ser Ala Ile Val Glu
            180                 185                 190

Met Ile Lys Thr Ala Phe Ser Ser Thr Asp Gly Leu Ala Ile Phe Glu
        195                 200                 205

Val Arg Ala Thr Leu His Leu Pro Thr Asn Ala Met Val Arg Pro Ser
    210                 215                 220

Gln Val Phe Thr Glu Lys Glu Ser Gly Ser Lys Ser Lys Ser Lys Thr
225                 230                 235                 240

Gln Asn Ser Arg Val Phe Gln Ser Thr Thr Ile Asp Gly Glu Arg Ser
                245                 250                 255

Pro Ile Leu Gly Ala Phe Lys Thr Gly Ala Ala Ile Ala Thr Ile Asp
            260                 265                 270

Asp Trp Tyr Pro Glu Ala Thr Glu Pro Leu Arg Val Gly Arg Phe Gly
        275                 280                 285

Val His Arg Glu Asp Val Thr Cys Tyr Arg His Pro Ser Thr Gly Lys
    290                 295                 300

Asp Phe Phe Ser Ile Leu Gln Gln Ala Glu His Tyr Ile Glu Val Leu
305                 310                 315                 320

Ser Ala Asn Lys Thr Pro Ala Gln Glu Thr Ile Asn Asp Met His Phe
                325                 330                 335

Leu Met Ala Asn Leu Ile Lys Gly Gly Met Phe Gln His Lys Gly Asp
            340                 345                 350


<210> SEQ ID NO 37
<211> LENGTH: 199
<212> TYPE: PRT
<213> ORGANISM: Vibrio cholerae

<400> SEQUENCE: 37

Met Lys Trp Tyr Tyr Lys Thr Ile Thr Phe Leu Pro Glu Leu Cys Asn
1               5                   10                  15

Asn Glu Ser Leu Ala Ala Lys Cys Leu Arg Val Leu His Gly Phe Asn
            20                  25                  30

Tyr Gln Tyr Glu Thr Arg Asn Ile Gly Val Ser Phe Pro Leu Trp Cys
        35                  40                  45
```

-continued

```
Asp Ala Thr Val Gly Lys Lys Ile Ser Phe Val Ser Lys Asn Lys Ile
    50                  55                  60

Glu Leu Asp Leu Leu Leu Lys Gln His Tyr Phe Val Gln Met Glu Gln
65                  70                  75                  80

Leu Gln Tyr Phe His Ile Ser Asn Thr Val Leu Val Pro Glu Asp Cys
                85                  90                  95

Thr Tyr Val Ser Phe Arg Arg Cys Gln Ser Ile Asp Lys Leu Thr Ala
            100                 105                 110

Ala Gly Leu Ala Arg Lys Ile Arg Arg Leu Glu Lys Arg Ala Leu Ser
        115                 120                 125

Arg Gly Glu Gln Phe Asp Pro Ser Ser Phe Ala Gln Lys Glu His Thr
    130                 135                 140

Ala Ile Ala His Tyr His Ser Leu Gly Glu Ser Ser Lys Gln Thr Asn
145                 150                 155                 160

Arg Asn Phe Arg Leu Asn Ile Arg Met Leu Ser Glu Gln Pro Arg Glu
                165                 170                 175

Gly Asn Ser Ile Phe Ser Ser Tyr Gly Leu Ser Asn Ser Glu Asn Ser
            180                 185                 190

Phe Gln Pro Val Pro Leu Ile
        195


<210> SEQ ID NO 38
<211> LENGTH: 230
<212> TYPE: PRT
<213> ORGANISM: Vibrio cholerae

<400> SEQUENCE: 38

Met Ala Thr Ser Leu Pro Thr Pro Ser Ala Ile Thr Thr Ser Ala Leu
1               5                   10                  15

Glu Tyr Ala Phe His Thr Pro Ala Arg Asn Leu Thr Lys Ser Arg Gly
            20                  25                  30

Lys Asn Ile His Arg Tyr Val Ser Val Lys Met Ser Lys Arg Ile Thr
        35                  40                  45

Val Glu Ser Thr Leu Glu Cys Asp Ala Cys Tyr His Phe Asp Phe Glu
    50                  55                  60

Pro Ser Ile Val Arg Phe Cys Ala Gln Pro Ile Arg Phe Leu Tyr Tyr
65                  70                  75                  80

Leu Asn Gly Gln Ser His Ser Tyr Val Pro Asp Phe Leu Val Gln Phe
                85                  90                  95

Asp Thr Asn Glu Phe Val Leu Tyr Glu Val Lys Ser Ala Tyr Ala Lys
            100                 105                 110

Asn Lys Pro Asp Phe Asp Val Glu Trp Glu Ala Lys Val Lys Ala Ala
        115                 120                 125

Thr Glu Leu Gly Leu Glu Leu Glu Leu Val Glu Glu Ser Asp Ile Arg
    130                 135                 140

Asp Thr Val Val Leu Asn Asn Leu Lys Arg Met His Arg Tyr Ala Ser
145                 150                 155                 160

Lys Asp Glu Leu Asn Asn Val His Asn Ser Leu Leu Lys Ile Ile Lys
                165                 170                 175

Tyr Asn Gly Ala Gln Ser Ala Arg Cys Leu Gly Glu Gln Leu Gly Leu
            180                 185                 190

Lys Gly Arg Thr Val Leu Pro Ile Leu Cys Asp Leu Leu Ser Arg Cys
        195                 200                 205

Leu Leu Asp Thr Arg Leu Asp Lys Pro Leu Ser Leu Glu Ser Arg Phe
    210                 215                 220
```

```
Glu Leu Ala Ser Tyr Gly
225                 230


<210> SEQ ID NO 39
<211> LENGTH: 603
<212> TYPE: PRT
<213> ORGANISM: Vibrio cholerae

<400> SEQUENCE: 39

Met Ala Lys Lys Gly Phe Ser Ser Phe His Arg Lys Ala Val Ser Ser
1               5                   10                  15

Gln Asp Thr Leu Glu Ser Ile Glu Leu Val Ser Ser Ala Asn Cys Leu
            20                  25                  30

Glu Ser Val Thr Tyr Gln Asp Ile Ser Ala Phe Pro Glu Thr Ile Ala
        35                  40                  45

Val Glu Ile Asn Phe Arg Leu Ser Ile Leu Arg Phe Leu Ala Arg Lys
    50                  55                  60

Cys Glu Thr Ile Val Ala Lys Ser Ile Glu Pro His Arg Val Glu Leu
65                  70                  75                  80

Gln Gln Asn Tyr Ser Arg Lys Ile Pro Ser Ala Ile Thr Ile Tyr Arg
                85                  90                  95

Trp Trp Leu Ala Phe Arg Lys Ser Asp Tyr Asn Pro Ile Ser Leu Ala
            100                 105                 110

Pro Asn Ile Lys Asp Arg Gly Asn Arg Glu Thr Lys Val Ser Thr Val
        115                 120                 125

Val Asp Ser Ile Met Glu Gln Ala Val Glu Arg Val Ile Ser Gly Arg
    130                 135                 140

Lys Val Asn Val Ser Ser Ala Tyr Lys Arg Val Arg Arg Lys Val Arg
145                 150                 155                 160

Gln Tyr Asn Leu Thr His Gly Thr Lys Tyr Thr Tyr Pro Lys Tyr Glu
                165                 170                 175

Ser Val Arg Lys Arg Val Lys Lys Lys Thr Pro Phe Glu Leu Leu Ala
            180                 185                 190

Ala Gly Lys Gly Glu Arg Val Ala Lys Arg Glu Phe Arg Arg Met Gly
        195                 200                 205

Lys Lys Ile Leu Thr Ser Ser Val Leu Glu Arg Val Glu Ile Asp His
    210                 215                 220

Thr Val Val Asp Leu Phe Ala Val His Glu Glu Tyr Arg Ile Pro Leu
225                 230                 235                 240

Gly Arg Pro Trp Leu Thr Gln Leu Val Asp Cys Tyr Ser Lys Ala Val
                245                 250                 255

Ile Gly Phe Tyr Leu Gly Phe Glu Pro Pro Ser Tyr Val Ser Val Ser
            260                 265                 270

Leu Ala Leu Lys Asn Ala Ile Gln Arg Lys Asp Asp Leu Ile Ser Ser
        275                 280                 285

Tyr Glu Ser Ile Glu Asn Glu Trp Leu Cys Tyr Gly Ile Pro Asp Leu
    290                 295                 300

Leu Val Thr Asp Asn Gly Lys Glu Phe Leu Ser Lys Ala Phe Asp Gln
305                 310                 315                 320

Ala Cys Glu Ser Leu Leu Ile Asn Val His Gln Asn Lys Val Glu Thr
                325                 330                 335

Pro Asp Asn Lys Pro His Val Glu Arg Asn Tyr Gly Thr Ile Asn Thr
            340                 345                 350

Ser Leu Leu Asp Asp Leu Pro Gly Lys Ser Phe Ser Gln Tyr Leu Gln
```

```
        355                 360                 365

Arg Glu Gly Tyr Asp Ser Val Gly Glu Ala Thr Leu Thr Leu Asn Glu
    370                 375                 380

Ile Arg Glu Ile Tyr Leu Ile Trp Leu Val Asp Ile Tyr His Lys Lys
385                 390                 395                 400

Pro Asn Gln Arg Gly Thr Asn Cys Pro Asn Val Ala Trp Lys Lys Gly
                405                 410                 415

Cys Gln Glu Trp Glu Pro Glu Glu Phe Ser Gly Ser Lys Asp Glu Leu
            420                 425                 430

Asp Phe Lys Phe Ala Ile Val Asp Tyr Lys Gln Leu Thr Lys Val Gly
        435                 440                 445

Ile Thr Val Tyr Lys Glu Leu Ser Tyr Ser Asn Asp Arg Leu Ala Glu
    450                 455                 460

Tyr Arg Gly Lys Lys Gly Asn His Lys Val Gln Phe Lys Tyr Asn Pro
465                 470                 475                 480

Glu Cys Met Ala Val Ile Trp Val Leu Asp Glu Asp Met Asn Glu Tyr
                485                 490                 495

Phe Thr Val Asn Ala Ile Asp Tyr Glu Tyr Ala Ser Arg Val Ser Leu
            500                 505                 510

Trp Gln His Lys Tyr Asn Met Lys Tyr Gln Ala Glu Leu Asn Ser Ala
        515                 520                 525

Glu Tyr Asp Glu Asp Lys Glu Ile Asp Ala Glu Ile Lys Ile Glu Glu
    530                 535                 540

Ile Ala Asp Arg Ser Ile Val Lys Thr Asn Lys Ile Arg Ala Arg Arg
545                 550                 555                 560

Arg Gly Ala Arg His Gln Glu Asn Ser Ala Arg Ala Lys Ser Ile Ser
                565                 570                 575

Asn Ala Asn Pro Ala Ser Ile Gln Lys His Glu Asp Glu Ile Val Ser
            580                 585                 590

Ala Asp Asn Asp Asp Trp Asp Ile Asp Tyr Val
        595                 600


<210> SEQ ID NO 40
<211> LENGTH: 330
<212> TYPE: PRT
<213> ORGANISM: Vibrio cholerae

<400> SEQUENCE: 40

Met Ser Glu Thr Arg Glu Ala Arg Ile Ser Arg Ala Lys Arg Ala Phe
1               5                   10                  15

Val Ser Thr Pro Ser Val Arg Lys Ile Leu Ser Tyr Met Asp Arg Cys
            20                  25                  30

Arg Asp Leu Ser Asp Leu Glu Ser Glu Pro Thr Cys Met Met Val Tyr
        35                  40                  45

Gly Ala Ser Gly Val Gly Lys Thr Thr Val Ile Lys Lys Tyr Leu Asn
    50                  55                  60

Gln Asn Arg Arg Glu Ser Glu Ala Gly Gly Asp Ile Ile Pro Val Leu
65                  70                  75                  80

His Ile Glu Leu Pro Asp Asn Ala Lys Pro Val Asp Ala Ala Arg Glu
                85                  90                  95

Leu Leu Val Glu Met Gly Asp Pro Leu Ala Leu Tyr Glu Thr Asp Leu
            100                 105                 110

Ala Arg Leu Thr Lys Arg Leu Thr Glu Leu Ile Pro Ala Val Gly Val
        115                 120                 125
```

```
Lys Leu Ile Ile Ile Asp Glu Phe Gln His Leu Val Glu Glu Arg Ser
    130                 135                 140

Asn Arg Val Leu Thr Gln Val Gly Asn Trp Leu Lys Met Ile Leu Asn
145                 150                 155                 160

Lys Thr Lys Cys Pro Ile Val Ile Phe Gly Met Pro Tyr Ser Lys Val
                165                 170                 175

Val Leu Gln Ala Asn Ser Gln Leu His Gly Arg Phe Ser Ile Gln Val
            180                 185                 190

Glu Leu Arg Pro Phe Ser Tyr Gln Gly Gly Arg Gly Val Phe Lys Thr
        195                 200                 205

Phe Leu Glu Tyr Leu Asp Lys Ala Leu Pro Phe Glu Lys Gln Ala Gly
    210                 215                 220

Leu Ala Asn Glu Ser Leu Gln Lys Lys Leu Tyr Ala Phe Ser Gln Gly
225                 230                 235                 240

Asn Met Arg Ser Leu Arg Asn Leu Ile Tyr Gln Ala Ser Ile Glu Ala
                245                 250                 255

Ile Asp Asn Gln His Glu Thr Ile Thr Glu Glu Asp Phe Val Phe Ala
            260                 265                 270

Ser Lys Leu Thr Ser Gly Asp Lys Pro Asn Ser Trp Lys Asn Pro Phe
        275                 280                 285

Glu Glu Gly Val Glu Val Thr Glu Asp Met Leu Arg Pro Pro Pro Lys
    290                 295                 300

Asp Ile Gly Trp Glu Asp Tyr Leu Arg His Ser Thr Pro Arg Val Ser
305                 310                 315                 320

Lys Pro Gly Arg Asn Lys Asn Phe Phe Glu
                325                 330


<210> SEQ ID NO 41
<211> LENGTH: 105
<212> TYPE: DNA
<213> ORGANISM: Vibrio cholerae

<400> SEQUENCE: 41

tgttgatgca accataaagt gatatttaat aattatttat aatcagcaac ttaaccacaa     60

aacaaccata tattgatatc tcacaaaaca accataagtt gatat                   105


<210> SEQ ID NO 42
<211> LENGTH: 48031
<212> TYPE: DNA
<213> ORGANISM: Homo sapiens

<400> SEQUENCE: 42

gtgggggccg ttggctccag acaaataaac atggagtcca tcttccacga gaaagtgagt     60

gtccgcgttc ggtggggagc tgtctgccgc gcggtggcgg gcgtggagcg cggcatcacc    120

gcctctcgga gggctgggtg gggcccgagt cgcccccatg ccgatctcgc ccggcgaggg    180

gcgacgccgc agcctcccgc ctcctcggct cgaggagggg agcatcacct acgcccctac    240

ttcccccgcg gcccccgccc tgggagccgg gagggagtat gggcggggcc gggggcgtct    300

cgggacacgg gagtggggtg gcgcccagtg ggtttgcttc tgcctttctc cgtcactttc    360

catcgctttt cggaggattc cttcacccct ccccaatcct tccctctccc tagggtctag    420

ctagagtcat ctctgggaca cctccctcaa cccctcctac cctaatcctg gcagaattaa    480

cttttcctcc tccggactgc tcaattctat attggagtct tccctacacg tagatctttg    540

gggtcttgtt cgtgtctttc ccctgcacta ggtccgcgag cctcccgagg gaggagacct    600
```

-continued

```
tggctcgccc actgtagggc ctgacattta ggaagtgaag taggaaaccc ggcgtgcccc    660
taaacaggga agtcgtcaca agagttttta ttacgggatg tttgggtttg gtttcttttg    720
gtactcccat ctttccggag caggcggcca gctttgtttt taggtattag gagtggactg    780
ggatgatttt gttgtagtct gcctagcctg ctgtcccttt aactcttccg tgaccatgca    840
cttgaagata ctgtttgtga tatgtaaaga aactcctcgt ttctctcata ctattatcca    900
gccatttgtg tgtgagtgaa gccttcccca ggacagcttt ggcacatggt atcatgtttc    960
ataatagttt cgtgtttgga aagagttgct ggtaaggctg ttatttaata ggaggagcaa   1020
agggtttttg ttttattaaa tacttataaa tgatcattta tcccagacat ttaaaattca   1080
cacacacaca acaaataaag caaagacaaa agaatacatt taccaaatgt aaatctgtag   1140
cataaatttt ttttaatttt tattttaaag atggggtctc attctgtcac ccaggcaggt   1200
gtgcaatgga gagatcatgg ctcactgcag ccttgatctc ctaggcacaa gcgatcctcc   1260
cgcctctgcc tccagagtag ctgggactac aggtgcatat cgccagggcc aggtaatgtt   1320
tttgggagag acggggtctc gctgtgttgc ccaggctggt ctcgaactcc tggactcagg   1380
tgattctccc acctcggcct ctcgaagtgc tgtgattaca ggcgtgagcc actgtgcctg   1440
gaacaaattg ttaagtacaa tgcttttcat tgtagaaaac atctcggaaa cttttgaaat   1500
aggctgatgt tcagtggggg aggaaggact cagtcgtata gttgtcacta attttttgac   1560
ttgattgaca tgactcgtaa atcatagaca atagagattt ggttgcttgg ctgagtagag   1620
tgcgtgaaaa atacacacgt actttttttt tttttttttt gagatggagt ttggctcttg   1680
tcacccaggc tggagtgcaa tggcgccatc atggctcact gcaacctccg cctccccgtt   1740
caagcgattc tcctgcctca gtctccccag tagctgagat tacaggcgcc cgccaccacg   1800
cccagctaat ttttgtattt ttagtagaga cagggtttca ccatgttggc caggctggtc   1860
tccaactcct gacaggtggt ccgcccgcct cggcctccca aagtgctggg attacaggcg   1920
tgagccaccg cacccggcca tatttttgtt attaatttc aaaggctttg gtgtgggacc   1980
acatttcaac atggaaggcc ttaaacatgt tccacactac ttcctgagaa ttagacaaga   2040
tttttaacaa tattgttacc tagttgggac acatttgtac tgacccatgg gatgaaaaaa   2100
agctgagtgc tagcctagtg aaaatctact tacccgaaag aaatccctct tagtctgggt   2160
gcagtggctc acaccagtgc tttgggaggc ccagacgggc ggatcatgag gtcagtagtt   2220
tgagaccagc ctggccaaca tggtgaaacc ccgtctctac taaaaataca aaaaattagc   2280
caggtgtggt ggcaggcgcc tgtaatccca ggtactctgg aggctgaggc aggagaattg   2340
cttgaacccg agaggcagag gttgcagtga gccgagaccg tgccactgca cttcagcctg   2400
ggcaacagag cgagactccg tctcaaaaaa aagaaaagga aaaaagagtc cctcttaatt   2460
atcagcatgt gtataggcct acagatactt caggaatacc tttaccatta tcatcaactt   2520
gtatctacat agcatgtgaa gattcaacaa tttagttttt tgggcgtcct caagagtacg   2580
cacctataac catatggccc aattgttaat ctcctataca gtccattctg ggaatgtttg   2640
ggcttactgt gccatttttc cgttcactgc cttcccctct gcaatatacc tttaaccctt   2700
gctaggtcct gggtttggag agccagagaa ccaactttgg ccctaaagaa gctgtgtagg   2760
tagcaatatc tgcctacgaa gggccttgca accatttcct cttggaacct tggtttcctc   2820
tttctgagta gtcactttga gtacccttta ttaagttaga atgtaaaaac agtttctcac   2880
tgatatatct gcagtgcctg agagagggcc tggcacagag taagtactca ataaatattt   2940
gaatggggcc gggcgtggtg agacctgtct ctacaagaat gaacaaaatt agctgggcgt   3000
```

```
gttagcacat gcctgtagac ttgggaggct gaggtgggag gattgcatga gtctgggagg   3060
tcgaggctgt agtgagccat gatcgcacca ctgcactcca gcctagggga cagagcaaga   3120
tcctgtctca aaagaaaaaa atgtatatat ttgaatggat aaagagatgg ctttgagttt   3180
ctgagatata tatggtgctg tttatctaaa gtaaacaagt tttctgtaaa tattttaagg   3240
ctttgcaggc cagctgtagt ctctgtcaca cattcttatt tgtgcatgtt tttcccaacc   3300
atgtaaaaat gtaaagtgca ttcttagcta ctggggcagg ttgaatttgg cccatgggct   3360
agagtttgcc aacccctaac ttaaaccttt gtactaactt tatgaccact actggatttt   3420
tgttgttgtt tgttttagtt ctggtgcctg ctttgttttt tttttttttt ttaatcctct   3480
tgctgatgtt tcttggtgca gttactgtgc catttgtatt ggtgctttta atgtaatgca   3540
aactggtaat aatatctaaa cttgctgggg ttgtacataa aattattgaa aagattgaaa   3600
agatgctgag cattgactct gtggcattca ttatgccctt ttgtgattgc tggattttag   3660
ccatctttag gacatttgag ctttaggaga agccaaattc tgtataaatg acttgaagtg   3720
ctaatagcac aggttttgaa acctctgcct gggtttgagt ctcagctctg ccttttacta   3780
cctgtgtgat cctgagcaag ttacttagta tccctgtcct ctagtttcct cctctgtagt   3840
gtggggataa taacatagac ataacctgag agttagagtg tagagaaggc tccctggcag   3900
atagtgctgt agaagtactg gccattgcca ttactcaggt gcttgtgttt gctgaacctc   3960
atagtaaggg ctcggagagc actaagagga ggtgagaaat gctgctagat tgacagcttg   4020
tccccagata gcccattccc gagagcacct taggtttata cctgatttgt gttgtagtta   4080
gtagtgtctc tggtaatttg aactagtttc aggttggtct tgaaaacctg gggaggttgg   4140
gggtaaatga tttggtagca gttctctttt gtgattttat acattatctt tgtagaactg   4200
cagtttgcta attctctgag cccaacacaa tgaagtctgg gcctaaaatc atagaatttc   4260
ttttattttt ttttttgttt ttaatttatt tattccctcc ctccctcctt tcttcctttc   4320
ttcctttcct ttctttcttt ccttccttcc ttccttcttt cttttctttc tttcttttct   4380
ttctttggag tctcactctg tcaccaggct ggagtgcagt ggcacgaact ttcttcagag   4440
tctcactttg tcaccaggct ggagtgcagt ggcgcgaact cagctcactg caacctccgt   4500
ctcctgagtt caagagattc tcctgcctca gcctcccgag tagctgggac tataggcatg   4560
tgccaccatg cccagctaat ttcttattt ttagtagaga cgaggtttca ccatgttggc   4620
caggatggtc ttgatctctt gacctcgtga tccacctgcc tcagcctccc aaagtgcggg   4680
gattacaggc gtgagctacc acgcccagcc tattttttat tttttgaggc agagtctcac   4740
tctgtcaccc aggctggagt gcagtggtgc aatctcagct cactgcaacc tccgcctcct   4800
gggttcaggt gattctcctg ccttagcctc ctgagcacct gggactacag gcgcctgcca   4860
ccacacctgg ctaattctta tatttttagt agaggcgggg tttcaccatg ttggccaggc   4920
tggtctcgaa ctcctgatct caagtgatca acctgccttg gcctcccaaa gtgctggaat   4980
tacagccatg agccaccatg cccagccaaa tcatgagatt tcaataccgc tgaactttga   5040
ttatggcaaa gtgaacttct gctttgatta aagcttgatg agagaggtgg ctggggatag   5100
tttgagataa gggcaaggca ggaaaatgca taatcttacg tgggctcatt gtcattgtac   5160
aattcttttg gtccatgtgg aatttgatcc gtcctatgac ttaagttatg tttatttttg   5220
tttttatttt tatttatttt gtgtcttttt gagagacatg atgttgctct gtcacctggg   5280
ccagaataca gtggcacaat cttagctccg tgtagccttg aactcctggg ctcaagtgat   5340
```

-continued

```
cctcccacct cagcccctca aacagttgag attatagtat gaaccactgt gcctagcctt   5400
aagtgatttt taaatttgta ctgaacagtt tgtcctttcc ttccattaaa tcatattaga   5460
agtacagaac ttgatatttc ctgtagcaat acagtttttc tttgatgaag tttgatttca   5520
agtacttatt tttcataatt taaagctatt ttttatagag agaattttaa tcaaatattt   5580
ggatgtcact attgctatat atggtattaa gtatggtgac catagtttgt aaactccaaa   5640
ctgacagcaa gacaggaaat ttgtgttagc aaaggctttt ttcttactgt ttgaattttt   5700
taaaaattag atacaataca gagaggagca cacaaatcat taagagtaca gctcagcgaa   5760
ttttcacaca gtgaacatgt gtaaacagca agtaacaaaa gatttacctg catcctataa   5820
cctcccatta ttccctttc taggtactgt ctctccactg cattcccacc aaatataacc   5880
actatgctga attctgacat cataaatgag ttttgcctga ttttgagctt ttgtgactgg   5940
aagtgtacag tgtatatacc ctttcgattc tgtcctcttt agtttaccat tgtttgagaa   6000
atttatccat actgttccag aattaactac tgttaattat tgttaattaa ctactgttgt   6060
agttaattca tcctcattgt tatctagtat tcttttgtga gtaaacacaa tttccattct   6120
actgtgatcc cagctatcca tttgggtcgt ttccagtttg gggtccatta caaatagtaa   6180
tgctatctgt aatgctattt tgtattacta caaatagtaa tgctatttgt ggcacaaaaa   6240
tactgctttt gtgaacattc ttatacatgt cttttgatga atgtatgttt gcattgctgt   6300
tgtttacatt atgtacctag taatggaatt gctagatcat aggagatgta tatattaagc   6360
tttagtggat gcattacata attattagtt attattggtt ataccaattt atcctctcat   6420
cagtagtata caacagtttc tgtatctcta atctccaaca ttttagccat tttagagttt   6480
gtgtactaac acattgtggt tttaatttac atttccctga tgactaataa agttgagtac   6540
ctcttttgtg ttctttatag ccatttgact gtcttgtgaa gtgcttgttt gtcttgccta   6600
tttttctttt ctttctttct ttttcttcct tccttccttt ctttctttct tctttctttc   6660
cttccttctt ttctttcttt ctgtctttct ttcttgtctt tcttgtcttt ctgtctttct   6720
tggtcttgcc ctgtcaccca tgctggagtg cagtggtgca gtctcagctt actgtagcct   6780
cgaccttttt ggggctcaag ttatcctcct ttctcagcct cccaagaagc tggactacaa   6840
gcacgcacca ccatgctcag ttaatttttt attttttgta gaaatggggt ttcaccatgt   6900
tgtccaggct ggtctcaaac ttctgggctc aagtaatcct cctgccttgg cctcccaaaa   6960
tgctgggatt acaggcatga gccaccgcag ccagccttgg ctatttttca aaaggatata   7020
agtagaacat ctgtatatcc cttcaatttg catattattc agtaagagtt gcactctggt   7080
agtagaaata tataaggagg agaaagaagt ggaaacaaaa agtctattct catgagaaga   7140
cttgggggat agtgttctct ctagctccaa gctacttatt ccttacgaaa agttgaagat   7200
aaacttatct cagactgagg ctgtctcaat gttgtcttcc tattccatta tacacatata   7260
acccatattt ttttcaccag ctgaattttg ctcctagaaa attgattcat caggaaaaat   7320
atccgtcttg caaggtggtt ctctttagag tctgctgtgt gacatagctc aggacaaatt   7380
gtgtgatgtc agataggttg ggttaaggaa tagaccttat tggggaaaga gagaacttgg   7440
agggccaagg ttagcaggag aaggaaatgt tctctcatct gccgtcaatt cagggagggg   7500
caaacctggt gtctgtgttc acagggaggg atccatccat ctgtgattct cccttcttat   7560
caggtagcat gggaaagcta cactgttgcg gggaggaggg tcacacgcag gctacttagt   7620
accaggcacc ctggacttgg attcaggttg ccagttgtgt gagaaactgc ccagcacctg   7680
aaggccctga acccatgaga agttgtacct acctcccatg aggaggaatc ctgtcatccc   7740
```

```
atgggagctg agcttgggtg cagtccctct tgctggcttg tccaggagtg agctccaggg   7800
ttgtttggga cagttctgct cattgcttta cactgtgtat acattatctg tagagttcca   7860
tgaagagaac ttcagcactg taactgcaag ttttaacatg gaacagaatt tttctcacct   7920
gtattaattc ttaagatttg aagttctatc aacaagcatt tagattgtgt ggagattttt   7980
ttatttttat ttttggagac agagtcttgc tctgttaccc agactggagt ggcagtggca   8040
tggtcttggc tcactgcagg ctctacttcc tgggttcaag cgattctcat gcctcagtgt   8100
cctgattagc taggactaca ggtacacacc accatgctgg ctaatttttg tatttttagt   8160
agagacgagg tttcaccgta ttggtcaggc tggtctcgaa ctcccagcct caagcagtcc   8220
acccacctcg gcctcccaaa ctgctgggat tacaggtgtg agccaccatg cttgactgac   8280
atcatcatgt taaaagaata aatgttctag ggagctgggc acagtgtcat gtttctgtag   8340
ttctagctgc tcgggaggct gaggcaggaa gatcccttga gccctggagt tcaagtccag   8400
cctgggcaac atagtgagat ctcttttttt aaataaataa ataactgttc tagggactaa   8460
aatttccttt caccattagt aatttactgt agaatctcca agaatgaact tattttaggt   8520
actgaaaatg agggagacta aatgttttat acagtagttt ttagtaaaat atgagatttg   8580
atgcatttga tagatgatgt ttgtttaaaa taattcttaa atttttgatc atgtaattat   8640
agtttcatta atggtagatt tgtaaaataa atgttaccaa atgaaaatgc atgtacctat   8700
gttaattatc cttatctaaa gctgaaagtt cagttcaact atgttaaaac atagtagggg   8760
cctggcaggg tggctcttgc ctgtaatccc agaacttagg gaggccaagg tgggcagatc   8820
acgaggtcag gagatcgaga ccatcctggc taacattgtg aaaccgtatc gctactaaaa   8880
atacaaaaaa ttagccgggc atggcggtgg gcacctgtag tcgcagctac ttggtaggct   8940
gaggcaggag aatggcgtga actcaggagg cagagcttac agtgagccga gatcatgcca   9000
ctgcactcca ggctgggtga cagagcaaga ctccatctca aaaaaaaaaa aaaagttggc   9060
caggtgtggc ggctcacacc tgtaatccca gcacttttgg aggccgaggc aggcggatca   9120
caagatcagg agtttgagac cagcctggct aacagagtga aaccctgtat atactaaaaa   9180
tacaaaaatt agccaggcat ggtggtgcat gcctgtagtc ccagctactt gagaggctga   9240
ggcaggagaa tcacttgaac ccgggaggcg gaggttgtgg taagctgaga ttgctccact   9300
gcactccagc ctggacaaca gagcaagact ctgtctcaaa aaaaaaaaaa attaatgatt   9360
aaattattta ggggagccgg gcgcagtggc tcacgcctgt aatcccagca ctttgggagg   9420
ccaaggcggg cggatcacga ggtcaggaga tcaagaccat cctggctaac acaggatgaa   9480
accccgtctc tactaaaaat acaaaaattt agccgggcgt ggtggcgggt gcctgtagta   9540
ccagctactc gggaggctga ggcaggagaa tggcatgaac ccgggtggcg gagcttgcag   9600
tgagccaaga tagcgccact gcactccggc ctgggtgaaa gagtgagact ccgtctcaaa   9660
aaaaaaaaaa aattatttag gggaagatac tatacaattc tgtttaacaa gtcacatttt   9720
aatttttttct tttggaaata ttagcaagaa ggctcacttt gtgctcaaca ttgcctgaat   9780
aacttattgc aaggagaata ttttagccct gtggaattat cctcaattgc acatcagctg   9840
gatgaggagg agaggatgag aatggcagaa ggaggagtta ctagtgaaga ttatcgcacg   9900
tttttacagg tactgatttt aaactcacta agtcacattt cttttttttt tttttttttg   9960
agacggagtc tcgccctgtt gcccatgctg gagtgcaatg gcgcgatctc ggctcactgc  10020
aacctctgcc tcccgggttc aagcgattct cctgcctcag cctcccaagt agctgggatt  10080
```

```
acaggcacac ggcactatgc ccggctaatt ttttgtatct ttgttagaga tggggtttca  10140
ccatgttggt caggttggtc tcaaactcct gaccttatga tccacctgtc ttggcctccc  10200
aaagtgctgg gattataggt gtgagccacc acacccggct tacatttctt ttaaaaatgt  10260
ggataccatt tagaaaagga tgggccattc ttcctatagg gatctgactg gtgaattata  10320
actgtgctgt taactttgga aatgggaatg cacaagatat tgttttaaat atgcacgcta  10380
atgacagttt gtatccttct ttccccaccc ccaccccttgc ttcaactacc tgtcaaaatt  10440
aacagcagcc ttctggaaat atggatgaca gtggtttttt ctctattcag gtaagtagtc  10500
acaagcatgt actatgtgtt gcttacatcc caggcaccgt ttcacagcct ttcaatagtc  10560
actgtaacaa ggcgaccttc ggaagttctt ctgtctacag agtatagatt atactctaga  10620
gtactagatt ttttttttct tgagacagag tctcgttctg tcacctaggc tggagtgcag  10680
tggcgtgatc ttggctcact gtagcctctg cctcccgggt tcaagcgatc ctcctgcctc  10740
agcctcccaa gtagctggga ttacaggcac ccgccaccac accagttaat atttgtattt  10800
ttagtagaga tagtggggtt tcaccgtgtt ggccagtctg gtctccaact cctgacctca  10860
gcctcccaaa gtgctgggat tacaggtgtg agccactgca cctggccaac tagagtacta  10920
gatttttata tagataaaca tgaaaggatt gtagaatctt catattagag tggggcattt  10980
aaaaattcct tcttgagaaa gattaatttg catctggatg ctaataataa ccttaattct  11040
ggccgggcgc ggtggctcac acctgtaatc ccagcacttt ggggaggccg aggtgggcgg  11100
atcacgaggt caggagattg agaccatcct ggctaacatg gtgaaacccc gtctctacta  11160
aaaatacaaa aattagctgg acgtggtgac acgtgcctgt aatcccagct actcgggagg  11220
ctgaggcagg agaatcgctt gaaccaggga gtcgtaggtt gcagtgagcc aagatcgcgc  11280
cactgcactc tagcctggtg acagagcgag actccatctc aaagaaaaaa agaaatcctt  11340
aattctaata agtcacaatg tctcaaactt accatctgtt gggtaaattt gagaaaatgc  11400
aataccttgc taccatcctt ttaaatcagc ctaccagact ggatttcctt attatggttt  11460
gtggcttttg attttttttt tttaatgtat agctctcttt gaattctttg gtggttatat  11520
atatatgtac tcgcaagatt cttttatctg tgggtctttc attctttttc taacactgtg  11580
agttgtatcc agagtacttt cggaacctct cctgagcgac ctatctctgc agatatcttt  11640
gtttatgttt cccttgtact gccctcctgg actcttcctc atccaccagc atttccatct  11700
agtgctttac cgtgccactg ctaacaggta atggctactg cagggctgaa atcagaggcc  11760
agagtaggcc cagcacttgg cgtttcctat ttgtgccttg ctgctcttgg tgcctgttca  11820
tgtgtgccca ctaccttgca ctcaatttct gtctttgctg gtacctggct cacttgcttc  11880
tttgttggct accttggagg gcagatagtg aattttcaga aatttccctt tttttgtcag  11940
acagattgaa ataaacaggt ttgcattttg ttttttctac aagcggcaag cccatgaccc  12000
tagaagtctg acatctatgg aaccttcagt ttaaatgccc agggagaact tattttggta  12060
gatatgattt ctgacattgc aggtagcaag ttgaatataa tttttctaaa gtagcaccca  12120
cagcagccaa attatcagat gtatatagta gactagtttt aagaaaagca cttatgggta  12180
gaatatacat ctggattttt gaggcagttt tatttaggaa ttgtgtggtt ttctggaaca  12240
tctcagagac ctggtatgaa aagcactctt ctaatatata tgtgtttttt tttatggatt  12300
tagtgatata tctatacaca cacacttttt aaaacctata gccggctggg cgtggtggct  12360
catgcctgta atcccagtac tttgggaggc ccaggcgggt ggatcacaag gtcaggagat  12420
tgagaccagc ctggccaaca aggtgaaacc ctgtctctac taaaaataca aaaatagctg  12480
```

```
ggtgtggtgg cgtgtgcttg taatcccagc tactcgggag cctcaggagg agaatcgctt  12540
gaacctggga ggcggaggtt gcagcgagcc gagatcgtgc cactatactc cagcctgggc  12600
gacagagcaa gactctgtca caaaaaaaaa aaaaaaaacc tatagccttc tagagaaatt  12660
tatatatgaa gtacacaact aacatagcta cacttcctaa atttggaatg gagtggttta  12720
gcttatgaaa agttgctatt tttcttaaca ggttataagc aatgccttga aagtttgggg  12780
tttagaacta atcctgttca acagtccaga gtatcagagg ctcaggatcg atcctatgta  12840
agattctgtt ttgcatttca tacatttctt ttcccaaatt tgatttttaa agttgtaatt  12900
tcttaaagaa gagaaataca ttttgaatac ttttgttttg atgttccctg tttcattcac  12960
tcagactttc ctatttcacc tttgtgatgt ccatgagcat ctgccctgta gccttcctgg  13020
caccccagtg tctgtggcag cacagagctg accccataag tggtgcatga ggccatcttg  13080
tggcacagca tcactaagct gctgcagaga cgttcatatg gttgtgtgat cttttaaaaa  13140
catcagtgac acttaactat aaatataatc ttaaattatc acaaatttta tataatattt  13200
gccagtagac aacataaata tgaattcaat atttcaagtt aatattgtct gttttctttt  13260
ttagaaatga aagatcattt atatgcaatt ataaggaaca ctggtttaca gttagaaaat  13320
taggaaaaca ggtaacattt cttacccttc cttgtctttt tttcttatat tgtaccccat  13380
ttaaaactaa aatgtgggcc aggtgtggtg gctcatgcca acagtttggg aggctgaggt  13440
ggggggatca cttgaagcca ggagtttgag accagcctgg gcaacaaagg gaggtcctgt  13500
ctcttaaaaa aaaaataaaa ataaaaataa aaataaataa aaaaaaaaac aaagagccag  13560
gcatggtggc tcacatctgt aattccagct tacttggaag gctgagtcag aaggatcact  13620
tgagctcagg agtttgaggc tgcagtgaac tatgattttg tcactgtacc ccagcctggg  13680
tgacagagta agactgttct ataaaacata aaaataaaaa aaatatattt aaaaattaaa  13740
aaaaaaaaag gattgctgac tttaaaatta ggaaactgac cagtaatgtg tgtgtgtgta  13800
gcatggttta tccttcttga tagatagaaa ttgtcatttt aaaagataat atcagttttc  13860
cttataaatt tatttgtgac aagtatatgc aatttaacta tatcataaga aaaattctat  13920
attaaagata atacaaatgt ggttactttt aagtgggttt ttatgtgatg actatgttct  13980
gtcagttaat tattacattt atagatttgt atttagcata gtgctgtcac aaagcctgaa  14040
atagtgtcaa gcatgaataa agcattcaat tatgtttgct ttagtgtaag attattcatt  14100
atgattccaa aagccatgta atacgtacgt ctacagaaaa tcacttctat tttttaaata  14160
aaacatgaaa tatgtcttga gcaagctatt ttaagaaaca atcatttaac gtccttgtta  14220
ttagaatttt gaatctttga aagagggtta ttgaaaacca gctaggacag taaaaaagaa  14280
taaactagtg atacatgcag caatatggat gaatctcaaa ataattatgc tgaaagaata  14340
acccacaaac aaaatactac ctgctgtatg gtatcattta ttaaaagtct agaaaagtgc  14400
agattcatct gtagtgatgg aaagcagatt gaccagcggt tgcctgggga cgagaaggct  14460
atggaggagt gagaggggag ggttacagag aggcacggga aacatggcaa tgaggaatgt  14520
gttcactatc ttggttgtag taatggtttc atgggagtac agtatacaaa tgtgaaaaca  14580
tttcagaggc cagatgcagt ggctcatgcc tgtaatccca gcacttttgg aggccaaggc  14640
aggaggattg cttgagctca aggagttcag gaccagcctg ggcaatggca caagacccca  14700
tctctaaaaa aaaaatgaaa gaaaaaaaaa ttggctaggc gtggtgatgc atggccgtag  14760
tcccaggtgc tagggaggct gaggagggag cacagaggtc aagcctgcag tgaatcatga  14820
```

```
tcgtgctact gcactccagc ttgggtgaca gaaggagatc ctgtctcaaa aaaaaagttt  14880
caaattatac actttaaata tgtgcagttt attatatgtc acttataccc caataaatct  14940
gtttttttta aaatgtaaat acaagccaaa aaaggtataa gtcaagaaaa tatattgaat  15000
taaatctgta agagataatt caaaaacaaa aaccctattg ttatctttta agtcacccaa  15060
atcaaatttg ggaaaagtca cctacttagc ttcatcctaa gttggttctt tctttctttc  15120
tttccttctt ttgagacgga ttcttgctct atcgcccagg ctggattgca gtggcgggat  15180
cttggctccc tgcaacctcc gccacctggg ttcaagcaat tctcttgtct cagcctccca  15240
aatagctgtg tctacagcca cgcaccacca cacccagcta atttttgtat ttttagtaga  15300
gacggggttt cgccatgttg gtcaggctgg tcttgaactc ctgacctcag gtgatccgtc  15360
cgtctctgcc tctcaaagtg ctggggttac aggcgtgagc caccatgccg agccctaagt  15420
tggttctttc ttaaagttct tcctgaggag ccaagagcaa gttaaggaga tgtaacctag  15480
aagcttacag tggaggctag ctgggtgcag tggttcacgc ctgtaatccc agcactttag  15540
gaggctgagg cagggagatc actgaggcca ggagcttgag agcagcttgg cccaacacag  15600
tgacaccttg tctctacaaa aaaaaaaaaa aaaaaaggca gcttacagca gtagaggctg  15660
atgcgagtgg gaatcacctc taggtaaaaa ccagtgtagc gtactgctga gattatttaa  15720
cctctgggtt ttatttatgt gtttttaaaa attatgatcc agtatttttt actttttttt  15780
gtataaagta agcactgaat ttttaaggtt gtattaattt gcaaataaat gtctatctta  15840
ttattttgag agatttaaaa aattttagtt cttcaaaatt gcattttcac attttgaatt  15900
acgttatctt tgacaaatac agaagatgtc aaattttggt ttattttctt tggttctaat  15960
ttatattttt gtttaaaact atatttttca ctatagactc tttctgtctc tcgaggtccc  16020
tgtataatga aaaagaaggc tggaaaaagt attaacattg tcaaaatcca ggaaaagtag  16080
ttggtcatga tattgatcgt taactttaga aactttttgt atcttgtggg ttaaattagg  16140
attactatgt ggtagtgata aatgatgtta attagggccg agtgcagtgg ctaacacctg  16200
taattccagc atgtagggag gctgaggtgg gaggatgtct tgaatccagg agtttgagac  16260
cagcctgtac aacatagtgt aagacccctt ctccacacaa aaaaattaga aaatttgtca  16320
agcatcttgg tgcacacctg tagtcccagc tgcttgggag gatgaagcga gagaatcact  16380
taagcccagg tgttcgaggc tgcagtgagc tatgattgca ccactgcact ccagactaga  16440
tgaccatctc ttttaaaaaa atgtgtttat atgttatatg tgatagtgct ttttaaaaac  16500
atttttaaat tatagagaca gggtctcact atgttacagc ccaggctggt ctcaaattcc  16560
tgggctcaag caatcctccc accttagcta acctcccaaa gtgctcggat tataggcatg  16620
agctgcatgc ccagctaatt tagtgatttt taaaaactga gctggtaatt ataaattctc  16680
ttcctggaac ttctgacttt ctcacaattg gaatcttttg acaaaaatta tcagtaatgg  16740
gaaaactttg tgtagttgtc atttttcctc ccatcagtgt gatagatatg attggagtta  16800
tgttggactg atattttgaa aaaagattta attatagcta ttaataaaga catttaaact  16860
actgactatg catttttatt cttttgggag ggtttaatgt ttatagttta aagcaaactg  16920
ttgtttttaa aaaagtatct aacagggccg ggcgcggtgg ctcacacctg taatcccagc  16980
actttgggag gcctaggcgg gcggatcaca aggtcaagag atcaagacca tcctggctaa  17040
catggtgaaa ccctgtctct actaaaaata caaaaaaata gctgggtgtg gcggcgtgcg  17100
cctgtagtcc cagctactcg ggaggctgag gcaggaggat ggcatgaacc cgggaggcgg  17160
agcttgcagt gagccgagat cgcgccactg cactccagcc tgggcgacag agcaatactc  17220
```

```
tgtctaaaaa aaaaaaaaaa aaaaaaaaaa gagtatttag cagaggccag gtgcagtggc  17280
tcatgtttgt aatcccagaa ctttgggagg ctgaggcggg cggatcattt gaggtcagga  17340
gtttgagacc agcctggcca atgtggcaaa tgtgctgtct ctaactaaaa atacaaaaat  17400
tagctgggtg tggtggtgca gacctgtagt cccagctact tgggaggctg aggcaggaga  17460
atcacttgaa cctgggaggc agaggttgca gtgatccgag atcatgccac tgcactccag  17520
cctgggttac agagtgagac tcttctcaaa aaaaaaaaaa agtatttaat agtgataaat  17580
ctgcagtatt ctcttgtagt ttttaagatc atattattca gtcaaagaaa agagctcaac  17640
ttgaaatatt tccagagttt aaacaatctt actaagcttt gatgggttgt atctattctt  17700
aacatgtgaa acttccttat tacctataat atacactaac ttaaatattg acaatttttt  17760
tccagtggtt taacttgaat tctctcttga cgggtccaga attaatatca gatacatatc  17820
ttgcactttt cttggctcaa ttacaacagg aaggtaagta acggctgaac attttgtaat  17880
gttacctttc gaagtagtta aataaccagg cacattagat gacagtgtga taaaactgtt  17940
tttctggcag tggcagtgaa acaatcttta gttttgacgt ggtgataggc tgtgatttgg  18000
gtgacgctgt tcagttagag ttctcactga cacctggccc ttcctcttct gaggatgctg  18060
ctttctttgc agcccttcta agtaatggct ttttctttta tacatcacat atcacacggc  18120
tgagaggagg gatagatgtt tttcttcttt gcctcttcta ggccactgtt cttccttata  18180
aactccagtt tctttgaaat acatgcccct aacggctggg cacggtggct cacgcctgta  18240
atcccagcac tttgggaggc tgaggcaggc ggatcacgat gtcaggagat cgagaccatc  18300
ctggctaaca cggtgaaatc ctgtctctac taaaaataac aaaaaattag ccggggtgtg  18360
gtggcggacg cctgtagtcc gagctactcg ggaggctgag gcaggagaat ggcgtgaacc  18420
caggaggcgg agcttgcagt gagctgagat cgcgccactg ccctccagcc tgggcgacag  18480
agcgagactc cgtctcaaaa aaaaaaagaa aagaaaaaaa aaagaaatac atgcccctag  18540
attaaactat cccttgtcct tttgcactca tccacaagtc tcttttcatc agtgatttta  18600
ggatctgact cgttgtcttt ttctctactt caactacttt tatcattctt aattatttct  18660
gtatcgtcaa tcaatccagt acctgcctct tagtttcaaa atcacttact cttgcttagc  18720
tattaccagt aatcataacc actgtcaaat ctcaattgca agcatattac tctttaacta  18780
ccacctccta tctttaaacc atgttttgtc tgttttttta ttccagccat tctttaaacc  18840
ctactgtggg gcccaagcat ttcctttata cgcattcttc ctttcttcta ctgcttattt  18900
tctgtaatcc gtcatcataa tcactccatt gcattcttca acgtgtttcc cctctctccc  18960
tccatcatac ttgaatgaca aaaatctcaa ccctggttaa accacatctt ggccttgtcc  19020
attcctgtac cagagtagct ggacgtggct aaaaaataac ataaaacatg atgattggtt  19080
ttactttttt cttaaatgat ctatccatcc attcacccat ccatctatca aagtgactag  19140
gcctatttct gaagcccagg ctggagtgca gcagcataat cacagctcat tgcagctcca  19200
aactcctggg ctcaagtgat tctcttgcct tagcctgttg agtagctggg actacaggct  19260
tgtgctacca cacctagcta aggttttact ttaaatttat tataatcaca aaattcagat  19320
gagcctttag tgctgtctga tatttctact atgttttctt agtgatgtac caccctccaa  19380
ggtgtttata aaaaattatg taccactctc caagaagttt ataaaaaata atgtgccacc  19440
ctccaaggtg actaatttca cagcttatgt ctttaaacct ttaagcactt tcctctccct  19500
tacacacctt ccttgtggct ttccgttaca ttctgctgag aacatagaag caattaaaat  19560
```

```
tatgttcttt ctaccagcaa atttatcaat ttgcttatat cttcacctgt gctttgagcc  19620

tatttaaata gatgaatggt cccctacctc taaccaaaac cagtccctca cttgtgggct  19680

ggatcccagc tcttctcacc tactcaagat gttcctgctt tcatctctcc actctcttat  19740

ataatcagtt ccccccccct ttttttgtaa tattcctata agcagtaaaa taagcttttt  19800

atttccattg attaaaaata aaaatcctct cttaattcca tgaaactcca gctgcctccc  19860

catttttatt ttttccttag gattgtctct agtgtgcctt ctccttttct tgaactctgc  19920

ctcctgggtt caagcgattc tcctgcctca acctcccgag tagctgggat tacaggcgtg  19980

caccaccatg accggctaat tttttttttt tttttttgag atggagtttc cctcttgttg  20040

ctccggctgg agtgcaatgg cgtgatctcg gctcaccgta acttctgcct cctgggttca  20100

agcgatttc ttgcctcagc ctcccgagta gctggattta caggcatgtg ccaccatgcc  20160

tggctaattt tgtattttag tagagatgga aggggtttct ccatgtttgt taggctggtc  20220

tccaactcct gacctcaggt gagccgccca cctcggcccc ctaaagtgct gggattacag  20280

gcatgagcca ctgcgcctgg ccccggctaa attttttttt tttttttttg tatttttagt  20340

agagacaggg tttcaccata ttggccaggt tggtctcgaa ttcctggcct cgagtgatcc  20400

acctgcctca gcctcccaaa gtgctgggat tacaggcgtg agtcaccttg cctagccatc  20460

ttttagtaat ggtatttgga gatcacaatt tgagtgctgg catgcttatt gctgctgggt  20520

ttgttatgta gttattgtga attcacattt aggaatatag ggtttttaat tctttgattt  20580

tagatacttg tatctttttt cttttatatt taaaaccttg gttcctgatg atatcccttc  20640

ttagaaaccc tgtctacctt tggccttcag cccaccatgc tgtggttttc ctaacttgct  20700

gcctgcactt ttcagattcc tttcatggat cttaaatatc atctgtaaat aagatctatg  20760

tgtcaataat taccaaactt ttatctttag tcttgacatc taccctgaac acctagcttt  20820

gactaactcc tagctttggc atctccactt ggaaatccaa aaagtgtttc aaactgaaca  20880

tgtctatgaa agacttattt ttttctctct atccatgcta tccatcaggt tttccatttc  20940

cataagggtg actcttgtac tctggttcct atatattata ccgacagagc agcccagagt  21000

gcttcttaac cagtgtaagg cctgttatgt cccaccctca ctctttgtcc ttcagtggct  21060

tcccagcaca cttagaataa aatctgaagt cttaggccgg gcttggtggc tcatgcctgc  21120

aatcccagca ctttgggagg atgagggggc agatcacttg aggtcaggag ttgatgagac  21180

cagcctggcc aacatggtga aaccctgtct ctaccaaaaa atacaaaaat taactgggtg  21240

tggtgttgtg cacctgtagt cccagctact cgggaggctg agataggaga atcacttgaa  21300

cccgggaggc agaggttaca gcgagccaag atcataccac tgcactccag cctgggtgac  21360

agaacgagac tctcaaaaaa aaattaaaaa aaaaaaatat gtgaagtctt gaataaaacc  21420

caagatcttt accatggccc ctgaacaggg cagagtatcc attcttcaga cactcttcat  21480

agaataccat ggtgagctgg catatttatt atacaataca gaaacaattt tactggcaga  21540

aaacacatta aaccgtctaa actctgaata cagttgtcct cataaaaaat gttcaacata  21600

ctattttgag gttttccatt aatagttctt ataatctttg tcccattatg tgttaatcca  21660

acaaaggata tccaataaca aacaccaaag tttaagaaaa atgtgctagg cgcggtggct  21720

cacacctgta atcccagcac tttgggaggc cgaggtgggc agatcacctg aggtcaggag  21780

ttcgagacca gcccagccaa catggtgaaa ccctgcctct cctaaaaata caaacattaa  21840

ctgggtgtgg tggtgggtgc ctgtaatccc agctactcag gaggctgagg caggagaatc  21900

gcttgaacct cctgggaggc agaggttgca gtgagctaat attgcaccac tgcactccag  21960
```

```
cctgggtgac agagtgagac tccatctcaa attaaaaaaa aaaaaaaatt aatgatagag  22020
aaacttaaat cagttagatt gttttaggta tagcccatcc ttggtttttg tgtgtagcat  22080
ctagcttggg gaaaccctgg atttctggaa tcatatttag acacagtcac actagactaa  22140
tgtaattctt ttgggatgca aaccacacgt ttgacacctt aaatagcttt taggtatttg  22200
gcttcccagc ccctattttt agttacaagg ggtgtacatg tgtgggtcag ggtgggggta  22260
gctctttccg cagatgatta gttttagcca tgttactagt tattgcacac attatctgtg  22320
tcctcacagc agccctgtga gtaagtgtat tagggttctc tagagggaca gaactaataa  22380
ggtagatgta tatatgaagg gtaatgtatt aaggagtatc gactcgtatg atcacaaggt  22440
gaagtcccac aataggctct ctgcaggctg aggaaccagg aagccagtcc aagtcccaaa  22500
acctcaaaag tagggaagct gacagtgcag ccttcagtct gtggcaaaag gcctgagagc  22560
ccctggcaaa ccactggtgt aagttcaaga gtccaaaaga tgaagaactt ggagtctgat  22620
gtttgagggc aggaagcatc cagcatggga gaaagatgaa ggctcagcaa gtctagtact  22680
tccacactct tatttctgcc tgctttattc tagctgagct ggcagctgat tagatggtga  22740
ccacccagtt tgagggtggg tctacctctc ccagttcact ggcttaaatg ttaatctcct  22800
ttggcaacac cctcgcagac acacccagaa acaataattt gtagccttca atccaatcaa  22860
gttgataata ttaaccatca caggaaggta ctagtatcat atgtttaaca gtagaaacca  22920
agacaaatgc agctaggaag tgggagaact gggatcagat gcaggcagtc tgattctaaa  22980
tcagttgctg ttacccactc tgacaacagt aagtgagtag cctgctcagt caagtactat  23040
attagtaggg ccctttacag acatatttat ttctcacagt cactcaatga gacggctctt  23100
ccagtcttac aatggagaaa gtgaggctca gagactttaa gtaacttacc ttagacgact  23160
ttactagtaa gtataagaat cattatttgg actaaagtct ttctgaatcc tcagcttgta  23220
tttttttcca gtgttctgtg ctgccttttt atctactagt gttttacatc aattttgaat  23280
ctctttacta actggttagg ttgatttttg cctttttttt ttaggttatt ctatatttgt  23340
cgttaagggt gatctgccag attgcgaagc tgaccaactc ctgcagatga ttagggtcca  23400
acagatgcat cgaccaaaac ttattggaga agaattagca caactaaaag agcaaaggta  23460
aaaatgaggc ctgcagtatg gaatatatgg tagtatttca ttatgagaat taaattttca  23520
tgcttagatt gaatatgtgg tccttgtgtt gttggcgact ctattttgga ccttatattt  23580
tagtgaagtt tattagttta aacttgaatc aactctttga aatacttaaa tatattaact  23640
tagttagctg gtatggtata ttcctagcac ttcgggaggc tgaggcaggc tgattgcttc  23700
aacccaggag ttcgagacca gcctgggcaa catggcaaaa cctcatctct acaaatagta  23760
caaaaattag ccagatgtgg tggtgtatgc ctatagtccc agctacttgg gaggcagagg  23820
aagaaggatc acctgaaact ggggaggtag agactacagt gagccataat cacactaccg  23880
cactccagcc tggtcgagag agtcagaccc tgtctcaaaa aaaaaaaaaa aaagaaacgg  23940
aaaaaaaaaa cttagttgga ttcaaattgc aacacaatca ttatattact agagcttatt  24000
tgccagaaaa cattttaagt tttgacttac ttaaagcctt tacattacaa atgcctttat  24060
gttatgtcta aaatagaaga ttggttgcag ttattaccag tgcttttgtt ctttagagtc  24120
cataaaacag acctggaacg agtgttagaa gcaaatgatg gctcaggaat gttagacgaa  24180
gatgaggagg atttgcagag ggctctggca ctaagtcgcc aagaaattga catggaagat  24240
gaggaagcag atctccgcag ggctattcag ctaagtatgc aaggtaaaga cattctgatg  24300
```

```
tgtgttgtat tcattgctga agaattgatt ccaattattc ttagatttca tggaagttaa  24360
tgtactctta gaggtgtttt gacaattact gcagaagcaa tagctatata gtgggctttc  24420
cctttagatt tcttataatg gaaatcactt tttacaacct atattttatt aggagtagtt  24480
atatttttac tcctggttat tttatttggt ttcaacactg tactaacaca atagtaaatt  24540
gtggttttaa tctttgtggg tatcagttga cccttatcca aatcagctgt tacataaata  24600
tgtgccatta gacactatgg aagggcctgg acagggaata taaactgatt ttacaaaaac  24660
ccaacattta ttggctatgc aacttaaacc gtaagcccac tttggtgggc ccagtttttt  24720
agtgatataa actatcaata gagaaaagcg aaaacatatc ccctagacaa tctaggcaaa  24780
gaaaaatgtt aagacatagc tcaaagtagc ttaattaaaa gtttgaagtg ggttttttgt  24840
tttatttttt tctaactcat atgtatttgc ttctactttc taatgaaatt atttatcagt  24900
tgatttcctt agatatctaa ataaaattga aatttcatta atgggaagat tatttttatc  24960
ctgaactttt cttgcctcta tgcatgcctc tgagtactcc atatggtgtg caatcccatt  25020
tttgattaat agagtcctgc tggattagca gggacagaaa tcagctttag atttctttct  25080
ttttttttt tctttctttt tttttttttt ttttttgag tcagagtctc actgtcgccc  25140
agcctggagt gcagtgatct tggctcactg caacccctgc ctccgaggtt caagcgattc  25200
tcctgcctca gcctcctgag tagctgggac tacaggcgcc taccaccacg cccagctaat  25260
tttttgtact tttagtagag atagggtttt gccctttttgg ccaggctggt cttgaactcc  25320
tgacctcagg tgatccacct gccttggcct cccaaagtgc tgggattaca tgtgtgagcc  25380
accacgccca gccagaagag tagaatattc ttaaagagaa aacgttttaa aggcttactc  25440
aaatgagtat aaacaaacat attgttgctt gaattggtaa atacagtgat tggtttttgt  25500
tgtgttgtgt tttgttttca ggtagttcca gaaacatatc tcaagatatg acacagacat  25560
caggtacaaa tcttacttca gaagagcttc ggaagagacg agaagcctac tttgaaaagt  25620
aaagtagttg gtacaagtta aagtagcatg tttaatattt gctttggcta ttttgtctat  25680
ttgtaaatgg ttactgcctg aatcctgtga atatttgaat gtattttttta aaaatttaca  25740
gcaaatagga cgggcacggt ggcttacgcc tgtgatgcta gcagtttggg aggccaaggc  25800
gggcagattg cctgaggtca ggagttcgag accagcctgg gcaacacagt gaaaccccat  25860
ctctactaaa aatacaaaag aatcagctgg gcatggaagc gtgcgcctgt agtcccagct  25920
gcttgggagg ctgagccagg agaattgctt gaacccggga cgtggaggtt gcagtgagcc  25980
gagatcgcac cactgccctc cagactgggt gacagagtga gactccgtct ccaaaaatat  26040
atgtatatat atataaataa aaataaaaat ttacggcaaa taacatgaaa caaaaaaacc  26100
ttgccccaat actggataaa ttttttaaac tgagtgaagg aaaccttata aaatttcatt  26160
tattaaaaga aaaatgaaat taggacaaga caagaagaat gccaattgat cctttggatg  26220
tacttcttgc ttacctgatt aaccctgcaa aattcctcta ccaatcagta cgaaaaacag  26280
ctttggaggt atgggagcgc attcccaaat agacgtggta gttcatttag ctgctcatgg  26340
ccgcttcagg cagtcctgta agcctgttag catcagggga atggatgcaa accataaatc  26400
tggatcaact cctaaaacct taccttgtgc ccagccttgt aagtgcttgc taaataggaa  26460
ttccaccata tgaaaataca ttcttttcaa gtaactatca ttcagacttt tgtcccccac  26520
tttttttttt taaagaaaaa taaaaggctg ggcacggtgg cttacgtctg taatcccacc  26580
attttaggag gccaaggcag gtggatcacc tgaggtcagg aattcaagac cagcctgacc  26640
aacatggtga aacctcatct ctactaaaaa tacaaaaatt agccgggcat ggtggtgggt  26700
```

```
gcctgtaatc ccagctactt gggaggctca gacaggagaa tcgcttgaat ctgggaggca  26760
gaagttgcag tgagctgaga taacgccatt gcactccagc ctgggggaca agagcgagac  26820
ttcgtctcaa aaaaaaagag aaagaaaact tcatgttaaa gattacaaga taaataatca  26880
gacccactga tcctaggtca gaaaacagag tcatagctca atctgactta ctatttgctg  26940
tatttcatcc attctgagat gcacatagtt tcacatttca atgtctctga aattgagaag  27000
catcttacag tcataattga cagtatatta gcagcaccta taaatattgg ctcattttac  27060
atttgatggt ataatgaaga aaatatttac cttttttctt gttttgtttt taagtcacaa  27120
ctcagaagta gatgaaggaa aattctgatc agctgacatc ctcttaatgt gagatatttc  27180
tagtctttat tcagtataga ttaatggcta attatatgtt aaatttcaaa gtagtgctta  27240
ttagtgcttt ttacttttaa gtttcaaaat taacttttttt attataataa actccaaatt  27300
tatacaaaag tagaaaaact agcatactcc tgtttatgac ccagattcaa caaatactag  27360
cacacggcca atcttgcttt tttttttttt tttttttgag atggagtctt gctctgttgc  27420
ccaggctgga gtgcaatggc acaatttctg ctcactgcaa cctctgcctc ctgagttcaa  27480
gcgattctcc cacttcagcc tcccaagtag ctgggattac aggtacacac caccatgcct  27540
ggctaattct tgtattttta gtagacacgg gatttcacca tgtcgtccag gctggcctta  27600
aactcctgac ctcaagtgat ccacctgcct cggcctccca gagtgctggg attacaggca  27660
tgagccactg agcccggccc aatctcgttt tataatactc ccatctccca ttctttccac  27720
tgtcccacct gcaagtttgg attattttgt aacaaatctc aatcatcata ttattctata  27780
accattttaa tatgtgtctc taaaatatat tagctttatt tttaacatag ttaaatgcta  27840
ttgtcataaa ataataatca taataattaa ttgtaattct atatcatcaa ttatctagtt  27900
aatgtaaaaa ataaatctaa ggccaggcgc ggtggctcac acctgtaatc ccagcacttt  27960
gggaggctga ggtgggcaga tcacctgaga tcaggagttc aagaccagcc tgaccaacat  28020
ggagaaaccc catctctact aaaaatacaa aaaattagcc aggcgtggtg gcgcatgctt  28080
gtaatcccag ctacttgaga ggctgaggca ggagaatcac ttgaacccgg gaggcgaggt  28140
tgcggtgagc cgagatcgtg ccattgcact ctagcctggg caaaaagagt gaaactccat  28200
ctcaaataaa taaataaata aataataaaa aataacttaa atctacttaa ttagaaaaac  28260
taacattcta aaaattttat tttaagaaat atcaaaattg gctgggcacg gtggctcacg  28320
cctctaatcc ctgcactttg gaaggctgag gtgggcggat cacctgaggt caggagggtc  28380
aggagtacaa gaccagcctg gccaacatgg cgaaaccctg tctccactaa aaatacaaaa  28440
attagccagg catgatgatg ggcacctgta atcccagcta ctcaggaggc tgagacagaa  28500
gaatcgcttg aacccaggag gtagaggttg cagtgagctg agatcacccc actgcactcc  28560
agcctgggtg acagagtgaa actccgcctc aaaaaaaaaa aaaagagaaa agaaatatag  28620
aaattaaagc atacatggcc aggcgtagtg gctcatgtct gtaatcccag cactttggga  28680
ggctgaggca ggcagatcac ttgaggccat gagttcaaga ccaacctggc caacatggcg  28740
aaagcctgtc tctactaaaa atacaaaaaa attagttggg catggtggtg cacacctgta  28800
atcacagcta ctttggaggc tgaggcagga gaatcgtttg aacccagagg tggaggttgc  28860
agtgagccga gattgtgcca ctgcactcta tcctgggtga cagagcgaga tactgtctca  28920
aaaagaaaaa aaaaaggctg ggcgcggtag ttcatgcctg caatcccagc actttgggag  28980
gccgaggcag gcagattacg aagtcaggag atggagacca tcctggctaa tacagtgaaa  29040
```

-continued

```
ccccgtctct actaaaaaat acacaaaaat tagctgggtg tggtggcagg cacctgtagt  29100
cccagctact ctggaggctg aggcaggaga atggcatgaa cccgggaggt ggagcttgca  29160
gtgagcagag atcacaccac tgcactccag tctgggcgac agagcgaggc tctgtctcaa  29220
aaaaaaaaaa gaaagcatac tctcacctcc ttcagtgact gatgttagta ttttggcaca  29280
ttctttttct gtgacatata cacacttacc ttgtaagtgt tgtactcatt tcctatgaca  29340
gtaaatagtc tttgtaacag gctgcatgat atttcataaa atgaatggat gtggcataat  29400
ttatatgtga gccttttgaa ttctgctatt ataattaata ttgcaatgaa caattcttat  29460
attgcctcta cacctcaaat gtcttatcat ttcttctagt ttttctgagg atgtcagatt  29520
attgggttaa aggatatgaa catttttaag gccttggaac agatttctaa attgctttcc  29580
agaataattc ccatgtgata ctttcaccat gtttatttca gacttttttt tttttttttt  29640
tttgagacga aatctcactc tgtcacccag gctggagtgt agtggcatga tctcggctca  29700
ctgcaacctc cgcctcctga gtttaagcga ttattctgcc tcagcctccc aagtagctgc  29760
ggttacaggc aagtgcctcc atgcctggct aatttttgtg tcttttgtag acatggggtt  29820
tcaccatgtt gcccaggctg gtttcgaact cctgagctca ggcaatctgc ctacctcggc  29880
ctcccaaagt tctgggatta caggcgtgca ccaccgcgcc cagccatcag agtctttttt  29940
gtcaaaataa aatggtctaa agacatacat catagagaaa ctataataca aaatttacag  30000
gtatatctaa gaaaagaaaa gtatatttaa agcataaaaa taaactgctc ttttacttaa  30060
aatttttaa aaactggatt aaaaatatga aacttccaac aaattgagct tttttttttt  30120
tttttttctt ttttgagacg aggtctcgct tttgtcaccc agtctggagt gcagtggcgc  30180
gatctcggct cactgcaacc tccacctccc tggttcaagc aattcccctg cctcagcctc  30240
ccaagtagct gggattacag gcgcatgcca ccacgtcggg ctaatttttt tgtattttta  30300
gtagagaggg ggtttcacca tgttggccag actggtctcg aactcctgat ctcaggcaat  30360
ctgccagcct gggtctccca acatgctggg attacaggca tgagccactg cactcggcct  30420
gaacttttta tagtagtaac gataattcag taatgtccaa taatgactaa gtaagttata  30480
acaagtacaa tgtcagcaat aactagtgct ttttagtaaa cagggtcagg caaccttgta  30540
ccctttttaaa aatgttcgaa tatcgatata cctccttcct acttggtgga ggattgattg  30600
aggaggaaag tgtgcagtga tggttaccag cttcagcctc ttggcttgac tttgcaaata  30660
ctggtgagaa tttggaaaga gcttgagaat atcttacata gtcacatgtt gctgagaaga  30720
gttaagaact aacttcttga tgttcatttt taacaatggc ttgcattcaa aaccttgtag  30780
agctcattag taggagctaa gaagctaata tttgcctttc actaaaattc ctgattactt  30840
agcctaggta gttcgttgtc tctctaggtt ctgtctttgg gagcttgggt ctaaggttat  30900
caagctaact ctttcttccc tctcaccctt cccaaattga ccctggtgct gatttgttat  30960
tcatacgatt ttctagtttt tcttttccct ttttgagtat ttgaagcttc atactgaata  31020
tagtaatcat agtattcatg cataaagaaa atcataaagt aattgcataa atgcataaag  31080
taatcatagt tttcatgcat taaaaaaact agttttggct gggcgctatg gctcacgctt  31140
gtaatcccag cactttcgga ggccaaggca ggcgaatcat ctgaggtcag gagttcgaga  31200
ctagcctggc caacatggcg aaacctcttc tctactaaaa atacaaaaaa attagccgag  31260
tatggtggcg ggcgcctgta atcctagcta tttggcaggc tgaggcagga gaatcacttg  31320
aacctgggag gcagaggttg cagtgagccg aggttgtgcc attgcactac agcctaggcg  31380
acaagagcaa gactccatct caaaaaaaaa aaaaaaaaaa aaaaaactcc ctattacaga  31440
```

```
ttcataattt atgagtcatt aaataatatt ttcaagccat gacatttttt ccagcagtag  31500
tctctaaatc tgttttacca tcataaaacc ccaagcaaaa ctctactaca tcagctgtgt  31560
cactgtaaaa cctgccttaa ctcacagaag catgaaatta agcaatgtgt gtgaaactat  31620
tttataaact gtaaagtatt ccatacatac atgttggcag ttattaatgt cttctctagg  31680
tgtggctttg aaatggatgc agatgctttc tgttacaaaa aacataagtt gcaaatgttc  31740
tataacaagg agagacacaa atatcttcat ggacatggat tgctatgagt gtttgattgc  31800
ctaatacttg agccaccact tcagtgatat ggtataattt atcaaacagt gttgagaaac  31860
agaaactact ggggatgttt taaagaggaa aatacttaat atagaaatta ggggtttaca  31920
taatcttaag aaaggatgaa ggtgcagctc ttagccaggc ctccacagta ccacaaacca  31980
acttgcagga agagctgtaa ccactgcccc agttgggaca atgggtaatg aggatattaa  32040
atttaagaac atactgctat agcaatgatc cttggcatag aaagctgcca ccacaattgc  32100
ctagagatgg gaacatgaag tctggccccc attgcaacag cagtgaagca gaattttggg  32160
actggcatct cccaaatggc tttgcttgcc accagagaac aaccaaagtg gagggagatg  32220
gctaggcctc atttctgcct attttatttt attttttgag acggagtctt gtctgtcgcc  32280
caggctggag tgcagtagtg tgatctcggc tcactgcagc ctccgcctcc cagcttcaaa  32340
caattctcct gcctcagcct cctgagtagc tgggattaca ggcacccgcc actgtgccca  32400
gccaatttc ttatttttag tagaggtggg gttttgccac gttggccagg ctggtcttga  32460
actcctgacc tcaggtgatc tgcccgcctc agcctcccaa agtgttgtga ttacaggtat  32520
gagccaccat gcctggccca tttctccctt tttttttttt tttttttttt gaggtggagt  32580
ctcactctgt tgcccagact ggagtgcagt ggtgcaatct tggcgcattg caacctctgc  32640
ctcccagttt caagcaattc ttctgcttca gcctcctgag tagctgggac tacaggtgtg  32700
tagcaccaca cctggctaat ttttgttttt gttttgtttt ttttgagaca gagtctcact  32760
ctgtcaccca ggctggagtg tagtggcatg atctgggctc actacaacct ccgcctcccg  32820
ggttcaagca attctcctgc ctcagcctcc agagtagctg ggattacagg tgtgcgccaa  32880
cacacctggc taattttttt gtatttttaa tagagatggg gtttcaccat gttggccagg  32940
ctggtctcga actcctgacc tcgtgatccg cccgcctcgg cctcccaaag tgctgggatt  33000
acaggcatga gccaccgtgc ccagacaagg tttgtatttt tagtagagac agttttgcca  33060
tgttggccag gctggtcttg aactcctcac ctcaggtgat ccgcctgcct tggcctccca  33120
aagtgctggg attacaggcg caagccactg tgcctgaccc gtttctgctt tttaaagctc  33180
atgtgagcac ttaatttgta accagaatcc tacttgtaaa ataatctaag acatgtagct  33240
tttagctttg taacctctat aatattgatg gcacagtggg agtggatgct gagtaccact  33300
tgaacatgtt ccacctcagt gtcttcacag ctggaaggtg tctacattgt ttcaaggtgg  33360
acaattgatt tacttctcat ttttcataaa ctaaaagtag aataaaggct attcctctaa  33420
aattgctatc tcacctgtca ctcccttgca ttctcacata ccttcttgag tggaggggca  33480
gagggcatgg agtgatagca gatgtgccag gaattctcca taactcagtc cgtccctctt  33540
gtgctatgtt gcagcatcag gatttgctaa tgggaggata ctgcccttac gtgcatcatt  33600
agccatgcac actaaggtct tacacctaca cacaggtcag tattctggct cagagaccaa  33660
cagggagaaa ttgcagttct cattagttga actttcttta ttgttcacag ttttaaaaca  33720
caaaattgag aggaactcta taaaaaatgt gccattctat taataattgt tgctggtaat  33780
```

-continued

```
ttaaaaatcc ttgttccttt tcaaattctt atataccttt tttttttaaa cacttgatct  33840
tagccaaaag accgagaagc aatctttttt tttttttttt tttttttaa cctatagctt  33900
ctcactgaga ttgtcagctg tttgtaagtt ttggtttttg gttttctgtg tttgtattta  33960
catatatgaa atacagattg agtatccctt atccaaaatg cttaagactg gaagtgtttt  34020
agatttgggg ttttttagga tttgtgaata tttgcactat acttaccagt taagcattcc  34080
aaatccaaaa tttcaaatct gaagtgttcc actgagcacc tcttttgagt atcatgttgg  34140
tgctcaaaaa gtttctgatt ttggagcatt tggatttctg attctcggat ttaggatgct  34200
tgacctgtaa tttcagattt acataaaagc agaaatagta cacagagctc cttatatcct  34260
tcacccagat tccccaatta ttggcctttc tgaaccattt gggaataata tgcagatatg  34320
attttccatt atgtctcagt tgttcagtgt atattttcta agtacaagaa tatattccta  34380
catatttaca tgataaccgt catgtttaaa cattttaaaa tggggatttg tattacattg  34440
tttctctttt tgaaaaaatt acagaggagc ttaatgcaat cagtattact taaaatctga  34500
taatgtgtgt taaatagtag ttttcattta tttcatttat caggtgttca gtgaatgctt  34560
actatgtaac agcacagtta tcagcactgg ggaaatagat gagtaagata agatttgcac  34620
tttcattagc ttacatgcca taaagaggga aataaagaga acaccagatg atgataagtt  34680
tatgctgaga attaaaatga agtgatgaaa taatgggaat gtcaggtggc tacttttggt  34740
gggatggtca ggaaaggcat ctctggggag ataaatttta agctcagacc tgagtgaaaa  34800
gaatgagcca gccatggaaa cattatgtta actcacatgg tagtttgaaa tgctttatct  34860
gatcaaaggt acttattttt ggtgactttc aacaatatta agggtctata aaccaacact  34920
catttgcata agaataacta ccagtgaatc tttttgtatg ataggttttt tgtttgttgt  34980
tttttgaga cagagtctcg ctctgtcgcc caggctggag tgcagtggcg cgatcttggc  35040
tcactgcaac ctctacctcc ccggttcaag tgattctcct gcctcagcct cccaaagtag  35100
ctgggattac aggtgcctgc caccacgcct ggctaatttt tgtattttta gtagagatgg  35160
ggtttcaccg tgttgtccag gctcgtgtca aacttctgac ctcaagccat ccacccgcct  35220
cggcctccca aagtgctggg attacaggtg tgagccacca ctcctggcca tgataggtta  35280
ttttgtgatg aaaataccta cctcttaatt tgtctgataa atttaaattt tatgtctaga  35340
tttcctaaga tcagcacttc catattttaa agtaatctgt atcagactaa ctgctcttgc  35400
attcttttaa taccagtgac tactttgatt cgtgaaacaa tgtattttcc ttatgaatag  35460
tttttctcat ggtgtattta ttcttttaag ttttgttttt taaatatact tcacttttga  35520
atgtttcaga cagcagcaaa agcagcaaca gcagcagcag cagcagcagc agggggacct  35580
atcaggacag agttcacatc catgtgaaag gccagccacc agttcaggag cacttgggag  35640
tgatctaggt aaggcctgct caccattcat catgttcgct accttcacac tttatctgac  35700
atacgagctc catgtgattt ttgctttaca ttattcttca ttccctcttt aatcatatta  35760
agaatcttaa gtaaatttgt aatctactaa atttccctgg attaaggagc agttaccaaa  35820
agaaaaaaaa aaaaaaaagc tagatgtggt ggctcacatc tgtaatccca gcactttggg  35880
aaaccaaggc aggagaggat tgctagaaca tttaatgaat actttaacat aataatttaa  35940
acttcacagt aatttgtaca gtctccaaaa attccttaga catcatggat atttttcttt  36000
ttttgagatg gagtcttgct ctgtcaccca ggctggagtg cagtgtcgcg atctcggctc  36060
actgcaagct ctgcttcctg ggttcatggc attctcctgc ctcagcctcc tgagtagctg  36120
ggactacagg cgcccgccac atcgcctggc taattttttg tatttttagt agagacaggg  36180
```

```
tttcaccatg ttagccagga tggtctcaat ctcctgacct catgatccgc ccgcctcggc  36240
ctcccaaagt gctgggatta caggcgtgag ccatcacgtc cggccagaaa tcatgaatat  36300
tagtaggtga aaaataaaca cattttacca cctggaaaat gaaaaatact tgagtataat  36360
ctaaataaca atgggaagtg cagagttact ttccaggtct cggtttaaat atgtcttaaa  36420
ctttggccaa ttagtagtag aagttgagag aaaaagtaac tatctgacaa agaaattata  36480
agcagaatat ataaagaact cttaaaactg aataatcaga aaacaactca ataaaaaggt  36540
gaaggatttg aaaagatatt tcaccaaata agacataggg atgacaaata agcacatgaa  36600
aagactctca gcatcactag tcacagggaa atgcacgata aaaccacagt gagacaccat  36660
ggcacccctg taggtatggc tttaatgaag aaataaaact gacaatacca agtgttggca  36720
aggatccaag cagctgagac tcatatactg ttaatgggaa tgtaaaagtg tacagctttg  36780
gaaaacagtt tggcattttt ttgataaatg tatacttagc catgtgatcc agcagtccca  36840
atcatgtata tataaccaaa agaaaagaaa acttaggttc acataaaaac ttatatcaaa  36900
tgcttatagc tgaccaggca tggtggccca tgcctataat cccagcactt tgggaggccg  36960
aggttggcag atacctgaag tcaagtgttc gagaccagcc tggccaacat ggcaaaaccc  37020
tgtctctact taaaatacaa aaattagcca ggcgtgatgg caggcacctg tagtccagct  37080
attcaggagg ctgaggcagg agaatcacgt gaacccggga ggcagaggtt gcagtgagcc  37140
gagatcgtgc cactatactc cagcctgggt gacagagcaa aactctgtct caaaaaaaaa  37200
aaaaaaaaaa agggctggac acggtggctt acgcctgtta tcccggcact ttgggaggcc  37260
aaggctgatg gatcacctga ggtcaggagt tcaagaccag cctggccaac atggtgaaac  37320
cccatctcta ctaaaaatac aaaaatttgc tgggcatggt ggtgggcacc tgtaatccca  37380
ggaggctgag gcaggagaat cacttgaacc cgggaggcgg agattgcagt gagccaagat  37440
tgtgccattg aactccagcc tgggtgacaa gaccaaaact ccttctcaaa aaaaaaaaag  37500
attatagcat ctttattcat cattgcccaa aattacaaac tgcctaaatg tagaccttca  37560
tttagttaat gaatgcacaa actgtggtat atccaaacaa ttgaataaaa aaaggaatga  37620
actggtactt ttttctattc ctcctgttta agtacagcca aaacacctca acatttgtat  37680
aaaacatgag ctgggctggg tgcggtggct cacacgtgta atcccagcac tttgggaggc  37740
tgaggcgggt ggatcaccta aggttgggag ttcaagaccg gtctgaccaa catggagaaa  37800
ccctgtctca actaaaaata caagattagt cgggcatggt ggcgcatgcc tgtaatccca  37860
gcttcttggg aggctgaggc aggagaattg cttgatcccg ggaagcgaag gttgcagtaa  37920
gctgagattg caccattgca ctccagcctg ggcaacaaga gcaaaactct gtctcaaaaa  37980
gaaaaaaaaa accattcagc tgaatctcaa aggcagagag aagacagact ggctagggac  38040
cttggaacca gaggagcagt gtggtgggga gtggactgga ttttcttttt gcctcattta  38100
tcctggactt ggtgctggag aagctatggg ttcagaccaa gagaaaaccc catgaaaagc  38160
ctgctctctc tagccaaaag aggcaaccta gcaagataaa aacctttaga taataagcac  38220
ttgactccag tcaaacaaaa cagaataaac tggccccatt cacccctgtc agcaaaggcc  38280
aagtgggagc caagatatgt accccaacct ggaagtcata aggtacactt ctcccctttc  38340
ccagccaagg tggtgttaga gaaggctgac tggggagctg ggattctcat tccctccagg  38400
aggtgataac actcctttca catggtgtca gtggtcacag ggaggctgaa cttccaccca  38460
gtaatacata ggcatctctc tggctcctat atgggtgatg ttggagaaga ggccgagtag  38520
```

agaatccaga ctgttgctga cacccagcag taacaaggac acctccacaa tgtccgtgga 38580
ggccatgtgg agatcagtaa caaggcactg ctctccctcc cagtcagaga gatgtcagtg 38640
gaggactagg gggctagaac tcccatgtgc gttcagcagt aatccccatg accgccactc 38700
cttgacatca caggccttga agaaacctgg actttcactc ccctctggtt gtagcgaggt 38760
ggcactccct tttccctgtt gccagtgctg tgtcagtgga ggcttgctaa attggaagat 38820
gtaaataaga ttcacattct cataacataa taccccaaat tttcaggatt taattgaaaa 38880
tcactaagct gggcatggtg gctcacacct gtaatcccag cactttggga ggccaaggtg 38940
ggccaaacac ttaaggtcag gaattcaaga ccagcctggc cagcatggtg aaaccctgtc 39000
tctactaaaa atacaaaaat tagctgggcg tggtggcaca tgcctgtaat cccagctact 39060
gggaaggcta aggcaggaaa atcactggaa cctgggagac ggaggttgca gtgatccaag 39120
atcgcactag tgtactgcag cctgggcaac agagcaagac tccatctaaa tttgtgtcag 39180
gattcccaga aggagatgag aaagggtggg gctgaaaaaa attgaggaag aagtcatggc 39240
tgaaaatttc ccaaatttgg caaaagtcag aaacctacag attgaaaaag ctgaatgaag 39300
ctcaaatatg ataaactcaa agaagttcac acagagacac atcacagtca gatttctgaa 39360
cactgcagac aaaaaatgaa gatctcgaaa ttagcaagaa atgaccttac ctaagcaatt 39420
tgaatgacag cagatttccc atcagagatc ataaaggcca gaaggaaggg gtacatacaa 39480
catttttct agtgctgaaa gacaaaaact ctaggctggg cacggtggca cacacctgta 39540
atcccagcac ttttggaggc tgaggcaggc agatcacctg aagtcaggag ttcgagacca 39600
gcctggccaa catggggaaa ccctgtctct actaaaaata caaaaattag ccaggtgtgg 39660
tggcacgcac ctataatcct agctacttgg gaggctgagg caggggaatc gcttgaacct 39720
gggaggcgac ggttgcagtg agccaaggtc gcgccactgc actccagcct gggcagttga 39780
gcgagactcc atctcaaaaa aaaaaaaatt atccaggctt ggtggtgggc gcctatagtc 39840
ccagctactt gggaggctga ggcaagagaa ttggttgaac ccaggaggtg gaggttgcag 39900
tgagccaagc tcatgccact gtactccagc ctgggtgaca gagcgagacc ttgtctcaaa 39960
aaaaaaaaaa aaaaaaaaaa acaagaaaaa aactctaaac ccagagttac atatccagtg 40020
aaatatcctt caggagtgaa gggaaaatta acgatttgtc ttcaggagac ctaccctaaa 40080
agaatggcta aaggaatttc tctaaacaga aaagaaatga taaaagaagt aattttggaa 40140
catcaggaag gaagaaagaa caataaaaag agtaaaatat gggtaaacac aatagacttt 40200
cccctccttt tgaatttttct aaattgtatg atggttgaag caagaattat agcactgatt 40260
tggttttcag tatatatatt ggaaatattt aaggcattat gttacagatg aaggagggtc 40320
aaaggatata aagggaggta acctttctat atttcttttg tactgatgca ggcactttgg 40380
aaaataattt cactatttgt ttaaaaactg aacataccct gaccatatga catagcatct 40440
atactcctgg gcatttatcc cagagaaaca gaaatttatt tatttttttt ttagtattac 40500
actccgtaag tgctgtaata ctagcactta gggaggctga ggcaagcaga ttgcttgagc 40560
ccaggagttc aagaccagcc tgggcaatgc tgcacagtca aaaaagaaaa acaaacattt 40620
agaaaactat tttaaaagtc tttaattgct gaatgcctct ttggctaata tttggaagat 40680
cattattatt atttttcttt tttaggcaga gtcttgctct gtcactgagg ctggagtgca 40740
gtggcgccat ctcggcttac tgcaacctct gcctcccggg ttcacgccat tctcctgcct 40800
cagcctcccg agtagctggg actacaggcg tgtgccacca tgcccggcta attttttgtg 40860
tttttagtag agatggggtt tcactatgtt agtcaggatg gtctccatct cctaacctcg 40920

```
tgatccgccc acctcggctt cccaaaatgc tgggattaca ggcgtgagcc actgtgccca  40980
gcctggaaga tcattattta gtcctacaac tgacacattg ttccactgac gcaattgccc  41040
aggctggtct tgaactcctg ggctcaagca atctgcctgc ctcggcctcc ctaagtgcta  41100
gtattacagg cttgagccac tgtgcccagc caaaaataga aatttatatt ctcacaaaaa  41160
catgtacatg aatgtttata gcagctttac ttgtcataat caaaaactgg aaacaaccaa  41220
aatgtcctac agtgaaacaa actgtagtac atccatagca tgtaatactc tactgtcagg  41280
attaaaaaga aacccactgt tggcacaggc agcaccgtgg ctggatctca ggggcattat  41340
gctgagtgca aaaaagcctc aaagggtctt acactgtatg attccacttg ttcaactaaa  41400
aatgacagct gtatagagat agagaacata ttagtggttt ccactagtta gagaaagtgg  41460
gtaaaagata ggtgggtggg aatataaatc gatagcaggg agatctttgt ggtattataa  41520
cacttctatg tcttgattgt agtggtggtg gttacatgaa tacacgtgtg ataaaatgcc  41580
atgtagaact acatataacg ttgtgccaat gtcaatatct aggttttagt ttgatcttta  41640
gttacataag atgtaactat tgggtgaaat tgggcaaaag agtacacgaa acctctctta  41700
aatatcttta caacttcctt tgaattgaca gtttttcaaa atagaaagtt gggtttttgt  41760
aaatacatga attgttgata tacacaacaa atctcaaatg cattatgcta cgtgaaagaa  41820
gccatattca aaaggctaca tacctactga tgccttttat atgacgtgca ggaaaagata  41880
aaactgtagg acagagaata tactggtggc tatctgggat taggaaatgg ggatcgacca  41940
caaaggggca gcatggggga attttctggg gcaatggaat ggttgtgtat cttgatggtg  42000
tatttgtcaa aatatataga actataaaag taaattttgc tttatatgta ttaaatcaaa  42060
aaaagaaact cgtgctcaaa tagaaataca ttttctgaga acttgccttt tgatgacttt  42120
gagaattttc tggaaatttt aaagaaatgt ggttttgttt cccaacaggt gatgctatga  42180
gtgaagaaga catgcttcag gcagctgtga ccatgtcttt agaaactgtc agaaatgatt  42240
tgaaaacaga aggaaaaaaa taataccttt aaaaaataat ttagatattc atactttcca  42300
acattatcct gtgtgattac agcatagggt ccactttggt aatgtgtcaa agagatgagg  42360
aaataagact tttagcggtt tgcaaacaaa atgatgggaa agtggaacaa tgcgtcggtt  42420
gtaggactaa ataatgatct tccaaatatt agccaaagag gcattcagca attaaagaca  42480
tttaaaatag ttttctaaat gtttcttttt ctttttttgag tgtgcaatat gtaacatgtc  42540
taaagttagg gcatttttct tggatctttt tgcagactag ctaattagct ctcgcctcag  42600
gctttttcca tatagtttgt tttctttttc tgtcttgtag gtaagttggc tcacatcatg  42660
taatagtggc tttcatttct tattaaccaa attaaccttt caggaaagta tctctacttt  42720
cctgatgttg ataatagtaa tggttctaga aggatgaaca gttctccctt caactgtata  42780
ccgtgtgctc cagtgttttc ttgtgttgtt ttctctgatc acaacttttc tgctacctgg  42840
ttttcattat tttcccacaa ttcttttgaa agatggtaat cttttctgag gtttagcgtt  42900
ttaagcccta cgatgggatc attatttcat gactggtgcg ttcctaaact ctgaaatcag  42960
ccttgcacaa gtacttgaga ataaatgagc attttttaaa atgtgtgagc atgtgctttc  43020
ccagatgctt tatgaatgtc ttttcactta tatcaaaacc ttacagcttt gttgcaaccc  43080
cttcttcctg cgccttattt tttcctttct tctccaattg agaaaactag gagaagcata  43140
gtatgcaggc aagtctcctt ctgttagaag actaaacata cgtacccacc atgaatgtat  43200
gatacatgaa atttggcctt caattttaat agcagtttta ttttattttt tctcctatga  43260
```

```
ctggagcttt gtgttctctt tacagttgag tcatggaatg taggtgtctg cttcacatct  43320
tttagtaggt atagcttgtc aaagatggtg atctggaaca tgaaaataat ttactaatga  43380
aaatatgttt aaatttatac tgtgatttga cacttgcatc atgtttagat agcttaagaa  43440
caatggaagt cacagtactt agtggatcta taaataagaa agtccatagt tttgataaat  43500
attctcttta attgagatgt acagagagtt tcttgctggg tcaataggat agtatcattt  43560
tggtgaaaac catgtctctg aaattgatgt tttagtttca gtgttcccta tccctcattc  43620
tccatctcct tttgaagctc ttttgaatgt tgaattgttc ataagctaaa atccaagaaa  43680
tttcagctga caacttcgaa aattataata tggtatattg ccctcctggt gtgtggctgc  43740
acacatttta tcagggaaag ttttttgatc taggatttat tgctaactaa ctgaaaagag  43800
aagaaaaaat atcttttatt tatgattata aaatagcttt ttcttcgata taacagattt  43860
tttaagtcat tattttgtgc caatcagttt tctgaagttt cccttacaca aaaggatagc  43920
tttattttaa aatctaaagt ttcttttaat agttaaaaat gtttcagaag aattataaaa  43980
ctttaaaact gcaagggatg ttggagttta gtactactcc ctcaagattt aaaaagctaa  44040
atattttaag actgaacatt tatgttaatt attaccagtg tgtttgtcat attttccatg  44100
gatatttgtt cattaccttt ttccattgaa aagttacatt aaacttttca tacacttgaa  44160
ttgatgagct acctaatata aaaatgagaa aaccaatatg cattttaaag ttttaacttt  44220
agagtttata aagttcatat ataccctagt taaagcactt aagaaaatat ggcatgtttg  44280
acttttagtt cctagagagt ttttgttttt gtttttgttt ttttttgaga cggagtcttg  44340
ctatgtctcc caggctggag ggcagtggca tgatctcggc tcactacaac ttccacctcc  44400
cgggttcaag caattctcct gcctcagcct ccagagtagc tgggattaca ggcgcccacc  44460
accacacccg gcagattttt gtatttttgg tagagacgcg gtttcatcat gtttggccag  44520
gctggtctcg aactcctgac ctcaggtgat ccgcctgcct tggcctccca aagtgttggg  44580
attacaggca tgagccactg cgcctggcca gctagagagt ttttaaagca gagctgagca  44640
cacactggat gcgtttgaat gtgtttgtgt agtttgttgt gaaattgtta catttagcag  44700
gcagatccag aagcactagt gaactgtcat cttggtgggg ttggcttaaa tttaattgac  44760
tgtttagatt ccatttctta attgattggc cagtatgaaa agatgccagt gcaagtaacc  44820
atagtatcaa aaaagttaaa aattattcaa agctatagtt tatacatcag gtactgccat  44880
ttactgtaaa ccacctgcaa gaaagtcagg aacaactaaa ttcacaagaa ctgtcctgct  44940
aagaagtgta ttaaagattt ccattttgtt ttactaattg ggaacatctt aatgtttaat  45000
atttaaacta ttggtatcat ttttctaatg tataatttgt attactggga tcaagtatgt  45060
acagtggtga tgctagtaga agtttaagcc ttggaaatac cactttcata ttttcagatg  45120
tcatggattt aatgagtaat ttatgttttt aaaattcaga atagttaatc tctgatctaa  45180
aaccatcaat ctatgttttt tacggtaatc atgtaaatat ttcagtaata taaactgttt  45240
gaaaaggctg ctgcaggtaa actctatact aggatcttgg ccaaataatt tacaattcac  45300
agaatatttt atttaaggtg gtgctttttt tttttgtcct taaaacttga tttttcttaa  45360
ctttattcat gatgccaaag taaatgagga aaaaaactca aaaccagttg agtatcattg  45420
cagacaaaac taccagtagt ccatattgtt taatattaag ttgaataaaa taaattttat  45480
ttcagtcaga gcctaaatca cattttgatt gtctgaattt ttgatactat ttttaaaatc  45540
atgctagtgg cggctgggcg tggtagctca cgcctgtaat cccagcattt tgggaggccg  45600
aagtgggtgg atcacgaggt cgggagttcg agaccagctt ggccaaaatg gtgaaacccc  45660
```

```
atctgtacta aaaactacaa aaattagctg ggcgcggtgg caggtgcctg taatcccagc  45720
tacctgggag tctgaggcag gagaattgct tgaaccctgg cgacagagga tgcagtgagc  45780
caagatggtg ccactgtact ccagactggg cgacagagtg agactctgtc tcaaaaaaaa  45840
aaaaaaaatc atgctagtgc caagagctac taaattctta aaaccggccc attggacctg  45900
tacagataaa aaatagattc agtgcataat caaaatatga taattttaaa atcttaagta  45960
gaaaaataaa tcttgatgtt ttaaattctt acgaggattc aatagttaat attgatgatc  46020
tcccggctgg gtgcagtggc tcacgcctgt aatcccagca gttctggagg ctgaggtggg  46080
cgaatcactt caggccagga gttcaagacc agtctgggca acatggtgaa acctcgtttc  46140
tactaaaaat acaaaaatta gccgggcgtg gttgcacaca cttgtaatcc cagctactca  46200
ggaggctaag aatcgcatga gcctaggagg cagaggttgc agagtgccaa gggctcacca  46260
ctgcattcca gcctgcccaa cagagtgaga cactgtttct gaaaaaaaaa aatatatata  46320
tatatatata tatgtgtgta tatatatatg tatatatata tgacttccta ttaaaaactt  46380
tatcccagtc gggggcagtg gctcacgcct gtaatcccaa cactttggga ggctgaggca  46440
ggtggatcac ctgaagtccg gagtttgaga ccagcctggc caacatggtg aaaccccatc  46500
tctactaaaa atacaaaact taagccaggt atggtggcgg gcacctgtaa tcccagttac  46560
ttgggaggct gaggcaggag aatcgtttaa acccaggagg tggaggttgc agtgagctga  46620
gatcgtgcca ttgcactcta gcctgggcaa caagagtaaa actccatctt aaaggtttgt  46680
ttgttttttt ttaatccgga aacgaagagg cgttgggccg ctattttctt tttctttctt  46740
tctttctttc tttttttttt tttctgagac ggagtctagc tctgctgccc aggctggagt  46800
acaatgacac gatgttggct cactgcaacc tccacctcct gggttcaagc gattctcctg  46860
cctcagcctc ccaagtacct gggattacag gcacctgcca ctacacctgg cgaatatttg  46920
ttttttttag tagagacggg cttttaccat gttaggctgg tctcaaactc ctgacctcag  46980
gtgatctgcc tgccttggcc tcccaaagtg ctgggattac aggtgcaggc caccacaccc  47040
ggccttgggc cactgttttc aaagtgaatt gtttgttgta tcgagtcctt aagtatggat  47100
atatatgtga ccctaattaa gaactaccag attggatcaa ctaatcatgt cagcaatgta  47160
aataacttta tttttcatat tcaaaataaa aactttcttt tatttctggc ccctttataa  47220
ccagcatctt tttgctttaa aaaatgacct ggctttgtat ttttttagtc ttaaacataa  47280
taaaaatatt tttgttctaa tttgctttca tgagtgaaga ttattgacat cgttggtaaa  47340
ttctagaatt ttgattttgt tttttaattt gaagaaaatc tttgctatta ttattttttc  47400
caagtggtct ggcattttaa gaattagtgc taataacgta acttctaaat ttgtcgtaat  47460
tggcatgttt aatagcatat caaaaaaacat tttaagcctg tggattcata gacaaagcaa  47520
tgagaaacat tagtaaaata taaatggata ttcctgatgc atttaggaag ctctcaattg  47580
tctcttgcat agttcaagga atgttttctg aatttttttta atgctttttt tttttttgaa  47640
agaggaaaac atacattttt aaatgtgatt atctaatttt tacaacactg ggctattagg  47700
aataactttt taaaaattac tgttctgtat aaatatttga aattcaagta cagaaaatat  47760
ctgaaacaaa aagcattgtt gtttggccat gatacaagtg cactgtggca gtgccgcttg  47820
ctcaggaccc agccctgcag cccttctgtg tgtgctccct cgttaagttc atttgctgtt  47880
attacacaca caggccttcc tgtctggtcg ttagaaaagc cgggcttcca aagcactgtt  47940
gaacacagga ttctgttgtt agtgtggatg ttcaatgagt tgtattttaa atatcaaaga  48000
```

ttattaaata aagataatgt ttgcttttct a 48031

<210> SEQ ID NO 43
<211> LENGTH: 300019
<212> TYPE: DNA
<213> ORGANISM: Homo sapiens

<400> SEQUENCE: 43
gatgtcccga gctgctatcc ccggctcggc ccgggcagcc gccttctgag cccccgaccc 60
gaggcgccga gccgccgccg cccgatgggc tgggccgtgg agcgtctccg cagtcgtagc 120
tccagccgcc gcgctcccag ccccggcagc ctcagcatca gcggcggcgg cggcggcggc 180
ggcgtcttcc gcatcgttcg ccgcagcgta acccggagcc ctttgctctt tgcagaatgg 240
cccgcttcgg agacgagatg ccggcccgct acgggggagg aggctccggg gcagccgccg 300
gggtggtcgt gggcagcgga ggcgggcgag gagccggggg cagccggcag ggcgggcagc 360
ccggggcgca aaggatgtac aagcagtcaa tggcgcagag agcgcggacc atggcactct 420
acaaccccat ccccgtccga cagaactgcc tcacggttaa ccggtctctc ttcctcttca 480
gcgaagacaa cgtggtgaga aaatacgcca aaaagatcac cgaatggcca tatcctttttg 540 cccgaacccc agcagcagct gcgcctcccc ctcctccctc cgcctcccct cttccaggct 600
gggagagaga cccgggggtt gatgggaggt ggggaggagg ggggtcttcc aggggctggg 660
agagggggca ccgggaggag tgtgaaagaa tctctccacc ccgagctggg ttgagctacc 720
ctggaggctt gggaatgggt ttgtgggggg ctggggggtg ggcagcggag agtggatcct 780
tcccaaggac cgactctaga atgagatctg gggcctgggg tcgtgcagga gccttggtgg 840
gggctttcga gccaagtccg gagggtttgg agttctacgg agtgagcttg gagcgggctc 900
gggcctgggc gcttctggcc agggcagggg aactatgggg gccttggttg ggttttcttg 960
gccgtcgctc actggagtcc acgcagggga agctggacag cctctccact actgctttcc 1020
ccaaggtggg gggccgccgc acttttaggg cagggcgctt gggggctccc agggctaaga 1080
gcaagaggga gtccatgtgg ccttcacact gagaagccag cactggccga agtgagtacc 1140
ccagggtggg ccgctgttcc tatctggaga ggatagtgat gggctggggg gcgcttatgt 1200
ttccctcatg tgtgcaggtc ccattgcctt taaccgctga ttggggaacc tcatcatctt 1260
tgggggtgtc gagaaagaga tcccacttgc tttatctggg cccctggcct gggaagacct 1320
gatctggaca ctttcagtaa gaaagacagg gcaacagcaa atgaggtggt gggtccattt 1380
tagagcacca tgtccagctt ttcctacccc gagtagccga gagggaacac caggagaatc 1440
agcacccatg tggacatctt aggtaggtaa atgcctttta aatttttttt tttttaatca 1500
aagatccaga ggaaaaaggt gaagcccaca ttttcttctg tggagatgct atcaaaatgc 1560
agatcttctg tgtttcttta aatccctgcc tgcttgaaat aaaccttgag gagggcttaa 1620
catctatcga gatgtaggca ggcaagggtg ggtaattagt cgggctttct agcagttatc 1680
taagcatgac ccagattcca ggaggggga cacaccctgc tgcccaggct ggctggccac 1740
tgtgccatgc ccagatgtgc cgcttctccg cacagttcca accagctgcc ctctgtgtaa 1800
aaatgaacgg gctggatggg tccctggggc tcagcgatga gtcccctatc ccttttgtat 1860
gtggttttgc agttatagac taaacggggc tgggccctgt gtggtctccg ggggttgctg 1920
tttgaggagc atggcgggtg gtagagggac tcacttcagg ggggttcaaa atcgagcctg 1980
gcgcttggat cctgggtgct gggattgcaa cagagggcac tgaggttttg gagtgtgtga 2040
gtggtctact ttgagggtgg ggaaaattaa gaagttcagc agaggtgctt ttgaggggag 2100

```
cataccteta actacgatgc catctccgtt ggtgcccaaa gcaggtgcca ggtctttgct   2160
tcctaagttt cagactctta aagaggctgg ttcttaaggt tagcaattcc tcaccatccc   2220
aggcccattg aagtgctcag ggtggcttg attactctgc ctatcaacag agtgaggagt   2280
gggagtgcct tgcaggagga cagggtattc atgggtgcac acccagttag ctccaggagt   2340
gagagggctt tgctcggctg acaggtttcc tcattgaaaa tggctttaga tcgccttctg   2400
gagcctggat ttggagactt ctaagaggaa aggaaggagg tggggagccc ttctgctgtg   2460
tccttagctt acctctgtcc agcctgaatc ctgcagattg gagggctgtt gggggagagg   2520
gggattgcag tggcccctcg gaagggggaa tcgtgggaga gggaggcagg tgaattgcga   2580
gtgttgcttg ccacttcatc tattctctgg ccagctcgcc cggggctttc ttgctcttat   2640
gatgagtttg tgcattatgc tctctgcaga ctgtttttgt tctctttgac ccgaggtaac   2700
aaacacatta tacagcccta ctctggaagg gaaaactccc cacctcacaa tctgtcatcg   2760
agctgggtca tccaggactg agctttctct gtcctggatg gagcggaggg cggtggcggg   2820
gtgggtggga gggttggaga tgagagggga tggacagaga cctggggagg gaggtagtga   2880
ataaaagaat tcaggccagt gtaaagagaa agacacgtgg aatgtcagag tcacgatacc   2940
agggcagaac attctacttt ttaatctaaa tatttctgcc attaaaaaaa aatgtttcag   3000
catatcctga gagtgaaaaa aaaagtgtgt aggtacttaa ataaagtcta atatatgtac   3060
aggcaagtac atatattcag atgcatagat ttttacaaaa tgaacacacc cacgtatcca   3120
gcacccaggt cccgatcagt gccctggaag tccccctccc cataccgcct cctagttgct   3180
cccccaacaa gggtaccgct cacctgactt ctaaggttca ttttgcctct tttaaacatg   3240
taaatggagt cacacagtac gttcttttgc cactggcttc ttttgctcac atctgtgtat   3300
gtgactctac tacaatctat ccattctact gttgatgggc atttgtgtca tttctgtttg   3360
tgccactggg aacattcttg tgtcttctat tattttttc ccacagttct cttagatagg   3420
agtggaatcg cccctgctac tttttgatgc atgtgttgtg ggatgtgtat ttggaaatgg   3480
tgttgactaa gggttgcagg tcgatatgga aagcaggttc ctccctgtct tgtttaagag   3540
aagtgagtga atgatccatg aacttgtcgg tatgctcaca gggcctaaga gtgctacttc   3600
caaatgtaaa ttctggcatg gtacactggt gaaggatgca gtcttgcttt ctccacactc   3660
ggggcaattt gtcactatga tttcttcctc tttcatccct cagtgggtca aacttgaagc   3720
catcaatgac aattaagaat cctcatttat ttcatttttt cccctcttcc taagtgagga   3780
aacccaaatg gaagtctttg atgttcaaat ttacattgcc gtgtttttct catgccaggc   3840
agcaagccgt cttgaccaca caccttggtt tcatgttttc attgactgga attgtgattc   3900
aaatagggcc atgagggtct ctgatgattg ccgaagagct cagatctgtc agctcaaaaa   3960
ggagcatctg tcagccttcc tagagttccc tccccactta atgccactca ctccttctac   4020
caagtgccaa ggtgaatgtc atctttccag ccctccctgt gccaccaggt ctcccactga   4080
acatgatgta gaaactcagg ccatcggagg aacactggaa gcaggtcagt gtattatcac   4140
gcacagttgc ctgaattaca cgtagaattc cagcttttca tccggtttgc agaaatctta   4200
acaagacacc taaagtcaca ttgacatcag gtgacatcac tttgacatct gtggacattg   4260
gctgattggc actcctctca tttttttttt tttttttttt tttaagaaaa gctctctaaa   4320
gagaaacttt ctgcatgaga agcgctggga gacatgggag caggttatca gactcttggc   4380
ctgtcctgag agatagaatg ttctagaagg tactgccgta gagggcagga tggtgtcact   4440
```

-continued

```
tacgtgatcc ttgtactaga ccggcttggc tggtatttcc agaggagcaa aattctgcga   4500
agtaaaattt agcacggctt ttccaatggg agtattttca aaaagggtgc aatttcttat   4560
ccacaattcc ccaatccaaa aagctccaaa aaccaaaaga cgagctcata tagaggtaaa   4620
acctaacctg aactgacttc agtttgaagt cttaatttac agttttcatt cattctactt   4680
ggtgtgcatt tgagtatgtt ttgcagcaga aatgttagat gtgcttgatg atgaggtgct   4740
gcttcagctc ctgactgtta ggtctgcatt gtagtcctgt caaactttca ggtgtatgga   4800
agttgtcttg ttaacaggat ggttctggtc cagcaggatt tgggtggggt ctgggattct   4860
gcttttctag ctagcttcta gggattcccc atgtggtaag ttcatgggct agggttggag   4920
tatccaggtt agatcataga gacatcttgt tatcattttt cttttcctta aaaatcaggt   4980
ttataggggc cgggtctggt ggttcacgcc tataatccca gcactttggg aggctgaggc   5040
cggtggatca tgaggtcagg agttcgagac cagcctggcc aacatggtga aaccccgtct   5100
ctactaaaaa tacaaaaatt agccaggcgt ggtattgtgc gtctataatc ccagctactc   5160
gggaggctgg caggagaatc atttgaacct gggaggcaga ggttgcagtg agccgagatt   5220
gcaccactgt actttttttt gagactctgt ctcaaaaaaa aaatagattt attgatgtat   5280
aatttatttg tagcaaaatt caccctttttg acatactggt ctgcaagctt tgacaaatgg   5340
atgtagttgt ggccaccacc caaatcaaga tatgggacag tttcatcaac cctaaaatac   5400
ccccacagtg cccctcttga gtcagcaccc cacttctcca gccccttcaa ccactgatct   5460
gttctccatc cctacagctt tgccttttgc cgaaggtcat ataaatgtaa tttcacagta   5520
tatagccttt tgaatgtgga ttcttttact cagactttga gattcattca tgctgttgcc   5580
tgtgacagta gcgccttcct ttttggtgtt gagcaggatt ccatgatatg gatggaccag   5640
agtttgcttc ccagccgaag gacattggga tgcttccagt ttcaatgatt atgaatagag   5700
ctgctataaa cattggctta tgggttttag tgggaacatt tcatttcata catttcattt   5760
ctcttgggta aattaaccca ggagtgagat tgctgagttg tgtggtaggt gtatgtttaa   5820
ttttataaga ggctctcaaa ctgttttcct aagtggttgt accattttac attcccatct   5880
ttgcaatgcg tctaaaagcc ctgagttctg aattccaaag cacgtctggc ctcgatggct   5940
taggattaag gatgtggatc tatggaaagg agtggaagta atagtgttaa atcccggtca   6000
gagaaataag aaagattaag gatgtcattc aaagctatgt gcctgcacta gagagagaga   6060
aagaaggggt tctcttgggt ggggttccac ccctccctgg tagttctacc attccccagg   6120
aaaaagtcaa gctctgaggc tgtgagaccc atgatcttta ccctgttctt caccactgca   6180
accccagtgt gtgggacaaa gcaggcgtcc tataaacgtt tgctgagcaa atgagaaaag   6240
gtacctgtct tcacccatta actaaattgt ataacatcta tctgatctac ccttgtgcca   6300
acgttttagg attttgatgg gttttagttg caggggggttg agagactgtc catgagatta   6360
tcagaccaat gaaagtttct gaaatgttag tgcttgagta gattggatgc agcggcccct   6420
tgagaatgaa gtctttcttc agggacttgg agtgggaggc atctgttggg tgcgtagggc   6480
ttatgcttcc ccctccctgt ttcccccccca gtagcaagca cacatataca ctttctcagc   6540
aataaaaagc accgccggga aggtggactc catccagaaa tgatcagagc ctaagagccg   6600
tgcagtaacg catttccgag aatgccagct cagctcctga gaaaagggcc ggatgggatg   6660
gtgcctgctc tgaaagaggg cagagaggag agggaaaaca ctccggactc tgggtcagac   6720
tggcccaggt tcacattatt caccagccat gttatcttgg gcaccagagc ctatttcttg   6780
acatgcatga tgaggatatt ccttctagta gcatctccct tggagggctc tcaggagatt   6840
```

```
aaatggggtc gtgcgtgaaa aatggccagc acagtctcca gcacagagaa aaaccccaaa   6900
acgccagagc cgtaatacta tggagtcatt taggttccag tgttcttttt ttggaaaccg   6960
gccagaaaag aggctttctg ggtgggaatg ggagcgaagt gccccccccc accacccccct   7020
gcgactggtc agtgtggatt gattaacctg atcgtggcgc tctttaaagc cacctttgga   7080
cattttgcat tctccgttct ctctggaagc tttcagggga aaaaaaattc gtggccactt   7140
gacccatttt tctattccct tgagtctaag gtaaaaatta attctctttc ctcctttggt   7200
ccctccctct ctctgtgggt gacaaggtga gggagtttta aagtatataa ttagcttccc   7260
tcttcccctt ttgcactccc tgtctcttcc tttggggccg gtcgagagtg cagcccagga   7320
tggccacccc aggtgtccac tgcaaactcc acagaaaaac tttgctcaac ttttggttta   7380
gaatttaggt acccccctcc ccttccaaac tttggtcttc tttctcctca ctccctaaaa   7440
aaataggaaa aacaaggaac attcctggcg agggaaccat gagtgggcac agcaacttag   7500
gtttcaaaaa ccactgggcc tcagttctta tctgagtagg gtgacccttc agccagggtt   7560
gcctgggact atcctgggtt tagcatctct ggaaactcac agtcctgggc aaactgggac   7620
gctggtcacc ctaatggtga gttcttaaca cctgagagag aagaatggtg caagagatgg   7680
tgccgttgac caagaaaggg ggagagtcag ttacttattc cctctgaaaa gccaagactt   7740
tttattggaa tgaatgcagc ttttagaagc cgtctttaag gcagctaata caagagagat   7800
tccagctatg aagggaaatg cctgagttaa gtccggatca agttttgaca tctcgcttcg   7860
gtcagacacg gctttatctg ccgttcagac tgggagcagc cgtgagtctt ccttaaaggt   7920
gcctgttgct caggcggcac ctgcagttag aaattagcag cctcccaccc ccagccccca   7980
aataacagga ttcaagagtc ccctctctga agccatgagg gaaacccaac ttagtcaccc   8040
acttgccagt aaataatatt catgctgtta agttctgttc tcattttagg cctatgtgta   8100
aaaaatatat gtaattttaa actgattttt aaagtatttt catacgaaca gcatttgcag   8160
gagggcgaag tctggatgtt accttttttgt aaaagtggat ggatttgtct tcaatgagac   8220
tctggggcag acttaaaact tggcccgcag tggtgttaca tggattctga tcttccagag   8280
tctgtcacgt tcttttatct ccatgatctt tattatcttc tttattgaga atgatgggca   8340
tggtgtgtgt gggtgggagg gctatgctga ccatcactgc agtgaaatgt gttcgtggca   8400
tgttgtggcg tctgcatagg aatgtgtctg tttgattaac agcacaagca gtggaggctg   8460
taaggaggaa aagaggaggg aaggtgatat tggatggagg ggagacatat agagcttggg   8520
aacagtccac cctggctgca aatctcagct ccagctcaca gttgtggagc ctcagtcttc   8580
tcctctgtaa aacggggaca gtagtcctat gtccgaggaa ttgtaagaag gttaaaagat   8640
actgtaccca gaaagcacat ggcatatata atcatcctgt gaagtagcca actcaatgaa   8700
ttttatttta tttattttga gtcagagtct cactctgtca cccaggctgg agtgcagtgg   8760
catgatcatg gctcactata gcctcgacct cctaggctca agcgatcctc ctgccttagc   8820
ctcccgagaa gctgggacta taggcatgca ccaccgtacc cagctttaac aacataaatt   8880
tatatatata tatatatata tatatatata tatatatata tatatatata tatatatatt   8940
ttttttttt ttttttttt ttttttttt ttgagatgga gtttcattct tgttgcccag   9000
gctggagtgc aatggcgcga tctcggctca ctgcaacctc cgcctcccgg gttcaagcag   9060
gacgatgggc atttgggatg tttctagttt ggggtggggg attgtttgtt tgtttgctgt   9120
tatgaacaat gctgctgtaa ggaatcaata attttgaatg aatgaattcg aggtgttaat   9180
```

```
tttagtctgt gtacttggaa atctagcttc acctagaatc agctgagatt catcagcatt   9240
tatggcagga gctaagacat ttcacagctt actcatcatt ttctctaaga ggctgggtca   9300
accggttagc tcttggtcct gcttgtattc tgagagtcag aacctgtggt ttagacactg   9360
gcaattgata tggttgtaga gaagcagcat ggttgagttg agagcatgga ttctggagct   9420
aggtggctgg ggttcaaatc ccagctctac tagtcactgg ctgcgtgatc ttgggcaagt   9480
cacttaagtg ttctgtgctt cagtttccca gtctgtccca gtggtgattc taatagctcc   9540
atggggatcc taatagctcc tatctgggag gattaaatga gttaatacat ctgatgttta   9600
gagtggtgcc tgacacttag gaagcactat atgtgtttat acatggaaga gtggatagat   9660
ggatggactt atgtgggtgg ccatatttgg gcttctctga tccactgctg agaatagtgt   9720
gtggcacaca gtaggtgctg cataagtgtt aatattctgc tctttcttgc caagtctctc   9780
aactcccttg atctctgtta tttttggcgt ctgtgttgtt aacccattct tctgaatgat   9840
cagctgaatc actgttgctc caatatataa gccaaggaga acacaatcac aaggtctcat   9900
tgattgtcca tactagaatt ccatgattcc taggcccaag taggattttc cccacgtctc   9960
agcaatcctt cttccatgtt tctaatcttt ttctctcatt tgttatgccc cattgccaga  10020
ctctccaatc tccccacagc ttccccttcc tctaactata ctgtctctag tcttaccttc  10080
tccctaaggg caccgtcttt gaagacatca aatacttcag agcaccaaat ataggttagc  10140
ttctctgagg gccttacaag gacatggagt gtttgggtct tacacaaatt ggaatggtca  10200
gaaatgttta gagacttgag ttgtctttga aagagttgtc agaatgcaaa tttttgactt  10260
gtggcctgtt tctgatcaca acgcagtctt ttaagttatg gatcatagct ggatgtttgt  10320
ggtttagagg ggatggaggc atcctctgca gttagtgttg gatgtctggg tggatggatg  10380
gatggatgga tggatggatg gatggatgga tggatggttg aacagatgca tggatgagtg  10440
gatggatgga tggatgggat gaaggaagga aggaaggatg ggtgattgga gggtaggtgg  10500
gtggataagt agattggtag atgactcgat gggtgggtgg acaaatggat gggtgaatgg  10560
atgactggat ggatgactgg atggattggt gtatgagtga atatatggct ggatgaataa  10620
ataggcagat gactagactg gattgagggg taaaaaatatg gatgactgga tgggtggatg  10680
agtggatgat agatggttga atgggtgggt ggatgggtgg atgttggata taagggtgta  10740
tggtagggta gctgtctatg tgtgggtctc cctgatattt ggtgttctgt ttgacttggg  10800
aatgaccaag tctctccgct taccacctta tttgtacctt ttccagtatc aagtgaattt  10860
tgcacacttt tgtaaaaatc aataagattg tatgtttagg actttgggag gccgaggcag  10920
gcagatcaca aggtcaggag atagagacca tcctggctaa cagggtgaag ccccatctct  10980
actaaaaata caaaaaatta gccaggcgtg gtggcgggca cctgtagtcc cagctacctg  11040
ggaggctgag gcaggagaat ggcatgaacc cgggaggtgg agcttgcagt gagccaagat  11100
catgccactg cactccagct tgggcgacag aacgagactc catctcaaaa taaataaata  11160
aataaatatt atatgcttag gttttaccta tgtaattaga aagctccttg agggtagggg  11220
acagtgattt gccttcctca catcccccca aagttcctgc actatatcat gcataagtat  11280
ttaattgagt aatggtgagg aaagtaaaca gtgttattga acaaagatta ttaaaattct  11340
ggaaacacct ggttttgttt cagcactggg actgaaagtg gaattccttg gattttgctc  11400
cattggtgga taggatagca tgtggtggtg gactggtaga ctctttctct tccaagcaga  11460
ttgggtaaat gccccagatt cttacccact agtcagagat tacagattac tgattgatat  11520
ggtttttctc tgtgtcccca cccaaatctc atctcaaatt gtaataccca catgtcatgg  11580
```

```
gagggacctg gtgaaggtga ctggatcatg gggtgattt cccccatgct gttcttgtga  11640
tagtgagttc tcatgagatc tgatggtttt aaacttgtgt gggcctcttt cctctctctc  11700
ctctcctgct gccatgtaag acgtgccttg ctttcccttt gccttctgcc atgatttgta  11760
agtttcctga ggcgtcccca gccatgcaga actgtgagtc aattgaacct cttttcttta  11820
taaattactt ttatagcagt gtgaaaacgg actaacacac tgatgtagca aggtccttta  11880
aggccccatg tgatctggtc cctgttttgt ctttgatctc atctctttca ttgtctacct  11940
tcctttcatt gtctattctg tctcagccct gctgaccatt ttactcacac ccatgtcatt  12000
tgcattacat gacattcctt ctgttcagca taagctattt cctctgcctg catcactgtt  12060
tctccaggtc tccccatggc taactccttc tcttcattta ggtctcagcc caaaagttac  12120
ctcctccaag aggcctatcc ttttcattta ctgaacatct catgtacaaa aaagaatata  12180
aaatatatgt atactctctc atccacaaaa aaatctctga agacatttta atgtatttca  12240
tcccatacct ttttatgcat gtaaactttt aggaacacat ttccatgcca ctaggtatcc  12300
ttgaaaaaat aagggccacc atgtatagtt gcacaggttg tgcactgcac aaagatagca  12360
tgtcacatat cttaagtatc atggagcttg tatgtctact atttcagtac cccagctgat  12420
aaaagcttaa gtatcttgtt ctagcaagat gaagctatta tgacaatttt tgacagagaa  12480
aggggtgttt tgtttaagtt cacaatcaga gaaatgggtg tcttgtttaa tttcacaacc  12540
agagaaaggg gtgtcttgtt taaattcata cagtggtgct gtatgggttg gtggcaaccc  12600
cagaaaagac tgttgttaat atctgataat gttccacttt atacgtgtat tatattcatg  12660
taacaatctc tggctgtttg ttttgccatt ataaataaca gtgcagtaaa catctttgtg  12720
tgtgaatctc tgtccaaggt tctgatagtt ttctgaatga aattcctgtc tatatatggc  12780
actccaagcc cataattgaa actctgctgt taccactttc tttgaatctg tagaaggaat  12840
tttgagaaca ggtgactggt atattcagga tgttgatgac aaggaacaga gaaagaacag  12900
ttaaatggtt tggaattttt cctgggctgc atgtaaagca gtgcttttga actgggagca  12960
atttttcccc caaggggact tttggcaatg tctggagacg tttttggttg tcacgaatgt  13020
agggggaggg ggcaagatgc tactggcatc tggctggtag aaaccaggga tgcagttcag  13080
catcttaaaa tgcacaggac agcctttctc agtaaagaat tatccagctc caaatgtcag  13140
taataccaag gttgagaaat cttgatgtaa tcgatgtcat gggtttcttc aagaggagtg  13200
ggtggattta gggtttttgg gtgacttaaa tttaatttac agtttgtctt cctagctggg  13260
tgtctaagcc agctttctgt gaactttaga tcccacacaa gaagcaacag gcttgctacc  13320
gacagattcg ttgatgtaaa tatagatgag tgtatagaag gaaatctcac ccagagctgg  13380
aaaatgttgg aatgaaaact gcggcggcct ccccttctct ctccttcccc ttctgttgcc  13440
ctgtttgaaa atcgtgcctt actttctttg gtctcctggc atggtgaatg ctgctggtat  13500
ggactgtgtt tctatatccc cttgatcccc acacccttag gaacgtacag gagagagacc  13560
ctggagcata tcagcttaga gatggagggg aatgggaagg agtgcgttca ttcattcata  13620
aatgttgact gagcacctac tgtatgctag gtgaatggga ggacgtgagg gcagggaggt  13680
gacaaggttg gcttattctg ggctttgtga actatggtga ggattttgtt tttttccaaa  13740
ggaaatggaa taaccactcc ttttttcccc ccgatatacc taaacttttt gattttcata  13800
acaaaaatgg gcttcctttt gtatatttgt tttgagacca gccgtttttc caccaacact  13860
gatcacactg cagtgagcat cctggtagag aagtctttgc acacttctgt cactgtttcc  13920
```

```
ctaggacaga ttcctggaaa tggtatggca aggttgtatg tcaggctttt gggccaggtt  13980
gcaagaaaca ggaagtctgt gccctttcaa attccaaggt cccctttccc tgacgacgtg  14040
gcccaatcag gcttgccctc ccttgatttt acatcttcac caatcagata agtgaaagtg  14100
aaatcctgtt gtggtatcct gtgcatttct ttggtgactt aagacataga gcattttcca  14160
gatctctgtg ggctgtttgg atatcctttc ctctgttttc tcaggcacat tctttaccga  14220
tgtctttgag ggattgagca agtttctgtt gaaattgagg catgtcatgg ctctgtgtgg  14280
ggcttgaggc agtccagtgt agtggaggga gggaggctgt ggagcctggc tgcctaggtt  14340
caaataccaa ctctgcttat ttccattcat atcattttag gcaaatcact tagccccctg  14400
ggcctgcctt tcctcatcag taaaagtggt ataacattag tgcctgcatt gtggggtggt  14460
tgtgaggaaa gcagcactca aaacagtacc tgacacacag tgggtgccaa ataagagtct  14520
gatgtattag tgttataggt atcggcctcc tccctcccca gtgcaatagt gtgtgtgcgc  14580
ctctgtgtac ctctgttggt gctgacaagc ccttttttaaa atttagaggt gaggtctcac  14640
tctgtcccct aggctggagc acagtggtgc aatcatggct cactgcagcc tcaaccgcct  14700
gggctcaagc aatcctccca gcttagcctc ctgagtagtt gggactatcg gtgtgcacca  14760
ccacacctgg cccttagaca gcccctttat ttcaaagcga aatggcagcc acaagattta  14820
gtgcaagctc tccaagcttt aggaccagct gcaactcctc taactgacca aacaggatcc  14880
cccatgtccc caaccccaa aacctgatga aaagcaaaca gaccattttc cacattcatg  14940
acggaaaggc ccttttcttg gctcctgccc ttgctcatgt caggatttca ctccatccct  15000
gataaagagg aagcaccatg tcccaggagg acatggaaac tctctgcttt gtggtgaata  15060
gttacagtaa cagtagctcc tctctgtggg gagcttatga gcccctaagc tttatagaac  15120
tgccctggca gtttatgaga acttcatccc agcccccaga gctcatggca cttatttttg  15180
cccccagttt gcagatgtgc acactgagac tcagagagct aacactgctt gccaaggtca  15240
cacatctagc aaatggagaa actttatgag acaggtgaag gcacagcaag gataaaaacc  15300
cagagggaaa aatactcaag ttttctccgg gaaaccattt gcattccaga gaggttggtg  15360
tgcgagtggg caagagatgt cgcgggacga tggttaaggg acagagtctg agctcaacta  15420
ggactaggtt tcttcctttc cttccttcct tcctttcttc cttccttctt cctttccttt  15480
gtctttctct ccctcccttc cttcttcctt tccttccttt cctttctctt tccctccctc  15540
cctcccttcc ttcttccttc cttactcctt tccttccttc ctcctttcct tcctttcctt  15600
tctctttccc tccttccctc cctcccttct tccttccttt ctttccttcc ttccttttc  15660
ctttctcttt cctttctttc ctttccttcc ttcctctctt cttccttctt ttctttcttt  15720
cttttctctt tctttctttc tttctttctt tctttctttc tttctttcct ttctttctct  15780
ctctctctct ttctttcctt ctttctcctt ccttccttcc ttcttttctt ttcttttcct  15840
ttcttttctt ttgtttttttg agatggagtc tcgctctgtt gcccaggctg gagtgcaatg  15900
gcacaatctc agctcactgc aacctctgcc tcccggttca agcaattttc ctgccttggc  15960
ctcccaagtg gctgggacta caggcacgcg ccaccacacc cagctaattt ttgcattttt  16020
agtagagatg gagtttcacc atgttggcca agctggtctc gacctcttga cctcgtgatc  16080
ctcctgcctc agcctcccaa agtgctggca ttacaggcgt gagctaccac gcctgggcta  16140
ggactaggtt tctatcggtg gtgtggcttt tgggaagcta cctaatctta accactctgt  16200
ttcgtcatct ataagataag cagtgtagca ttttcttgca ggaatgttgc aaggattaag  16260
tggatggtga ctgtaaaaca tcatgcgtgg cacatagtaa attctcagca ggtagtcatt  16320
```

```
gctggtcatt tacttttctc taatgaccag caagctctta atttcctcct tggcatgggc  16380
actgggacgt agatggacaa aacacagaga gaaataaaca cacggacaaa aatccccgcc  16440
ctggtgtggc tgatattctg ggtggggaga gagagggagt ccaaggacca gataaacagg  16500
taaaggatag tttgagtgtg gtaagtacta aggctcaaaa ataaagatct cccaggtgat  16560
cttagctgca tttggaggtg acaggagata caactgagaa actgagatag gaggaaaccc  16620
aaggggagat gtgggcttga tttagggtga tctgaggagt aggagaagtc aggggctggt  16680
gtggggaggc tctgatggtt ctctctgggg agtgaagcag ggattcgttg gggagaccca  16740
aggggacagg tgaaggcccc tgaacaggtg gccagtgctg agaaaggaaa ggtggaggac  16800
ccaagtgagt tcctaatttc ttcattgctc ccctaaggtg tttgtctcac ccttggccat  16860
agtcttggat cacttacaga tgcagaccag gctgggctca atggcttgtg cctgtaatcc  16920
cagcactttg agaggctgaa cccaggagtt tgagagcagg ctgggcaaca tggtgaaacc  16980
ccgtctctac aaaaaaatac aaaaattggc cgagggtgtt ggcacatgcc tgtagtccca  17040
gctacttggg aggctgaggt aggaggatct cttgagcccg ggagacctat gctgccaaat  17100
aaggtaggca gtagccacac atggctattg caattttaga aattaattac aggccacatg  17160
tggtggctca cacctgtaat cccaacactt tgggaggccg aggcgggcag atcatgaggt  17220
caggagatcg agatcatcct ggccaacatg gtgaaacccc atctctacta aaaatacaaa  17280
aattagctgg gcatggtggt gcacacccgc agtcccagct actcgggaga ctgaggcagg  17340
agaattgctt gaacccagga ggcagaggct gcagtgagct gagattgcac cactgcactc  17400
cagcctgggc aacagagaga gactccgtct caaaaaaaaa aaaaaaaaaa aaaaaaagaa  17460
aagaaaagaa attaattaca ataaaaacag tccctgagtt tcactggcca catttgaagt  17520
gcccgatgac cctgtgtggc ttagtgacca ctgtgctgaa tagtgcagat ctagagcatc  17580
ctactggaca tgttgccagg gtccctgaac caacagaatt agcatctcct gggagcttgt  17640
tggaaatgca gaatctcatc ccctacccca gacctgctca atcccaatct gctcttcagt  17700
gagattcctc aggtgatctt gactgcacct tctaatcact tggaagcttt aaaaatgctg  17760
aggctgggca cggtggctca cgtgtgtaat cccagcactt taagaggcca aggcgggtgg  17820
atcacctgag gtcagaagtt tgagaccagc ctggccaaca tggtgaaact ccatctctac  17880
taaaaattac aaaaattacc caggtgtggt ggcacacacc tgtagtccca gctacttggg  17940
aggctgaggc aggagaactg cttgaacctg ggaggtggag gttgcagtaa gctgagatgg  18000
cactgctgca ctccagcctg ggtgacagag tgggactctg tctcaaaaaa aaaaaaaaaa  18060
aaaaaaaaaa gaaaagaaaa aggaaaatgc tgatgcccca agctccaccc ccacagatgc  18120
tggagagatt tgtccagggc ttcccctgga gtggggaatg tttgaaaact ccccaagggt  18180
ttctaaagtt cagccagagt tagcagaaag cccattaggt ggctaagcag gtagactgaa  18240
gttggagctg tgtgaccttg ggcaagccac ttaccctctc tgaaccacaa gctcccttct  18300
ctctaaaact agagacctgc tggcacctcc ctcccagggc tgtgagaagt aaatgatggg  18360
atgattcaaa gtgctgagta gggtcagatg cagtggctca cacctataat cctagcactt  18420
tgggacgctg aaatgggagg attgcttgaa gccaggagtt tgagaccagc ctgggcaaca  18480
tttaaacatt acccaggtgt agtggtgcat gcctgtagtc ctagctgctt gggaggccga  18540
ggtgggggga tcccttgagc ccaggagttc aaggctgcag tgaacaatga tggtgccact  18600
gcactccagc ctgggggaca agagtgagac cctatttcta aaaaagaaag aaacccaaaa  18660
```

```
tgctgagcga gtgccttgga ttgatagtaa gcagtgcctg tgtaataagc atgaatttta  18720
aaaaatgagg tcagcagcct tagagctaat ggttaatggg tttgggtgtg ggattttttt  18780
ttttttaatt tttaaaacat tgagataaaa ttcccataac ataaaattga ccattaacca  18840
ttttaaagtg tacagtttgg tggcatttaa tacactcagt gttgtgcaac catcacctct  18900
ctgtagttca aagaccccaa aaaggagacc ccgtactcac tgagcgctca ctccctgtct  18960
ctccccgctc ccccagcccc tggcaactac taatcttctg tctgtataga ttgacctatt  19020
ctgattttgg gggtttttga actcgccttc cctggctgac aacctctcgc catccaggtg  19080
agactgtgtg aaagcccagc tccctgcatt tctgggtctt cctctcccca ctgggggctg  19140
cccccacctg tttccccctc tgggcaccct ggttctactc atcagcctgg cttaatccca  19200
gcagcaggtc catgttctgc tctcctgtgg ctgccacaaa tgagaggttt catctcagct  19260
gggtttctcc tagttaaata tttaataaat aagacctaca acttgtgatg ctgggagtgt  19320
ttgatagtga aattaatgat ggggagagag tggcaggcgg cccacaggtc catgctggag  19380
ctgggatgag gcgccctggg caggcgtccg tgccactgat gcttgggaac cacggtgggc  19440
catgccatcc catttccccc agccagggcc tctttttag cactgtgtcc agcacagggt  19500
agccacctga taaataagtg ttaaaagaaa gagaggctgc gtgtgtaggg aagaaggaag  19560
agacagagga gacaaagagg agacacagag agagagagag agatgagaga gaaagaaaag  19620
tggaaggtga gaaagagaca gagatggaag gggagagaag gacctggatg gaggaagtgc  19680
aaggaaggca atggtgaggg aaaagagaga gagacaaaga tggaagggat gaaggagagg  19740
gagagatatg gaggtagaga aagagagaca gaaagaagag agagaatatt gcttcttgta  19800
tcttcccctt ctcctgttat ccttgaccat cttattattt ttttcttttt tctgtctctc  19860
cagttctcat ttccttaccc tcgccgtctt gccaactcgt catctctttt catttcctgt  19920
gtctatgtta tcttttaatt ttctgtctgg gtattttccc cttttctctt tctcagcata  19980
aactgttggt tggtgtatgt gtcttctttc ttttttagtc tttaactgac gtgtgtgtgt  20040
atgtgtgtgt gtgagagaga gagagacaga cagacagaga gagagagaga gagacagaac  20100
aaacctagag agcagtgtag gaacatagat gaacatttta aagaccaaac catgaagcgt  20160
acacccattt tacccaggtc aagagccaca gggccaccat cagattctcc ctcatgctca  20220
tcctcaatca cagccactcc ttccctcctg gaggaaccac tattggagat tgtatgggaa  20280
ccattcgctt gctttcttgt gtggttgtac cacctaagta cgcatcctga agcaatatag  20340
tcagatatta tgtggttttg agttttatat gaataaaatc atgtgagagg agttgttttg  20400
tattttgctt cattggtttg cagttacctt tgtgagattt catcctcatt gtggtcactg  20460
cagctccttc atgatcttgt ttattcattg atgatgagca tgtgactttg ttctcttttg  20520
ggcactggca taagcagctt tgttggttgt ttatggattc tgctgctcgc ttgcaggggt  20580
ctctctggag cacatcgctc tgtgtgaaat tgttggatac taagatttgt acattttcac  20640
cttgactaaa cactgccaaa caattttcca aagtgcttgt gctaatttac actcctgccg  20700
gtggtgggtg agcattcaag atgcttcaca accttgccaa cacttggtat tgtcaggttt  20760
ttaagttata gcctttctca tggtgatttc tcattgtgat tttagtttgc atccccccgat  20820
tgcaaattag agtgaacata gtttaaaata tttattgact attcaagctt gcttttttgt  20880
gaagtgcctc tacatgctct gtccattttt gattaggtca cttttaaaaa aaaaatattg  20940
atttgtgggt gatccttaca tagcctggaa actgattctt catcattata tgttgtgcaa  21000
tattttctct tggcttggct tttgatcttt tttataatgt cttttgatca ccaacagttc  21060
```

```
ttaattttga tgtggttgat tttagaaatc ttttccttta tagtttgtgg gctttgtatc  21120
ttatttaaga aaatcatttc taccctgagg ccatggatat attttatgtt atttctgaaa  21180
gttttacagt tgtgttcact gtatgtcttt aatcagcttg ggattgattt ttatatgtgg  21240
tggtaggtag ggtccaattt tcctttttat tccataagaa ttgtcccagc atcatttatt  21300
aaaaagccca ttcttgcccc aatgatctgc aagacaacct cttgactgtt taacttttac  21360
cttctttcat ctggtctgtt tttatactca acctttgaag ccacaaatat ttattgagtg  21420
ccaactgtgt gccaggcact gagttacagt gacggatatg acagatgcaa tcatggcttt  21480
catggagttt acagtctggc aaggatgaca tgtaaatagt tattactact tataatttaa  21540
aatgttatag gccttgcaaa aagggacaag tctggcttgc tctaaaagaa acatgtgaaa  21600
caacatcttc cagggaagtg ctgataaact gagtctttag tgggcctctg ctattgtagg  21660
ggtgggaatg gtggaaaaga tgttttggcc acagggaaca gcatgtgcaa aggtcctgtg  21720
gaaggtgctt aggagtttga tatttatcct aaaggcactg tcaggctact gaagcagtaa  21780
tacaatgatt ttatgtctgt gaatagttcc actggttgct gcatggagaa tgtattggaa  21840
tacagcaaga ataaaaagcc atgagaccaa ttaggaaatg atttcactca ttcagggaag  21900
tgtgccttgg gctggcatgg tggctgtgga gatggaaatc attgatcaga ttaaaagaaa  21960
ttttgagctg gcatgatttt tcccctctct cccctctctc tatctctgtt tcttttctgg  22020
ttgtgtttc tgggtgagaa aagcagtttg tgatcctgcc aagggtatgt gctctggagg  22080
atgtatttgc cacagatggt ctttggaatt ctggccaaga gagtcactgg acagcccctg  22140
gcccccaggg tttctggagc caattcaaca atgactgttt attaacaaca gcaaggatga  22200
gttgctagcc tttccttcag agcacctttt aactgttacc ttactttgtt acccaaaccg  22260
acactatgga attggtgggg gagaagtgga agggttttta tctccatttt ttatagaacg  22320
ggggaagtta attggcactc ttgaaatcat acaaaagatg ttggtttcag gattggtttc  22380
tggactttca gcccaatccc aattactcaa gctcacacac ccaatcccca aacatactct  22440
tttgcaaata atttccctac tgaggtgctc ctggccaatt taaaaggtcc ccatttcctt  22500
gcctataaaa tgggaattaa agtaaaaata tctacctgtt gacttgctgt gaggtcagtg  22560
ggcctgacac atggtgtgga ctcattatat ttacctatgt gaatccctta gttcccttta  22620
cttggaagag gtggaaaact caaaggggct taaacaagaa gtggggattg tattggctca  22680
tgagactgaa gagtctcagg agtgtccagc ttcaggcttg tttggatcta gggatcagat  22740
aacaccatta ggcctctgtt tctgtttctt ggctctactt tttgcagctg gctccattat  22800
ccatgactta gctgcacttc cagccctcca gtctgcccaa gaccatattc agagagagat  22860
tcttctctct ttttcagcta tcttcccgga attttcagca aatgctttct tgcttttgat  22920
tggctgttgc tgaggtcgtg tgctcatgcc agaaccaatc actgtgggga aatgggaggt  22980
ggagaacggg gtgctctgat tggcttaggc ttgggtcaca tgactttatg gagttggggt  23040
ggagccaact tctccaagtg gggaagagca gtcttcttaa aggtgtatta ggatatgctt  23100
gctgctgtaa caagcaaccc ccaagtctgc agtagcttaa ggcaatacga atgtacttct  23160
cactcaccct aaatccaatc agataatcag caagtggcat tccatgtggt gatttcagga  23220
cccggctctt tccatctgtg gctccaccat cccctaagat cagaaagtcc ttcacttccg  23280
gcctgtagga aaagagtatg aaggctcaca caggaagttt tgggaggcca catatagaag  23340
tagtgaacct tacttctgcc tgcattctgt ggactggaat ttcatcccat ggtgtatgag  23400
```

```
agagggtccc agtaggaaac ggaagacaca gaccaagaat caaattaaga gatagcttaa  23460
gaatcaaatt aagagatagc ttacaaaggt gtgggccctt actgaaatag agaaggagga  23520
agagaggaag gaggcagaga cagagagaga ctgagactca caaagacaca cacacacaca  23580
cacacacaca cacacacaca cacacacaca caagttgaga gaaagaaggg gggagagaaa  23640
gagagagagg gagcatttcc taacaggaag ctggcagaat aaatgtcccc cattgtccaa  23700
agccagaggg ctgggagccc agtgagccca tccacacagg tcagcccccc atgtgacagt  23760
cctagaaggg taaagaagga aggagagtgg atttggggta atggaagaca gccaataccc  23820
atggtccatc tgactgcagg gggaactgag aaattcagtc catggagaag aaggtttagt  23880
ggacacgtca ctttgtcttt ttcacaaagt gaaactaggt tctcaggtgg aaaaaagaaa  23940
aagaaggttt gccttgctgc tattcttttt tttttttga gacggagtct cactctgtca  24000
cccaagcggg agtgcagtgg cacgatctcg gctcactgga agctctgcct cctgggttca  24060
cgccattctc ctgcctcagc ctcccgagta gctgggacta caggcaccca ccaccacgcc  24120
cggctagttt ttttgtattt tagtagagac ggggtttcac tgctagccag gatggtctcg  24180
atctcctgac ctcgtgatcc gcccgcctca gcctcccaaa atgctgggat tacagacgtg  24240
agccaccgca cccggcctcc ttactgctat tcttattatt ggtggtagca gtggtggtga  24300
tggttattgg ttcttagttc cctctacatg ccagtatctg ctctcttctt tttttctccc  24360
ttacttcttt ccttgttctg caaattcttt ccctttaagt gaaaatcttt ccgtgttctc  24420
caagggagat aaattctatg ccaagcttga gtgtggggtc ctctgcttgg atagctgtct  24480
tctccaggag atgaggtaga actgagatag tgggggtctc tgcaggcagt ctgtgcccct  24540
ggcaagcccc tcaccttaac ctgaggctgg gtggggaaag atgccttgat ggagtcagaa  24600
cagaaagcaa gtgatcgctg cctgaaccaa gcagtcactt tcctggaggt gaaacctaga  24660
aacggtccct caggctgggt ccagggaggt ggacttgggt cccaggggca ggaagcaacc  24720
tgcccctcac ctgctcctac ctctttgtag cctatcttgg caaccagaag taggtataca  24780
agtgacgttg aagctgggca tgttaacaat ggtgtgagcc cgcctgactc caatctggtc  24840
cagctgtact ggccgtgcat cctcatctcc agcccccagg gtcagcccag cggctgtaac  24900
aatggtctgt cccctccccg ccccacccac ttctttgaac tcctccaagg atctgtgatg  24960
atagggctgt cactgtctta gcttccacca ttcaagctta accggccttc ttcccctcca  25020
tggagaacgg aagagcaacc cctcattgcc tctggcagct gaccagcagg tccctgcctt  25080
ctgcccactc ccaggtctag gacaatgagg tgagaggtag acaggaccaa gttccccagt  25140
gctgtcttct aggtccacct atcatgagag ccgtgattcc tagtttttat caccctctcc  25200
ccaactttgc cagctctcca cttctggcag tggtggctgc ccatgacttc accttcccgt  25260
gcctcagttt cctcatctgt aaaataagga cagccatggt aatgagagtt ctggtcaata  25320
tgccaggcac ctcgcttgca tcaatttagc tcatcctttc agtgccctga ggggtgggta  25380
ctgttatcat cccgtgtaac aaaaagagaa aaccgaaaca gagagagaga ctcactatct  25440
gaggtcttgc acccctcaag caacaaaagt gggatttcag cctaggctat ctagattcgg  25500
agtccacggt ctcaatgaat aataacaaca ataataatat tgtcctaatc tgatgagttt  25560
ttgatcagat tcaatacaag agcataggca gaaaagctta gcccagtgcc cagcacatgg  25620
taagaactca gcatgttatt tataatagta ataaaccatt ttatgttatg taattatata  25680
ttcatagata aatatagttg actcttgaac aacatagggg ttggggcaat gacctcctgt  25740
gcagtcaaaa atgtgtgtgt aacttttttt ctctattttt tagaaatttt aaaattagag  25800
```

```
acaaggtctc gcttttgttg ctcaggttga tctcgaactc ctgggctcaa gtgatcctcc  25860
tgcctcagcc tctcaaagtg ctaggattac aggtgtgagc cccgcaccc agcctgtgta  25920
taacttctga ctcccccaaa gcttaactac taacagtcta ttcttgacca gaagccttac  25980
cagtaacata aacagtcgat gaagacagat tttatatgtt atatgcatta tatactgtat  26040
tcttacaata aagtaagcta gggaggagaa agtattattt taagaaaatc ataaggaaga  26100
gaaaatatat ttactattca ttaattggaa agggatcatt ataaaggtct tcatcctcat  26160
tgtcttcaca ttaagtaggc tgaagaagag gaggagttgg tcttgttgtc tcaggggtgg  26220
cagaggtgga ggtggaaggg gaggccagaa agacaagcac gcttggtgta actgttattg  26280
gaaacaaatc tacataagtg gacccataaa attcaaacct gagttgttca ggggtcaact  26340
atatatgcta caaatacgta atatgctaat atagttgtat gttattgtta tagtacgggg  26400
atcagaaaat gttttctgca aaggattagc tagaaaatgt ctagtaaata ctgtctcttt  26460
gggaccactc tactctgcca ttatagcaaa ggcagctaca ggcaatacgt aaatgaatgg  26520
gcatggccat ttgccaataa aactttgttt acacaaacaa gccatgggcc agagtttgtc  26580
aacggctggt atagtatatg ttattatata ttagctttac tttttctgtt gctttgttta  26640
tgttcttctt tgcccttcct ttcttaaagg ccagcctttc tttctctctg ttggtctgtc  26700
ttttaggaca gcatggcagg ccactgggac atgggctctc ctgactccag gcttgtttgt  26760
ctgataagac atgaagagtg aaggtggcag gactctgagc tcaggcctgt cctcctcctc  26820
ttccctctct tcgtttttttc tttcctcttt cctcttttct tcccaagctc cagaagttgc  26880
cattttcctt tcccattgct gattttctct gccttgggag aaagcccgag aagatcactt  26940
ggaaaagccc acgagcatct ctggcctcac tcacccagct cctgccattg tctttactct  27000
tcctcagaca caccaggcac agtcctacct cagggccttt gcactggctg tttcctctgt  27060
ctgcattgtt cttctctcag gtgacctcat ggcttctccc tcctctcctt caggacttca  27120
ctcaaaggcc accttctcag catttgcctc ccgcccttct gccttatttt cccctttgga  27180
acttttcacc ttcttactta ctcatctgtc tgctatctgt caccctacat cactatgatc  27240
tccacaaggg aaggtgattt tattcgtttt ttgttctgtt ttgttgaaga tgaggttttg  27300
ctcttgttac ccaggctgga gtgtggtggc acgatctggg ctcactgcaa cctccacctc  27360
ccggattcaa gtgagtctcc tgcctcagcc tcctgagtag ctgggattac aggcacccac  27420
caccatgcct ggctaatttt tgtattttta gtacagatgg ggtttcacca tgttggccag  27480
gctgatctca aactcctgac ctcaggtgat ccacccacct cagccttcca aagtgctggg  27540
attactgtga gccaccacac ctgatctttt ggttttaccc accaatgtgg actagaacag  27600
cctagatcag caggtggcat gcagtaagca gttgataaat atgtgttgga tgagtgagca  27660
ctgtggcttc tgtcattctg ttgctcaata gcattcatct ggaaataacc acagtttgtt  27720
tatccattta cctgttgatt ggcatttctg ttgattctcg tttgggccat tatgaacaaa  27780
gctgctgtga aatacttata cctttgccca attcttcact tggtgaaccc ttataaatcc  27840
tttaggccag gtgtggtagc tcacgcttgt aaccccagca ctttgggaag ccgaggtagg  27900
aggatcgctg gaggccagga gttcaaaacc agcctgggta acatagcaag acccgtctct  27960
acaaaaaaat aaaaaattgg ctggacgtgg caatgcatgc ctgtagttcc agctacttag  28020
gaggctgagg tgggaagagt gcctgagccc aggagttcaa gaccgcagtg agtgatcgcg  28080
tcctgcactc caggctgggc gatagagtga gaccctgtct gtaaaaatga cagcaacaac  28140
```

```
aacaataata aaacctttag gtttcctctt aaaaggaaca tccttagagc ttttcctgac  28200
ccagcaactc accccaagtc tgaattagac ttcaccccat ttctttcata acatttatca  28260
caatgacatg tttattttgt gggggcgggt ggcattctgg ccagaactgt cgacttccag  28320
agtgaaaata cggaagaacc aaataaaaca caacacacac atttgcacag cagctcgagg  28380
gaggtgctta gttctttgag tttccaagaa cagagagacg aagatttgtc tggggaggaa  28440
aaatcaggga ctgcttcttg gaggaggtgg actgttgctg ccccatccac ccacacattt  28500
gcagatgtgg tgatgagaag atgactgtca cgaggtctct gagcccaggg ggcccatggt  28560
tgagtgcaaa gatagtgggg ttgacaaata atcgtcgtat aacaaaagaa aagccaccac  28620
agttgcataa tggaaaggcg gcttctatag aacattcaga tcatagttga aggcatgtca  28680
cactgtgtta ctcagaggcc actgtcagag ccaaaagtga gagtggatga gagtttgggc  28740
aggaaacaac tgaaccagat acagcatcac ctccatgagg gctcagcttt atctattttg  28800
tcttctgttg catccccagc ccttagaaca ctgcctggtc catctttgct gtgtgaataa  28860
taataaggaa cgatcgctgt gttgagtttg ggctgtgaat tcagacagtt tgctgctgca  28920
tacctgatta tgagtctcag ttttcctcct ccataaaatg ggcaaaacag tccttgcctc  28980
atggggctgt gcatttgttt agcaaacact gaaggagtat acatggtggc caaggcactc  29040
ttcaagacac aggaagcaga caaaagtccc tgccctctgg gagcttacat gctcatgggg  29100
agagatgtat gataagaaac aaaaatagta ggtaagttgc atagtacttt agaagattat  29160
aagggtaatg ggaagagaac agcagagaaa gggctgggga ggcagttgct gtattagata  29220
gagctttatc gaggcgatgg cattggagcc aagacttgag gaagctgtga ggatgtctag  29280
agaaagaagg aacagctggt gcaaaggccc tgaggtaggg gtatatgtga catgtgtgac  29340
agtgaggagg cagatgtggc tgaagccagt gagcaagaga gagggaaggt gcaaggataa  29400
ggacagagag gtgacgggac aggttttgga gggccttatg ggctgcgggg aggactttgg  29460
cttttgctct gagggagctg ggagccacgg agggcttttg agcagaggag ggacgtgacc  29520
tgactcagat attcataggc tcctctggct gctgtgaaaa gaacagactt tgaaggttgg  29580
gggcaggcag ggcagaagct ggggaattag gaaggaggtg acagtgttgg tcctggcagg  29640
taatagtggg ggtggaacca ggttgttgtc tgtggagata ataatgagtg gctggattct  29700
ggttataatt tttaagtttt tttattgtga taaaatgaat ttttttattg tgataaaatg  29760
aaatttacca ctttgaggtg tgcaattcca cagcacttac tacagtcacc ctgttatgca  29820
acagtcacct ctatttaatc tcagaacatt tcatcccccc taaaggaaac cctgcaccca  29880
ttagtagtta cttccagttt ctcccttccc ccagcttctg gaaactacta attctggata  29940
taagttgaaa gttgaccagt aggatttcta ggcagacagg tggtgagggc tcaatgcatt  30000
catgcacaga aagtactcag gtggcatatc ataggtgctc aaaactgaaa tggtgatgat  30060
gagttggcaa tgatggtgag tccttccaga atccctgctc tagtgctaaa ctgacctacc  30120
tggctgtgta gaattctcac ctgctggccg ggagggtggc agaaccagga tcccttctta  30180
cttccagtct ggcttgggtt agggataggg gaggaatgat cagaagaacc aagctagcac  30240
catctgttct ggaacatcat ccaactcttg tccagatttc ccagaactga gcaggaaaat  30300
gtccagggag gaacagtgca gctgatggaa gtcctggtaa gccctggccc cagcttcctg  30360
agctgctgtt gcaccaacta gcatttgttg gaccttcagt ctgagccaag atggcagctt  30420
cagaggaaga acaagaagtg tacaagtttc tttcatggtt gtgtccccgc ctccttatat  30480
agcctcatat aaacccctgc actatcccgt tactgtttgc ctctccctga aaagagtgta  30540
```

```
aaactccccc actttttccc tacttttcac aatgtgtttt ggtttctaaa gatgaaactc  30600
ctttaattat gttctggttg taattttctg gctcctttta tttctccctt acttgatgta  30660
ttattttccc ttgttccttc tgccccctgc ctccattgat gtttctcttc actgctatct  30720
agatttaatt ctcaactcct gccaagttca gggtgatagt gcaaaaagac atggaccatt  30780
tagtcttgaa ttcaggtccc acttctgaca ccttcaaagc tgctttactt tgggcaagtc  30840
atatgatctt cctgaggggg tatcctttac cttgttcagc taacatttct tgtttttctc  30900
tgggcacaga gtagagtgtc attttcccca cctccctgaa gttaggtatg gctgtgtgat  30960
ttggtttcat caatgaaatg tgaggggaag tgacgtgagt ccttccggac agaagcctta  31020
agggtgagca tgggattcac catgtttcct ttttcctgcc tccactgtca tggatgcaca  31080
aagatggacc ctctctcaaa gtaagtgctg gagagaggat gacatagatc agtccccatc  31140
ccacttcata gcatgagtag aaaaatagac ctggggtgtg ttcaaccact gagatctggg  31200
gattgtttgt tactgcagca ggacatagac taggctgact gtatacctca ttatctgcat  31260
tttggggctg atatctaatc acagtgtctc caggaagatt atgttgatgt atgttttagg  31320
gatggatatt catattttcc tataagggct caataggttt ggaaatgtca catgcatgta  31380
aacttctgat taacaaatat ttcttgcttt ccaatttctt cctatagtgc ttctaatttt  31440
cctgtttttc aatcttgaat aaaatgtgag aagtgtttga cttctccttc gaggagatta  31500
atggtttcta aagcctgggg cattgattta gtcattctca acctccttgt ttctatgacc  31560
tttttttctc cttctctggt cacttagtgt ctgctaaggg gtgaaggaat gtctgtttta  31620
actcattgca tttttttttt ttttgagacg gagtctccct ctgttgccca ggctggagtg  31680
cagtggtgtg atgttggctc actgcaacct ctgcctcctg ggttcaagtg attctcctgc  31740
ctcagcatcc caagtagctg ggactacagg tgtctgccac cactcccggc taatttttgt  31800
atttttagta gagacggggt ttcaccatat tggccaggct ggtctcgaac tcctgacctt  31860
gtgatccgcc cgccttggcc tcccaaagtg ctgggattac aggcgtaagc caccacacct  31920
ggcaaactct ttgcattttt aactcttgac atcttcatct tctttttccc acctcccctt  31980
tgcctgttcc tcccctgctc accccaccag ggagtttata atcaggttct agaacctgca  32040
atgtttttct gttgttgtct tccatcttcc ttgagtctta tgggaatcgg ccatagtcgc  32100
aaattaacaa atagctctga agcgcctcaa gcttggaggc atttcctttt gctcacctaa  32160
gcaagatcct ggagctgttg caaatatcct gccccctact gtaaatctgt cttcatggtt  32220
gtaagagatt cagtcggggt cagtgaagac ccgagcagga gatcttggcc gaggctcctt  32280
gatgttctgt ctgcgctggg tgttgtcata ttgattaagc tcctgggact gctgccagca  32340
gcctctagga ttaaatcaat agagtttgca aaagtaaaag cttcttttgg agacacagaa  32400
tatgtgggtt tattttttaa tgataaagct tcaaggagaa tcttcatgga tggcagaacc  32460
agtgatggaa aaggcgaggc agacccaaat atttggggaa gtgcagtggg gagcaagtga  32520
gggaggtttc attgggaggc cggggctttc cagaaaatct gtttaactgg agttgctaat  32580
gcaacagctc agagttagaa gtgaaggtgg aagatgcaag aaggactgcc gctgagatgt  32640
aaagagaaat gaaggagagg tggatccatt tgctcattca ataaacattt tgggaggcag  32700
gggggtgggg gggagcctgc catgtgcctg gaactgggat gtacatggtg gggacatgac  32760
agtgggcagg acagatgtgg ttcctcctgg ccctcctgga acttgtaaca ggaaaagaag  32820
gcataaaata aggaataggc aaatacagac ataattacta attgtggtaa gtgtttggga  32880
```

```
gaaaaccagc agggtcctgt gtttgtttcc tagggctgcc aggacaaatt gccatgaact  32940
atatggctta aaacaacata aatatattgt cacccagttc tgaaggctgg aagaccaaaa  33000
tcaaggcatc agcagtgctg agctcccttg gacggctcta gagaagaatg cttccttgat  33060
tcttccagtt tctggtagtt gttagcatac attggcttga ttggcttgtg gctgcatcac  33120
tgcagtctct gcctctgtct tcacatggcc ttctccttca tgtcagtgtc ttctcttcct  33180
cttctctctc tctctttttt tttttttgt cagggcctca ctctgtcacc ctgtacaaga  33240
gtacagcagt gcaattatag ctcactgcaa ctgctgcttc ccagcatcaa acaatcctcc  33300
cacctcagcc tcctgagcag ctgggactta caggcgtgca ccaccatact cagctaattt  33360
ttaaattttt gatagagatg ggatctcact atattgccca gactggtctt gaacttctgg  33420
gctcaagtga tcctccctcc tcagcctccc gaagtgctgg gattacaggt gtgagccact  33480
gcacctggcc tcttctgtct cttataagga tctttgtcga tggattttga gcccgtcaga  33540
taatccagga caatctcatc ttgagatctc taatttaatt atacttgcag aggccgtttt  33600
actaaataag gtcatggcca gaggctccag aggctaaagc atgggtatga ttgcaccact  33660
gcactttagg ctgggtgaca gagcaaggcc ccatctctga aaaataaaat aaaataagta  33720
acctactaca ggccctttgc gtagaggata attagaagta caggggtacc acgtaagtga  33780
agacctgaag gttgttaagc acagagcaga gtgtgaacag aatgagacag agggaggaag  33840
agaatcccag gcagagggaa cagcatgtgc aaaggccctg ggaaggaac aagttcatca  33900
tgttaaaaat gagccagtgt agctagagtc tgatgagcaa agggactcac aggtgggaag  33960
acacccaaga agttggcaga gacaggtcac acaagacctt ctaggtcaag ttccggaggt  34020
gaactttatt ctacatgcaa tgagaagtcc tcagagaagc ttaagtggga tgggacagaa  34080
ctgctttact ttaaatatat atacatatat acaaacatat aatattacat atataaagca  34140
tatatatgta tacatatata catatctatc tacctgtcta tatatttttt agctgggcat  34200
ggtggctcac acctgtgatc ctagcacttt gggaggctga ggtgggagga tcacttgagc  34260
ccaggagttc aagaccagcc tgggcaacat agggagaccc catcactaca aataaaaata  34320
aaaattaaaa attagctggg tgtgatagtg tgcacctgta gtcccagcta cccgggaggc  34380
tgaggtagga ggattgctgg agccccaaag gttgaggctc cagtaagccg tgattgtgcc  34440
cctgcactct agcttgagca acagagtgag atcctgtctc aataaaataa tttttgtatt  34500
gaggtgaaat tcatgcaaca taagttaacc attttaaaat gagcaattca gtggcattca  34560
gcgcattcac aatattgtac aacctccacc tctttctagt gctgaaatat tttcatcacc  34620
acccctccag aaaaccctgt atccatgagg cagttgctcc tcatcctccc ctcccggtat  34680
ccccccaacc cccaccactc ctggtaacta caaatttgtt ttctgtttct atggatttac  34740
ctatactggc tctttcatat aaatgaattc aggcactgtg tgacctttcg tgtctggctt  34800
ctttcactta gcataatgcc ctggcttctc tctggagaat gaaatggata gaccactttg  34860
gagtctactg agattataga tatttctgtg ggaagggaca gtggcttgac cttgggtggt  34920
gctgaagagg caatgctgag caggaggatt caaagtctaa tttcggaagt agaattggtg  34980
gggtctgatg atacatcagc tgtaggggga ggaagatgta ggaactggga aggtctctta  35040
gggtaacctt acctgattga gctccttact aggcagctgg tggtacaatt cataacaaag  35100
gttaatagag aaagagacat gggattaggg agggaatgga agagtttggg ccttggacac  35160
tgtagtggtt tgaatcctgt ccaccaaaaa ttcagatgca tttggaactt cagaacctga  35220
gacctcattt gaaagtagga tctttgcaga tgtcattgag tcagggattg agatgaggtc  35280
```

```
atcctggatt acagtggact cgagattcca tggtaagtgc ttttatatga gaaggtacag  35340
gggagaaagt catgtggcaa tagaagcaga gaatggagtg ctgcagccac aagccaaaag  35400
acatgtagag gcaccaaaag cgggaagagg caaggaagga tcctccccta gagcctttga  35460
agggaaaccc cctaatttca gaaccttgcc tccaggatga cgagagaata aatttctgtt  35520
gttttaagcc acccaatctg tggcaatttg tcatgactgc cctaggagac taatatagac  35580
actcctatga gatgctctaa gaagacacag agtggtatag ctattgctaa gaccacacac  35640
tgtagcaggg aggaaatcaa atggagaaat gccccaactc cccctcctct ctgatctctt  35700
gctggtgcct cccgttggcc aagccaaccc agaaggcaga agatgtggtg gagggcagcg  35760
ttgcagggct tggatgatgc agtcacagaa gtcagccctg cctctaccag gatgccaaac  35820
agggcaatga gtggatattt tagggagaaa gggcaacaag agaatggcaa aatacatcga  35880
aatgcatgca agctctagaa agaggataga gatagataaa gggtgattac ctaggattaa  35940
gccccaggga agaccaacat ttagagattg gatagaaaaa gaggagcaaa aagggaagat  36000
tgagaagtag agaccaggag gataggagga aaactagaac aacattaaga agggcatggt  36060
caagtaatct gggcacagaa aaatggccct gggatttggc agcctggggg tctttggtga  36120
tcctctttgg aagagttttg gttgagtgat gggggctaga aaccagcctg gggagggtag  36180
gagaagaatg tgcagtgagg aagtggcagg aacacgtgaa ggcaactctt catgaagggg  36240
agtagagaaa ttggttggtg gctgaaggaa aattttcagt caagggtgga ggttttaatg  36300
atggaagaat attgatttct gtaaattggg tcattcccat ccattatacc aatatgcacg  36360
ggtgtcttct ctgatatagg atgctgggat tctcaaatgc ccatttgagt ttagcatcat  36420
gaatttaatg tcaccagccc agatagttga tctcattcag gaatgctcca ctgcccaggt  36480
atggggaagg caactagttg agttcatgca gggatggatt ttttccagga gagaaacagg  36540
aggcaagaaa gtgcgatata atcaacctat gtaaggttga caaggcagga gagggtcctg  36600
agaaatggcg gggtcagtgg gttgcagggc tcgatgggat ggacgttggt ttgcatttaa  36660
gggagttagt gagctgggag gtggttaaag aggaggtggt tcagccgggc gcggtggccc  36720
acacctgtaa tcgcagcact ttggggagcc gaggcgggcg gatcacaagg tcaggcgatc  36780
gagaccatcc tggctaacac ggtgaaaccc tgtctctact aaaaatacaa aaaaaaaaaa  36840
aaaaattagc caggcgtggt ggcgggcgcc tgtagtccca gctactcagg agcctgaggc  36900
aggagaatgg cgtgaacccg ggaggcggag ctgctgtact ccagcctggg cgacagggcg  36960
agactccgtc tcaaaaaaaa aaaaaaaaaa aaaaaaaaaa gaggtggttc aagacaagga  37020
tgctggaaac aggtgttttg gaggtggctg gtgtagcttc tgagcatgca tagctggagt  37080
ggcttggagg agacattggt tattgatgaa gaggtaggga catcctccag tgatcaagga  37140
agcaggggac cagcatggac aatggtctct ccacagggaa attggaggtc atcaaatgtt  37200
aacaggttcc gtcggagtct tagctcccag cttctgtttt cctgtggatc tcaggatctt  37260
ggctgctggt gctacctctg actttggact tcccattgag cccagcagca ctgggaggga  37320
ccttcatggc attggctggt ttaaggaaga cttccttggc tttgctgact ttcttggggg  37380
ccttcttggc tacacctgct tttgagggag ccctcctcac ctcacctgac ttcttggggg  37440
caccttttcc accttatctg agttgggaag gtctttcttt gattctcttg ctttcttggg  37500
gcccttctca ctggtttttc tgggggccat gatggtggac atattccaga gctgagcttt  37560
ccttttgttc ttaggaacta atttgaggct gccagtggcc ccaccttggt cttagagttg  37620
```

```
atggtctgca gggaatttcc aggttaaagg ttttttattt gtttgtttaa ttttgagaca  37680
gagtcttgct ctgtcaccca ggttggagtg cagcggcacg atcttggctc actgcagcct  37740
ccgcctcctg ggttcaaaca gttttcctgc ctcagcctcc taagtagctg ggattacaag  37800
cacgcaccac catgcccagc taacttttgt atttttagtg gagacagggt ttcaccatgt  37860
tgaccaagct ggtctcaaac tcctgatctg aagtgatccg gccaccttgg cctcccaaag  37920
tgctgggatt acaggtgtga gccactgcgc ctgacctcca ggtttaagtt taaaccatga  37980
agtagatgga ctgtgtagag agagaccagg gaaatggagg attttactga ccactgaaca  38040
gggatgtcac tattgccaga gaggaaaagg attccccctt ggtagagtga acatataagg  38100
gaaagtggtt gaaaattgaa tcaggagaca gagacctcac accactcaga ggtccctaga  38160
gaactttact gacctagaaa aaaagataaa cagggagaag gtcttcagtt cttgtttgga  38220
atctgacact gaagcatcct cactcctcac tctcttcccg accccgagag tctgaaattg  38280
attaatactt tttgtttaaa acttggcttg ttgttttgtt ttttctttct gttttcatca  38340
agggatcttt attttacttt tgtgtatttg tgtgttttcc atgagtcatg ttaattcttc  38400
catgtttaaa ctttttggcc cagaggaatt tatacattta aattatggat ttaatttcag  38460
aaggtacata cacacacaca cacacacact cactcatctc actttttaaa aactgtaaaa  38520
tatagccctg taaatatcca gaaaatatct aatgtgggcc gggtatggtg gctcatgcct  38580
gtaatctcag cactttggga ggccgaggtg ggtggatcac ctgaggtcag gagttcgaga  38640
ctagcctggc caacgtggtg aaaccctatc ctcactaaaa ataaaaaaat tagctgggca  38700
tggtggcagg tgcctgtaat cccagctact cgggaggatg agacaggaga atcacttgaa  38760
cccaggaggc agaggctgca gtgagccgag atcaccccac tgcgccccag cctgggcgac  38820
agactgagac tctgtctcac aaaaaaaaaa aaagaaaaga aaaagtcagt gtgcatcccc  38880
tctgacatcc agcaacttca catcttggaa tttatgctgc aggaaaaatta tcacaagtgc  38940
acaaggatgt atggtgagat agttattatt atcattttaa aagatagggt ctcactgtgt  39000
cacccaggct ggagtgcagt gaagtgatca cagctcactg cagccttgac cttctgggct  39060
cgagtgatcc tcgtgcctca gcctccccag tagctgggat tacaggtgtg agccaccatg  39120
cctggcatcc cccttttttt aaaaaaaggt tttaattatg aaaagaatat gggcttgttg  39180
ttttgtgtgg ttttttaaaa gcttaaaaaa tgtgtagtgt gtcatttaga aggtgaaaag  39240
cccttacccc atcccacctc ccagagataa cctctgctag caatttcgtg tttgtctttc  39300
aaattttttc ccacacacat tctttgtact ggctgcttcc cctcctgggt tactcttctc  39360
ccagacagaa acagggctca ttcccttgcc tcctccagct tttattaaaa cattaacttc  39420
cctgtagctg gatgcagtgg ctcacgcctg taatcccagt gttttgggag gtggggaggc  39480
aggaggatag cttgagccca ggagtttgag actagcctgg gcaacatagc gagacccatc  39540
tctacaaata aataaataaa taaataaata aataaataaa taatggaaat ttaaaagaga  39600
gagggaagga ctcttgaaaa ccgtccatat catgcttctc taaatggttg agggctcaga  39660
ggaaaaaaaa tcagcaattt cacatcacgg aatttattct gcagaaaaat tctcacaagt  39720
gcacaaggat gcgtggtcag atgatgatga tgatgattat tattattatt attgaagaaa  39780
gtagcagcag cagcagcagt attttaaaag acagagtctc ggatgggcat ggtggctcac  39840
gcctgtaatc ccagcacttt gggaggttga ggtgggcaga tcacttgagg tcaggagttc  39900
gagaccagtc tggccaacat ggtgaaaccc caactctact aaaaatgcaa aaattagcca  39960
ggtatggtgg tgggtgcctg cagtcccagc taccagggag gctgaggcac gagaatagct  40020
```

```
tgaacccagg aaatggaggc tgcagtgagc caagatcgtg ccactgcact ccatgcactc  40080
cagcctgggt gctgacccag gttaggtgca agactccgtc ttaaaaaaaa agaaaaggaa  40140
aaaaaaaaaa aaaggacaga gcctcactgt gtcgcccagg gtaaagtgca atgagtaaag  40200
gcccatgatg ggaaccctga ggagagagtc aaggggaaag aaaaaaaaaa aagcaaaacc  40260
aaaatggaat ttaaaaaaaa tcaggtgcaa tttgcataac agaaaattaa ccattttaaa  40320
gtgaacggct ctgtggcatt tactgcactc caactgttat gtaactacca cctctgtcta  40380
gctccagaac attttcacca cccctaaagg agaccttgta cccattaagc agtctctctc  40440
cttctcccct ccccaccacc ttcctccagc ctctggcaac cacccatctg cattctgtct  40500
ctatggattt acctattcta ggtagtcaac aggatgagat atcccaaaag tccatccatg  40560
gatgaacaga taaaccaagt gtgatatgcc ttcctcagat attagtctgc cttaaaaagg  40620
aatgaaatac taatctttgc tacaacatag atgaacctca aaaatatgat gtggctggac  40680
acagtggctt acacctgtaa tcccagaact ttgggaggct gaggtgggcg gatcgcttga  40740
gcccaggtgt tcaagaccac cctgggtaac atagcaaaac tccatctcta caaaacaatt  40800
tacaaaaaac tagccaggtg tggtgacatg tgcctgtagt cccagctatt caggagactg  40860
aggcgagagg atcgattgag cccaggaggc cgaggctgca gtgagccatg atcataccac  40920
tgcactccag cctaggcaac agagtgagac cctatctcaa aaaacaaaac aaaacaaaac  40980
aaaaaagttg atgctgagtg aaagaagcca gacacaaaag gcaacatcgt gtttaattcc  41040
atttacatga aatgtccaat gaagattttt tttggcaaca tttattttga gtataatatt  41100
cagtgagtgg accacacata tgcatgcact gcagtatgtt cttggaaaca tttcagattt  41160
gagaggtctg ttcagctatg atgacggtag gtattgtccc ttccctccct ccttgaagaa  41220
aaggaactaa ggctggacgc ggtggctcat gcctgtaatc ccagtacttt gggaggctga  41280
ggtgggcaga tcacttgagg tcaggagttc aagactagcc tggccaacat ggtgaaacca  41340
tgtctctact aaaaaataca aaaaattagc caggtatggt gctgcacgcc tgtagtccca  41400
gctactcggg aggctgaggc aggagaattg ctcgcaccca ggaggtggag gctgcagtca  41460
accgagattg caccattgca ctccagcctg ggtggcagag caagactctg tctcaaaaag  41520
aaaagagaag agaagagaaa agaaaagaaa ccaaaagaaa aggaaagaaa agaaaaggaa  41580
ccaagaccta gaagggcaaa aataggaaaa gttggccggg cgcagtggct cacgcctgta  41640
atcccagcac tttgggaggc caaggtgggc agatcacaag gtcaggagat cgagaccacc  41700
ctggctaaca cggtgaaacc ccgtctctac taaaaatact aaaaattagc cgggcgcggt  41760
ggcaggcgcc tgtaatccca gctactcggg aggctgaggc aggagaatgg cgtgaacctg  41820
ggaggcggag cttgcagtga gccgagatag caccactgca gtctggcctg ggcgaaagag  41880
caagactcgg tctctaaaaa aaaaaaaaaa aaaaaaattg gaaaagttat ttactattag  41940
cagcaattgt cataaagtaa tgaacattta ttgcatgatt acaatgagat aaattgtatc  42000
ctgtttttat aagcatatta agttttcttt tttaaaaaaa tgtatgtatt tatttatttt  42060
aagagatagg gtcttgctct gttgcccaga ctggagtgcc atggtatgat catagctcaa  42120
tgcagcctca aattcccagg ttcaagcaat cttcttgcct cagtctctcg agtagctagg  42180
actacaggca tgtgccaaca tgcctggcta gttttcttat ttttaaatgt atttttgtag  42240
agacaggatc ttgctgtgtc gcccaggctg tcctcaaact cctggcctca agcgatcctc  42300
tgccttggcc tcccaaaggg ctgagatgat aggcatctac ctctgcattt ggcccacatt  42360
```

```
aaattttcta gtcatcatgg gaaccaaaat aaacaatata aaacactcac attccttgag  42420
cacttactat atgcagggcc ctgtaataga ttattgtgtg tatcagctca ttccattctc  42480
acacaaccta tgaggttgat gctattttct accttttata tatgaggaaa ctgaggctca  42540
gagaaggaaa ctgccttgcc caaggtcaag gccacgtctg atccccaaat cctttcaact  42600
cctctgcact actatttttt agtgcagata ttgccagttt tctaagcaga agcatgattt  42660
agcagccctg agtagacttc tcatttcaga accaaagtgt tggacattgt tggataaatat  42720
gaaaaacaaa tgacacacaa acctatttga tactgttttt aattttctct tcatttgatt  42780
ttcctgatga catgattaat ctttttgcc tctaccctgt atgtgaaatg taggtctttg  42840
cagatgtctc agagagtgtt aatagttgct gctggttttg ttttctctcc ccggggattc  42900
ccatccctgg gtgcaagtga aattaaactt gtgcctcttt gccgctggcc gtggtgctga  42960
aaacatcccg ggcagcgcta gggttgccct tgttagcatg ccatccctgc taagagtctt  43020
aggctgatca gcgagtggag agatcttttc caggcttcat tttggttaga actgtgtgtt  43080
gaagatttta aagcccatgt ctgggaactg gagactgttt ggattgtttg aagttgaaat  43140
agtcatgaat aattcctact tgagatgggc ttatgagggc gtggactagc atgcaatggt  43200
tggcctttac taaactgtgg ccattggttg ggacttgggt gaggtgtaac ccatttggtc  43260
taatccatat ggttagggcc ccaagtgcac ctgcattcta ttttttttt tttttaaata  43320
aaggcaaacc catctatctt ctaaccagga tagctcctga gtggtctttg gggaccacca  43380
gcttaaaagc atagactgtg ggctgggcac agtggctcat acctgtaatc ccagcacttt  43440
gaaaggccaa ggtgagagga tcgcttgagc ccaggagttc aagaccagcc taggcaacat  43500
ggtgagaccc tcatctctac aaaaatgtta aaagttagcc aggtgtgttg gcatgcacct  43560
atagtcccag ctactcagga ggctgaagtg ggtggatcgc ttgagcctgg gaggtcaagg  43620
ctacagtgag ctgtgatcgt gccactgtat ttcaccctgg gcaacagagc aagaccctaa  43680
ctcaaacaaa caaacaaaaa aaggcataga ctgtggagtt gggcagacct gggtgtgagc  43740
cccagctctg ccagtacctc ctatgtgacc ttgaaaattt gtttaatctc tctgagcctg  43800
gattttcttg tgtggaaaat gaggcttacc acagaaccca ccttgtagaa atgttgcaag  43860
gaattaactg aaacaaagtg cttaccacgg tatctgccca aagaagcagt tggaaacaag  43920
gcagctgtaa ttatggtcgc tgtgcttgtt aatggcccca taatagttga tcatattgca  43980
gagtgaaatt ggggtatgtg tttaatggac caaggaatat gtcttaaacc catatatcta  44040
gggttctggt accctctact ctttttcctg gtgattgtga tgagcatgga acttacatga  44100
aaatgaggtc tgtttggctt cttcacacaa gctcaatgac ctggctaact gctacaagta  44160
tctgtttcct tagaacccac ccatcagcag tccccatagt ggagacaagg tcacaaagag  44220
ttgacaaacc tgatttgatt tccgcaccaa ccacaggagg cttgaaatga gatgagggtg  44280
aagggcacca cagagggatg caaggattac ttggacactg caaggtcttg ctaagggatg  44340
ggaaccatca gccacgccca ctttgagaat tttccttcat gttctgaatc tgaagagcaa  44400
ggtcctgttc tcagatgcaa gccctccttc ttccctacgc agagtcaaac ttggtctttt  44460
ccagggtcac atacagcctc tctctggggc ctctgcaggt cctgatcaat ttcattgtgt  44520
atagagctct gtgtctcctc acctgcctgc agggctgtct gctatcctga cttccgagag  44580
ccatttcgga agccagcttt tcctcccatc agggatgctt ctcttctttc agccccccgcc  44640
ccgctttggc ctcctaggat ggctgatttt tctggatccc gctgacacag gtgctttctc  44700
tccgagccaa tcagggagca gaaaggctca gctcagctaa cagaggcatt gctcaccgca  44760
```

```
gctgtgagtt agaactcagg ctttctaaat cgggaggatc aggcatgact tgaggttggg  44820
ctgagaaagc ctcgcctgcc ccccagctcg actacccagt gaaacctttg gcttctgcct  44880
cgggcgaggc atctcttacc atgccaagaa ctcagcagcc catctttctt tcatctgggc  44940
accaagtaca tcattgcata tttcaggggg tttcattgtg tccttaacat gctcatggag  45000
acttggcttg agatgaagtc ggggtttcta ggcagcagga cccatgtccc cttccttcat  45060
ttcctccacc ggtgattttt gttttgtttt gttttgtttt gttttgtttt gttttgtttt  45120
tgagacggag tctcgttctg ttgtccaggc tggagtgcag tggcgttatc tcggctcact  45180
gcaaactctg cttcccgggt tcaggtgatt ctcctgcctc agcctcccaa gtagctgaga  45240
ttacaggcgt ctgccactat gcccagctaa tttttgtatt tttagtagag acggggtttc  45300
accatgttgg ccaggctggt ctcgaactcc tgacctctgg tgatccaccc gcctcggcct  45360
cccaaagtgc tgggattaca ggtgtgagcc accgcaccag gcccttccac tggtgttttt  45420
tgagcatcta ctatatagag aatgctctcc tgggcacaga ggatgaagca gtgaacaaag  45480
tagacaaaaa atccccacgt gcatagagtg tgcagtctcg tgggagagac agggaacaag  45540
ataaagaagg aaaaaaatag cagatgcttg actggggacg gggactaaag aaagaaaaaa  45600
ataagcaggc taagggggtt gatggatgtg acctttgagt aaaggcctaa aggaagtgag  45660
ggagggagtc atgtggatgt ctggggaaag actattccag gagaatgaac agcaggtaca  45720
aaggcccctg ggtacaaatg tgcctgggga gtttggggaa taaaagggag gccggcgttg  45780
ctgtagctga gtgactaagg gagagaatag aggagatgag gggagggagg taatgggagc  45840
aggtcatgca ccttgctggt gctggaagga ctttgttttt gcttttgagt gagatgggat  45900
ccatgggaag gctttgaata cttccacatg cattaggctg aaattttctt ttctgctttt  45960
gtcgcattcc aacattgctt ttatttcatc aaaatcttcg gtttcttctc aggctcttta  46020
cccaagtggg agcagaaggc tggtacccag ggctgttcag ttctccccct ggggtcagaa  46080
cgtggaggag aaagcttgga ggagaaacag gaacccccac ctctttctgg atgactcaaa  46140
accgcaatta cctgagctcc tcctcctatc cctgaaatag aggcacttag cacttcctaa  46200
acttcccggt gcacacaaat cccctggcga tctttttaaa tgcaggttct gactcagcag  46260
gtggatgcaa ggtctaaggc tgcattccta accggtgctg gttctgggac cacactttga  46320
gtagcaaggg tctgaggtca ttgttgcaga tgtccatctg gggcatgtct gtggacactt  46380
gcgggggtgc gggtgagcag agggaggggg gatgatgttg gaaaagcagt gtgagtatct  46440
gtgtttgata agaagtaaga aaatgaagca aggtgggaga gtagaacctc tttatttttg  46500
cctacgtgct aaggttttat tgccataccc agagagccct gggtctgaaa tccaggcaac  46560
actggccagt tgaaaccctg atattgcagc ccataaaagt gctgcatgct gcatggtgga  46620
cttctgggac tcttcctgga accttcagtg ccagagccgg tccaaaggaa gtcacatccc  46680
tgccattgag gggcaggaga ccagggaacc ggaggagtgg gatggcagaa gcgcgtgtaa  46740
ggaggctgag ttggcaggga gagaaagcga agtcagcttc aaatcatagc gagaggagac  46800
cagggaaggg cttggcgttg ctgctctgtg tacaaatatt gtctcttatt ttccaggctg  46860
cagggtgagg cagagtggag tatttgtgca acacagccca gctttgttct ctgggctcct  46920
aatgcctgtc agctcagagg cagaaagcca atcagagatg atcgtcggca aggccggctt  46980
ttgttggctc cccaaattgc cctgagtctc ggattttgct tttcagagtg tgctttcagc  47040
tggaggcaaa ggctgaagct ggtgacaaaa ggaagcctgg ttttcctggc tttccgagac  47100
```

ttttactgag ggggtttcta tttcagactc cgttttccca cctggaaagc aggttccact 47160
ctccctccgg cctggaaggg atggttttat ggtgcttcca aaatgccaaa cctaactcca 47220
gggcagaaga ggagactgaa accaattaat tttccaaagg ttagagctac gaggagggga 47280
gaggtttagc atggtcaagt tccccaagac atactaattg atctctctac agaatgcggg 47340
atttcagtgc ccccagggga cactcagcaa tgtttagaga ccacttgagg ttgtcatcac 47400
tggacaggag gggctgctac tggcatctag cacacacagg ccagggatac tgttgaacat 47460
gctgcagtgc ccagacagcc ccaccaagga gaatgatcca cccctaaacc tagtgctgag 47520
gttgggaaat cctgctccgg agtaaccaac accctatggc tttttcactc aagcagccgc 47580
ttctccagcg cttacacctc ctcagagatt gccagatcca tatgcagagc ctgttggcgt 47640
gggacacttc tgaggggtgt ggcagggaga cagcggacat tcccatttac cagctgatca 47700
gcaggttagg agctaatatg aaatgaacaa gatagaccct ccccacctgc cctgcagatc 47760
ctctggtggg acactaggga gggaggcctc ctaaacccaa atgacagttc ccaggatgca 47820
gggaggagtt tacctatgca aactggagag aatgcaaatg gggcatctag agatacttac 47880
tggacgaccc ctcccctgcc tcgggtcttg gaagaacaga ttctcagagg tctgccctga 47940
tcactgtaat ttttttttta ttgaggtaaa attaatataa cacaattaac cattttaaag 48000
tgacatttag ggctgggcac agtggctcat gcctgtaatc cccgcacttt gggaggctga 48060
ggaagaaagg tcgcccagga gttcaagacc accctgggca acaaagtaag actctgtctc 48120
ttacaaaaaa aaaattaggc acacatggtg ttgtgcacct gtagtcccag ctactcagga 48180
ggctgaggca ggaggatcgt ttgagcctag gaattcaagg ctgcggtgag ctatgatcat 48240
gccactgcac tccagcctgg gtgacagagc aaaattgtgt ttctttaaaa aaataaaagt 48300
aaaaataaat aagaaaagaa aggagagggg aggggagagg cgtttagtac actcacaatg 48360
ttgtgtaact gtcaccttca tctagttcta aaacattaag cagccactcc catttccctt 48420
gccattcccc aggaacaaca aatctgctgt ctgtctctgg atttgcctgt tcgggatatt 48480
tcatatacat ggaatcatac aatatggggt attttatgtc tgcttctttc gcttggcata 48540
atgttttcaa ggttcattcc tgttctatca tgtatcagta cttcattcct tttttttttt 48600
tttttttgaa acggagtttt gcttttgttg cccaggctgg agtgcaatgg cacaatcttg 48660
gctcactgca acctccgcct cccgggttca agcaatcctc ctgcctcagc ctcctgagta 48720
gctgggatta caggcatgcg ccaccacacc cagctaattt tgtacttttt ttagtagaga 48780
tggggtttct ccatgttggt catgctggtc ttgaactccc aacctcaggt gatctgcctg 48840
cctcggcctt ccaaagtgct gggattacag gcgtgagcca ctgcacccgg cctacttcat 48900
tcctttttat ggctgaatac tattccattc tatgagtaga ccacattttg tttatccatt 48960
cacccactgg tgaaatttag gttgtttcca tcttttggct gttgtgaata gtgctgctgt 49020
gaatatttgt gtatgagtgt tcgttggaat acctgtctta cgatcctttt gtgtttatac 49080
cttggagtgg agttactgtg tgtcacatgg taactctgtg attaactttt tgaggaacca 49140
aggaatggtt ttctatggca gttgcactgg tgtttttttg ttgttgttgt ttttgttgtt 49200
gttgttttga gacagggtct cactcccatt gcccaggctg gagtgcagtg gtgcagtcat 49260
ggttcactgc agcctcaacc tcctggggct caagcaatcc tctctcctca gcctcccaag 49320
tagctggcac tacaggcctg cgccactatg cccggctaat tttcatattt ttttgtagag 49380
atagagtctc agtttgttgc ctaggctggt ctcggactcc tgtgctcaag taatcctcct 49440
acctcggcct cccaaagtgc tgggattaca ggcatgagcc accgcatctg gccagctaca 49500

```
ccattttata ttcccaccag catgagggtt tcaatttctt cacatcttca ccaacacttg  49560
ttttctgttt gtttgtttgt ttttaatagc tatcctagtg gatgtgaagc agtatcccgt  49620
tggggtttga tttgcacttc cctgatcact aataccctca tgtacatatt ggccatttga  49680
ctgtcttctt tggagaaatg tctattccag cctcctgtcc atttttcaat tggattatct  49740
ttttgttgtt gtgttgtaaa tgttctctct ttattttttta tttttttgag acagagtctc  49800
gctctgtcgc ccaggctgga gtgcagtggc acgatcttgg ctcactgcaa gctccgcctc  49860
ccaggttcac gccattctcc tgcctcagcc tcccgagtag ctgggactac agatgcccgc  49920
taccacgccc ggctaatttt ttgtattttt ttagtagaga tagggtttca ccgtgttagc  49980
caggatggtc tcgatctcct gacctcatga tccacccgcc ttggcctccc aaagttctgg  50040
gattacaggc gtgagccacc acacctggcc gtaaatgttc tttatatagt actagaccct  50100
tatcagatac atgatttgca aatagcttct cctattctgt tacttgcctt ttaactttct  50160
tgataacgtc ctttgatgca caaaaggttt aaattttgat aaagcccagc atatctgttt  50220
tttcttctgt ggatcatgca ttaggtgtca aatctgatca taatgtttta tttatttatt  50280
tacttattta tttattattt tatttatttt tgagatggag tcttgctctg ttgcccaggc  50340
tagagtgcag tggcatgatc tcggctcact gcaacctcca cctcccaggt tcaagcgatt  50400
ctcctgcccc ggcctcccaa gtagctggga ctacaggtgt gtaccaccac gcctggctaa  50460
tttttgtatt tttagtagag acagggtttc accatgttgg ccaggctggt ctcaaagtcc  50520
tgaccgcaag tgatccaccc accgcagcct ctatctattt ttaatttatc tctttttttt  50580
tttttttttt tgagacaggg cctccttctg tcacccaggc tggagtgcag tggtatagtc  50640
attgtacact gcagcctcta cctcctcggc tcaagcaatt ctctcgcctc agcctcccaa  50700
gtacctggga ccacaggtgc ctgccatcat gctggccctg ccaccatatt tgaaattgca  50760
gccctgaccc cttccactgt ctatagtctt caccatctta ctacataaca tagcatatat  50820
gatgtactgt ataacatggt atatgcagtg tactgtatag catagtatac atgatgtagt  50880
catctcattt atttgcttct cctctgggaa gcaggaggaa gcttctcctc ttgtctgctt  50940
tgctctcaac tgtgtcccta gcccagaaca gagtctggca cacagcaggt actgaatgaa  51000
tatgtgttca gtgaatattg tgggtgagat agaaggtgaa tatccacatt tccctttaga  51060
agtcacctga tctgggtttg agatctgcag ggatctactc cagacaggag aacgaataat  51120
tccacctgtg ctgatgagtt ggaaggatct agagggcttg agatctttcc actggggtca  51180
gtgggggtgg gtgcacctcc aacacccttc ttttctttga acaagatttt tccttaattc  51240
cccaatactc cctttgaata tatgatttta gccaccatca tagcgaattg catcgtcctc  51300
gcactggagc agcatctgcc tgatgatgac aagaccccga tgtctgaacg gctggtgagt  51360
gatgtctttt ctcagggtct tctccttggc tttagcagga cattaatttt tgggggagtg  51420
gagcagggca cagaggaggc tctcagtcct ggagcccaga gccagatcat gggaagccta  51480
aatttccttt tcatttttttc ttgaaccaga gtctcgctct gtcacccagg ctggagtgca  51540
gtggttcagt catagctcac tgcagcctcc acctcctggg ctcaagccat cctcccactg  51600
cagcctcctg agtagcaggg actacaggtg ccaccatgcc cagttaattt tcttattttt  51660
atcttttttt gtagagatgg ggatctcact aggttgctta ggctggtctc aaactgccca  51720
ctttggcatc tgacataatt tcaggcagta tactcaaatg aacattgtta atgttaataa  51780
ttatgtcttg gccagacact gtagctcatg cctgtaatcc cagcagtttg ggaggccaag  51840
```

```
gcaggtagat cacttgaggt caagagttcg agaccatcct gaccaacatg gtgaaagccc  51900
gtctctacta aaaaaataca aaattagctg gatatggtgg tgcacacctg taatcccagc  51960
tacttgggag gctgaggcag gagaatcgct tgaacccggg aggcagaggt tgcagtaagc  52020
caagatcgca ccattgcact ccagtctggg caacaggagt gaaactccat cttggtgggg  52080
gggaggcgaa aaaaaagaaa caagaatatt acaaaggata cagatgaaga gatgcaaagg  52140
gtgagatata ggagaagggt gtggctggca gcttctaggt agcttcagga gggggactgg  52200
tcaccagaaa gaccaaggca tgattcgagg gttgcgactt tcagccccac cccccaacct  52260
ctgggagggc agaggggctg aaaatcaagt tgatcaccaa cggtcaatga tttaaatcca  52320
aacctctaat catgccttgg ttttcccggt gaccaacccc catcctgaag ctacctagaa  52380
gctgccagcc atcagtcaat ccttagcctg caaaaagaca tccctttgga gatcccaagg  52440
gttttaggag ctgtacacca ggaaacagtg tcaaagacca aacatacatt tcacaatgtc  52500
acagtcttct aaaaactata actagcctag caaacctatg atttctagat ctttgcattt  52560
tcacttaaaa taaagctaaa taaaaagcgt ccattgaaag actggtaagc aagtagaagt  52620
accagtggca agctaatgtg gaaaaaaaaa atcattcagg cagagtgaaa atgattgtag  52680
ctcgagaaac gttgctgtaa cagatgggaa aacattcaca ttggggctct gatggagaag  52740
agcttgtagc ttaatttcaa atatgataga ttagcagctg gaagccagaa ccagccggag  52800
gttctgcaga ggaactggag gtgaggatac tggccactta tcagccagta cagaagtcct  52860
attccaaacc tttaacaatc tacatgccag ctgagaacca tcctaagggg tcagatttag  52920
gagtgaggtc aatgcacaag ctctagcctc aaataccttg aacgctgcat gtgacaagta  52980
aattctctaa accaatgctt tccattagaa ctttctgcag tcacagaaat gatctccatc  53040
tgccctgtcc aataggattg tcacttgaaa tgtagccagt gtgactgcag aactgtgttt  53100
tttattttat tgcatttaaa ttaattttaa ttgaaatagc cacatgtggc ctgtgactgt  53160
cgtattgaat aagacaggtg caaacaaata attctgttta gctgagtgat atgtgaggtt  53220
ggcccaaaag gaatgaagga ggaaggtgcc ttctctaggc attggctttg ctcgcaaaag  53280
gctttggaca agagaactct gcaagaggca gtgaggggtg gtgagtgcag gagggtcagg  53340
ggaagtgaga gggtgatagg tactgatttc taggtgggct ggttccctga tcttgtcaac  53400
atctgcccag cccaagacgc tgaccttgcc ttctctccct tccaggatga cacagaacca  53460
tacttcattg gaatttttg tttcgaggct ggaattaaaa tcattgccct tgggtttgcc  53520
ttccacaaag gctcctactt gaggaatggc tggaatgtca tggactttgt ggtggtgcta  53580
acggggtaag tggcgcgtgc tatacgcttt ggatttaact agctgaagga ttacgaggct  53640
tttggttggt gtggtccggg ccaggctcag gaaggctgag cccttgtgtt ctccctcccc  53700
ttgttatgcg cctgcctcct ttctgccaac accccacctc catgtctcag ctgtatatta  53760
cagcagatgc tttctgttac aattaaaata atagctcatt attgttggct gcttccagag  53820
tgctttatgc ccattctcta atttaatcct tgcaacaacc cactgaatta ggaaatatta  53880
atattcccat ctgaccactg aggaatcaga aactcagagt gtaacttgct taaggccacc  53940
cagcaagtaa gtgatggaac tgggagatga acagaagatt atgcattcca gaactcaagg  54000
ttttaagtgt tgtacgtgca tgggtctctt gatttgcttg aggatatctt gcttttattt  54060
caacttggtg aatgtttttt gagaatgtct gggtgcaagg gattgtgatt atgacaaagg  54120
agaaaagcaa gctaaataag gtacagttac tgtcttcaag gagttttcag atccatatat  54180
gatgaactgt ggttgaaatg tgtatatgct ttcctctaag caccctgtat gaggtagcac  54240
```

```
ttgctggtat aacaaaagat ccaaagctag gaaatgactt aaacacggca gaagtttatt  54300
tgtcactcat agaaaattca aaattgagct gggtgtggtg gtgcatgcct gtaatctcag  54360
cactttggga ggctgaggtg ggaggatcac ttgagctcag gagttcaaga ccagcttggg  54420
caacacagtg agaccacccc cccatctgta aaacataaaa taaaataaaa attaaccagg  54480
catggtggta catgcctggg agaattgctt gagctcagga gttggagggc acagtgagct  54540
atgatcatcc aaccgtgctc cagcctgggc aacagagcaa gaccccatct cgaaaaaaaa  54600
aagtccaaaa taattgttcc tagttgacag gctcatctcc tccaatgact gacggaccct  54660
gacccttgcc atattgtggc tcttcattgt cagcccacat catccaataa ctccatgctt  54720
gtctgtatca aaccaggaag gagaagtgag catagaaggt gatacttgga aaggtttatg  54780
agtttggaag gggtgtgacc catacctgtt ccattcatat cctattggct agaactcggt  54840
cacatgacca cacatcactg caagggaagc tgggaagtat cagattgtgc ttagaagaaa  54900
agggaaatgg atttggagaa tgacctacta gtctgtcagg gaccttaaaa acttttatta  54960
gattccagta gggacattag tatctggtac caatggctgg ttcctcctct tcccactctc  55020
tactctcctc tcagctaagt ctgggctctt ctattctaag acccttcttc actggacacc  55080
tttttcatag taatcattta caggatcata gctttccatg ttttgttgct gctccaggtt  55140
ctgtctctct tggcggatgt gatgggttgc agcacccaca ctgtgctggc cgggctctca  55200
caatgcagat ttgtttcaga gcaatgttgc ctctcacaga aggagctgtg gcctattggg  55260
ctgtttctgt agaggccttc agatgtcagc agtctgttgt aaggactctg ggctagctct  55320
catgggcttg ggtgttcaca gagggatctt tgttggctgt gctcacagtt cggtggcttg  55380
ggaccttggt gggttccaag ggcatattat ggtactgggc acttttctct tagtctacta  55440
ggaaactcat ctagaaacag cctagtggct aacttttttta ttgtttaaaa aatgtaaagc  55500
tgggcagggt ggctcatgcc tgtatcccag cacattggga ggccaaggtg ggaggattgc  55560
ttgggcccag gagtttgaga cgagcctgag caacatagca agaccacatc tccacaaaat  55620
aaaaattaaa agtgtataaa gctgggtaca gtggcacatg cctgtaaccc caattactca  55680
ggaggctgga gagagaggat tgcttgagcc taactagttt gagaccagct tgggtaacct  55740
agcaagatcc catgcaaaac taagtagaga ataatagagc aaacacctgt gtatacattc  55800
atttattcaa tgactattta ttgaacactt ctgtgtgcca ggtcctgttc taggctctgg  55860
gacacagcag taaacaaaat agaaaaatcc cctgtcctca tggagctgag agtctactga  55920
tggagatgga cacaattgat gaatgaatct agtgtgtcag atggcggtga ggggtacaga  55980
ggaaaaataa agcaggggag ggatgggatg tgtggcaggc aggggtgagg ggtgctggaa  56040
gccagggaag acttcactgg gcatgtgaca tctgaatgaa aacctaaggg aggtgagtga  56100
gtgagccatg aggagagctg gaacagagtg tcaggcaaag ggaacagcca gtgcaaaggc  56160
tctgaggctg gactgtatct gacatgtttg atcaacagta agaagaccca catggctaga  56220
gaaggtgacc agaagaatgg ggagaattgg ggatagagaa gtaatggagt aacctgctat  56280
caaaacacaa cctttctctt tttttttttt tttttttttt tgacaagagt ctccctctgt  56340
cacccaggct ggagtgcagt ggtacaatct cagctcactg cagcctctgc ctcccagttt  56400
caagtgattc tcctgcctca gcctcccaag tagcttggat tacaggcgtg taccacaaca  56460
tctagctaat ttttgtattt ttagtagaga cgggtttacg ccatgttggc caggctggtc  56520
ttgaactcct gacctcaagt gatccacctg gcatggcctc ccaaagtgct gggattacag  56580
```

```
gcgtaagcca ctgtgcccag caaaacaaaa cctttctaac ctttctaatc cctgttttct  56640
ccctccctag acccattcct ttctctcccc catccagggg cactttcctg aattttatgt  56700
ttattatttg catttatgta ttcacacttt ggctgcctaa gtatataaga aatatatgct  56760
acctattttt acacttcaaa atattttta aatagcatca gagtgagaat agtttacact  56820
ttgactacat gcatagataa gaaatatgtg ggctgggaat ggtggctcac acctgtaatc  56880
ctagcaattt tggaggcaaa gatggaagga ttactttagg ccagaagttt gagaccagcc  56940
tggccaatgt agtgaaaccc tgtctctaca aaatgaaata aaatgtaata aaatattcag  57000
ctgggcatgg tggtgtgctc ctgtggtccc agctactcag gaggccaagg cgggaggatc  57060
acttaagccc ataaggtcga cgctgtagtg agctatgact gcactccagc ttgggcaaca  57120
gagcaagacc ctgtccctaa aaaatgtttt ttgttgttgt tgttgttttt tgttttttg  57180
tttttttaat aaaggccagg tgtgatggct cacacttgta agcctagcac tttgagaggc  57240
cagggcagga agactgcttg agtccaggag tttaagacca gcctgggcaa catggtgaaa  57300
ccccatctat aaaaaaaatg caaaaaatta gccaggcatg atgacgcacg cctgtagtcc  57360
cagctactca ggaggctgag gtgggaggat cacgtgagcc caggaggtcg aggctgcagt  57420
gatccgtgat tgcaccactg cactccaggc tgggcaacaa agtaagacct tgtctcaaaa  57480
aaataaaata aaataaaaaa taaaaaaaag aaaagagaaa gaaaaaaaga gatatgtggt  57540
actgttttc aaacttcaca tttctctaac ctgacttttg tgttcaacat gagataaatc  57600
tgattaataa aaatagtttc catgcatcca ttttcatgac tgcatagtat tctgtggtag  57660
gagtatgctg ccgtgtattt atctatttgg attgtttcca gctttgggct attttgaccc  57720
aaagtgtccc tgctttctcc caagtgagtt tctctagggc acgtacccag gagtggaact  57780
gctgagttgt atactgtgtg catcctcagc cccactaggt attgccaaat tgctctgcaa  57840
agtggttgtg ccaattcatg ctccctgggg gctggcttct gctggctgag gctggcttga  57900
ccttgctggc aggaaggagc cttaaaaatc cctgtgtggt tttttttgtt ttacttttat  57960
tttaagttta ggggtacaag tgcagatcta ttacatgggt aaacttgtgt cttgggggtt  58020
tgttgtacag gttatttcat cacccacgta ttaagcctag tacccattag ttatttttct  58080
tgatcatctt cctcctcccg ccctccaccc tccaaaaggc cccagtgcgt gttgttcacc  58140
tctgtatgtc catgtgttat catcatttag cccccactta gaacacgcag tatttggttt  58200
tctgtttctg cattagtttg ctaaggataa tggcctccag ctccgtccgt gttcctgcaa  58260
aggacatgat cttgttcttt ttcttggctg catagtattc catggtgtat atgtaccaca  58320
ttttctttat ccagtctatc attgatgggc ttttgcagcc ctgttttttt ttttttttca  58380
taataacacg gttatgggaa cacttaggga agctcatata ttattgagca gtgtgatggt  58440
taatattgag catcaacttg atcagcttga aggatgcaaa gtcttgttcc tgggtgtgtc  58500
tgtgagggtg ttgccaaagg agattaacat ttgagccggt gaactaggag aggcagactc  58560
acccccaatc tgtgtgggca ccatctaatc agctgccagt gtggccagaa taaaagcagg  58620
cagaagaagt tggaaagagt agacttgctg agtcttctgg ccttcatctt tgtcctgtgc  58680
tgaatgcttc ctgccctcta aaatcagatt ccaagttctt cagcttttgg actcatggac  58740
ttacaccaat ggttagccag gagctctcag gcctttggcc acagactgaa ggctgcactg  58800
tcagcttccc tacttttgag gtttgaggac tctgacggat ccaccactgg cttccttgct  58860
cttcatcctt cagatgggct atcgtgggac tttaccttgt gattgtgtga gtcaattctc  58920
cttataaact ccctttcata tatacatcta tcctgttagt tttgtccctc tgaagaacct  58980
```

```
tgactaatac agacacctag tgggtcccaa taagtgatca ttaaactgaa ggcagtcatt  59040
cagtaggtca gtttgtcact tgtgtttgta tctccctgct tacaacaagg tggcctttct  59100
tctagtttcc tgtcatctga tggaagagat tctagactca ttcctctaga ggagaaatac  59160
ttcatctaga acagataggt cctaagggtg agagctcatc gttgggatga atgaacccac  59220
tgaaatttta tgcaagaaga aaattgtgta tatgtatatt tttttttctg gtctgtagtt  59280
tttattagat tctcagggaa tcctgatcct atcatgaaga ccttctattc tagattgggt  59340
tcctttcaca tccccttctc ctttcttgtt gaattctcca tgcatttctt tcacttgctt  59400
ttcttgctct tatttctctg gtagtcagtt atcctttttg tctggtggtt ctatctcctt  59460
caaatgaggc acattgctca aattttatta ctccaaattc caaggtgctg tttagtgtcc  59520
tgttgggttg taagctagga acagggaggg gaaagtaaaa cattctgcat gagctgggtg  59580
cagcgggcaa gcacctggaa ttccagctac tggaagctga ggtgggagga ttccctgagc  59640
ccaagggttt aaggccagcc tggcaacaa agtgagattt tgtcttaaaa aaaaaaaaaa  59700
tcccagctgg gctctgtggc tcatacctgt aatcccagca ctttgggagg cagaggcggg  59760
cagatcgctt gaagtcagga gttccagacc agcctggcca acgtggtgaa accccatctg  59820
tactaaaaat acaaaaaaaa aaaaaaaaaa gcctggcatg gtggtgtggt gtgcactggt  59880
aatcccagtt atttgggagg ctgaggcagc agaatcactt gaatccagga ggcagaggtt  59940
gcagtgagct gagattgtgc cactgcactc catcctggat gacagagtga gactctgtct  60000
caaaaaaaaa aaaaaaaaga aagaaaaaac acgcgcgcac acacacacac atcatgcaga  60060
cctagccttc tgccaatgtc aatggtagag aaacacagta gacacttaat tctatgtttc  60120
agagaggagg ggactcaaat atattaattt gacattgaga cagtgatgac tttaatgagt  60180
actttctttc cttttttttt tttttttttt cgggacagag tgcagtggtg ggattttggc  60240
tcactgtagc ctccacctcc tgggttccag cagttctcct gcctcagcct cctgagtagc  60300
tgggactaca ggcatgcact gctgtgcctg gctaattttt gtatttttag tagagacggg  60360
gtttcacact atcagccaga ctggtctcga actccggacc tcaggtgatc tgcccacctc  60420
ggcctcccaa agtgctggga ttacaggcat gagccaccgt gcccggccta atgagtactt  60480
tctgattaac ctgttgccct ctcagattcc tgaagcaaac cacagcgtta aaacgtgatt  60540
cattttgtgt ggaccaccac ggtgtttacc ttcttcttgg gtgaagtttg gtggaaaaga  60600
tcttaccccg gacatctgtt tgttctttgt aactcagagc ctcagagaaa tcctaacttt  60660
ataatgttgt caaacccttg taaggcatgt ttttattgta tttgtgttct gatcatgaaa  60720
ctgaaaatgt gtaagaggaa gatttcagaa gcttggctgt atgtctgaga tgacagttct  60780
tttactgtca ttctcaaata tatataaata ttgaagagat caaataacac aaatcgtgca  60840
tgttaagaaa agagactgtg aacctcacca gagaggggtg agcacaattt tttttctttt  60900
ttattcacag ggttagcact gtccctttca cataataaat gctcagtaaa ataaatggtt  60960
gttaagccgg aaaagggtaa cacttctgat aatgagtgtc ctgggaaatt tactaagctg  61020
tttagaagat gggaccaaca cactgataga aatagtcaga tagtccagaa gtctatggca  61080
gatgccctga acatcagatg agatataaga cagagaagct ctgggtcttt gccagctctg  61140
acattttatg actctatgaa acggaaggtt cctttttaga agggtctata aactgtctca  61200
ggctttgggc cattttgttg aagatcagag gcaaggaaaa gacacaacta cacaggaacc  61260
atcagggaaa gatgttgttt tttggtcttg aagcatcatt gaattttttt tttttttttt  61320
```

```
gagacggagt ttttctcttg ttgcccaggc tagagtgcaa tggcatgatc tcggctcact  61380
gcaacctccg cctcccaggt tcaagtgatt ctcctgcctc agccttctga gtagctggga  61440
ttacaggcat gtaccaccaa gcccgggtaa tttttttgta tgtttagtag agacgaggtt  61500
tctccatgtt ggtcaggcta gtctccaagt cctgccctca ggtggtccgc ccacctctgt  61560
ctcccaaagt gctgagatta caagcgtgag ccaccgcacc gggccgcatc attggatttt  61620
aaggctccat ggattctggc aggtccagcc cttctgtttt actcacaaac aagtggtttg  61680
tccaaagtca cacagagatg gtggcaagag atctagaata agaaggtgtc ttcaagtcat  61740
ggagccagga accctggctt tttgggcaat ggaagtggta taaatgttta atatcacccc  61800
tcaggttctg ccactagagc ccagctctct cttccttcct cttgccccct gactagccta  61860
tggcctcttt ccagagaata agaaagggat cctcagagaa taatcccagt tcctcgcttt  61920
ttattatata gttgaggaaa ccaagtctca gaggggtcag tgtcttgacc atacacctct  61980
catgtcctct ctccttttg attaattgaa taaatacatg tagttgcttc ttacctcctt  62040
tctttcttca cccctgcccc atgcacctgc tcttagttgc cttcacatgt aaacagcatt  62100
ccaacaacaa caacaaaaca caaccagcat tctaactcat gagaccagca acagttccta  62160
taaataccag cagcatttta ttttaatgtc tctctgcagt agtttctccc ctccatggat  62220
cagtcatcct tggtaccaaa aggattcccc actgtgacac aaatgctttt tgtcattctc  62280
agtgagttat accattgaga gagcatcgat ctttttattg ttcaaagctt ttggttgtca  62340
tgatatttgc tggaccatgt ttcaccagga accacatcac ttcctagcag caggagctat  62400
tttcttccat cttctaacaa caccagcagt gacagtgata ataatgatgt tagctgccat  62460
ggtcgttatt cttatcattt attgagtact tactatgtgc cagggactac attaagagtt  62520
ttatgtgtat tatcacattg agcctcgcta gcctttgtac agatgaatct gaggctcaga  62580
gaggttaagc tgctcacaag ggagtcacac agctggtaag gggtggatca ggatctcagc  62640
ctctctgcta ggacacttct ctaaacctag aataatactg ggcctgtgtt aagttcagca  62700
aagagctgta ttcaacccag tgtccttagg aatgtaatgc ctgttattaa caacagtggc  62760
aacattgata agctgaaact tatgaggtgc ttacaatatg atatactata tattatatac  62820
atacataggc acccacctat aatctcagca ctttaggagg ccaagtcagg aggatcactt  62880
gagcccagga gttcgagacc agcctgagca gcatagcaag atcctgtctc tgtaaaaagt  62940
ttatttttc agttggccag gtatgttggt acatgcctat agtcccagct aatgaggagg  63000
ctgaggcagg aggattgctt gagcccagga atttgaggct gcagtgaact atgatcacac  63060
cactgcactc cagcctgggt gacagagcaa gactgtctct aaaaataaaa ataaaaataa  63120
aattatttca actctcaagg ttaaataaat actattatta ttcccattta cagatggagc  63180
aactgaggct caaagacatt aaatgcttac tgtcttagtc tgttttctgt tgcttatagc  63240
agaacacctg aaactgagta atttataaag aaaaagcaat ttatttctta cagttatgga  63300
gactggaaag tttaagatca aggctgcatg agctataatg cacacacact attgcactcc  63360
aggctgggtg acagggtgag accccgtgtc aataaataat aatataaaat aaataaaaca  63420
aatttcaaca tgagttttgg aaggtttgaa atattcaagc cagagcatct gtctcataag  63480
tggtggaccc aggatttgaa ctaaggcaga tctggatcta gaacccattt tcttgaatcc  63540
tacgctattt ctctaaggtc aagtttgcca aggaaaataa acttgagaat ttgaatagag  63600
ctctctgaca tgggaagtca gggtgatcct tccttcccct ccctgatctt gggttccact  63660
atggctgggg gaaaacagga gcagaagaga tttcaagaaa tgagagattg gcctagcgcc  63720
```

```
atggttaaga cctggacttc agagtcagag gaagctcctc cctctatgac agtgagaatg  63780
tgggttgaac tcactgaacc tcagttttct cacctggaaa aagggagtaa aactagtgcc  63840
tagctcctag ggtttgcatc acacacgaaa gttggtgaac tgaaggaaaa aaacttaaat  63900
tcttgtgggg gagcatgtga tagatgctac aaattctcca tgccttattt acctagctta  63960
cgtctaagtt cacctgcagc ttcctcttgg tacactccca tctctctaca tctctgttgg  64020
agggcagtct ctggcatcac agagtttgct gagccagatg cttaacaacc tcggtagcat  64080
ccctcaacca gtgagctagg gagtcagtgt ataaataccc tggcttcccc attgctcagt  64140
gggaaaacac tgaaatatgt tatacagcat catagaggtg cctcagtaaa attgaatcct  64200
agttgttcac ataaaaccca ttcactagtg taccctttac caatctctct cttcctcatt  64260
cctcacttgt aattccttgc attacctccc aaattaacca ttggacccta gtttttgcct  64320
tggggtctac tcggcgctaa ctcaaggagc ggaagttgga agcttagcgg gttacaggtt  64380
tcagcaccct ggacagctcc cagcacaccg tattgtgcta aaatgttctc ttccctccct  64440
ctgcctccag ctggggtgga gagggactga gtaaaggcca gatggccagg tgaccttgtt  64500
ccatactgag cttcttggcc attttccctg tggggctgga gaagaccttg ccatccatct  64560
ctccgcaggt ttgggggccg actgaggtct tgttttctcg aattgctatg acaaatgcca  64620
gcctgcctcc aaggggcatc tgtcccactg cctctacagt ttgcatgcct aatgactcct  64680
ctcctctcac cagggcaggg aggtggctgc ctggtgggcc gcttgaagcc gggagaccaa  64740
gatcatgcca ctggactcgc aacaaaccga gactcttttt tttttttttt tttcctcgag  64800
acagggtctt gctctgttgc ccaggctgga gtgcagtggc gcgatcttgg ctcactgcag  64860
cctccgcctc ccaggttcaa gcactcccac ctcagcctcc caagtagctg ggattacagg  64920
cgcacaccac catgcctggc taatttttgc atttttagta gagagggggt ttcaccatgt  64980
tggccaggct gatctcgaac ttctcccctc aggtgatcca ctcgccttgg cctctcaaag  65040
tgctgggatt gcagctgtga gccaccatgc ctggccaaca gaataggact ctgtctcaaa  65100
aaataatttt ttttaaacat tgctttgcaa cccagctgct tcttgtgcag gcatctctaa  65160
atgaggacag ccagtctaca tagacacgta aggaagcata gtggttaaga cctggtcttt  65220
ggggttagag tggattccca acctgactcc actgtttcca agctgtgtga ccttgggcaa  65280
gttactgtac ctccctgaat cttccatttc ttcatctgga aaatgagagt agtagcatcc  65340
cctgacttgg tggggcatgg tggctgatgc ttgtaatcca aacactttgg gaagccaagg  65400
tgggtgaatc gcttaaactt gggagttcaa ggccattctg ggcaacatgg tgaaactcca  65460
tctctacaaa aacaaaacaa agcaaaaatt atctgggtgt gatagtgtgt gcctgtaatt  65520
ccagctactc aggaggctga ggtgggagaa tcacttgagc ccaggaggtc aagtctgcag  65580
tgagccgtgc ttgcaccact gcagtccaac agagcgagac cttgtctcaa acaaacaaaa  65640
caaaacacaa aacaacaaca aaatactacc accttatgga gttgttttca aggttcaatg  65700
agttaatgtc tgacccatgc tgggctgggt ttatggatgt tacttgccca gggacagtct  65760
gaagaaagag aaagtgatat agtccattgg gcctcagctt cctcatctgt ggaatgggaa  65820
taataattgc acctacctca aaaggtaaaa gtcagtgaga tacatataag gcattcagaa  65880
caaaaactgg cacagaataa gtgctcaatt atattagcta ttgtaagact aataactatc  65940
attataatga tgataataat tattactact tccccaggcc cagttccata gaccagttag  66000
ttaactgtag ggaacgtttg ctattattag ttgggttccc aatatctgac ctccctttcc  66060
```

```
aatttaggga gaatcctccc ctttctataa agtactgctg gtctatggga tcccaccctc  66120
actaataagt tgaaggtgaa agggattcat tgtcacccca tcacctggta gtcagggcat  66180
gtgatttaaa caaccagggc caggcgcagt ggctcacgcc tgtaatccca gcactttggg  66240
acgccaaggc aggaggatag cttgagccaa gcccaggagt ttgagaccag actgggcaac  66300
atagtgagac ccctatctct taaaaatttt ttaattagct gggggtggta gcacaggctt  66360
gtagtccccg ctactcagga ggctgaggca ggaggattgc ttgagcccag gaggtcaagg  66420
ctgcagtgag ccgtgatagt gccactacac tccagcccag cctgggcaac agggcaagat  66480
cctgtctcaa aaaacaaact aataaaaaac tcaaccagtc acgttttcct acccaggaat  66540
ttgaaaatgg accaagtgat ccaaacatga tggtttggac tctttcatgg cctcctgcta  66600
caggagaagg tcaggctggc tacattgttc ctgctgattt cccaaatccc ctcttctggc  66660
cccctgttga ttatctgagt ttcctaaaaa tcccttttat gcctaagata gccggtcagt  66720
gtttggtttt gcaatcaaga acccagactg ggccaggcac ggtggcccac gcctgtaatc  66780
ccagcacttt gggaggccga ggcgggcaga tcatgagatc aggagatcga gaccatcctg  66840
gctaacgtgg tgaaaccccg tctctactaa aaatacaaaa caaaaaaaaa aaaattagcc  66900
aggcatgatg gcggtcacct gtagtcccag ctactgggga ggctgaggca ggagaatggc  66960
gtgaacccgg gaggcggagc ttgcagtgag ctgagatggc accactgcac tccagcctgg  67020
gcgacagaac gagactccgt caaaaaaaaa aaaagaaaaa agaagaaccc agaacccaga  67080
ctgatcctga gacaaagatt tgagggcaac gaatcacgag gtcaggaaat cgagaccatc  67140
ctggctaaca tggtgaaacc ccgtctttat taaaaataca acaaattagc tgagcgtggt  67200
ggtgggcgcc tgtagtccca gctactcggg aggctgagga aggagaatgg cgtgaacctg  67260
ggaggcggag cttgcaataa gccaagatcg caccactgca ctccagcctg ggtgacagag  67320
caagactcca tctcaaaaaa aaaaaaaaaa aatttgagga caagtggttt gtttggcaat  67380
accaggaaac aggggaacag gatagtcaga aaagaaagag aaagctgggc atggtggctc  67440
actcctgtaa tctcagcact ttgggaggcc aaggcaggtg gatcacctga ggtcaggagt  67500
ttgagaccag cctggccaac atggtgaaat cccgtctctg ctaaaaatat aaaaattagt  67560
cgggtgtggt ggcgtgcacc tataatcaaa ataaaataaa atcaggatat tttattttaa  67620
aactctgtct tagtgtaact catatttacc tcttctgtat gctcctttgc atcagttata  67680
tattgccata atacggctgt gtaacaaaca atccccaaga cccagtggct tataatgaca  67740
agcatttatt tagctcatga ttctgaaggg tggcagttta ggctgggccc agttgggtgc  67800
tttatctggt ctcagttgag ctcattcatg catctttggt cagctgcggg tcagctgggt  67860
ggctcttctg tttggctgtt agctggctgc agactggtcc aggatgacct cggctggaat  67920
gactgtgctc cactccctat ggtctttcac cctccagcag gctagcctga gctagttcac  67980
atggcagctt ttcatcctcc agcaggctag cctgagctag ttcacgtggc agcaatggga  68040
ttctaagaga aagaggaagt gttcagcctt cttaagggct agtcccagga atggcacaac  68100
atcgtgttgg ccactgttgt ccaaagcaag caatgaagct ggtccagatt caaggaatgg  68160
ggcaacagag cccatctggt atttacctgg ggccactggg gccccattcc tgttccctgg  68220
ggccttttgc cctgacttct gtgggccctc agagcatatt ttcagattcc tttccatccc  68280
tgaccctcag caatcaatgt agatgacgtg tcattactgt gtcacttgca cagagaaaag  68340
gaggaaaaaa tgtcagcaaa aactctgctg agagcagagg gcccatcata cagcaagctg  68400
gaaagaaaag tgggaatgat tacacagcct cctcagatgc ttccagcttt tatcaaatct  68460
```

cactgtgata tctgagttct gaaccctcac aggtggttgg cgtgcaaggg aagagatttc 68520
ttgtctgcca tgctgacatg cacagacacg caacctggct ccctctgtcc actggggctt 68580
tggattttgt ttgttgaaat gttacccact cctgatcaga gctggatgga aacctggctc 68640
tgattccatt ggctcagggg ctcaggtggg ggcagaggcc aggctggttg ggtgtctatg 68700
tggagacctt aactcttctc cctcccgccc caactctttt tgtttctttt tttttttttt 68760
tttttttttg agatggggtt tcactcttgt tgcccaggct ggagtgcagt ggcgtgatct 68820
tggctcactg caacttctgc ctcctgggtt caagcaattc tcccacctca gcctcctgag 68880
tagctgggat tacaggagca cgccaccata cctggctaat ttttgtattt ttagtagaga 68940
cagggtttcg ccatgttggc caggctggtc ttgaactcct gacctcaggt gatccaccct 69000
cctcagcctc ccaaaatgct gggattagag gcgtgagcca ccacacctgg cccttttctt 69060
ttcttagctg cctccacctc tcttcccttc tgcagtgtta ggtttatgga aaccgaggcc 69120
ggcgtagaga tcaacttcag agagcatgaa ctgagcatct gctgggtctt agatccttta 69180
catagcttat catcttcaaa ccttctcaca gttctgtgtg gctagagcca ggatttggac 69240
acagctctgc cccactgtag aaccaggctt ccttctgtcc actgtcaaat tttagaggga 69300
gaaaataggg aaagggacac cagccttctc cacgagcagc ttctgcccac tcaccccagg 69360
gactttgcac atgctgtgtg cctgtgtctg agatatgctc cctcctctgt atctgcttaa 69420
ttcttaccca gacatgatac ataaagtatt taacatccag gtggcaggga caccagctaa 69480
cctgaaaaga ggttcccctg ttgtgccaca tgtgtactca ttgtttgctg cattgtgggg 69540
gcagtccagg ggccttgaag aggggccaag gtgccaaagg ggcactctca ggcctcaagg 69600
aagtacatgt ttactgatat gatactgtct cttcctccag gaaggaagcc ttccctgatc 69660
tccccactgc atgcccacta tgataccagt ttaggtcccc tctttatggc catctgtggc 69720
atcagtgtga atcctcttaa tgttgtctat ttggttaatc atctgtctcc ttcctctggg 69780
gggtaaagac agaaccacag agcctcgtgt agaacttgag aatggggttc agtaaaaatc 69840
tgttgaatgc ataaatgggt gattgagtga atgaatgaat gagtgaatga atgagtgagt 69900
ggatgaatga atgagtgaat gaatgagtga gtgaatgaat gaatgagtga attaatgaat 69960
gaattcatag ctgataatac aggcttcatg gcttttgtta ggcttgccca gacattgcta 70020
ggggatggac agaaggaaga agagctatac ttaattccag tcctgttgtt ctgtagcagg 70080
aggagaaaaa cagggactgc ccagcctgct ctgggtggat tcaggagcag ctgaggttcc 70140
tctcttattt gcaaacaggg aattcaaaaa gccccaacct cagaatcaca ctcgcctcag 70200
cagctgtacc agccaagggg acaatgtggg aagccttggg caccaggaat gctgagtgct 70260
tcgaaaaagc gaaggctcag ggaacaatcc ctgatttttc attcccttgt cctttctgaa 70320
gaaacaggca aaggcaggcc aggcacggtg gctcacacct gtaatcccaa cactttagga 70380
ggccgaggct ggtgaatcac ttgaggtcag gagttcaaga ccagcgtagc caacatcatg 70440
aaatcccatc tctactaaaa atacaaaaat tagctgggtt tggtggtgca tccctgtaat 70500
ctcagctact cgggaggctg aggcatgaga atcacctgaa ctggggaggt ggaggttgca 70560
gtgagctgag tctgcgccac tgcactccag cctggatgac agagtgagac tccatcttaa 70620
aacaaaacaa aacaaaaaca agtaaagcct tgtgtgtttt taaattgtag gttcagcagc 70680
aaagctctgt aataaggagc tggaccctgc agtcagacag tcatgggctt ctccagtgcc 70740
cagccgagtg acccgaggga gttatgataa acaccaacat tcatccacaa tttgtaccta 70800

```
gtgctattct caatatcttg agtaaattat ctcatttaat cctccaggca catctttctt  70860
ggtaggtgcc gtcattgtcc ccagtgtaca tctgggaaaa tgaggacagg ctggcagagc  70920
acccttcctg ctcacctctg ctgctctgct gacctctggc aagactgttg tctctctgag  70980
cctcagtttc cccatctgaa aattggggcc tgtattagcc cgttctcaca ttgctataac  71040
gagatgcttg gctggggctg ggcgtgatgg cttatgcttg taatcccagc actttgggag  71100
gctgagttgg gcagattggg agtgtgagac cagcttgggc aatatagcaa gaccccatct  71160
cttctaaaaa aaaaaaaaaa ttagccaggc atggtgatat gcacctgtaa ttccagctac  71220
ccaggaggct gaggcaggag aattgcttga acccaggagg cagaggttgc agtgagccaa  71280
gattgcgcca ctgcactcca gcctgggaga cagagtgaga ctccatctca aaaaacaaat  71340
tatttttaaa aaattaaaaa aaaaaatgcc tggctgggca cagtggctca cacccataat  71400
cccagtactt tgggaggcca aggtgggaag attgcttgag cccaggagtt ccagaccagc  71460
ctgggcaaca cagtgaaatc ctgtctctac taaaagtaca aaaattagcc aggtgtggtg  71520
gcacgcgcct gtggtcccag ctactcagga gggtgaggtg ggaggattgc ttaagcctgg  71580
gaggtcaagg ctgcagtgag caatgattat gccactgcac tccagcctgg gcgacagagt  71640
gagaccttgt aaaaataata ataataataa taaataaata aaaaccctga gactggggta  71700
atttataaag aaaagaggtt taattgactc acgattctgc aggctctaca gaaagcatgg  71760
cagcatctgc tcagcttctg ggaaggcctc aggaaactta caatcatggc agaaggtaaa  71820
gctggagcag gtgtcctcac atggccagaa caggaggaag agagagagtg gggagatgct  71880
acacaccttt aaatgtccaa tctcacaaga actcactcac gatctcgaga atagcaccaa  71940
ggcggaaatc tgcccccatg atccaattac cttccaccag gccccacctc caacattggg  72000
gattacaatt cgccataaga tttggttgcg gacagacaca gatccaaagt acattaaaag  72060
taatggcaaa aaccacaatt acttttgcac caacctaata tctcaggggc tcattgtacc  72120
tatttcacag gacaaatgaa ggtatcagta ataacagtag cctgtagtcc cagctattca  72180
ggaggccgag acaggaggat cacttgaacc caggaggtcg aggctgcagt gagctatgat  72240
cacgccactg cactgcaccc tgggtgacag ggcgaaaact tatctctaaa aataataata  72300
acaacaacaa tagtgaacac agatataaca tgtgtgtggc caggctgtgc ccttagggct  72360
ttgcagggat tatttcattc actctcaatc tccccatttt acagatgaga aaactgacgt  72420
tcagaaaagc tagaggactt gccccaagcc acacggctag gaagtggtgg aattggggtt  72480
taaatgagga agcttgactt cagtgtcgaa gctcttaact gccacactca atacatggag  72540
tagaggttgc tgattctgtg attatctgat tctggaaagt aaagaccctg tttccagacg  72600
tttgctgctt gacttagttc ccaggggatg gccactggat gatgcagtgt tgcccaggag  72660
aggttagcta gacacactgc aaccattcca ttgctaatac ttatacttgc tcttgttctg  72720
ctgggtgcta tgcagggaag ggctgtctga gccctttgca agaattctcc cattggtgcc  72780
tcccagagat tctgaggttg gggctttttg catcccttat tagcagatga gacaccaaag  72840
cccaggtcaa taatctgacc tgcatccccc gcctaccagc cagaccaagg tcacttcccc  72900
acaatgcagg ccctgatcca aggctctggg tgcaaaccag tttccatgtc cctgggggtc  72960
catcttcttc agctgacttt tttttttttt tttttttttt gagacagcgt cttgctttgt  73020
tgccgaggct ggagtgcagt ggtgtgatca tggcttattg cagccttgac ctcccaggct  73080
caagcaatcc tcccacgtca gcctcctgag tagctaggac tatgggcaca cgccatgatg  73140
cctgggtaat tttttttttt ttttttttga gacagagtct cgcactgtag cccaggctgg  73200
```

```
agtgcagtgg cgcaatctcg gctcactgca agccccatct cccaggttca tgccattctc  73260
ctgcctcagc ctctcgagta gctgggatta caggtgcctg ctacctcgcc tggctaattt  73320
tttgtatttt tagtagagac ggggtttcac cgtgttagcc aggatggtct ccatctcctg  73380
acttcgtgat ccgcccacct cagcctccca aagcgctggg attacaggca tgagccagat  73440
gcctggctaa tttttaagtt tttttataaa ggcggggtct tgctatgttg cccaagctgg  73500
tctcaaactc ctggcctcaa aaagtcttcc tgcctcagcc tcccaaagtg ctaggattac  73560
agacatgagc cactgcaccc agcctgactt tttttctaac tgaaaaatta attatatata  73620
ttcatggagt acaatgggat gttctgatat atgtttacat ttttgaatga ttaaatcaag  73680
ccaattaaca tatccactac atcgcatact tattttttgt ggtgagaacg cttaaaatct  73740
actcttttag caattttgaa atatacaata ccttatgttg tatattacat tatgttgtat  73800
agtacgttga aacatacact acaatacgtt atcattaatt gtggtcacca tgctgtgcaa  73860
aagatctcta aaacgtattc ctcctgtctg actgaaactt tgtatccttt gcctaatatc  73920
tccccaatcc ctccaccacc agcccctggt aaccaccatt ctctctgctt ccatgggttc  73980
aaatttttta tttttttgaaa tttttaattt ttatttattt atttatttat ttatttattt  74040
atttttgaga tggagtctcg ctctgtcacc cagtctggag tgcaatggtg ccatcttggc  74100
tcactgcaac ctccgcctcc tgggttcaag cgattctcca gcctcagcct cccgagtagc  74160
tggggttaca ggtgcttgcc accaggcccg gctaattttt gtatttttag tagagacggg  74220
gtttcaccat gttggctagg ctggtctgga actcctgacc tccagtgatc cacccacctc  74280
ggcctcccaa agtgctgaga ttacaagcgt tgagccactg cacctggcct aaaatttttt  74340
tttttttttt tttttttgag acggagtctc actctcttgc taggctggag tgcagtggca  74400
tgatctcagc ccactgcaac ctcagcctcc cgggttcaag cgattctcct gcctcagcct  74460
cctgagtagc tgggactaga ggtgtgcacc accacgccca gctaattttt gtatttttag  74520
tagggacagg gtttcaccat gttggccagg atggtgtcaa tctcttgatc tcgtgatctg  74580
cctgcctcgg gcttccaaag tgatgggatt atgggccacc acgcccggcc tcaaattttt  74640
tagagctcac atataagcga gattgtgtac tatttgcgtt tctgtgtctg gcttgtttca  74700
tcttagtata atgtcctcca ggttcatgca cgttgtcgca aaagatggaa tttgctcctt  74760
tttaaagact gaatagtact tcattgtgta catatacacg ccatattttc ttcatccatt  74820
cctttactga tggacatttg ggttgtacct gcatcttggc tattgtgaag agtgctgtca  74880
tgaacatggg tgtgcagctg actctgaggt gttagaggga ttacagctcc tccaaaagac  74940
caccgtcacc caaacctgct cctcctgccc tattttctgt ttaggtaaag gcggctttaa  75000
ccccctgcag tgctctggcc tcagacctcc agatcttcct ctatgcctct atgcctcttt  75060
ttctccaccc cctgcatcca atctgttagc acatcttatt ggctctacct tcagaatcta  75120
cccagaatcc accacccacc tctcaccacc ttcacagccc caccccggtc cagcccccat  75180
ctttgctggc ctggactaaa ccagttgccc ctccacccca atctggtctc ttaacttcag  75240
tccttgcccc acccccagga ctgttcccca cacagcagcc agagggcacc tgtgagccac  75300
tgagtcagga cctggctcct ctttgctcac aacctcactt ggagaaaaag cccaaattct  75360
cctcacaggg acccacaaac tctgcccctg tgatccccca tccccctcta ttcccactct  75420
cctctccact cactcggctt cagctacaca agttccctgc tgtcccttac acaccaagca  75480
ctccccagcc tcagggcctt tgcacaggct gttccctctg cctggaacac tcttccccca  75540
```

```
gatatctgct tggctccccc ctcacttcct ttgggtcttt gctcaagtgt ccttctaaca  75600
tgtaactgcc tcacctgcac tgtgccaccc cactccccgc ctctaggctt aatttccctc  75660
tacacccctg aagagcatct gccaagctat atttacttgt ttattggtta ttgccaatcc  75720
cctgccccca ctagaatgcc agctccatga gggcagggac ttctgtctgt tttgttcact  75780
gctattcccc cagagcctag aacacagcct ggcacatagt aagtattcac taaataattt  75840
gtaatatgaa ttgtgccagt aaaatcttcc aggggcatca agcccctgcc atgactaggt  75900
ggtaacatcc tcacccccctg tccatgtgct atctcctcct gacctgcttg tctcattgtt  75960
ctaatggtgg ctcacgcctg taatcccagc acttggggag gccgaggcgg gcagatacct  76020
gagttcagga gtttgagacc agcctggcca acatgatgaa accctgtctc tactaaaaat  76080
acaaaaatta gctgggcgtg gcattgcacg cctgtagtcc tagctactcg agaggctgag  76140
gcaggagaat cgcttgaacc cgggaggtgg aggttgcagt gagctgagat catgccattg  76200
caatccagcc tgggccacaa gagcgaaact ctgtctcaaa aaatatatat atatatttca  76260
ttgtggtaac atatgcataa cataaaatgt accatttttt aagtgtttag ttgagcggcg  76320
ttaagtacat tcatattgtt gtgcaaccag gaccgccatc catctccaga acttttgcat  76380
cttgcaaaac tgaagctctg cccccaggaa actctcactc cccgctcccc cttcccctct  76440
ccccgactcc cccttccccc ctccccactc cccccaccct actccacact ccccactccc  76500
ccagcccctg gcacccgccg ttctagtttc tatctctgtg aatttggcta ctttgggtcc  76560
cccctgtgag tagaatcata cagtatttgt ctttttgtga ctggtttgtt tcgtggagca  76620
taatgtcctc cagtctcatc catattgtag catgagtcag aatttccttc ttttccaggc  76680
cgaatcgtat tccattgtgt ggatggacca cactttgctt atctgttcat ccagatgggc  76740
acttggcttc caccttttgg ctattgtaaa taatgctgct gtaaacctgt gtgtacaaat  76800
agctgagtcc ctgctttcaa ttcttttgga tatagaccca gaagtggaat ttttttttaaa  76860
tcaagatttg acccactggg gcccttagag gtctcattgg ctctgaagct tttttttttt  76920
tttttttttg gacgctttga aactaaaaat aggagtgagg ggcacagtga ggggggcaca  76980
catctctcgt gtcagcgttt tttaaaaaca ccccgggagg aagatgtgtg aaatccctcc  77040
cttccccccg ctcccacccc ctccaagatc tcaaaatacc tcttgtttta ggaagcggct  77100
gtgacatcag gcaggcagcg tgtggcatct gagacacaat atcgcaagtg gctgggagcc  77160
cagagaaacc aggacaggcg tgctggggat gtggactaga gatggagcta attttagtgg  77220
ctgaagaggc tgcaagaaga gagagaaaga ggggtgtgtg tgtgtgtgtg tgtgtgtgtg  77280
tgtgtgtgtg tgtacgcaca gtgatagagg ctggaggggg agaaatgaca gataaatcag  77340
cttgggcaaa gaaagctaat gggcagagga gcgagaccca gctcagaagg tggtcagcaa  77400
atctaaagat gtgtgcccga gggtcaaggt ggtgggggga ttcataggca agtggtagag  77460
aggctattcc atttgcagag gctctctctg tttgaggcgt gattcacctg tgccgtcctc  77520
aaggccattc tgagaacacc actgttgttt tcctcctttt atgagtaggg aaactgaggc  77580
attgaactgc ttctattctt cagtaagaag caggggggaac atatggtaga agcaaagaaa  77640
tacaaacatg agggctctcg ggtctacgt gattggctgt gacatccatg agagcggatc  77700
gcaggttgaa ggaaacactg gtggcagaaa gtagctgaac atttggattt gggaatccca  77760
gtggacgtgg cgaaaattct ggcttttccc ttcacaggct gcggggccac tctgacctgc  77820
ggtttcctta tctgtgaaat ggaacgatgc cacctgtctc agcgttgttt tgaggatgcg  77880
aggagatgat ccgtgtaata tgcccactag gggcctgct ccagggtaga ttctcagcaa  77940
```

atggtagtca tggtttttgt tacatttggg gatattggca ggtaaaaagg aaatacttca 78000
ttcattccaa aattgctcac tgaggttcta ctatgtgcta ggccctgatg acacatcggt 78060
caacaagaca ggcctgcttt ctgcccttgt aaaacttcag ttcaactgca ttgcactcat 78120
cagcctaata atccaggtaa attgtgatga gaataacaac tagcatttac tatgagccct 78180
ttacaaatat taacccattt aatcttctaa agagcctata agataagagc tcttgccctg 78240
cgcagtggct cacgcctata atcccagcac gtcgtgaggc caaggcaggt ggatcacctg 78300
aggtcaggag ttcaagaata gcctgaccaa cagggtgaaa ccctgtctct gctaataata 78360
caaaaattag ccaggcatgg tggcaggtgc ctgtaatccc agctacttgg ctgaggtagg 78420
agaatcgctt gaacccagga ggcggaggtt gcagtgagtc gagatcactc cactgcactc 78480
caagagtgaa actctgtcac acacacaaaa aaaaacaacc tgttattatc cacattttac 78540
ctatgaggaa accgatgccc agagaggtta agtaactgtc caaaggtcac acagctacgg 78600
agtggtagag ctgggattca gacccaggag tgtgatccca gagtgtgtgt gtatgtttgt 78660
ttgtttgttt gtttgtttgt ttgtttttac cactgtgttt tcctgcttct gcaatagaag 78720
taatcaccag taacactgag cagttgttat gtgccatgcc cttaacacac atctccttgg 78780
atctttggaa agaatcctaa aagggttgtt tttcatgatc cacattttat ggagagagag 78840
agatcaaagc atagagagag gaagtaactt gcccaagatc ctgcagctga agactctagg 78900
gttgcaaatt tgggacggcc ctggaccctg cattccagct tctagcagct catagggga 78960 actctttatt tatttattta tttatttatt tatttattta tttattttga gatggagttt 79020
cgctcttctt gcccagcctg gaatgcaatg gcatgatctc ggctcactgc aacctccgcc 79080
tcctgggttc aagtgattct cctgcctcag cctcctgagt agctgagatt acaggcatat 79140
gccaccacgc ctggctaatt taattttttt tagtagagac ggggtttctc catgttggtc 79200
aggctggtct cgaactcctg acctcaggtg atccgcccat ctcggccccc caaagtgcta 79260
ggaatacagg cctgagccac cacgcatgcc ctggggggga ccacttttat cggtgcattt 79320
cttccatttt ccctgtgtct gtgtaaagat aaacaccccc aagccccttg actatgaact 79380
gtgggccata attagttaat ggaaggtaaa tgttttagag acggaaattg ctgtgccatt 79440
tttccccgct aggcattgtt gcctgcatgc taatgcaaca caatgtgcct ttcttctgtc 79500
aggcattttt agacaaattc tattttccct aaaatatttt gccaaagaaa atagcaaatg 79560
gggaagacat tcagaggctc aggcagagag aggacaccat tcccttgggt ttaaacagaa 79620
tggcagagtg gataacagca cagatcttga gttaggtgga tgccaatttg tgatttattt 79680
cccagcaaac caagatgctg gctctctgtg tgcctcagtt tacttatttg tcaaatgagg 79740
agaataatgg tacctgtctc tcaccagctt accagttgcc tctttagcta tgtctaatct 79800
gctattaacc acgcccacta tgtctttaat tccaagtatt agaattgttt tcttcctaca 79860
agctgtctga tcttttttaa tcctgcttca tcttttgcag tattgttttc ctacagcagg 79920
atttctcaac cttggcacaa ttgacatttt gggctaggta attcttggcc gtgagctacc 79980
accctgtgct aagatactta gagcatccct ggcctctcac cctactaaat gccagtagca 80040
gcccctcccc agttgtggca gccaaaaatg gctcagacat tgccaaacga aatgtcccat 80100
ggagggtaga aacgccccca cttgagaatt gttctatagg tattttcaag catgtcttac 80160
atttctttaa gtataatatg caaaagaaaa ggctaaatct aaaaaaagcc cataatatgc 80220
gaagaatttt tataatcagt gtccaataac ttaagtatct aaaattgtta tggctttttt 80280

```
tctgctgtct cttgtttcct gtgattcctc attctggtgc cttgttttct tgaatgtctt  80340
gttatctttg gttgtgtgaa gctcattttc catgggacac tattttttgt tttgttttgt  80400
tttgagacag agtctcgctt ggttgcccag gctggagtgc agtggtgcaa tatcagttca  80460
ctacaacctc agcctcccag gcccaaatga ttctcctgcc tcagcctcct gagtagctgg  80520
gattacaggc gtgtgccacc acacccagct aattttttttg tatttttagt agaggcaggg  80580
tttcaccacg ttggccaggc tggttttgaa ctcctgacct caagtgatca acccgcctcg  80640
gccccccaaa gtgctgggat tacaggtgtg agccaccgtg cccggcatcc atgggacact  80700
gttgaaggga gttcattgag gcctgcgatg aaggcgaacc ctccatggac aatttgcatt  80760
tactttttcc aggtgtctgg gaaactccca gtctaggacc atcttagact tttagaccaa  80820
caatgtgttg agaatttagg tcaccagtgt ctgcaaaagc cagcttgtgg ttataatttc  80880
tcaaaaactt ttgtttttct ccttttctgc aaagtgccaa agtaacttcc tcaaaaatct  80940
ctgggaatgg aaagacggga gtaaattaac ttcaggtttc ttacctgaaa gtgatagcct  81000
attggggccc catcctactt ggggagtggt gtgtctcctt tgagactttc taacacgtgt  81060
gtaccctgga ctttgcccca cccctgctcc ctaggaggcc ataaaacttg aagcagcagt  81120
tccatgggtt agacagatgc ccttggggca aaagtggttt taatgctctg gtagatgctc  81180
aggttacctc tgggaaattc ttgacttcac ttatttattt ggggctgata actactaatt  81240
gtcaggcctt tcttgtttca acaacatgga cttcagattt tatgcaggat ttgtcatcgt  81300
tttcagcaag agagtcagtc ttattaccca gcttactgca ttagaaatag atgtctgggc  81360
caggcgcagt ggctcacacc tgtaatccca gctgtttggg aggctaaggt gggcggatca  81420
tgaggtcagg agttcgagac cagcctggcc aacatggtaa aaccccatct atactaaaga  81480
tagaaaaaat tagctgggtg tggtggtgcg tgcctgtaat cccagctact tgggaggctg  81540
aggcaggaga attgcttgaa cccgggaggc agaggttgca gtgagccaag atcgcaccac  81600
tgcactccag cctgggtgac aggacgagac tctgtctcaa aaaaagaaat agatgtctgt  81660
tgtgtggatt atttaaaaga gtagatggcc aagaactatg acttatgcct gtcatctcag  81720
cactttgaga ggctaaggtg gagggatcac ttgaggccat gagttagaga ccagcctggg  81780
aaacatagca agacccccat ctctgcaaaa gtaaaataaa ataagttagt gtgcatgatg  81840
gtgcaggcat acctctagtc ctagctactc aggaggctga ggcaggagga tcacttgagc  81900
ctaggagttt gaggctacag tgatctatga tcatgccact gcactccagc ctgggtgaca  81960
gatcaagacc ctgcctctaa aacataaaaa taaatacaaa ttaagttaaa aaataaaata  82020
aataagtaat agaacatcca gcacagttct tggcatgcat tgactgttgt tgtttgtttg  82080
tttgtttgtt tgtgacggag tctcactctt gttgcccagg ctggagtgca atggcatgat  82140
cttggctcat cataacttcc acctcccagg ttcaggtgat tctcctactt cagcctcctg  82200
agtagctggg attacaggca cgtgccacca ctcctagctg ttttgttttg tttgtttgtt  82260
tgttttgtat ttttagtaga gatggggttt ctccaagttg gtcaggctgg tctcaaactc  82320
ctgacctcag gcgatctgcc agcctcggcc tcccaaagtg ctgagattac agacgtaagc  82380
caccacgcct ggccagctgt tttgattgtt aaatgaaggt ggtatgaaag ggaaggaaga  82440
acagtgacat ttgcaaggga cactccctgg agggcagggc aagggggctg tggaggggag  82500
aagtcagaga gtatgataca ggttgccttg ggtgatgttt tagattttag ccaacattgg  82560
caaagagcct catttatctc tcagagtagc tctggctact ggaaatgctg cacaacttca  82620
ggcggacttt ctagaagaaa actcttggcc aggtgcagtg actcacacct gtaatcccaa  82680
```

```
cactttggga ggctgaggca ggtggatcac ttgagctcaa gagtttgaga ccagactggg  82740
caacgtggca aaacctcatc tctacaaaaa aaaatacaaa aattaaccag gcgtggtggt  82800
gcatgcctgt atcccagcta cttgggaggc tgaggtggga ggattgcttg agcctgggga  82860
ggtggaggtg gtagtgagcc aagattgcac cactgcactc ccatttgagt gacagagcaa  82920
gaccttgtct caaaaaagaa aaaaagaaaa gaaaagaaaa gaaaattctc tctgggattc  82980
aatcctggcc cacacagcat tggcttcact tcacctcctt ctcccctgag atacacagca  83040
ccattccccc aagcttcatc aacttaatct ctgatctggg tgctgtgact tgtccccatt  83100
cctggccaga atttaaggta gggatgaacc cactagccct ccatcacgca ctctgccata  83160
aaagcacacc acgtgctgat tgctgtcttt ggtctccttt ctgccttgcc ctctagactc  83220
tgagctgctt ggagacagag gccagttttg tccatctcca aatcccctaa agtcctgtgg  83280
ccagcaagca ggtaggacat ctgaaagttc gtcagagagg gaattgcttt tctcttgaga  83340
tgcaactaga acaagaatct tattgacctg gagtagcttc aaggttgtaa gagtatgtgt  83400
cagggttctc caagaccact ctcaggtttg aaggtttgct aaaagggctc acgggaccca  83460
gaaaagctgt gaaattcagt tatggtttat tacagtggaa gaatacagat aatacagatt  83520
aaaatctgca aagcaaaaga tgcacaaggc aatgtccagg ggagatcagg catgagcttc  83580
cagctgttca ctcccagtgg agttatgcaa acagtgctca attctcccag caatggtgtg  83640
tgacaatgta cagtgtaccg ccaaccagag aagctcacct gagccttggt gtccagggtt  83700
tttattgggg ctcagttaca ttgacatgga gcacccatgt gactgacttt aactgctggg  83760
tctccagcac actccaagat caaactgata ccgtgtgtcc cagggcccca gctgaacaca  83820
aacaggcagt caccatagat cccattgtga gcataagcta ccaggcatgg cccaaagccc  83880
tagatataca gatattcttt ccaggagcca gccaagggcc agtccttcct ttggaatatg  83940
cagagtttga actccccaac cccaaggagt taactcttta ctacacagaa tataaatctc  84000
accaagtctt tcttcttgtc aagtcctctc aaggtgaccc attgctttta gcagtgtctt  84060
tgagaccctg cgtcatctgg ccttgaccca tatcacctgt gttatctctc cactctagct  84120
acattgaact tttcttttt gagatgtggt ctcactccat cacccaggct gaagtgcagt  84180
ggtacagtca cagctcactg cagcctcaaa ctcctgggct caagtgatcc tcccacctca  84240
gcctcctgag tagctgagcc cacaggtgca tgccattaca cccagctaat atttttattt  84300
ttagtaaaga tgggttctca ctatgtttcc caggttggtc tcaaactcct gggctcaagc  84360
agtcctccca tcttggcctc ccaaagtatt ggcattacag gggttagcca ccacatccag  84420
cccattgaac tttttaagga tcccctagca tcctatactt tctgtcactg gatagccttg  84480
gaattatttt tccttctttt tgaaatactc ttcttctttc cacccttttgc tgtcaagtct  84540
cagaataggc attatttcct ccaaaaaccc tctcctgacc ctccaaatct ggatgaggac  84600
acttcctttg cccagagagc acctgtttta atcctctcag gtggctataa taaaatacct  84660
taaactgggt ggcttataca cctcagaaat ttattttcca cagttctgga ggctgggaag  84720
atcaaggcac tgacagattt ggtgtctgat gaggggccat ttcttgtttc gtagaagggg  84780
tcttcctact gcatctttcc atggtgaaaa gagttgaggc agctctctga aacctctttc  84840
atgagagcat gaatccctct gtcttcatga tctaatcacc tcccaaaggc cccacttcct  84900
aatatcttca cattggtgac taggtttcaa catatgaatt tgagaaagac acagacattc  84960
agaccatagc agtgctcttc caccaggttt tttatccccc tgtattataa ttgaggttta  85020
```

```
aattatctgc tttccttccc ttagattgta agctccatga gagcagggcc ctacccatcc  85080
agtcattgtc ctatccccca tgactacaac ttcctgggta cataattaat atttattata  85140
ttatgtagca aaggtatgct gccatactaa gagacccaaa aggccaccgg attaaaacct  85200
taaagaaaaa aaaataattt ctctcctata atagctgcaa ggttagccat gcaggttggc  85260
agggaagctc acttccacaa agtcactcag ggattcaggc tcctgttgcc ctcttctttt  85320
ctaccaccaa atgatcttca gcaccatttg cacaatcaaa acttaactgg tcttgaatag  85380
gcagaccttg aatttctgaa gtctcagacc caaaagtggc agctgtcact tccactgaca  85440
tatcactgat ggaaacttaa tcatgtgatc ataccaaact gctagggatg ctgggaaatg  85500
tagttttgtt gggaactcca tgacttggct aaaattccat tactgtagaa gatggtgggg  85560
gatgggggag tggtggacat ccagtggttg ctaccatatt tattgaatca aattgtcaaa  85620
caggacctat ctgataaggg gttcttttcc agaattaact gaagtattaa atcaggggca  85680
aaggcatgtc acctcatctt tctctcccta tattggcttt ctagggctgt tataacagag  85740
taacatgaac ttggcggctt aaaacaacag aaatttattt tctcttagtt ctggaggcta  85800
gaagcctaaa atcaaggtgt cagcagagcc accttgacaa ctgctctagg aaagaattct  85860
tccttgcctc ttctggtggc tcctggcaac ccttggtatt ctttgtctgg catccacttc  85920
aatctctgcc tccatcttca tttgcctttt ttctctgtgt gtctatgtcc tttcctcttc  85980
ttagaaggat accagtcatt gaatttaggg cttactctaa atccaggatg atctcacctc  86040
aagatcctta attagttaca tctgcaaaga gcttatttca aaacaagatt gcattctgag  86100
gtttcggtaa acacgaattt gggggaaata gtattcaact caattcactg ctttacttaa  86160
gaaaagagac catgaagtga gcctccttct gcttgagaga gagagcgagc ctttctgtgc  86220
aataggtcaa tgaatggatg cagctgaatt ccacataact ttataaaaat agatggccag  86280
cccatggggt ttgctgaccc ctgcccaaaa attccaaagt caacagcagt ctctttttta  86340
atcatttctc tattttttaa tttattttta tttttatgtt gagatagagt cccgctctgt  86400
cgcccaggct ggagtgtagt agtctcggct cactgcaacc tctaccttcc agatacaagt  86460
gattctcctg cctcagtctc ctgagtggct aggagtacag gtgtccgcca ccatacccag  86520
ctaatttttg tatttttaat agaaacaggg tttcaccatg ttggccaggc tggtctcgaa  86580
ctcctgacct caagtggtcc acccacctcg gcctcccaaa gtgctgggat tacaggcatg  86640
agccaccatg cccggccagg attttcttca ttttaacagc attcttactt gtcccacatc  86700
cattctatcc tgggtctaat tagataacaa aatctacaga tcttgtttaa ctgacattgt  86760
cctgggggat actttttatc ttttgagaca aggtctcact ctgttaccca ggctggagtg  86820
cagtggcctg ataacagctc actgcagcct cgaccacctg ggttcaagcg atcctcccac  86880
ctcagcctcc agagtagctg gaaccacaga tgcatgccac cacacctggc taatttttaa  86940
atttcttgta gaggtggggt ctccctatgt taccaaaggc tggtctcaaa ctcctgggct  87000
caaaagagcc tcccacctta acctcccaaa gtgctgggat tacagatatg agccactgtt  87060
tccagccttg gaaatatagt ctaagaactg agtcaatagg cgattttgtc attgtgtgga  87120
catcatgtag agaacttaac acaaacctag atggtataaa ctactgcaca cctcagttat  87180
ggggcatacc ctattgcacc taggctgcaa acctgcacag caggttactg tcttgaatac  87240
tgtaggcagt tgtaacacaa tggtaagtat ttgtgtatct aaacatatct aggccgggca  87300
cggtggctca cgcctgtaat tccagatcac ctgaggtcag gagttcgagc ccagcctggc  87360
caacatggcg aaactccttc tttactgaaa aatgcaaaaa ttagccaggt gtggtggcag  87420
```

```
gcacctgtaa tcccagctat tcgggaggct gaggcaggag aatcgcttga acctgggagg  87480
tggaggttgc agtgagctga gatcatgcca ctgcactcca gcctgggtga cagagcaaaa  87540
ctccatctca aaaaaataaa aaataaaaaa catatctaaa cagaaaaggt acagtaaaaa  87600
tacagttata accatatggg accaccattg tataggcagt ccgctgttga tcaaaacata  87660
tcaaaacatc gttatgtagc acatgactgt accataaacc acacggcttc aaacaaggga  87720
aatgtattct ctcactgttt tggaggccat aggtctgaaa tcgaggtgtc accagggtcc  87780
ctccaaagga tccgggggag gatccttcca ttggatttgg agttgcttca ctccagtctc  87840
tgcctcagtg gtgacagggc gttctcctct tccctctcaa agttccctct tctgctgtgt  87900
cataaggata catatgactg catttaggcc ccactcagaa aatccaggaa taaactcttg  87960
ccctcatatt cttaactaaa tcgtacctgc ataccttatt ttttctaaat aaggtagcat  88020
tccagggatt aggacatcaa cataacttct ggagggttca ctgttcaacc cactacagcc  88080
agaatgcgct ttgaattcag gttctgacat ctgggactgc ctcccacgta cacacaccac  88140
taccttgtac tgaatgcctg aagggttctg cccccacctc cactccccca aatatttgct  88200
gtggacctga gaaagctgac ttcatggaag cttcattcca ttgttctaag gacttttcat  88260
acattaacaa atgtcttctc tctatgggga aaaccacaga gaaatcaaga cagagtgggg  88320
ttaagtaact cacctgagga ggaacagtaa gtggcagagc caggattcaa accaacatgg  88380
ttttgcacag ttttgacatc atttgcaaca caaatattgt cacagatacc tttttgagca  88440
tctactgtgc taaccgccag gaaggaaaag aacatggggc cgggagagct cttgacaggg  88500
gacagggctg gccatggagg tctgtgtctt ggtggaagat gctatggttc tctttttttt  88560
tttttttttt tgagatggag tcttgctctg tcacccaggc tggagtgcag tagtgcaatc  88620
ttagctcaca gcaacctcca cctcccgggt tcaagcgatt ctcctgcctc agcctcccaa  88680
atatctggga ttataggcac acaccaccac gcccagctaa tttttgtatt tttagtagag  88740
atggggtttc accatgtggg ccaggctggt ctcgatctcc tgaccttgtt gtgatccacc  88800
cgcctcggtc tcccaaagtg ctgggattac aggcatgagc caccacactg ggcaactatg  88860
gttctctttt aactccttgt gctgaaatta ttgcagaagc ccaggccagt tcatccccag  88920
aaagtgaggc ataaacaggc agagctctac agaaacagag aatccacgac tggtttgatg  88980
gaggctgcct cactacctac agaatgggct ctgggtggat tgttctatct ggggagccag  89040
cccacccacc agtctcagcc cttggcgact ctttcctgct gtcacagcag ctggacattc  89100
agaaaccgaa acatgacagc cttccctccc tgttcctgcc cagtggagtg gaaacccctc  89160
gggacccaca taccgagcgt gcacagcagc acagagttgc acagttaaca cagcgcttct  89220
tctccagccc tccggatgca agctgacaga ttggcagctg gctgacttcc aaggtccagt  89280
gagttcttgg cagtcgcttt ctgacctgga cgagtggctg ccacctcctg gaacatcagg  89340
ctgccccctt ggggagaggg tgacggtctc tctggaaaga ctgtgagctt tgaggtggtc  89400
atcaaaagcc attcttggaa acattctttg agctgtaccg tgcaattcgg tcaccaattg  89460
cacgtatttg gatattaata tccgtatgtg gatattaaat tggttttggg ttttgttttg  89520
ttttgattgt ggcaaaatat acacaacaat cctcctgcct cagcctccca agtagctaca  89580
ggcatgcacc accataccca gctaattttt ggattttttta aatttgtttg tttgtttttg  89640
ttttttgaga tggagtgtag cactgttgcc tgggctggag tgcagtggcg cgatctcagc  89700
tcactgccac ctccgcctcc tggattcaag tgattctctt gcctcagcct cctgagtagc  89760
```

```
tgggattaca ggcgcccgcc aacacgccca gctaattttt tgtattttta gtagagatga  89820
ggttttacca tgtcggccag gcttgtctcg aactcctgac cttgtgatcc acccgcctca  89880
gcctcccaaa gtgctgggat tacaggtgtg agccaccgcg cccggccgat tttgtagtt   89940
ttagtagaga cagggtttca ccatgttggc taggctggtc ccgaattcct gatctcaggt  90000
gatccaccgc ctcggcctcc cgaagtgcta ggattacagg catgagccac cgcacacagc  90060
ctaaatgctg tgcctcacgc ctgtaatccc aacactttgg taagctgagg ccagaggatt  90120
gcttgagccc aggagtttga gaccagcctg ggcaacatag gaagacccca tctctataaa  90180
aaataaaaat aaattagcca ggcgtggtgg tgcaggcctg tggtcccagc tactcgggag  90240
gatgaggcag gaggatcgct tgagcccaag aggtcaaggc tgcagtgagc tgtgattgtg  90300
ccactgcact ccagcatggg tgaaagagca agaccttgtc tcaaaaaaaa ttaagcgaaa  90360
tttaaaattc tgtttctcac tcacacaggc tgcacttcaa gtgcttaatc atcccttgtg  90420
ggtggtggct atcatattgg acagcatgga tagagaatat tttatcagc gtaggaagct   90480
tcatcagaga ggaccgctca gaggcctgtg ggaccagca cagtgcagta gaagacacag   90540
gccagctggt gagagactgg tcttctgatc ccagatctgt ccctcacttg ctaggtgacc  90600
ttggacagct ccctcagtcc ctctggagtt ttctcttcat tgttaaatca ggaaattggc  90660
ctcagtgaat tctgaggccc catctacttt tttttttttt tttttttttt tttttttaat  90720
tgagacagag tctcgctctg ttgaccaggc tggagtgcag tggcatgatc ttggctcact  90780
gtaacctccg cctcccaggt tcaagcaatt ctctgcctca tcctccccag tagctgggac  90840
tacaggcgtg caccaccatg cctgggtaat tttgtgtttt tcagtagaga ccgggttttg  90900
ccatgttggc caggctggtc tcaaactccc aaccttgagt gatcctcccg cctcggcctc  90960
ccaaagtgct gggattacag gtgtgagcca ccacgcctgg cctcatctag ttctaaatgt  91020
tatgacccac tcagctctga agacaaggga ggaacatcct ctcagtctag ctctgacatg  91080
cagaagcctc tcaccctgtc ccccaggtca taaaggcagg cgtgttgtga agagcacaga  91140
atgggctgag aaaaatatgc agggattgcg tctatctccc ttccttccgc acgtttcctt  91200
gtcggcacca cctgcctcta ttccgcgccg cacacacacc cgccttctct ctgtctcgga  91260
ggaagacagg atcttccatc ccccaaatcc tgccctgatt cctactctga agcctctgcc  91320
ctgactcctt taagctccct gggaatacag cccatctcct atgccctcct catcccagta  91380
gttcctacct tccccaaaat cgctttggga aagtccccca atgagtaacc agctgtccta  91440
catgggcatc tcagaacttc tcttctgttg ttgttgttgt ttgttttgct tttgttttga  91500
gacaggatct ctctttttca cccaggctcg agtgcagagg tgtgatctca gctcactgta  91560
gccttgacct cccaggctca ggcgatcctc ccccctcagc ctctggaata gctgggacta  91620
caggcacacg ccaccacacc cggcaaatt ttttttagga cttttggtag aaatggagtt   91680
tcgccgtgtt gcccaggctg gtctctaact cctgggctca agcgatccgc ccactttggt  91740
ctctcaaagt gctgggacta cagacatgag ccaccacacc cggcagagct tctatttctt  91800
gagtgtgttc tcagccatgc taagacattt tctcttctca gcctgatgat gcttttggct  91860
tgtgtttctt tgtttttaat taccccttcc cagtcgctgt catgggatca tgagggtctt  91920
ctgtccatct agatgacacc tttcttgtgc cacgtgtctc caacattccc tggtttttaa  91980
acccttattg ctttcaagat actatccaag ctccttaatg tggcacattg tccttcgctg  92040
ctatctgcct gctttttttt tgagacagag cctcgctcta ttgcctaggc tggagtgcag  92100
tggcgcaatc acagcttact ctgcagcctc gacttcttgg gctcaagcaa tcctcctgcc  92160
```

tcagccttct gagtagctgg gaccacaggc atgcaccatc atgcttggct aatttatttt 92220
tatttatttt tatagagaag gagtctccct atgttgccca ggctggtctc aaactcccgg 92280
actcaaagtt cattgcagtt tcaatttttt ccttggctca aggatcctcc cacttcagcc 92340
tcctgagtag ctgggactac agacgggcac caacacacct ggctaatttt tgtatttttt 92400
gtagagatgg ggtcccacta tgttgcccag gcttctatct gcttttatct caccttccac 92460
tcttccatcc ttcctttctt ttcttttatt tcctttccct tcccttgcct tccttttctt 92520
tctttctttc tttctttctt tctttctttc tttctttctt tctttttctt tctttctttc 92580
ttgacagagt ctggctctgt cacccagact gaagtgcaat ggcaagatct tagctcactg 92640
caacctccac ctcctgggtt caagcaattc tcctgtctca gcctcccgag tagctgagat 92700
tacaggtacc tggcaccaca cccggcaatt tttttttttt ttttagtaga gacggggttt 92760
cgctatgttg gccgggctgg tcttgaactc ctgacctcag gtgatcctcc cacctcagcc 92820
tcccaaagtg ttgggattaa caggtgtgag ccactgtgcc tggccttttt tttttttttt 92880
ttttttttta agacaggacc ttgctctgtc actcaggcca gagtgcagtg gcactataat 92940
cactttctgc agccgtgacc tcctgggctc aagggatcct cttgccttgg cctccctagt 93000
agctgggact acaggcatgt gccaccacac tggctaattt ttaaaacttt ttgtaggccg 93060
ggcacggtgg ctcacacctg taatcccagc actttgggag gccaaggcgg gcggatcacg 93120
aggtcaggag attgagacca tcctggctaa cacagtgaaa ccccatctct actgaaaata 93180
caaaaaatta gccaggtatg gtggcgggcg cctgtagtcc cagctactcg ggaggctgag 93240
gcaggagaat ggtgtgaacc tgggaggcgg agcttgcagt gagctgagat cacgccactg 93300
cactccagcc tgggcgacag agcgcgagac accatctaaa aaaaaaacaa aaaaaaaaaa 93360
caaaaaactt tttgtagaga tggattcttg ctaggttgcc caggctggtc tcaagcttct 93420
aggctcaagc agtcctcttg cctgtgcctc ccaaagcctt gggattacag gcgtgagccc 93480
ccacacctgg tcctaaccca ctttctgaac ttccaaccac accattttgt cctaatattt 93540
aagtcacacc ataacatgtc ccacttcaga aatgcctacc aaagtagtct tcaaatcttt 93600
ttaaatcagt ggaccctttc taccaaacaa atgttatttt ttaaatattt attttagagt 93660
aatttagact tttagaaagg ttgtagctgg gcgcagtggc taacgcctgt aatcccagca 93720
ctttgggagg ccgagacagg tagatcacct gaggttgggc gtttgagacc agcctgggca 93780
acatggtgaa accccgtctc tactgaaaat acgaaattag tcaggtatgg tggcacgcgc 93840
ctgtagtctc agctactcgg gaggctgagg caggagaatt gcttgaaccc aggaggcgga 93900
ggttgcagtg agctgagatc gcgccactgc actccagcct gggtgacaga gtgagactcc 93960
atctcaaaaa aaaaaaagaa aagaaaaaaa agaaaggtta taaatatatt ataaagagtt 94020
cccacatacc cttcacccag tttctcctgt tgtttgtatc ttatattatc accatatgct 94080
tgtcaatgct aaggaattgc tgggtgcaga gtggcacatg gctgcagtcc cagatactca 94140
ggaggccaag gcaggaggat atcgcttgag cccaggagtt caagtctagc ctgggcaaca 94200
cagtgagacc tcttttctgc aaaagaaaac aaataaaaca tctaaaaaag aatacactgg 94260
aggcggcgtg gaaacaagga tctcatttgg gagttgtctg caatgttctg agcaagcagt 94320
aacggaggcc tcaagtcagg gctgtggtca tggaggtggg gaggggtggt tggtttcact 94380
atctgtgttg acttaatttt agatttgcag actcaactga gtatgaactt taagagaaag 94440
agagaggcca ggcacggtgg gtcacacctg taatcccagc actttaggag gccaagtggg 94500

```
gaaggccgct tgagcccagg agtttgacac cagcctgggc aacatagtga gacccctgtc  94560
tctacaaaaa aaaattttta aattagccag gcagggtgat gtgtccctgt aatcccagct  94620
actcaggaca gtgaagcagg aggatcattt gagcccagaa agttgaggct gtagtgagct  94680
gtagttgcac cattgtgctt cagcctggga gacaaagtga gaccctgtct caaaaaggag  94740
aatggggaga gagagagaga gagagaagga gaaagagaga gaaagagaga gagggaagtc  94800
aaggagaacc ccacattttt tgacatggtg tattagtctc ttctcacact gctaataaag  94860
acatacctga gactgggtaa tttataaagg aaagaggttt aatgcactca cagttccaca  94920
tggctgggga ggcctcacaa ccatggcaga aggcaaagga gaagtaaagg catgtcttac  94980
atggcagcag gcaagagagc ttgtgccatt tataaaacca tcagatctca tgagacttat  95040
tcactaccac aagaacagta tgggggaaac tgcccccatg attcagttat ctccacctgg  95100
cgccgccctt gacacgtggg gattattaca attcaagttg agatttgggt gggaacacag  95160
ccaaacccta tcacatgggc aagtgaaagg atgggtttgc catcaaataa aatggggaag  95220
gagactgact aggtgggcag attaggaact cagctttcta tgaagtgcct actgatggat  95280
agagatattg tgttggccat ctattaggtt ggtgcaaaag taattgcggt tttgccatta  95340
aaagtaatgg caaaggaaat aacctttgca ccagcctaat aggaattgga gtctaaaatt  95400
caaaaaaggt aagtcagagc tggagatcca aaggcaggag tcagcctcct gtggaggcta  95460
tttaaggaac tgaataaggg catagatgca ggagagcacc caggactgag cccagggctt  95520
actctccatc attaaagagg ttggggaaga tgaggaggag ccagcagaga agactgaatt  95580
ggagcaaatc agaagaatgt gggtgctggc tgtcatgcaa ggaaagtgct aagccatttc  95640
aagtatgagg gaatgatcaa tgatgtccac tgatgctgat gtgttgactc aaatgaaaaa  95700
tgagaatcaa ccattggatg tagtggcatg gagatctttc gtgacctgag ccagagctgc  95760
ttaggtgaag aggtgaaggc aagaggctac tggaaggatt actactagct cttttaaaga  95820
gttctgctgt gaagggtaga ggaagagaga tggggcatgt gttagctggt gggggaagtg  95880
gatttcagag gtttgtttcc cttaaaaaaa aaaaaaaaaa gaaaaaagaa taaagaaaaa  95940
aaaaaggcca ggcacaatga ctcacacctg taatcccagc attttgggag gctgagacct  96000
cgggaatttg agactagcct ggacaacata gtgagacccc atctctacaa aaaaaatttt  96060
tttttaatta gctgggcatg gtggtgcatg cctgtggtcc tagctacttg ggaggctgag  96120
gtgagaggat ctcttgagcc tgggaggtcg aggctgcagt gagctatgat cacaccactg  96180
cactccaggc tggacaacag agcaagaccc tgtctcaaaa aaaaaagatg ggagacctaa  96240
cagcagattt tatgctgata ggaataacct attaggggag aaaaacatga ggatgctgga  96300
ggaagaagag tgtcaggagg acatctcttg gtggacgaga ggggatggca tttggtgtac  96360
aggtggaagg tttcacttta gatgacagca cacacagtta tctatagaaa caggagaaaa  96420
tgcactatat gggcatacat gctgggaggt agagagtaaa taatagtggt ggttgcttgt  96480
ggaaattctc ttctaatgtt tttatatttt tatggtttat caaggacaat ttatattttt  96540
acagtttact gcaaacaaca agttctaatt tattcaataa ttatttgtgg gtagaccgag  96600
tgcagtggtg catgcctgta atcctagcac tttgggaagc caaggtggga ggattgcttg  96660
aactcctgat tcacttctga gcttgaatca ggagttcgag atcagcctaa gcaacatggc  96720
aaaacactgt ctctacacaa aatacaaaaa ctagccaggt atagtggcat gcacgtagtc  96780
ccagctattc gggaggctaa aacgggagga tcatttgagc cctgaaggtg gaggttgcag  96840
tgagccaaga gcgagccact gcactccagc ctgggtgata gaataagacc ctgcctcaaa  96900
```

```
aagaaattct tattcttctt cttcttatta ttatttgagg agacatttac tttgtaccag  96960
gcgctgtgct agatgctgga gatacagaca tcaacaatga caaggctaag tgcctggcgt  97020
atttgtactt tgagtctaat aaaagacatc acacagacac acaacacaca cacacacaca  97080
cacaggattg tcaaaggatc aaccatttca catgtcaaga tcaggaatga tattggtcta  97140
ctactgcctt accatatctc ctaccatgac ctcatcttcc tcttgccaga ttttaagtct  97200
ttatacctca actcccagaa ctctcttcgc ctcacaccct atcacaatgt catccgtacc  97260
ccacggccaa tactccatca ttcgggaaag caaagttcca aagcgtcaag attgtatcaa  97320
tggacctgtc tctatggcaa cagtcctgaa tgagccaagc aaggtaaccc tggagatggc  97380
gtgaatgaga aagtggcctg ttgccacgga gacgtgctga atgggaaggc ccccacgagc  97440
caggctatgt cacgaagccg aaacagtcag catgaagtcg gtatgtctat tttcaactcg  97500
gaattacaaa aatacatttt aatagagctc atgacccatc tccttcctcg tccctgcctc  97560
ccaccccact cttcagcctt catcctacaa cacaatcgag cctcaccagg aacccttcaa  97620
acccctcaag gacaccttac tgttccttca gtacacagtc cccttcctgg gctgaggtgg  97680
tattcctttg accaactact gtctcccctt tgggaccaac agtattctca aaagccatga  97740
gcttatggga agaacattaa ctacattctt tggggcaaga acagttgctc acctgtgaac  97800
cagctcagct tgcatctgtg agaatgattg caatgggtag accagttctc catcaaagaa  97860
tggccctagc accccacaca cagtggtata atctgatcat gctggtgtat tgaacatata  97920
atgttagtgc cacatgaaag gaatttgtaa aaggacttag tgcctagaaa ggtacctttg  97980
aagatcttgg aatctctgaa acttacccag gttccttata ccctgctcaa agtattcctc  98040
catttatttc ttcattcatt agttcttttg tttcaccaca tatatatttt tgaaacgggg  98100
tctcactctg ttgcccaggc tagagtgcag tggcaagatc gtggctcact gcagcctcaa  98160
cctccccatc tcaagcagtc ctcccacctc agcttcctga gtagctggga caccacaggt  98220
acaagccacc acgccaggct aattcttgta atttttgtag agacggggtt ttgccatgtt  98280
gcccagtgta ttcgtttgtt ctcacattgc tataaagaac tacctgagac tgagtagttt  98340
ataaagaaaa gaggtttaat tgactcacgg ctccacaggc tgtgcggaag gcatggctga  98400
ggaggccaca ggaaacttgc aatcatggcg gaaaatgaag gggaaacaag cacatcttca  98460
catggtggca ggagagagag agtgaggggg ggagtgctac aaaaccaggt ctcacgagaa  98520
ctcactcact gtcatgagaa aagcaagggg gaaatctgct cccaggatcc aatcacctcc  98580
taccaggtcc ctcccccaac attggggatt acaattcaac atgagatctg ggtggggaca  98640
cagagccaaa ccatatcacc caggctggtc tctaactcct gagctcaagc aatctgcctg  98700
ccttggcctc ccaaagtgct aggattacag acgtgaacca tatttattaa gcattgttac  98760
agcaaagaga agcattgttg cagcataaca attggaagac tccattgatg gacgtctcca  98820
tcaacaagaa ctgtcggata aactatggta cacccatccc ttagcgtgtt atgaagtcat  98880
tacaaaaaga agaagcagat ctctgagtgt caataagagc tagtacttat agggtgtcta  98940
ctgtatacaa gtgctgttag aaagtgagta ttaactcatt taattcttgt aacaagcctg  99000
tgaggtggat tctttcatat ccccatttta cagagaagga aataggaatc tctatatcca  99060
agatatgtta tcaggtgaca aaagcagttt ttgaatggtg ccgccatttt ctcgtaagag  99120
caaatctgga agattccatg agaaattaat aattgtgttt gcctctgtag cggcaccctg  99180
aaagatttgg aagtaggtgt ggaaaggaaa cttactttct tgtgtctttc tgaattttgt  99240
```

```
actgtctacg cgttttgtct ttcacaaaac caaacagaaa atgaccattt ggtgcatttt  99300
gtgtgtcagg cattcttcta gtctagagaa gcacaggaga gcaaaatatt ttactgacga  99360
gaaaaatgag gcatggagaa gttaagtgac ttgcccaggt agcagagctg ggattccaca  99420
tcatagggtt tatacaggaa acaggtaaac agagctgtgc ttgtgtgtgg gtatgtgtgt  99480
acacatgcat acatgtgtgc atgtgtgtgt gtgtttgtgt gtgtgtgaat gtgcttgtgt  99540
gttgggagag ggaaatggca agagaagaac ctacagaagg tcagcaggaa ccaacccatg  99600
ttttgaggag tttggacttt atcctgaagg cacaagggag ccatggaagg atttagacaa  99660
ggggtggttg tgcttagctt tttatttaga aggatgactc tggctgaagg gtgatggccc  99720
agaatacagg tatatgtgaa ggactcctcc tgccctagta ggaggatgcc cacccaccct  99780
ctctgcccag tgcagtatca aagggcaaat tgggtacaga gaattctcac caagctgggt  99840
agaatccact ctgatgctgg ggagtggaca ctgaatgcac cagcctctcc tcctgctcaa  99900
tccctgaatt gaagctgttc cactaatgtt agggatcaga ttcccttcat atatatatat  99960
atatatatat atatatatat atatatatat atataatttt ttttttgaga cagagtctcc 100020
ctctgtcacc caggctgaag cccattgtcg cgatcttggc tcactgcaac ctccacctcc 100080
caggttcaag caactcttgt tcctcagact cccaagtagc tgcgattaca ggcacccgcc 100140
accacacctg gctaattcta tatttttagt agagacaggg attcacctat gttggccagg 100200
ctggtcttga gctcctgggc tcaagtgatc agtctgcctc agcctcccaa agtgctagta 100260
ttacaggcat gagccaccat gcccgtcctt tttatattac cttttttat agagatgtgg 100320
tttcactatg ttgaccaggc aggtcttaaa ctcctggcct caagcgatcc tccctcctca 100380
gcctcccaaa atgctaggat tacaggtgtg agccactgca tctgtccaga ctctgttctc 100440
cataaagctg gcatatggaa agagggaaga ccatccaggc aatatcgaag tcccattggt 100500
gctgatgtgg ctgctgagac cacatgaatg gatgcattct gactctgcca cctctcagct 100560
atgtgaccct gggccagtca gcaagtccct ctataactca gttttctcat ctgtaaaatg 100620
gcgtcaacag tagccaaccc cagcaaatac tgtgaaatat acagaacatc attataatgg 100680
tgaggatgat agagatgcta tgttatcaga atacctgggc ttgaaccagc tccccttctt 100740
gcaagctgtg tgacttggag ctgatgccca aacctctgtg ggcctcattt gtttcatctg 100800
ttcaatgggg ataataacac tcttacttca tacagttatg gaggatttat tgaaataatt 100860
gacatacagc tcttagaaca gtatccggct ccttgtaagc gctcaagaaa tattacagac 100920
tgttgataat aatgcaatac tactaccaat aatatggcca ggagcaatgg ctcacacctg 100980
taatcccagc actttaggag gcagaagcag gctgattgct tgagcacggg agttcgaggc 101040
cagcctgggt aacataggga gactctgtct ttacaaaaaa taaaaataaa aatacaaata 101100
attagccagg tatggtggtg catacctgta gttccagcta cttgggaggc tgaggtggga 101160
ggattgcttg agcccaggaa gttgaggcta cagtgagctg tgatcacacc actgcactcc 101220
agccagggca acagagtgag accctatctc aaaaataata ataatggccg ggcgcgctgg 101280
ctcatacctg taatcccagc actttgggag gccaaggcgg gcagatcact tgaggtcagg 101340
agtttgagac cagcctggcc aacatggtga aaccccatct actaaaaaca caaaaattag 101400
ccgggtgtgg tggcggggtg cctgtaatcc cagccactca ggaggctgag gcaggagaat 101460
cgcttgaacc cgggaggtgg aagttgcagt gagccgagat cacaccactg cactccagcc 101520
taggtgacac agtgagactc catctcaaat aataatatga gtaataataa taatatcatt 101580
tttatcatca ttcttactaa cagtctctca ctccttgccc tgcagttttg cctgttttct 101640
```

tggaataaca ctcttccaca cctttcccct cagggatggt tcacgtttag catcatgacc 101700
cacccctggg gattagttag ctcatttctg gaaagcactt tggagctgta ggtgctttgc 101760
aggctggaaa catcacggga cttgtaccat atttaagcaa tgccagatta ttctgcctgg 101820 caggggggagg acacagagga tacggccctg gtatcttttc tccctgccta cctcagcttt 101880
gctctgaacc attttctgtc ctgttcaggg cagcctgggc cacttgccac ttccagcttt 101940
ctcgggagag gatgccttcc tgatggcacg cctcttaaca cacacctggt gctgttgttg 102000
aaaaagcaac aattgactcc agcgccagca ctgagaggct tgtccttaaa attagcagga 102060
gctgttggaa ggtcgctgtt agctcttttg actggaacac actgttcccc aggtggcatg 102120
aggctgaata cagtgcaggg attggctctg ctctcaggtg gcctgctcca cgctcctgag 102180
ctccgggtgg aagctgtgac cattatttcc ttaacagaaa catatatagc agcattaact 102240
atgaacctta ttactgtgtg tgtgtgtgtg tatatgtgta tatatatata tgcacatatg 102300
tgcatatgtg tgcctatgaa cctgttctga gcactttaca aatgtcaatg tattttatcc 102360
tcccaacaac ccattttata aataagactt gaggcacaga gaggttacgt tactgcccca 102420
agatcacaca gctggagagt ggtgaggcca agatttgaac atatgtacca ttgtaccata 102480
tgtaccaact tttttttct ttttgggatg cattcttgct ctgtcaccca ggctggagag 102540
cagtggcatg accacggctc attacaacct caacctccag gttcaagcta tcctcccacc 102600
tcagcctctc aagtagctag gaccacaggt gcataccacc atgcccagct aatttaaagt 102660 tttttttgt ttgtttgttt gtttgtttgc agagatgggg tctccttata ttacccaggc 102720
tggtctagaa ctcctaggtt caagcaatcc ccccacctcg gccttccaac atgctgggat 102780
tacaggcatg agccactgca cccaggtcct ccctccttat aaaggtcgcc aagcacaatc 102840
ttgtgagcct ggccctatcc acacccatac gcaacatggt gtgtattttt caaacaaaaa 102900
ctgaatgaac acctctggtt tgggttcccc tcacacttgt cccgggtttg ttgactctgt 102960
gttgtgggcc tagacaaagc agtgtctgga gctcctagac ccagggacca gacagtctgg 103020
gttcaaatcc tggctcttcc acttctgcct gagtgctctc tctgaacctg tctttcttta 103080
tctataaaat ggagataatt tttttaaact catcacttgg tcaaactgct ttgagcatgc 103140
aaatgagttc atatgtataa acctcttaga atgtcccagg caaagaacaa cacttcactc 103200
agatcaacat ttatttagca tctactgtgt acccatgact attctaggtg atgaggagac 103260
cctctggttc ttatgaggta gtgaggtggg ggagggtgag aaccctaaac attaacgatg 103320
gtgtgttcgc aggtgggaaa atcagtaaag tcgggtaaag ggaatttggg agtgctgtgc 103380
tcaagtcctg gccctgccac tttctggggt gcaagataca gcattgaata gggtggtcag 103440
ggtaggcctt attgggaaag tgatatttga gcagacgatc tagatgtcgg cacatattgc 103500
tactgtttga tggtactaat atgagtttga gtttcacttg caagtatata tatatatata 103560
tatatatata tatatatata tatatatgtg tgtgtgtgtg tgtatatata tatgtgtata 103620
tatatgtata tatatgtgtg tatatatgta tatatatatg tgtgtatata tgtatatata 103680
tgtatatata tgtatatata tgtgtgtata tatatgtgta tatatatgta tatatatata 103740
tgaaatttgg tccatttatt tatgctgatc aattaattga tgttgaaatt ataattgaat 103800
gttttattaa taaacagata cccacatact attttttcag aaattgttag gttttggggt 103860
tttctttaga ttttgattat ttttatttgc ttaattttct tttttctttt ttttaatttt 103920
atttttccat aagttattgg ggtacaggtg gtatttggtt gcatgagtaa gttcttcagt 103980

-continued ggagatttgt gagaacctgg tgcacccatc acccgggcag tatacactgc accatatttg 104040
ttgtctgtta tccagtgctc acctcctact cttcccccca agtctctaaa gtccattgta 104100
ccattatttt actcacccac attctttggc ctgagatgct gagtggtcat gactcccaga 104160
tcccttcttg tttctgtatc aaagatcttt actaagatcc tggcctaggg aacctattcc 104220
ctttcctcat ccccaatggg agaaggggct tcttccccag cttatttgcc aactcatagg 104280
aaaggtatga aggagaggac tgtagttgtc ttgaagctgg tcagatgttg aagagatgat 104340
aatatttgct gatcaagaga gacaaagcaa tgctggaaga agaggctgtg ttagttaaca 104400
ccagctgcaa taaccaataa aaccaaaaat ctctggctta agagtatgca tgagtgagaa 104460
atcaacttct aaagtacaac tggtggccgg atgtggtggc ttatgcctgt aattctagca 104520
ctttgggagg ctgtggtggg agggtcgctt gaccccagta gtttaacgcc aacctgggca 104580
acacagtgag acaccatctc tactaaaaat aaaaaaataat aaagtgaaac tggtgagggg 104640
tgcaatgagg tggagtggtg ggtgactcaa atatggctcg actccatgca gtcactcagg 104700
gatccaggct gttggaggct ctccctgctt aaacatgtgg cttccaaggt tgttctaaga 104760
gcctacattg agacagcagc tggggaaaag ggaaagtgga gtgggaggta cttatgaggg 104820
ttcctggaag tggtgaacaa cacttctgcc tgcattctat tgggtggaat ttagtcatgt 104880
ggcccaggct agctgcatgg gaggctggga aatgtagtct ctgattaggc tgccatttcc 104940
cagtcccact tgtgaatctt tagtgggaag ctcaccatgt ttgcaccagg gattcagtct 105000
acctcccact catgcctcaa ctatgtatca ggcactgtcg taagtacttt acatatcagc 105060
ctacctaatg caaacaacta ctcagtgggt gctttattgg tcacatgtat tagtgagaac 105120
atggaaaccc agagccgtta aatatcttgc ccaaggtcac acagctagga agtggcagag 105180
ttggaatttg aatccaggaa atctggctgc agagccccac gcttagtata aattcattgt 105240
agtttagaaa gaggcagaag gaccctaaaa ttggcataat ccatttttttg gtccctaagg 105300 aactgactga attgactact tgtaaaagtg agtcctggac aggcaacagt ggctcaggtc 105360
tgtaattcca ggactttggg aggctgaggc gggcagatca cctgaggtca ggatttcaag 105420
accagcctgg ccaacatggc aaaaccctgt ctctaaaaaa atagaaaaat tagctgggtg 105480
tggcggtggg tgcctgtaat tccagctact caggaggctg aggcaggaga atcgtttgaa 105540
cctgggaggt ggaggttgca gtgagcaaag atcacgccac tttactccaa cttgaatgac 105600
agagcaagac tctgcctcag gaccgccatg gccccctggg ttctaggtca gagtttctcc 105660
gccacagcac tgatgacttt gggggctgca ttattagctc caaaatggga gctatcctgt 105720
gcactgcctc aacttacttg atgccagtag cgcccgcgcc ccagttgtga gaaccaaaaa 105780
tgtctccaca cattgccaaa tgtcccctgg gaggtgaaat cacccctggt tgagagtcac 105840
tgttctagat tgttaaatat tatcttacac tctagcacaa gtccaaggca aactgactta 105900
gaaattacca accttgcaaa aaatagaaga tttcttaaag tcagtgagca tgatggtggc 105960
aagctgctga aatcacaccc ccagacatta gcagatggga tctggacagt attcatctag 106020
ttaaaaattg acaaggactg ggacactgca ggctcttcaa aagagaatca tttgaataac 106080
aaggggtcaa gacaggggta attggtgaaa gcccctgctc ataatttgaa aatataaata 106140
ggcatcatga aaattcatcc tgcaaaagtc aaaagtcgaa tgtgcagtgt tatacatgat 106200
cagttgattt gggaggggaa attgcatgca cacacatgag agcttgcaca cccacacaca 106260
cacacctgtt caagtgtgtg tgccagtgct cagtgaggac catctcccca acctgtctga 106320
tcatcttgct ttggggtgac cctatgggtg aggcagaaat tcttggatca tagttttcta 106380
atgaatatta taattgttaa cttctgatgg gtgctgactt tttcatcttt gcaacactgc 106440
gtaggtattt ttactctccc cattttacag atgagacaac tgaggctcag aaagattgat 106500
tagctctaca cgaagccagg atccaggctt agcctggctc caggaatcat gttttgagtt 106560
acgtagcttc cctgattctg agggacctcc ccacttctga aatcttctac tgttactccc 106620
catggccctt tcctattgac cggaggcacc ccagctcctc actcgtccct tatcttatga 106680
aacatgacca tgatgtctga attcaaagga gagcctgggc tttgtgggga aaacgaagca 106740
gaaaaagaaa ggtggaggtt ggtggttgtt tttggcatgg tgaggagcct gtcgttgctt 106800
gaggaaagca agaaaggaga ttgctggggc ttggatccat ctctgggtgc ctgtgggtct 106860
gtctgtaaaa atgagaactg gtcgtgctca ttagaggatt tgaccgttag gccttgggat 106920
agcgatttgg gaactttttt ctgctaagac aaagaataat atggttcagg ttcattttgc 106980
tcctgctttc ccaagcccta catctcttct gggctttttt ttttttcctt ttctctcctt 107040
cttcttcttc ttcttcttct tcttctcatt tttggatctg gacttctgct gactcatctc 107100
tctgagcaag gaaggaggga ggaagtcaga attgctcatt aaccgttttc tttagtgact 107160
cagctgtgat tcacatttta attaatggag gagaaaaacc tgatcagtcc taaggcatct 107220
gcccaatcac gcataactcc aggctggtga taataataat acttgaaaaa agtggggtgt 107280
cctgaattaa actatggctc attccccaca ttagtcttga ggactccacc aggccctcta 107340
agttccaggt ctcaatgggg ctccctgaac cagagcagct agtccaagcc ccgagcagca 107400
tttctgcaga gttagtctga ggtcaggaca agaaacagag gctcaagccc tcctgggatc 107460
gcaggaggat catgggaatg taatattgtt tcctgagctg gtctttggct ataatcccag 107520
gctcaagcct ggcctccctc ccctcggggc ctgaaatttg tcagagccta ttgcaggggc 107580
agcttctgtg ctttttgttt gcccagagaa tgagaaaagt ccagataatc atgaccgcta 107640
cttcctgagc acttactatg catcaggtgg tgtgctcagc acttctcatg aatgatcacg 107700
ttgaatcctc actctgtcca caaaaagaaa gagcttttat ataattctcc aacctcccta 107760
tgaggaaact gaggcttggc aattgcccaa tgtagacaat tagtaaataa tcaggcagga 107820
tataaaccca accctttccc acctgggagc cagagcttgc atctactata cttctctgct 107880
ttccagtcag ctgcaaagaa aaattggaag ctgatagctc attcaacaaa cacttattga 107940
acccttccac ctgctcagcc ctgttctaga caccagagat ccatcagtga accaaagagg 108000
caaatccatg gtctcatgaa actgacaatt tacctgccca agtgtattag ttactgttta 108060
taagttccta ttaagtgtat tagatatgct tgcagctgta acaaagaatc ccaacatgca 108120
taagggctca aaacaataaa aatttcgttc ttgcacagat aaagttcaaa aggtgtattc 108180
tttttttttt tttcttttgc gacggagttt tgctcttatc ctccaggcat gagtgcaatg 108240
gcccagtctc ggctcactgc aacctccacc tcctgggttc aagcattctc ctgactcagc 108300
ctccccagta gctggaatta caggtgcccg ccaccacacc tggctaattt tttgtatttt 108360
tagtataggt ggggtttcac catgttggtc aggctggtct taaactcctg acctcaggtg 108420
acccacctgc ctcggcctcc caaagtgctg ggattacagc cgtgagccac cgtgcctggc 108480
caaaaaaaaa atgtattctt aaacagcagg cacctctcct ctaagcagta agtcaggggc 108540
ccaggcttgt tccatattgt agctcctcat cttcaaccca tggcttccaa agtctccatg 108600
cttcttgata tcaagccaca gaagggaaaa gagcatgaga agggcacagg agaaatgttt 108660
ctgggacaga cccagaagta gtccatatga cttccatcta cctcccactg gctagagctt 108720
acatggcggc acccacttgc agagctggga aatggagtct aactgagcat ccaggaagga 108780
gagacagaca tgagtctttg cgtgggtcct cactgagaat caagctccac attttgatcg 108840
atgtcaccag agcgtacatg gcggcgccca cttgcagagc tgggaaacgg agtctaactg 108900
agcatccagg aaggagagac agacatcagt ctctgcgtgg gtcctcactg agaatcaagc 108960
ttcacatttt gatctgtgtc acctccttgc aagccctacc ttaggacaat tttaagggac 109020
attcctatct tcttccaccc ttaggacagt tttaagggac actcctgagt tcttccaccc 109080
acctcctctg tttcttgggc ttccagctct caggatttgc ctttgcctta caatggggtg 109140
aagcaagaat ctggaagaat gtctctcccc acaatttgaa gtcttatttg aaaaaaagca 109200
gtagagcatc cctccctctt gaggtaggga aatctagaat caaatcctgc ttctccagac 109260
tttgacctca gaaactgggg ggacttcaag gtcttcaggt gggcagcttt catgaaccat 109320
tcattcctcc cacctcatac caatcagggt cctaacagga aaaagaatta acttctagat 109380
ggttcaaaag aagaccatgc catgaagaga ctccttaaag agataggaac aggtgagaga 109440
aatagataac ggctgtttga ggtcctcaga gagaagccat cgcgagccct acatttcctg 109500
gaacccagtg gaggcagagc tgtgcagaag ggactactgt cagaaccagg gagggagcag 109560
ggaagcaata ttccaatctc tttccctccc ctcatcttct gccagcgctt cccctcagcc 109620
aaaccaaacc ggaaacggag caaagcattc tgggagttgt agtcttcaag ggtccgcctc 109680
gagggcacag agcccgctgg agcattgacc tagagggcac acagggaatg actagtttgc 109740
accatcatgt gacggactgc acgccctcga ttatgtaatc cactctataa ttcaactgca 109800
gagctgcatg gtacagcagg atagccacta gccacacgag gctatttaaa tataaatgta 109860
cattcattaa aatttaacca aatgaaaatt ttagccactg agccccattt caaatgctca 109920
ttagccacac gtggctcttg gctaccatat tggacagatc agaatagaac atttccatca 109980
tcccagaaag ttctaggggc cggcgcagct gtggtgtaac ctgagcccat gcatgttatg 110040
gaatggagaa gagagaaaac agcacaagag gcagttttga agggagacag agagctgtgg 110100
atcagtaggg aggagactct ctaggcaaag gagcagttga gaagcaagaa agttgagtga 110160
gctgctttgc tgcgatggag gcttccctca cggggaagag tagagtcaga aagctttagt 110220
tcaagttcag ctctgaaatg aaccaatgag tgttctgaca agacacctgg ccttccggaa 110280
ccttggtttt gtagtggcca agggcttgac cctctgaagg ttcactgaaa aaaatcaact 110340
cacaaggcat attaattgga gaaaaggcag gcagatttat ttaatgtgtt tgcacgagag 110400
ccttcagaat gaagacccaa agctgcaggg gaaattgtcc gttttttaag cttaggttca 110460
acaaagtatg gacagcggtg tagaaatatg attgaacaaa aagtgtacaa tgtaaatgct 110520
aatagactga gtggggaaac ccaaaaaggg ctgtcttgat tctccttggt ctctctgagc 110580
atgcatttct tccgggtatg ggacaagacc ctctctggaa tggagggggg gctctcttgg 110640
ttctccttgg tctctctcag catgcattcc ttccgggtat ggggcaggac cctctctgga 110700
ataagggggc tgtcttgatt cttcttggtc tctcagagca tgcattcctt ctgggtatgg 110760
ggcaggaccc tctctggaat gggatcctta taacctacgg tcaaataacg taagttagat 110820
aatttctttt tttttttttt cttttttttg agacagagtc tgattctgtt gcccaggcta 110880
gagtacagtg gcacaatctc ggctcactgc agcctctgcc ttctgggttc aaatgattct 110940
cctgcctcag cctcccaagt agctgggact acaggtaagc accaccatgc ccagctaatt 111000
tttgtatttt ttagtagaga cagggtttca ccatgttggc caggctggtc tcaaactgct 111060
gacctcaagt gatccaccac ctgggcctcc caaagtcctg ggatttgtaa tcccagcatg 111120
agccactgtg cccagccaga tcatttcttt ttctttttct ttttcttttc tttttttttt 111180
tttttttgag atggagtctc actctgttgc ccaggctgga gtgctgtggt gcaaactcag 111240
ctcactgcag cctctgcctc ctgggttcaa gcaattctcc tgcctcagcc ttccaagtag 111300
ctgggactag aggtgcgcgc caccatgccc agctaatttt tgtattttta gtagagacag 111360
tgttttgcca tgttggccag gctggtctta aactcctgac ctcaagtgat ccacccacgt 111420
cggcctccca aagtcccggg atttgtaatc ccagcatgag ctaccacagc tggccagata 111480 attttttat aactagtttt tacaaagaaa ggtggaggga aagttagagt aacattttta 111540
ggtgttaggg ctgactttgg ggaaaagagg tctggtttct acgacccgcc ttagggaaga 111600
gggattctag tttttgtggc tagccccagg ggagaatggg actaagagat agaagggcag 111660
gagaaggtca gagaaaaact tttgcttctg tggctgcttc ggagaacttc attttggggt 111720
attgttttct gagccccaac agtttgctta tcagtgaagt gggtataggc gcccacctcc 111780
cacagtgacg atgctgtgaa cagggctttg gaagagtaga actatgaaat atttgttgtt 111840
gccttgtggg gaaatggtcg ttaaagccaa aattgttcaa gagaagaagc aggaagagtt 111900
cctttctttc ctgcaggtat cctcttaagc tgagtcttca gaatcccctg acaacgttta 111960
atcaacactt tattaaattc accccaaccc tgcttcaaac cttcacctgg tcctcgagat 112020
cttccaactg tttcttgatg aagttagcag gcaattgtat ggcgggatca tcatctcatg 112080
ttttgttttg tttttttcct ttttaccctc tgactttgag aaatccttgt ccttttactt 112140
ttccaaacct gagagcattg cagagaagtt agaattgagc aggacatggg cttaagaccc 112200
agcccagcca tgtgctagct gtgtgaactc gaagcagtga ccccacctct ctgacctgga 112260
aagtagaggg aatgatagga cccaccaccg ccacacttgt agggtcatca tggggattga 112320
ataaaataat gcataagact tggcccacag caagcactca agaaatgtta gctacttcct 112380
aaatatattt ttaacctttt attgaatata acatacatac agaaaagcac atgtatcata 112440
caagtagagc ttgagtgatt ttcaaaaact gagcccagtc atgtaaccag cgcctagttc 112500
aagaaacaga acatagccga gtgaggctga ggcaggagaa tcacttgaat ctgggaggca 112560
gaggttgcag tgagcagaga tcatgctatc gctccccagc gtgggcaatg ggggcggagg 112620
ggaagagaga gagagagaga gagagagaga ggaaggaggg agggaaggaa ggaaggaagg 112680
agggagggag ggagggaagg gaaggaaggg gagagagaga aaaggaaaga aaagaggaag 112740
acagaaagag agagagaaag gtaaagaaag aaaaggaaag aaagagaaag aaagaaaaga 112800
ggaagacaga gaaagaaaga gaaagctaaa gaaagaaaaa aaggaaggaa ggaaaatagg 112860
gagggaagag gaggaggaag aagaagaaga aggggggag ggagggaaca gctgcagctt 112920
cgaggaagga aggagggagg gaaggaagga aggaaaggaa ggaaggaaaa aaaaacagca 112980
ccaacgttta gaaacccccct tgtgcctctg aggtcaccag taactccatc ctgacttcaa 113040
acagtctaga ttagttttgc ttgtttttga actttaagca catggggtca tacagcatgc 113100
atgcattgac ttctttccct tgacgttgta tgtgtgagat tcatctgtgc tgttgctgtt 113160
catttgttct catcgctgtg tgtgctgaac cacctgttca tttactctac taatggtggg 113220
cagtttggtg ctttctactt tggggctatt ccagagaaag ctactttgaa cacactcaga 113280
tatgtctgtg ggtgaccact cttcatattt ctatgggaga tattcctagg accggaacat 113340
ctgagtcaga gggaggaatt ggtttagctt tggtaggaac tgcctaacaa ttggccgggc 113400
acagtggctc atgcctgtaa tcccagcact ttgggaggct gaggggggca aatcacttga 113460

```
gctcaggagt tcgagaccag cctggccaat gtggcaaaac ccctggccaa catggcaaaa 113520
ccccgtctcc gcaaaaaaat acaaagatta gccgagcatg gtggcgtgtg cctgtaatct 113580
cagctactca ggaaactgag gcaggagaat tgcttgaacc tgggaggcag aggttgcagt 113640
gagcagagat tgcactactg tactccagcc tgggtggcag aatacatgaa actccatctc 113700
aaaaagaaga aaggaaggaa ggaagggaag gaaggaaagg aaactgccca acagttttcc 113760
caagtgtttg ggatggaagg aaggaaggaa ggaaggaaaa gaaactgcct aacagttttc 113820
ccaagtggtt ggaccagtta aaactcccac cacctgtgaa tgagagtttg tttttatttt 113880
gctcctggag tgcctctcct gtagcaggtt cccactgaat gtctgggaat tcaaatgtaa 113940
tgcacttgtt catttcctca agagcttcac tccatcaatt ggattcatcc attggctctc 114000
ccatctccac tgacactatg ttctcacctc tatttggaag acatcctgcc tccacctgcc 114060
caagtcacat tatcttctca ttccagcctc tcaaggagag ttttctcttt caccacctcc 114120
tctagccctg gtgattggca aggtctcgca acagtaccct tcaaaacact catgactgtg 114180
aatgcactgg ccttcactaa gtttcccatt cttctctttc tttctttttt cttttctttt 114240
cttttttttt gaacagagtt tcactcttgt tgaccaggct cgagtgcagt ggcacaaaca 114300
cagctcactg tagcctcaac ctcctgagct caaggtatcg tcctgcctca gcctccttag 114360
tagctgggac cacagacatg caacgttgtg cccagctgat tttctttttt ttcttttttt 114420
tttttttttt gagacatggt ctcaccctgt caaccaagtg cagtagcatg atcacagctc 114480
actgcagcct tgacctcccg ggctcatgcg attctcccac ctcagcctcc cgagtagctg 114540
gggctacagg cacaagccac catgcctggc taatttttgt acttcttgta gagaccaggt 114600
ttcaccatgt tgcccaggct ggtcttgaac tcttgggctc aagcagtcct cctgcctcag 114660
cctcccaaaa tgctgggatt acaggtgtga gccagcacgc ccggccatgg ctaatttctt 114720
catttttggt aaagacaggt ctcactttgt tgcctaggct ggtcttgaac tcctggactc 114780
aagcaatcct cctgtctcag cctcccaaag tgctaggact accgatgtga gccaccgcac 114840
ccggcaattt ccccttcttg acttctccag agctctcatc cctctcgagc tcctgtctct 114900
tctagaatca cttacctcac caccttatgg ggtttttgcc tctgttccta ctcctcttta 114960
tttaagaaaa cactgtactt taagagggct tcagaaacca cccgaaatag aaacatgtcc 115020
ttttgttcaa tcctttactt taaaagacaa ataaaatgaa gaattgctct ccatgtagaa 115080
ggttaaggag cttgggagga ccttctgtga gtggggagaa ctttacatta aaggaaaaaa 115140
aatgctggag aatagctgtg aacccaggaa gggagaagga cttcctccac tgaacttgta 115200
aagcacaaac tctaaggcaa aaaaagacat gattacatga aaactaagat atttgttcaa 115260
ataaagatgc aattggggcc aggtgcggtg gctcacgcct gtaatcccag cactttggga 115320
ggccgaggca ggcgaatcac gaggtcagga gatcgagacc atcttggtca acatggtgaa 115380
accccatctc tactaaaata caaaaaatta gccaggaatg gtgtcacgtg cctgtaatcc 115440
cagctacttg ggaggcttag gcaggggaat tgcttgaacc agggaggtgg aggttgcagt 115500
gagctgaaat cacgccactg cactccagtc tagcgacaaa gcaagactcc gtccaaaaaa 115560
aaaagatgca atagcaggtg gttcgggaac caaaccttac atccagatgc tggttgtccc 115620
atttcctgtg aatccttggg tgagttatca acctctctga gcctcagttt cctcgtcaat 115680
aaaatggaga aaatagtatc tacctatgga attgttgtga gttttgaatg agttaatatt 115740
tataaatcat ttagaatagg aattagcaca tggtaaatag tggatagaat cataaaaaaa 115800
aaattgatca ggggttaact tctaactgct gtttgttata gaggtcccta gcactgtgtg 115860
```

```
gtcattttaa atttagatga tttagaatta aatgaaattt aaaactcagt tcttcattca 115920
cactagccac attttaagtg ctcaaaaccc acaggtgact agtggctacc atatttggca 115980
gcacagattg agaacagatt tatcatccag aaagttctgt cagacagtgt tgatcaaggc 116040
tacatgaggg tctgggtgca gtggctcaca cctgtaatcc cagtgctttg gaaggccaag 116100
gtgggaggat cactggaggc caggggtttg agaccagcct gggaaacaga gagacctcat 116160
ctctaccaac attttaagaa ttagccaggc aaagtgttgc atgcctgtag tcccagctac 116220
tcaggaggct gagacaggat tgcttgagcc caggaatttg aggctgcagt gaactatgag 116280
cgcaccgctg cactccagtc tgggtgacag agtgagacct gtctctaaac ataaaaaata 116340
aaaatgtagg tggggcatag tggctcccgc ctgtaatccc agcactttgg gaagccgaga 116400
tgggcagatt gtgaggtcag gagatcgaga ccaccctggc taacatggta aaaccgcgtc 116460
cgtactaaaa ataaaaaaaa attagccagg catggtggcg catgcctgta gtcccagcta 116520
ctcgagaggc tgaggcagga gaattgcttg aacctgggaa gcagaggttg cagtgagctg 116580
agattgcgcc actgcactcc ggcctgggcg acagagcgag actctgtctc aaaataaata 116640
aataaataaa taataataaa gtaaaaataa aaatgcaaag actacctgag ggaatgtctg 116700
caagtcaacc agaataacac agcaacccca ataggaaaac aggccgaaaa tgtgaacagg 116760
cggatcaggg aagtgaagtc tgaaaagcta atcagcctat gacatggtac tcaaagtcat 116820
ttgtaaccag aaagatggaa atgaaagcag tatctctgta cacctttaat attggggaaa 116880
aaatatgtga ataagccaag ggtttccagc gatgcgggca cagaggaaag tcttgcacca 116940
ctcaaagggg tgtggcccag ggaggccact ctggagacat atcggtagta ctcagtccag 117000
tgaggtccag caccatcagc gcttatgtcc ccaggcatcc atcccaggga cattcttacc 117060
aggtctgtta ggggcaggta cgagaatgct tactccagca ccatctatat aaggggagct 117120
gaaggccacc tggtgtccct cctggagacc aggaggcggc atgtgacagc ggcacccatg 117180
gagcaccaga atgagtgaga gctccagacc gcatatccga cagatactac gggatggggc 117240
ttttagaaat atggttgttg ccgggcacgg tggctcatgc gtgtcatccc agcactctgg 117300
caggccaagg cgggtggatc acctgaggtc aggagttcga gaccagcctg gccaacatgg 117360
tgaaaccctg tctctattaa agatacaaaa attagctgga cgtggtggcg ggtgcctgta 117420
atcccaacta ctcgggaggc tgaggcaaga gaatcgcttg aacccaggag gcagaggttg 117480
cagtgagccg acatcgtgcc actgcactcc agcctgggtg acaagagcaa aactctgtct 117540
caaaaaattt aaaaaacaaa aaataaaaat atggttctgg gtgaaaacag gaaacaacag 117600
aatgtgtcta acttcatcct gcttatgtca gttaaaaata gacacactca aaatatcgca 117660
cgtgtttttg cgagaatgca ctcctataag gccaaattaa acattctctc agttgtctct 117720
gggagggaga agaatgaaag tagggtatag agagatatag gggaattaat gcatgaatga 117780
atgaaggtat aaacaagaga caggcgtcat acagaccaaa ggtaaagata tcccgtaacc 117840
tgaggagagc aaagaacttg actctgcatt tgaagattca gaaaatgaat ttcagaaata 117900
gttttctcgc cagggggtgg ctcacgcctg taaccccacc actttgcgag ggcgaggcag 117960
gtggatcact taaggtcagg agttcgagac cagcctggcc aacatgatga aaccctgtct 118020
ctactaaaaa tacaaaaatt agccaggcat ggtggcatgt gcctgtaatc ccagctactc 118080
aggaggctga ggcaggaaaa tcacttgaac ccgggaggca gaggttgcat tgagctgaga 118140
tcacaccatt gcactccagc ctgggtgaca gagcaagact ttgtctcaaa aaaaaaaaaa 118200
```

aaaaaaaaaa aaaaagaaga ggaagaaatc gttttttcaa gaaggggaaa gctgggtgat 118260
ttaagaatga acttgaagag gatcactcag tcctcaacct aggagtggca agaatataga 118320
ctgtatggga agtggttctg ctccttggta cccatcttag aaatatttgg cctgagtctg 118380
taagaggcag gtactttatc taacctgagg ttagggggcc actacatccc catcccctcc 118440
cctgctttct aaccatgcta acatcttctc actctcctgt ctcctctcct tctcactccc 118500
ctaatctgcc tattcacatt ttgggcctgt tttcctattg ggttgctgt gttattctca 118560 ctgatttgca gacattcctc tgtgtcatct ttttaatttt gttttaattt ttagaggcag 118620
gatgtcattc tgttgcactg gctgtagtga cgtagctcac tgcagcctca aactcttggg 118680
ctcaaactcc tgtcctctgc ctccacttct caactggtaa cctcacttct cttcatgagg 118740
tctctccagc cccagggcct ttgcacatgt tcccctctct tctgagtggc atatggtagt 118800
tgctcctctg taaatattta ttgacatcct gacttccaac cagcagagaa ttgacctcct 118860
tcccatgctc aggctagtga aggcatgagt ttggctgagg tcccagtggg gaaggtgagt 118920
ggggtggcag agttaaccag gagcagcatg gtagaatggg taaaaccaga cgtagcacgc 118980
aggcaccaca tgttagctgg acaagtagtt taaccccatg ggtctcaatt tccccatcaa 119040
tgaaagggag aatagaacaa gtccctggta agcagcataa aatgagctct cagaatgtaa 119100
agtaacaagc acacaacctg gaagagaata catttagtga atattggctc ctttaatcag 119160
caggttctga tatgacttag ctacaattaa gaaaataaaa atggaggccg ggcgcagtgg 119220
ctcatgcctg taatcccagc actttgggag gccaagacgg gtggggtgga tcacctgagg 119280
tcaggagttt gagaacaggc tggccaacat ggtgaacccc atctctacta aaaatacaaa 119340
aattagccag gcgtggtggc gcacgcctgt agtcccagct actcgggagg ctgaggcagg 119400
agaaacattt gaacccagga ggtggaagtt gcagtgagcc cagattgcac cactgaactc 119460
cagcctgggc gacagagtga gatttgtctc aaaaacaaaa gaagtctgga ggccaggagg 119520
ttggttgcag ggttggttcc ttggctcaac aatgtctcca aagagtcctt ccatctttcc 119580
actctaacat cgtcactgta aggacttttt ttaacattta ccactcacag ccccaagacg 119640
actgcgtcag ttctttcttt ttttccttca gacagagtcc cgctctgtcg cccaggctgg 119700
agtgcagtgg catgatctcg gctcactgca acctctgcct cctgggttca agcgattctc 119760
ctgtctcagc ctcccgagta gctgggatta caggtgcctg ccactgcatc cggctaattt 119820
tttgtatttt ttttagtaga gatagggttt caccatattg gtcaggctgg tctcaaactc 119880
ctgacctcag gtgatgcacc tgcctcggcc tcccaaaggg ctgggattac aggcgtgagc 119940
cactgtgccc ggccgatgac tgcctcagtt ctaaggtact tacccagcca tccacgtaga 120000
cagacacaaa agcatccggc caaagaagag ggagaggaag ggctgtctct taccatgtga 120060
ctcatctcac ggggaaaaaa tccttttcca gaagcaccca gcagattttt cacccagatc 120120
ctgttaggcc tacgaatggg tcatgtgaca agtgctctta ttgcaaggaa tcttgggaaa 120180
aagagactat taggcatttt ctgcctcttt gatgggaggt gggctctgcc agtaaggcgg 120240
gtagtggtgg tggctcttgg atggacaact gtgtcttcca ttcttcttct tcttttttt 120300 tttttttaa gagacaaggt ctcactctgt tgcccaggca gaaatgcagt ggcacaatca 120360
cagctcactg ctgcctcgac ctgccaggct caggtgatcc gcccacctta gcctcacgag 120420
cagctggagg agtgtaccac catggccggc taatttttat attttttgta gagatggggt 120480
ctctttatgt tgcccaggct ggtcttgaac tcctgagctc aaacaatcct cctgcctcag 120540
cctcccaaag tgctgggatt acaggcataa gccaccacgc ctggactctc ttctttaaat 120600
actgagcctt ccacctcttc tagaatatac tctgttaatt atcaaccaca cttttctaca 120660
tttttgcttc attattcatt cagtaaacat ttattgagtg cctactgtat gccaggcaca 120720
gctttaggtg ctggagatgc tatgaacaaa acagatgaaa atttctaaaa aataaaataa 120780
aaaataaaaa taaattttgc aaagccaggc acagtggctt aggcctatag ttccacctac 120840
tcaggagtcc aaggcagtag gatctcatga gactgggagt ttgagtccag cctgggcagc 120900
atactaggac tctgtctcta aaaaagaaaa gaaggccggg cgcagtggct cacgcctgta 120960
atcccagcac tttgggaggc cgaggcaggt gaatcgcaag gtcaggagtt tgagatcagc 121020
ctgaccaaca tggtgaaacc ccgtctctac taaaaatgta aaaattagcc aggcatggtg 121080
gcaagtgcct gtaatcccag ctacttggga ggctgaggca ggagaatcgc ttgaacctgg 121140
gaagcggagg atgcaataag ccgagatcgt gccactgcac tccagcctgg gcaacagaat 121200
gagaccctgt ctcaaaaaaa aaaaaaaaaa gaaagaaaga atagaaaata tctgccctac 121260
ggggatggac atgctagaac atcaaagtcc aatggaactt tctgcactga tgaagtatgt 121320
atgtatgcac cagccacatg tggcttggga gcacttaaaa cgtgactggt acaagcgaat 121380
ttttcattta atttaaatga atttaaatct gtatttaaat agccatgtgt ggctagtggt 121440
tactttattg ggcggtgcag ctctctaaag gccaagagat acatcatcaa cttctctccc 121500
ttgacccata ttcagttctc tcccaccctg aaaatctcct ctcctaccca ggctcacatt 121560
tccagttctt ctcctcttgt tctccctcaa ccatcagccc ccgcaagact gacgtgaccc 121620
tgatgccgta tgaaatgcat tcttcatcct ttactcttac tcacctctgt gcggccctgg 121680
agaccagtga cctctccttt ctcaaaatac tttatttctg tgtgtttttg ttgttgctat 121740
tgtttttggg gggttttctt gagatggagt ttcactctca tcacctaggc tggagtgcag 121800
tggtgcgatc tcagcttact gcaacctctg cctcccaggt tcaagcgatt ctcctgcctc 121860
agcctcccaa gtagctggga ttacaggctc ccgccaccac ggctggctaa ttttcttgta 121920
tttttggtag agacggagtt ttgccatgtt ggccaggctg atctcgaact cctaacctca 121980
ggggatccac ctgcctcggc ctttcaaagt gctgagatta caggcatgag ccaccgcacc 122040
cagcctcaaa atgcttttga acttgactgt caggtatgcc attctccaca ccagtctcct 122100
cccatgtctg tgtcttctcc ctctccactg gggacccttg gctttttcca cttcactcat 122160
ctaccctggg ttatctggtc ttccataacc ctgtcctctg ccacacctca cttattcacc 122220
caccacaata tttattgagt actcactagg ccatgaaaga tgctatacaa aaaaagcccc 122280
tgtcctcgtg gagctgacat tctagaagaa agcatgaata ataaatacga cttaataaac 122340
agtacggcca ggcatggtgg ctcacgccta tcatccaaac actaagagac caagatgaga 122400
ggatcacttg aatccaggag tttgagacca ccttgggaaa cgtactggga ccctgtctct 122460
acaaaaaaaa tattaaaaat tagctggata gggtaatgca tgcctgtagt tccagctact 122520
tgggaggaca aggtggaagg attgcttgag cctgagaggt caagtccgca gtgagctgtg 122580
actgtgcact gcacgccagc ctgggtgaca gagtgagatc ctgtcttaaa aataaataaa 122640
taaacaaaca aacaaacaat ataattccag agagtgaaga ggcaggatct ctttagctag 122700
gaagttgagg gatgttctct ctgagaaggc agaatctgag tttcaacctg aagaattcga 122760
agaggccagc taggcaaaag atgagagttg aaggaatggg gacggcagag gagacagcca 122820
atatagtaat tctcaataaa gcagaaagtg agcttttcct gctggcagaa cagaaaggaa 122880
gtcggagtgg ccagggtgtt gtgggacaag gtggtcagca ggagtcacat cacgcaaggt 122940
catgtggtca tggtagactt taaattttac tccaagcctg atggaagcca ttggaagatt 123000
ttaactaagg agtgacggaa aactggcatc tcaaactcaa catgtctaca acccagttct 123060
tgatctttga aaccttcttc ctccatcttc cccatctcca ttgacagcaa cttcatcctt 123120
cagttagctc aggccaaaac cctggagtca cccttgatac ctctctcctg ctccacactc 123180
agtctttcca ttggaagccc taggggctgc catattgttc tccatagcac ttcacaccgt 123240
ctgacatact atatcttttc ccactattgc tttgtccttg gtagcatctt taggcactct 123300
ctgaatatct ggcacatagt acgtgctcac taaatccttg ttgaataaat gaatgaacat 123360
cactccgtgg tcctttcaga accagagcca ttcttctctt tcttcaccac cgttgcccct 123420
caccccgccc aactagtcac aggagttgaa ggatgacaca gtagagaact gggattctgg 123480
agtcctgtgg ctggtctggg gttcgagttc ttactcagtg gtaggaacct ccatgtggga 123540
ttaacttatc tggtctttag tttcctcctc tgtaaaatgg gcctcaaact gccaaccgct 123600
gggatgcagg gaggatttga tgagcccagg caggctccct ggagcacagc aatcaatggc 123660
agctatatat aaaccggggc ctcttttgta ctcccactgc ctttgtccta gttccagccc 123720
tcattacacc agcctgctct tgcggctccc tcctaacttc tgctccatca ccaccaatct 123780
gtcctttcag ctgtcaggct tgtcttctga acgccaaccc taatcacatc ccttcctgct 123840
ccaaaacctt acatgactct cactgtccac aggacaagac ccagcctcta gttgacagcc 123900
tccactgtcc agcttaccca acctctcccc taccacatac cctgagtgga gccttctgcc 123960
tccatagggc tttcttagcc agagaagcct ccccttatctt cctgttctcc tcctaattcc 124020
ttcttatcct tccagggagg aggctgtgag gtaatgcatc ttgggagcca gctgggattg 124080
cacagggtgg tgagattatc tgcatttccg aggcttgaac aagttaaggc aatgggaaag 124140
gtcacacaat gagaaaatgc agggccagga tttaacccgt ctgagatgtt ctgactgtgc 124200
tatgctgcct ccccggacat gagctctgcg ataatgctgt ccccaggctg taatcattcc 124260
ctctttcatc cctgcctcct ctatccctgg ggtcagaggg acttgtagtt gaatctctca 124320
ctcactcatt ggtgtggtct ctccctaaag cagggtggag tttgtcttag cgttatcact 124380
gcatccagca caacctccct ggtccaggct tatcagcgtt caactgcgtc aatgcagttg 124440
cctcctcctc aatctcccag cttccggcct tgccccctag agagatcata ttttaataca 124500
agtcagatta catccctcct cccctcagaa ccctccatgg ctcacacctt actcagagaa 124560
aaagccaaag tcctctccac aacccacaaa gccctgcacc atccatcacc tcactgcctt 124620
cgtcccctca caccctcccc cttgctcgct ctgcttcagc cacaccaact catctctgtt 124680
tctcaaatac accaggcatg gcctagctat taaatgcacg gtccagcctg gtgcatttga 124740
agaacacgga tgaattggtg tggctggaac agagtgagtg agggggagag cgggaggagg 124800
acctttgcac cagctggacc tttgcaccgg ctgttccatt tgcctagagt tttccctgac 124860
atattcatat ggctcactct cttgcttccc ttgctttctc ccagtcttta ttcaaatgtc 124920
tatttctctg cacttgtgct gtttgataca gtcaccgctg gccacatgtg gcctttgagc 124980
acttcagttg aaacacatga aagtgtagaa tattgaccag attccaagga aaaccatgtg 125040
caaaatatct tttatctctt aagatacagg gtctcgctct gtcttccagc ctggaatgca 125100
gtggcacgat cacagctcac tgcagcctca aaatcccaaa ctcaagtggt cctcccacca 125160
acagcctccc gagtagctgg gattacaggc acacaccaca atgccccgcc cattttttta 125220
attgttatta ttttttttaa tagcgacaag gtcttgccat gttgctcagg ctggtctgga 125280
actcctggcc tcaagcgatc ctcctgcctc agcctcccga gtagctgaga ttacaggcag 125340

```
gagcttttgt gcccagcagg tctacgatct tcttagaatg cttcaggctg ggcatagtgg 125400
ctcatgcctc aaataccagc actttgggag gccaaagcag gcagattgct tgagctcagg 125460
agttcgagac cagcctgggc aatatggtaa aaccctgtct ctccaaaaaa aatacaaaaa 125520
ttagctgggc ttggtggctc ccacctgtag tcccagctac ttaggaggct gaggaaggaa 125580
gatcacctga gcccaggagg cggaggttgc agtgagccaa gattgagcca ctgcactcca 125640
gcctagacaa cagggagacc ctgtctcaaa ataaataaat aaataaataa ataaataaat 125700
aaataaataa acaaacaaac aaacaaacca ataaatgaat tttacctgtt tctttttact 125760
tttttaatgt ggctactagc aaattttaat tttttttttt tttttttttt tttttgagac 125820
agagtcacgc tctgtcaccc aggctggagt gcagtggtgt gatcttggct cactgcaacc 125880
tccacctcat gggttcaagc agttcgcctg cctctgcctc tgagtagctg ggattacaga 125940
tgcccaccgc cacgcccagc taattttttg catttttagt agagatggag tttcgccatg 126000
ttggccaggc tggtctcgaa ctcctggcct caagtgatct gcctgcgtcg gcctcccaaa 126060
gtgctgggat tacaggcatg agccaccgcg cctggctata aaatttcata agtagctctt 126120
aatagatttc tcctgggcag tgctggtcta aacacttttt tttttttttt ttttttttga 126180
gacggcatct tgctctgtca ccaggctgga gtgcagtggc gcgatctctg ctcactgcat 126240
cctctgtcac ccgggttcaa gctattctcc tgccttagcc tcccaagtag ctgggactac 126300
agacacccgc caccacgccc agctaatttt tgtattttta gtagagacgg gttttcacca 126360
tattggccag gctggtctcg aactcctgac cttgtgatcc gccagccttg gcctcccaaa 126420
gtgctgggat tacaggcatg agccaccgca cctggctata aaatttcata agtagctctt 126480
aatagatttc tcctgggcag tgctggtcta aacacttttt tttttttttt ttttttttga 126540
gacggcatct tgctctgtca ccaggctgga gtgcagtggc gcgatctctg ctcactgcat 126600
cctctgtcac ccgggttcaa gctattctcc tgccttagcc tcccaagtag ctgggactac 126660
agacacccgc caccacgccc agctaatttt tgtattttta gtagagacgg gttttcacca 126720
tattggccag gctggtctcg aactcctgac cttgtgatcc gccagccttg gcctcccaaa 126780
gtgttgggat tacaggtgtg agccaccgcg cccggccctg taacactttt aacactgaac 126840
tgtttgcctt ccaggtggta aagagcaggt gcctttactg atagaaatgt caccactccc 126900
ttcatcccgc cagccccatg tcactgacgc gtcctttccc cttgctctgt ggtaactttc 126960
tcctaagcac tcatcgccct aacatctgtc atacaggtat acctcagaga cactgctggt 127020
ttggttccag gtcgccataa caaagcgaat attgcaataa agggagtcgt gccttttttg 127080
gtttcccagt gcacataaaa gttatgctta cactatagtc tgttaagtgc atgatagcat 127140
tatgtctaaa aaaaaatgta cataccttaa ttttaaaatc catcaaggct gagcacagtg 127200
gcttgtaatc ccaacacttt gggaggccaa ggcaggagga ttgcttgagc ccagggattt 127260
gaaaccaggc aacaaagtga gaccccgttt ctacaaaaaa attcttttta aaaatagctg 127320
ggtatggtga cgcatgcctg tggtcccagc tacatgagag gctgaggtgg gaggctcact 127380
tgagcctgag agattgagac tgcagtgagc tgtgatcaca ccactgcact ctagcctggg 127440
ggacagagtg agaccgtatc tctcaacaaa aattaaaaaa aaaaaaaaaa aaggctgggc 127500
acagtggctc atgcctgtaa tcccaacagt ttgtgaggcc aaggtgggtg gatcacttga 127560
ggtcaggagt tcaaaaccag cccagccaac atggtgaaac cccgtctcta tgaaaaatac 127620
aaaaaaatag ccgggtgtgg tggtgcacac ctataagccc agctactcgg gaggctgagg 127680
```

```
cacgagaatt gcttgaacct gggaggcggg ggggagattg cagtgagccg agattgcact 127740
gctgcactcc agcctgggtg acagactgag actctgtctc aaaaaataaa taaataaata 127800
aataaataaa taaatgtttt attactaaaa aagttaacaa tcatctgagc cttcagtgag 127860
tcctcatctt gctggtgaag ggtcactggc tcagtgttga tgggtgctga ctgatcgtgg 127920
gggtggttgc tgaagattgg ggtgcctgtg acattttctt aaaataagac aagaaagttt 127980
tccgcatcca tcgactcttc ctttcacgaa agatttctct agcatgagat gcttgttgac 128040
agcaatttta cccacagtag aacttttttc aaaattggag tcagttcttt caaaccctgc 128100
cactgctttg tcaactaagt ttatgtcata ttctaaatct catgttgtca ttttaacagt 128160
gttcacagaa ttttcaccag gagtagaatc catctcaaga aatcactttc tttgctcttc 128220
cataacaagt aacgcctcat gcattgaagt ttgatcatga ggctgcagca attcagtcac 128280
atcttcaggc tccacttcta actctagttc tcttgctagt tccatcactt ctgcagtgtc 128340
ttcctccagt gaagtcttga actcctcaaa gtcatccatg aggatcggaa ttgacttcct 128400
caaaattcct attaatgttg atattttgac ctgttcccac gaatcacaaa tgttcttttt 128460
gttgtttgtt tgttgtggat tgttttttta tttttaattg agttgaggtc tcactatgtt 128520
gcccagactg gtcttgaact cttggcctca agtgatcctc ctgccttgat ctccctaagt 128580
gctgggatta caggcatgag ccactggaac agccacaaat gttcctaatg gtatctagaa 128640
tggtgaatgc ttttcagaaa gttttcaatt tcctttgccc agatgcatca aaggaattta 128700
tctatggcag ctatagcctt atgaaatgta tcccttaaat cataagactt gaaatagaga 128760
attacttctt gatccatggg ctacagaatg aatgttgtgg ctgggcatgg tggctcacac 128820
ctgtaatccc agcactttgg gaggctgagg caggtgggta acttgaggtc aggagttcaa 128880
gaccagcctg gtcaatatgg tgaaacccca tcactactaa aaatacaaaa attagctggg 128940
catggtggcg tatgactgta atcccagcca cttgggaggc tgaggcagga gaattgcttg 129000
aaccctcttg aagacagagg ttgcagtgag ccaagatcac accactgcag cgacagagtg 129060
agactctgtc tcaaaaaaaa aaaaaaatgt tgtgttagaa gtcataaaaa caacattcat 129120
cttcttgtac atgcccatta gaggtcctgg ataaccagtg cattgtcagc agtaatattt 129180
tgaaagaaat ctttttctg gctgggtaca gtggctcgca cctgtaatcc caccactttg 129240
ggaggccgag gcgtgtggat cacctgaggt cgggagttca agaccagcct ggccaacatg 129300
gtgaaacccc aactctacta aaaatacaaa aaaattagcc aggcatggta gcaggtgcct 129360
gtaatcccag ctaccctgga ggctgaggca ggagaatcgc ttgaacctgg gagtcagagg 129420
ttgcagtgag ctgaggtcgt gccattgcac tccagcctgg gcaacaagag tgcgacttca 129480
tctaaaatac atatatatat ataacatgtt atatgtaata taaattatat atataacata 129540
tatgtaatat aaattatata tcacatataa catatatcat gtgttatata tatcacatat 129600
aacatatgtg ttatatatca catataacat gtgttatata tcacacataa catatattat 129660
gtgtatatat gtcacatata ttatgtgtta tatatgtcac atataacata ttgtgttata 129720
tatatcatat ataacatata ttatgtgtag tgtatcatat gtaacatata ttatgtgtag 129780
tgtatcatat ataacatata ttatgtgtag tgtatcatat ataacatatg tgtagtgtgt 129840
tatatataac atatattatg tgttatatat ctcatatgtt atatataaca tatattatgt 129900
gttatatatt atatatatat ttttttctga gtagatctca acagtgggct taaaatatca 129960
gttatccatg ctataaacag acgggctgtc attcagtctt cattgttcca tttatagagc 130020
acaggcagag tagattcagc ataattctta agaccttagg actttaggaa tggtaagtga 130080
```

gcattggttt caacttaaag tcaccaggag cactagctcc taacaagaga gtcagcctgt 130140
cctttgaagc tttgaagcca ggcattgact tctcctctct agctatgaaa gtcctagatg 130200
gcaacttctt ccaatagggc atttcatcta cattaaaaat ctattattca gtgttgccag 130260
cttcattaat aatctcagct agatcttctg gataacttac tgcagcttct ccatcagcac 130320
ttatcacttc accttgcact tttatattat ggggacacct tctttcctta aacctcatga 130380
accaagatct tctagcttca gatttttctt ctgcacttcc ccacctctct cagtcttgct 130440
gtgggcttgc tgtggattag gctttggctt aagggaatgt tgtggctggt ttgatcttct 130500
atccagacca ctaaaacttt ctccatgtca gcaagaagcc tgtcttactt tcttatcatt 130560
catgtgttta ctagagtagc ccttttaatt tccttcagta atttttcctt tgcattcaca 130620
acttggctaa cctctagctt atggcctttt gtttgtttgt ttgttttgtt tttgagacag 130680
ggtctcactc cgttgcccag gctggagtgc agtggtgcaa tcaccgctca ctgcagcctt 130740
gacttcctgg gaccaagtga tcctcccacc tcagcctcct aagtagctga gaccacaggt 130800
gtgcaccacc acacccagct aattttttta ttttctgtag agatagggtc tccctatttt 130860
gcccaagcta gtctcaaact cctaggctca agccatcctc tcacctcagc ctcccaaaat 130920
gctcggatta caggcatgag ccaccatccc tggccctatc tcagcttttg acacgccttc 130980
ctcactgtgt ttaatcattt ctagctttta atttaaagtg agagacgtgc aactcttctt 131040
ttcacttgag cacttaaagg ccattgtaca gttatacact gacctaattt caatattgtt 131100
atgtctcggg gaataggaag gcccaaggaa agcgggagag atggggaaat ggccagttgg 131160
tagagcagtc agaacacaca caatatttat cgatcaagtt tgccatcttc tatggatgtg 131220
gttcgtggca cccccaaaca atgactatag tcacatcaaa gatcactgat cacagaccac 131280
cataacagat gtaataatta tgtaaaagtt tgaaataccg taagaattac cagagtgtga 131340
cacagagacg caaagtgagc acacgctgtt ggaaaaaaaa tggccctgat agacctcctt 131400
gacacagggt tgccacaaat cttcaatttg taagaaacac aatatctaca aattgcaata 131460
aagcaaagca caatgaaatg aagtcttcct cggccggtgt ggtggctcac gtccataatc 131520
ccagcacttt gggaggccaa ggcaagagga tcccttgagc ccaggagttg gaggccagcc 131580
tgggcaacac agggagactc catctctaga acaaaacaaa acaaagcctg cttatattta 131640
ttgggtttac tctcagtctc ccccacacag agatagggcc tggcttgtta ttagtgctca 131700
gttgatgttt gtgaagtgaa atactaagga cttaaccact gcctgttctt tgctgttcat 131760
gccctgacag cttttatgtg ccagcacaga agaaaacaag gtgcaagaag agaatagtga 131820
tctctaagtc agaatttgag gaacccaaat tagtaccaga aagctgggag gagaagagaa 131880
aaataaagta aatcaaatta aaagttgaat gggccaagtg cagtagctca tacctataat 131940
cccagcactt tgggaggctg aggtgagagg atcacttgag gccaggagtt ctagaccagc 132000
ctgggcaata tagcaagacc ccatctctac aaaaaaaatt ttttaatttt ctgaatatgt 132060
tgttgtacac ctgtagtccc agctgcttag gaggcagagg tgggaggatc gcttgagccc 132120
aggaggttga ggctgcagtg agctgttgtt gcaccactat actcaagcct gggtgacaga 132180
ataagtccct gtctccaaaa ataaaaataa ataaattcat tttttgtaaa gttgtatgtc 132240
atggcccctg cctactctgg cttcatgact tgctgcttga acctcaccat ccaaatccca 132300
gtggtgacac catgtcattt cttgaatttg ccaagccctc tttcagtccc aagctctctg 132360
tcatggccac tctcagcctg gaaagttctt tccccactgg ccagatttct ccccctcatc 132420
tatgggaact tgacttgaag tagggggtat cccaggccct ggactagtta acacgacctg 132480
ctgtgtgccc ctcaaagcca ttgtcttcct agctgagaag gcatcacacc tgcaacagat 132540
tcactcattg tgtgcatgtt tttcttaacc acttctcttc tgcatcagct ccatggggca 132600
gggatagtct catatgtcac tctacccagc acataggata cgctcagacg cccacttgtg 132660
gatggtggaa aaggtcagcc caacctaata tgcccatctc tcctctaggg gtaatcttga 132720
gaaaaaaagt tgggaacttg ctttgtgtta gtttaggatg acccagaata gatcctgaaa 132780
caagaattta gggcaatcct tgtgcaagta gttcatctga gaggtgaccc cagaagggtt 132840
ggagaaggag aggggaggtg gggcaaggaa gggtgagttg tcctgtaggc aactgagctc 132900
cgtcctactg ggagcccacg tggaactcac ctcttaagtg atccagaatg aagggtgagg 132960
gagctgcggt attgatccac caactcccag caatctttgg ttgagggctg ctcccttaaa 133020
gttcattccc tgggcctgcc ccagatttgg agacagccct aaggcaagag gtacagatac 133080
cagttggcca cagactgaag tgttaagacc caagcccctg gataaaactg aaaaatcaag 133140
ccagatgtgg tggttcccac ctgtaatccc agctactcag taggctaagg caggaggatt 133200
gcttgagccc aggagttcaa tgctgtagcg agctatgatt gcaccactgc attccagcct 133260
gggcatcaga gcaagacccc atgtctaaaa taaaaataaa ctgaaaaatc cccaagttat 133320
ttgctgtgac caaccttcca ttaaccacag accctctggt attcagcatt tcttgtccat 133380
tatatgaagt tctgatgaca gtctctttta ttgtattgtg ccttgaccac gcactgtaca 133440
tcacttagct ctgaaatgga catgttcagg aaacagggcc aggtgggacc ctgtgtttca 133500
acagcaatac ttttacaaat gaggtctcat gacagggtct tgctcggagg gtttctatgg 133560
aagcctcatc ccacctactg ctatcatcct tactaacttg catttacaaa agggactctt 133620
tttgaccaga ggcttggggt ctgtagctgc cttctagcca gctgatgctg gctggtccac 133680
acaagcagga tcacacccat ttttttgttt tcttatttat ttctgaatag gttagcatac 133740
cggtaacctg tgtgcctggc attgtgctga ccacttttttg tcaacttact gaatcctcac 133800 aaccccttgga ggtattgata ctattgttat ccaggttata caaaaggggg aaactgaggc 133860
acagagcagg gatgtccctt gcccaaggtt acccaactgg aaagtggcag atctgggatc 133920
tgaacccatg caggctgggc tcttaacact gaactacttt cctgccattt gttaaagagc 133980
cacaaaccag gccaggcacc atggctcacg cctgtaatcc cagcactttg ggaggccgag 134040
gcgggtggat cacctgaggt caggagttca agaccagcct ggccaacatg gtgaaaccct 134100
gtctctacaa aaatacaaaa aaaagtaccc gggcatgatg gcgggtgcgt agtaatccca 134160
gctactcggg aggctgaggc aggagaatcc cttgaacccg ggaggcagag gttgcagtga 134220
gctgagatca caccattgga gatcgcactc cagcctgggc aacagagtga gactctgtct 134280
caaaaaaata aaataaaata aaataaagag ccacaaaccc cgaaaggtct gccattcccc 134340
cagggcccca ggccacccca caatctattg tcattgtagg ttgtgaaata tactgaatgt 134400
caccccaacc ttgagccatg gggaagattc catttctctc attgcaacat ttgtgcaaca 134460
tgaaccatct gttgggggtc ttcgtaaatc accttttatc ccgtgaggca ggtactgtta 134520
agaccatttt acaggtgaca aaactgaggc cagtggtgtc gagtcacctg cctgtggtca 134580
cccaaccaat acaggacagc ttggaatccc aagcaccccc gccctgctgt ctgaccccca 134640
aaacccaccc tctgttctcc attctggctt ctttctttca gcatcttggc gacagttggg 134700
acggagtttg acctacggac gctgagggca gttcgagtgc tgcggccgct caagctggtg 134760
tctggaatcc caagtgcgtg agtttccgac cctgacaagg ggtttgctca cgggccccag 134820
gagccctcag tttcccctat gcagagcatc tcaggaggcc acatcctgcc accagcctgt 134880
gtgagggcag tctcttcttt gggactccct atagggaacc ccctaggaat atgactgtag 134940
ctccccatga gctcctgaaa gcaaactagg agccacaccc atttattgag cacctactgt 135000
ctatcgggag ccatgctaag caccacgtgt gatctcattc agtactcaca gccctatgaa 135060
gttgatagga ctgatgtctc tattttatgg agggggaaac tgaggctcag agtggctgaa 135120
acattggagc agggttttgt ggctgagaag tggcagaact aggagtgagc aagtgtgact 135180
ccaagcctgg gccgtaccac tggtggcaat gaccattccc atttaatgag tgcctgctgc 135240
gtgcagggca ctacagaagg actttacatg aattacctta tttcatcctc acagtcaccc 135300
agcgaacacc cattttacag atgagacggt tgaggcttaa ggaggttaaa ttactcacct 135360
gaattcttag agtggacagt aatgagctct aaaattcata ctcattcctt gctgctttct 135420
cattctccac agatacatct agtccccgtt taagggtggc tgccatatgc agggtcaaga 135480
ttaagtgtag gttgagccaa aaaaaaatgt aaaaagcaaa aataaaacag ggctgtcctt 135540
tttctatctt cttgtcttgg ttaataataa taatttagcc aggcatggtg gctcatgcct 135600
gtaattccag cactttggga ggatcacttg aggccacaag ttcgagacca gcctgggcaa 135660
cattgtgagg aacaccaccc ccaccccccc gccaatatct acaaattttt ttttttttt 135720 tagaaattag ccaggttgac tgggcacagt ggctcacacc tggaatccca gcactttggg 135780
agaccgaagc gggcagatag agcgagctca ggagttttaa gaccagcctg ggcaacatgg 135840
cgaaaccctg tctcaaaaaa aaaaaaaaat tagcaggcat gatggtgcac acctgtagtc 135900
ccagctactt aaaaggctga ggcaggagga tctgagccca ggaggtcaag gctgcagtga 135960
gctgtgatag caccactgca ctccagcctg gacaacagag tgagaccttg tctcaaaaaa 136020
acagacaaca aaaagtttaa aaacaaacaa tttataggct gggtgcagtg gctcatgcct 136080
ataatcctag cactttggga ggccaaggtg gatgggtgga tcacctgagg tcaggagttc 136140
gagacctgcc tggccaaaat ggggaaaccc cgtctctact aaaaatacaa aacttagccg 136200
ggcgtggtgg cgggcatcta taatcccagc tactcgggag gctgaggcag gagaatcact 136260
tgaacccggg gggcggaggt tgcagtgagc tgaaatcacg ccactgcact ccagcctgga 136320
tgaaagagtg aaactccgtc tcaaaaaaag aaaaaaaaaa attaaaaagc acttactatg 136380
tgccagacat tattctaagt atttccattt ttttaaagtc ctttatcctc ccaacaagcc 136440
tgtgaagtag tctcttttat tatcaccatt ttacatttta ttggcttcgt tcttccggtt 136500
cattgctacc caggtttaaa gagtaagatt tcccagagga tcaccagcag gatctttttg 136560
tagaaagaag acacttctat ccaaggtctc tgcaagatcc cagcagatgc ctgcatcata 136620
ttaaattaag ggccatccca aatctaatag tcaaaagagc caggtgcagt ggctcacacc 136680
tgtaatccca gcactttggg aggccaaggc aggacgattg cctgaggcta ggagttcaac 136740
accagcctgg gcaacaaagt gtgaccctgt ctcaaaaaat atatgtatat tataatagca 136800
gtagtaacaa gagtctctgt ttaatgacca cctatgactt accaggtact tcactgtgtg 136860
tgaactctct catctaatcg tatgagggag gtactattgc agtccccatt tacagatgga 136920
gaagctgagg tttggaattc actagtaagt ggatgactag gtcaggttcc cttgaagcgg 136980
atacttaggt gggtgttcag atgcacctgc tttattgggg gacggctctt gggagagaca 137040
gcaggagatc agcagggtgg ggctggggaa tggatagagc agggacgcaa tttcagctgg 137100
agtgtgtgtg acaccagagt tgtcctccaa tgcatggcaa ggatgccggc cttttgtact 137160

```
tctatagtca gtcactgtgg atgggaggta gagacgcagt agctcccagg tgagatagct 137220
tttgatcacc aagggcaatt ctactaagaa gagaggcagc tgggaggcat tagcaaccaa 137280
catccatagc agctggaggg cgggtacacc agaaagaaaa tgggatcttg gccagacacc 137340
aagagtatcc agcaccttaa ccactgcacc acactgcatc tgttagcacc cacattacat 137400
ttttttttt ttttttttt tttgagacgg agtctcgctc tgtcgcccag gctggagtgc 137460
agtggcgaga tctcggctca ctgcaagctc cgcctcccgg gttcacgcca ttctcctgcc 137520
tcagcctccc gagtagctgg gactacaggc gcccgctacc acgcccggct aatttttgt 137580
atttttagta gagacggggt ttcaccgtgt tagccaggat ggtctcgatc tcctgacctc 137640
gtgatccgcc cgcctcggcc tcccaaagtg ctgggattac aggcgtgagc caccgcgccc 137700
ggccagcacc cacattacat ttttaagccc ttggagtggc atggccccctc gagctatcct 137760
gacagcttcc ctctcttact gtggtctcca cccatcaaga gccatgggaa gttcctgcaa 137820
tcaagaagca aagcctcagg ctatatgttt gaaccttcat tttgatcata gactttccta 137880
gtagatacca tagtggttac aaacatagga tgttgtcatc gttcagacct gagttaatag 137940
cctcaagaaa aaaatggtag tggaaccagg tatggtgaag tgtgcctgta gtcccaccta 138000
ctcgggaggc tgaggcagga ggctcgcttg tgcccaggag gtcaaggctg cagtgagccg 138060
tgatcatgcc actgtattcc agcctgggtg acagagcaag cccatctcaa aaaaaaaaaa 138120
aagccaatga taggcagaga aatactaact aaggctcttg ctctgtcgcc aggctggagt 138180
gcagtggtgc aatcacagct cagtacagcc tcaacctccc cagactcaag caatcctacc 138240
atctcagcct cccaaatagc tgggactcca ggcacacagc accatgccca gttaattttt 138300
ttgtattttg tagagacagg gtttcaccac gctgctcagg ctggtctcaa actcctgagt 138360
tcaagtgatc cacccgcctc agcctcccaa agtgctggga ttacaggtgt gagccaccac 138420
gcttggccag ctattattat tattaacatt cttcgagtct tacaacagtg gaacttttag 138480
tgcaggatgc gaatttcagt attaacccct tcctctccca aaaggatttg aagcccagag 138540
taattcagcc gccatgaatg aaccatttgt tagatgagag gctactggag gctgagcttg 138600
gtaggataag agcttgcatg gggtccctga ttgatgacaa tacccccaga tttaggtctt 138660
cagatgccca gttgggtgtg tcttctgttc cactgtgtcc cttcggggac tgttccctgc 138720
cttctttctt tttgagatgg aatctcgcac tttcacccag gctggagtgc aatggcgtga 138780
tctcagctca ctgcaagctc cacctcccgg gttcacacca ttctcctgcc tcagcctccc 138840
gagtagccag gactacaggt gcccgccacc acgcccagct aattttttg tatttttagt 138900
agagacgggg tttcaccata ttagccagga tggtctcgat ctcctgacct cgtgatctgc 138960
ccgcctcggc ctcccaaagt gctgggatta caggcgtgag ccaccacacc tggccccctg 139020
ccttcttatt caccaccatc tttctgaatt gggttgctca gaacagagaa agcaacatca 139080
gcacatgggc aaacatgggg cttcatttca gatggacctg ggttcaaatc ctagttctgc 139140
cttttttttt ttttttttt ttttttgaga cagagtcttg ctctgtcacc cagactggag 139200
tacagtggcg tcatcttggc tcactgcaac ctctgcctcc caagttcaag caattctcct 139260
tcctcagcct cccaagtagc tgggattaca ggcgctggcc accatgccca gataattttt 139320
tgtattttta gtagagatgg ggtttcacca tgttggccag acttgtcttg aactcctgac 139380
ctcgttaatc cgctggcctc ggcttcccaa agtgctggga ttagaggcgt gaaccgccgc 139440
cgcgccctgc ctagttctgc catttctcat gcattctctg ggtgaatcac agcatctctg 139500
ttagccttgc ttcccacttc tgtaaaatga gagtgacttt acatgtatgg ccacctcagg 139560
```

ggcttgtcac tagaagccag tgaaataatg ttgagtctgg ttccttgggg ttgaaattgg 139620
gaccgccaac cgctttccta cccagagcag caactagcct atatggcggc cttttatgaa 139680
tgaggaaaag acaccgcctc ttggcagaaa aaaaaaatta agaaaatggc tccctcttct 139740
gggtgcaagt tgcccaacac ccaggaatat ggctccaaaa gcaatggact cccacccctt 139800
tcttgcccaa aagatcatca aatggaacag catgtcaaat acctttatta agtactttaa 139860
agttggctgg gctctgtggc tcatgcctgt aatcccagaa ctttgggagg cagaggctgg 139920
aagatcgctt gaggtcagga gttcgagacc agcctggata acatagtgag accctgtctc 139980
tataaaatat atatatagat ttatttgaga cagcgtcttg ctctgccact caggctgggg 140040
cgcagtggca caatcatagc tcactgcagc cttaacgatc ctcctgcctc agtccctaga 140100
gtagctagga ctacaggcat gcaccatcat gcctggctaa ttaaaataaa taaataaata 140160
aatactttaa agttaaaagt gctttttaaa aaataataag gccaggcgtg gagactcacg 140220
tctgtaatcc cagaactttg gaagaccgag gcgggtggat cacgaggtca ggagatcgag 140280
accatcctgg ctaacacggt gaaaccctgt ctccactaaa aatatgaaaa attagctggg 140340
cctactcggg aggctgaggc aggagaatgg cgtaaacctg ggaggcggag cttgcagtga 140400
gccgagatgg caccactgca ctccagcctg ggcgatataa caagactctg tctcaaaaaa 140460
aataaataaa ataaataata ataataatag gggccaggta tggtggctca cacctataat 140520
cctagcactt taggaggctg aggagtttga gtccttggag accaggggtt tcaggccagc 140580
ctgggcaaca tagcaagacc ccatctctac aaacaagttt taaaacttag ccaggcatgg 140640
tggtgcatgc ctgtagtcct agctattgca gggactgagg caggaggatc acctgagccc 140700
aggaggttga ggctgcagtg agctgtgatt gtgccactgc actccagcct gggcagcagt 140760
gcaaaaccct gtctcaaagg aaaaaaaaaa cctaggaagt gttgttccca tgataaggat 140820
cagcctccgt gtggtgcttc cttcaccatt gcccaatccc caggctcctg ggtgcttaat 140880
attccctcag gaacacacct gctttgtctg ggagagacct gggcgtcttg gtggcggggt 140940
ttgggggtac ttgctcatgg gcttatgggg cctctctctg tgtccccccca ggtttacaag 141000 tcgtcctgaa gtcgatcatg aaggcgatga tccctttgct gcagatcggc ctcctcctat 141060
tttttgcaat ccttattttt gcaatcatag ggttagaatt ttatatggga aaatttcata 141120
ccacctgctt tgaagagggg acaggtaggt ccacggagca tgatgcatct ttccagtttt 141180
ctccttcagg gacaagctct tgggaggatt aggcaggggt gtgcttcttt ctcctggcag 141240
ctgggaggac cgtctccttc agagagcact acaggagagg cagtgagtga aatagcctct 141300
gagatcttag ctgttgaaag ggtggggtt ccacagaagg tgacccagca gagaaagagt 141360
ttatttggga atgatcccag gaagcaccat cgggggaatg aggaagtgag cagagaaaga 141420
agggatcttt taaagagtgt gctatcaagc gggttaccac ttaaaactgg gactggatcc 141480
ccctgggcac ctctgggaga cagcaaagaa cacacaactc agctggtcac ggtggctcac 141540
gcctgtaatc ccagcacttt ggggggccaa ggcgggtgga tcacctgaga tcaggagtca 141600
gagaccatcc tggccaacat ggtgaaaccc catctgtact aaaaaataca aaaattagct 141660
gggtgtggtg gcaggcacct gtagtcccaa ttactcagga ggctgaggca ggagaatcac 141720
ttgaacccgg gaggcagaag ttgcagtgag ccaagatcac accactgcac tccagcctgg 141780
cgaaagagtg agactccatc tcaaataaat aaataaataa aaatataaat aaaaaaagaa 141840
cacacacctc agagccgtcc cagccaaggg gcaagggagc tggggtattt atacactggc 141900
ttctttttga cattggtgag gactgctcct agagtgggaa ttaatgcctg gcacatctgg 141960
ctgagtggaa caggtattct gggtgctttc agacctcgac cagtcctgac ttctaaagca 142020
agcaagaagt ggggagagtt gggccagaaa agggttattg cctcaatgca ttgtgagtgg 142080
taccttgtgg aaggtgagag acagagaaga ttccaggcac aggtgccatg ctaaacgata 142140
gttctcattt attataggaa cccatggatt tattttgttc tctgccctga gtgctgggtg 142200
agagtactgg atgagtcctc ctggtctccc ccaaccccca ggatgtacca gagatacccc 142260
aattgggagt cctggcacca accaatcaga acctagcact cagcagcatt ctgcccctcc 142320
ctgactatgc ccacattaac ccttcagtgg ctgggtctgg gggtagggtg agccccggaa 142380
aagccaggca gcgcagagac actctcccag ggctcagctc tgaaccagca gtgtggaagc 142440
agtgtgtcca ccacgatcca cactcaggaa ccaaatagcc cttggatacg ttttcagtta 142500
aatctttgcc atccaaactc tagctgcttg ctctctaaag ctccagaatg aaatggaatc 142560
aagtaggaag ggatgccttc agtatttcag tatttggacc actggccatc tgggtgcaga 142620
cagactgaat agcagttctg gttctgatga tttgggtcaa gggagctgtg aattgaagga 142680
gtggatagaa ggaatcaaga agcccaaagg ggaacccagg tgggcagaga aagaggtttc 142740
aggcccctta tttgggaaag gcagccacag aagaagattc tgtctgggag tggatttcca 142800
cccaccctct ccacccagtg acccccaagt ggatccgcag aggcagcccc tgagccctcc 142860
ctccccactc ctccccacgg ggagggaaaa cccactgggg aaggtttatt tgcaatggtt 142920
ggaggtttgg gttttttttgt gggttttggt ttgttggttt ttttttcct ctttttctct 142980 tgctcctcct gtctctttct ctcctgggct tgtgaagttt gctcaatatg gaatgtccta 143040
attatttctt tccccgatga agaaggtgtt aattgaggca gagctatttc tgctcctggc 143100
ctcgtcaccc aggcggaaat gcgagagaga gagagagaga gagagagaat gaatatgggg 143160
cagggcctct tggaaaaatc agccgtgagc agagaaacca ggactcctgg atcctaggtt 143220
tctgtgaagt tttattttat gtttttctac cctagactag ctaaaggaga agaggccatg 143280
gggttggctt gggtccgagt ggggttttga ggggacagat gtgggtggtg ccaccagagg 143340
ggaggaagcc tcgatttagg agaaagactg aaaagctagc tcacgattaa aaatataaga 143400
cgtgtgagta agagacagat atatacagac acccaggcag tgggttaatt ttaaaatgta 143460
tttataaccg aattcctcag acactctgga cgcttgtttt tctagaagca acgctcagag 143520
tgtttcgtgt cggtggttgg ggggttgagg gggattgcaa agctgctaaa gatagacccg 143580
ttttcagtag cattcctcag tgtcgggagc ccagttcctg tgtgcccagc accgtgccaa 143640
tcgcttagaa ggaagcaaag ataaagtgga aggcttcctg ctttctaaga gcttccaaaa 143700
tagttagagg aaacaagacc cctcatttgc agccattttt aacagtgaag gctaatgtgt 143760
gattataccc acgccccccct aaatatgaaa attcagtagc tattgtatgc ctgaaagggg 143820
ccaggtgcag tggctcacac ctgtaatccc agcactttga gaggctgagg tgggagtatc 143880
ccttgaggcc gttagtttga gaccagccta ggcaacatag ccagaccctg tctctgctaa 143940
aataaaaatt taaaaattgg ccgggtgcag tggctcacgc ctgtaatccc agcactttgg 144000
gaggccgagg caggcggatc aaaaggtcag gagttcaaga ccagcctggc caacatagtg 144060
aaaccccgtc tctactaaaa atacaaaaaa aataaattag ccgggcatgg tggcgtgtgc 144120
ctgtagtacc acatacttga gaggctgagg caggagaatc acttgaacct gggacataga 144180
ggttacagtg agccgagatc acgctactgc actccagctt gggcaacaga gtgagatttt 144240
gtctcaaaat aaaaaaattt aaaaattagc catgagtggt ggtacatgcc tatagtccta 144300
gctactcagg aggctgagga agaaggatca cttgagccca ggaattggag gctgcaaggc 144360
tgcagtaagc tatgatggtg cccgcactcc agcctgggtg acaaagtgag accctgtctc 144420
aaaaaaaaaa aaaaaaagag agagaggaag gaaagaagga aggaagggag ggagggaggg 144480
actggggctg tgttaactgg gctacacaaa gaggctacat ggagggtggg aattgagcca 144540
gacttggaca tggcgtggag acagagaaga ttccaggcac aggtgccatg ctaaacgata 144600
gttctcattt attataggaa cccatggatt tattttgttc tctgccctga gccttatgtt 144660
taaaagattt ttgccttcca acctgtattt atcaaataat agttcatgta ccaagtccag 144720
cataagtgag gaaggcgttt ccaacaactt aagttcatgg cgaggctaga cttggagttt 144780
ctattcagcc agagcttgaa aggccaacaa gattcattca ttcagcattg gtttatttcc 144840
ctctgctgtg tgctcagtca agggagcaga gaattggtgc tgcgaagtct gtagcacata 144900
cattgagaga tatttttgtt gagtaggaag cttgagttta cacacactca gctgtttgtt 144960
ttcttgtccg acaatgccac ggtcgtcttt gaaaaccttc aaaagcatcg ctcacagaat 145020
aaggtcctct cagacccgct gtgctggtaa aatgaggaca ctcccagatg tgagctttcc 145080
tgcctcccta ccccatcaat accttaagat ttggactgac ctttagcgtt cagcctgact 145140
gccacctccc caggaagctg tctttggttt ccagcaaaag gggtgtctgt tggcacgttt 145200
ctctctcctt gtggcatttt cacagcctgc ctcctgctat ttggggagaa agctcagctc 145260
ctgttcctta cccttaggca agggtaggaa ctgtgtgtac tggtgtccct cacccccaga 145320
acagctccct gagcccagta catcccaaga agaaaaaaat cagcaaggct tataggagaa 145380
taacacaatg cgcttgacaa atttgtccta atggatgtcg gaagaaggct gcacttacca 145440
gctacaccat gcacacggca catttactaa aactgactat attatggacc ataaagtttg 145500
tctcaacaga ggtcaaaaag ctgaaaaaaa tacaaataca aaacatattt tctgaccgta 145560
atgcaattaa gctggaaatc agtaacaaaa agagaactct aaaagtgttt gcagattaac 145620
agacatgcct ctcatttatg gatgaaatga tatgatgtct gagctttgct ttaaaaatat 145680
tctaggctgg gtgcagtggc tcacgcctgt aatcccagca ctttggaggc cgaggcgggc 145740
ggatcacttg aggtcaggag ttcgagacca gcctggccaa catggtgaaa ccccatctcc 145800
actaaaaata caaagattat ccaggtgtgg tggtggccac ctataatccc agctacttgg 145860
gagcctgagg caggagaatc ccttgaacct gggagtcgga gattgtagtg aggtgagatc 145920
atgccattgc actccagcct gggtgacaga atgagactcc gtctcaaaaa aaaaaaaaaa 145980
aaaaaattct agtggcaagg caaagtgttt ggaggggata cagaggaata gatgaaacaa 146040
aatttgccag aagtaaatag gtaagtgtct aaattggtga taggtacatg gtgaatcatt 146100
atattgtttt atacttctct ctcgctctct ctctcccccc gttctctccc tgtcttcctc 146160
tcccctctgt cttcatatat atatatatat atatacacac acacacacac agacacctaa 146220
taagtttttt taaaaaacaa atacatctaa attacccata ggtcaaagaa gaaataataa 146280
tggaaattag aaaatatttt acttgaacaa taatgataat gcatgacaaa atgttgagat 146340
gcaggtaaag ccacacttaa aggcaattta tagccttaaa ggcagttaat ccatccatct 146400
caaaagttta ggaaaagaat agaaaaaaaa aaaaaactca tggaaaacat aaagagaaaa 146460
gtagtaaagc tcagagaaga aattaatcaa tagaaaacca ataatagacc cccaaagcca 146520
aacattgatc tctttgaaga ctgatcacgt ttgtcccaaa agttattcgt tccaacagca 146580
ttatagagtc actggtccct atttctcaga gctggttttc cctgctcctt cccctgactt 146640
ttctcccctt cccttttgta gatgacattc agggtgagtc tccggctcca tgtgggacag 146700
aagagcccgc ccgcacctgc cccaatggga ccaaatgtca gccctactgg gaagggccca 146760
acaacgggat cactcagttc gacaacatcc tgtttgcagt gctgactgtt ttccagtgca 146820
taaccatgga agggtggact gatctcctct acaatgtaag tgatgctggg acagtgtgtg 146880
tggacaatca gagtctcagg gaggtggcct cctgggacca gtgagactcc aaggctgcaa 146940
tggagggacc ctgagctggg aaaggcagcc caaggacaac acagccccac tgaagctggc 147000
ctgaggctca ggcttttgaa gattacaggg gctcatgagc agaactctaa ctatagggca 147060
tagaagtctg gagggccccc agatgcaaca tcatttttca ttgtgcaagt gtttagatat 147120
aattttagat ttttgaatac ggaaaggtta tgtgatccaa aaaccaacac agataaaaga 147180
tagagtaata tctttggacg taggcgaggg gtccctgccc tgaggctcac ccagtccttc 147240
tccagccata ccactccccg tgggatgaga agttcctgga gccaagggga tgtgtctacc 147300
aagagcttgt gccccacttt gtaggccatg ttttaagtta ccaggatcct ggaattccct 147360
gcccatggcc agattccatg aacttgcgtg caattctcat atggatctgt tcgtaaccca 147420
actgagggcc aaggacatcc gaggggtggc tgttaacaca aatgtggcca gagcttggat 147480
gtacaagctg gaatgcccac acatatgtgt ggagcccctc tggcaggaca gagccatgac 147540
taagaagaga aagggacagg acagggctgg ctctccccac accttgaccc agtgcagata 147600
tccggattct aaattccacc ctgaccttcc aaagtgtaaa ggaaggtata tttgcaaagt 147660
agaagcacac agcatgtttt atttagttac cttttcaata tttccccgta gtatgtggtc 147720
tgcttttgta ctcttgccct agatcttaaa aatgttaggg atgtttctgg aaagatgtat 147780
ccctgccccc acttgcatgc tacttcctct tcccacaata tgcaacccct ttagttcctc 147840
agaatatcct tccaatgttt atttatgcaa ttataattat aagcataatc gaatctatgt 147900
cctcccccct ctttcttatc ccaaggagta gcattctata catgctgttc aattctgtga 147960
tttttgtttt ctcataacca cacgttctag agatctttcc actgcaggac atggacagtc 148020
tcttcacggg tgcacactag tatgcccagc taatttttgt agagacaggg ttcttccgtg 148080
ttgcccaggc aggtctggaa ctcctgggct caagcaatcc tcccgcctct gcctcccaaa 148140
gtgctgggat tacaggcgtg agccaccacg cctggccttc tttattcttt tgcacagctg 148200
catagcattc tattgtgtgg ctgcccatag ttttatttgt ttgccattaa gagaaatgct 148260
tgactggctt cctgtccact gacatggaac atgatgctgc tctgccagga gcatgttgca 148320
cgtacctctt catacttttg cagatatagc taggggggttg gagggtctcc attcccagaa 148380
gtgggattgc aggatcaaag actaaatgca tttataattt tatttttggg gaagattttt 148440
gttttgtttt tttggagaca aggtctccct ctgtcgtcca ggctggagcg cagtggtgta 148500
atcatagctc actgcagcct taaactcctg ggctcaggtg atcctcccac cccagcctcc 148560
tgagtagctg ggaccacagg cacacaccac catacctagc taatttttaa gaacaatttt 148620
atagagatgg ggtctcacta tgtttcccag gctgctctca gactcctggc ctcaagcaat 148680
cctcctgcct cagcctccca aagtgctagg attacaggtg tgagccactg cacccagcct 148740
aaatgcattt ataattttga tagatattta ggtgtgcaag ttttaaaccc cactctgtcc 148800
tcaccacagt tcaccttccc tcacctacta tgcaggtaag cagtccccag gcaggtcact 148860
tgtcagcagc tggagtgggg cagagccaag gattcaggat caaacacaag gatgccacaa 148920
ctgtagtgac cccatagagc accctggggc tgctccatac acacagctct gttgaccagt 148980
ggaggtctcc tcttcacctg ccctaagggc tgaaattacc attgaagttt aggccagcgg 149040
ttggcctgac ccgggagcaa tacctggctt cctcctcctg tacatagaga agctgaactt 149100
tcctcttggt cctagtgtat gttccttaac aacccattta tgcctagtgt tccattattg 149160
gaatgctaat cctgtgggag ttatttacat cctgctgctc aaggtcatca ctaaggtcgg 149220
atttttcaca cacacaaaaa ttgcaacctc cggcataaat gggttaagga atttccccac 149280
ttgtgggtgg agggagattt gcaaaaactc atccttgtaa tcctgatcaa caaaggcccg 149340
ttttagttgg gagtaggcag caaaaggagc cacatgaaca gttgcgcctg tcacgcactg 149400
cacaagaatg tcattcatat catagacaac atacgatttc tactgttatc ctgataattt 149460
attgacagaa aaaaggatgt ggggaaggga catggtgttc taatttgcat gaaaacctcg 149520
tctgagtgta gcatctctgg gaacatgcag cagatccgag ctcaggccct ctcttggccg 149580
tcacctgcaa acagcttgga caaagggtca gcccaattgg ccaaaactca ctggggaatt 149640
tttgtgggtt ctaggttttt actttgcaag gctggtgtga gaggaggttc cagcaggaaa 149700
tgaaccctcc tgagagggaa agagactggg aaatggagaa ggctgggaac tcagggagag 149760
aatgggagtg gggaatggga gctgaaaaaa attgtgagca taaaaaaggg atatgtcaca 149820
gggttggatg accagagaaa gcgtctgggg gttcagatta agatgctggg ggcgtgccca 149880
gtggtgggac aggaagcatg aatttccaga gggctcggtt ataaacatca ttgtccaatg 149940
ggtgtttccc ttggaagcct ctaagcttag agctaagcca cctctgggga cacaaactga 150000
gtggttaaga gcagagactc aggtgtcagc ctgtctgggt tccttccgac tcttccactt 150060
ccttgctgtg cagccttcgg caaggtgctt ggcctctctg tgccactatt tccacatgtg 150120
caaaacgaag agaagcatag tcccacctca caaggcacga ggactaagta aggtggattc 150180
gcatgaagtg tttagaactg atcctggccc ggggtgacct ccgtgtaagt caaattcccc 150240
accctgcatg gtgttccttt tagaaatgtg catgaatttt tcattagaac agctccagca 150300
gtgcctgagg aagtggagtg aggtgtgaga ggtcttactt tattcccctc gctggccctg 150360
ctattaacca ctaactcaga gtagctttct agcactttcc acacatttac atcccaccct 150420
cgtcctttgg ttagcagccc atgcaatgat ttggccttaa tgtgaaccta gaacacagct 150480
tctcgcccag ggatgatttc tgcccccagg ggacacttgg cagtggctgc agacattttt 150540
ggttgtcaca actggatggg aagaaggagg atgctattgg catcaagtgg gtaaaggcca 150600
cggatgctac tcaacattct acaatgcaca gcatccccca cctctgcccc accatagaga 150660
atgatccagg cccaaatgtc agtaaggttt ctgtcaggaa accctgggtc agaagaccaa 150720
ggttccttga ggacggggat gccttatact gcaatcagct gtcactctct gcctctctct 150780
ggggctgctg tgatcacctg gcctgcatgg acaaccccta ggagcagccc ccatccagtg 150840
cctggagaag tcagtggata aataccccag ctccctccct gtcgggcgtt ttgctctgcc 150900
ctgcatctct ccagtgggat caggctctgg ttgcccgcag ggttaacctg gtcacgtaca 150960
caccccttcac ttgccacctt cccttccctg tctggtattt cctgggatga acttttagat 151020
ttatttcctg ggctgctat aatgaagcac cacagactga gtagcttaaa acaacaggaa 151080
tttatggtct gacagttctg gaagccagaa gtccaacccc aagatgttag cagagctgac 151140
aacacgcccc tcaaaagcct ccgggggagg atccttcttt gcttcttcct ggcttttgct 151200
ggtttcccac aatctttggg attccttggc ttctagagcc ttcattctcc attccagtct 151260
tctgtcatct aatagcatcc tcccagcccg ggcacagtgg ctcacgcctg taatcccagc 151320
actttgggag gccgaggcag gcagatcact tgaggtcagg agtttgagac cagcctggcc 151380

```
aacatggtga aaccccatct ctactaaaga tacaaaaatt agccaggcgt ggtgggcggg 151440
tgcctgtaat cccagccact tgggaggctg aggcaggaga atcacttgaa cccgggagat 151500
ggaggttgca gtgagccaag atcatgccac tgcactccag cctgggtgac agaatgagac 151560
tccgtctcaa aaaaaaaaaa aaaaaaaaaa agaaaaagaa aagcatcctc ccttcgtgtg 151620
tctgtgtgtg ttctcctctt cttagaagga catcagttgt attggatcag aacctaccct 151680
actccagtcc aacctaattt taactaatta cgtctgcaat taccctattt ccaaataaga 151740
tcacattctg aggtaccagg gggttaggac ttaaacattt ttgtgtgtgt agcaggagga 151800
cgtaattcca tttataactc ctcctaaata aaacgacttg catgtgaact cttgtctggg 151860
gcttcccaaa gtgagataac ccctctctct accccctaaaa caacgagtag cgtctgtcaa 151920
tgccagggtg caggggctaa ggtgcccatc tttgagtttc tgctgaggag gacacagctg 151980
ctacgttgga gcactcttgg gttctgcctt cgtgcccagc catctccctt gggctagccc 152040
tgccctgggt ctatcctaga atgagcctcg atctgtttgg ccataggcaa gcagagtgtc 152100
tggaaatctt tgtcctccat gactggtgct ggagccgaag ccagtgggtg tggccttgcc 152160
agccaactcc atttacccag ctctgaacaa gctagtagtt gagatcaacg gagagtccag 152220
acagtcgctc caagcatctt ggaatccatg gacacaggtg taccgcagag gcttccccacc 152280
tgggtaggca gccctttgta agatcctggc accacattta ttctcttaac atcctttcag 152340
ttatccagta atcatttatt gagcacctac tgtgtgccag gcaatgatta ggtgattgga 152400
gacactgcaa cgaagaagac agactaaaat ctccaccctg gtaggagaga cagatgcaaa 152460
tggtaaacat gataaataat caatcaccca gaaagcagga gacactaagc aaatgtgtat 152520
gtactatggg aagcccaata ggaacgaaag ctacacaaga gaacaagtga tgggtggttc 152580
cttagtctag gtcaggcaat cagggagggc ttctcagagg aggtgatgtt tgagcagaga 152640
aggagggagc caggcagatg ttttggaaac agcattctca gcatggagaa cagtggcagc 152700
tcacctacag gatgtgtttg attcccttcc agattttgta ttcgtttctt gtttttctcc 152760
cttggcttcc tggtttaaat gccttttgaa gaaatctaag ctcaactaat cagcgatgct 152820
gttgaaggtt tatatcagga tatgcatccc agagttattt acaaaattag aacaaaactg 152880
gaagcaattg aaagcctgac aataggagat cagttaaata ccgtatggtc cttccgtatg 152940
atggcatatt atgtcatcat taaaaatcgt ctgctgggag aatattaagg atacagggga 153000
aaggctcacc atataatgat gagtgggggt gctgggcgca gtggttcatg cctgtaattc 153060
cagcaatttg ggagtctgag atgggtggat cacttgagcc caagagtttg aggccagcct 153120
gggcaacaca gtgaaaccca atctctacaa aaaaaaaaaa acaaaaatac aaaaatcagc 153180
caggcatagt ggcgtacatc tgtagtccca gctactcagg aggctgagac aggaggatag 153240
gatcacttga gccctggagt cagaggtggc aataagccgt gatcacgcca ctgcactcca 153300
gcctgggcaa cagagtgaaa ccctgtcaaa aaacaaaaca aaaaaaatga tgagtgggag 153360
aaacaagttt ttaaacaggg atcaaggagg ccaggcatgg tggctcacac ctataatccc 153420
agcactttgg gaggccaagg caggcagatc acctgaggtc aggagtttga gaccagcctg 153480
gccaacatgg cgaaacctca tctctactaa aaatacaaaa attagccagg catggtggcg 153540
ggcgcctgta atcccagcta cttgggaggc tgaggcagga aaatcgattg agcccaggag 153600
gtggaggttg cagtgagctg tgatcatgcc actgcactcc agcctgggca acagagcgaa 153660
agctgcacga gagaagaagt gatgcatggt tccctagtct aggtcagcca atcagggagg 153720
gttcctaaga ggaggtgatg tttgagcaga gaaggaggaa gccaggcaga tgttttggaa 153780
```

```
acagcattcc cagcatggag aacagtggca gctcaccctg tctagaaaag aagaaatgat 153840
aagaggggaa aatgagtttt taaaaaggaa tcaaggggag gtaaacctta tgatctcaaa 153900
ggtacaaata tgaaaatata agtaaagaaa aactggagga cactgtacca agctgacctt 153960
cgggtggtgg gatttgggaa tcttgatatt ctcaatactt ctttgtatct tcaaatttct 154020
ctatgatgat cacagtttac ttttttttt tttttttgag atggagtctc actctgttgc 154080
ccaggctgga gtgcagtggt gcgatcttgg ctcacttggc tcacctctgg ggttcaagca 154140
attctcctac ctcttcctcc caagtagctg ggactatagg catgcaccag catggtcagc 154200
taattttttg tatttttagt aaaaatgggg tttcatcatg ttggccaggc tggtctcgaa 154260
ctcgtaagtt caagtgatcc accaacctca gcctcccaaa ttggcttgag ccaattaaac 154320
ttgtcttgct aaatggttag cggggagaaa gaagaaggtc tcgggtcatt cctagaccag 154380
gaggcaggga gaaagggagg agaatgaacc tttcttaggc aaacagtgtc ctaggtgtcc 154440
ttatcttaca taatctgtcg agagagtcac actaaaataa atcattgatt gattgattga 154500
tacatcaata ataaatggcc agccttggtg gctcacatct gtaatcccag ctacttagga 154560
agctgaggtg ggaggattgt ttgagacaag gagttcaaga ccagcctggg aaacacagca 154620
agactcatct taaaaaaatt ttttttttta attagccaga tgcggtggct cacgcctgta 154680
atcccagcac tttgggaggc cgaggcgggt ggatcacgag gtcaggaatt cgagaccagc 154740
ctggccaaca gggtgaaacc ccgtctctac taaaaataca aaaattagcc aggcgtggtg 154800
gcacacgcct gtagtcccag ctacgcagga ggctgaggca gaagaatcat atgaacctgg 154860
gaaacagagg ttgcagtgag ctgagatcac gccattacac tccagcctgg gcaacaagag 154920
caaaactaca tctcaaaaaa aatgtttttt aattagccgg gtgtggtggt ccatgtctgt 154980
agttccagct acttgggagg ctgaggcagg aggattgctt gagcccagca gttcaaggct 155040
gcagtgagct atgatcccgc cactgcactc cagcctgggc aacagcaaga ccccatctct 155100
taaataaaca cataagtaaa taaatgatca tttttatttt attattaaat acacaagata 155160
aatgaaaaac aggcaaatct ttcttacaaa agaattccat ttaaagtatg taaacttcac 155220
tccccactgc cccaggaggt ggagactaat ctcccctact ttgagagtgg gctggattta 155280
gtgactcatt tccgaagaat agagtaggta aaggggaaaa tagaagtttt atagcggagg 155340
aacagataga taccacttta accaaatgat gaagattagt atcccccagg gatgtggata 155400
ttatgtaacc cttgatttta tgcctatata gcgttcttcc caaaaactcc taatcccagt 155460
tttttggggt tttgctctgt cttctaagct ggagtgcgat gatgcaatca tagctcactg 155520
cagctcaaac tcctggtctc aagcgatcct cccacctcaa cctcctgaat agctagggct 155580
gtaagcacat accatcatgc ccagctaatt gtattttttt ggtagagaca tgttctcaca 155640
cattgcccac gctgtcctcg agctactggc ctctagtgat cctcccaccc cagcctccag 155700
agtcactggg attataggca tgagccactg tgaccagccc agaatttttt tttaaggagt 155760
tgtgatgtcg tttaagagat gtgattcttc ataacacatc aacaacaagt cccagcgatg 155820
ggttggataa gtcttgggat ttcatgggag tattaagctt aaaagacttt gcatgatatc 155880
tgtgaactat atgtgatttc tgttggtaat gggggtcact gattctgcgg tttgccacct 155940
ccaatcatca tggaagaaaa tgttccactt ccagtgaaag taagaggaag taaaggggta 156000
attattttct atctaaattc acgaactcct tgaattctgt ccacagaccc ctaagtgttt 156060
cctccccaag gtgaaactga gagaatcttg ccagtgcctt ccgcagtcac tgtggctaga 156120
```

aaacccctca gaagaggtga tagtttagca ggtaactgga gttctcacca tccgtgtctg 156180
gctcagcccc catcacaacc agttacccag cccaaaatgt cagtagtact gaggttgaga 156240
ggctctgctc taggaggcca ggcctctcag aggaaggagg attggggtac tggctgggcc 156300
tcaagatgaa cctacccccct aagagctttg ggatggcgtg agtttctgtc catacccaag 156360
gactacaaat gcaggtttac tggaaattct gtgccaaaag tgaggtccaa ctcacttcta 156420
actgctacaa aacaaacctc catcaacata gcccatctct gttcttgacc tggaagctcc 156480
aaggtatcca catggctccc atgcccacta gacgggcctc ttccctggac cttcctgggc 156540
cagagaaggc tctgggtagc cttgtggaat caagatgggt gatcagccac ttcctctgtg 156600
ccaccctgtt ttggctactt ccctaggcat cagcctggga ttccttgatg gtaaaaatat 156660
aaaactctct gagctagggc ctttaatatc cccattttac agatgaagaa actgagtccc 156720
agagctgtgc acagcgattg agagtcagaa ttcagctctg tctcactcag tgtcaacatc 156780
ctcagattct gccatttata gcctcccaca gcaaatagga ttgagggctg cttctctgag 156840
ctcaagggga tagaatgggg aaccccatga gtactgcaac aaaactgttt gctggagaca 156900
agagctggtg gctctgtgtt gttctagtga caggtggcct catttcacag ggacccccctc 156960 accctatgtg ccccatgtgg ctcagaaaag ccagaaattg tctccactct cacaggggaa 157020
ggtccctgac cccctctttg ccagctgggc caaggcaaat tggggtcact tcatggggta 157080
caggacctac cctctcttgg ttgcccccaa ggaggggatg tggaggggct ggggacctgg 157140
caggaccagg gtgtcttgag ttaatttggg gctgccttta gccgagggct tctgtgtgcc 157200
tggcatcagc tttacattgt gtcttgatcc gtaaaacagc cctgtgagga aagatatttt 157260
taaccccatc ttccagatga ggaaacggag gcccacaggg tgacgtgacc tgccaaggtc 157320
ccctagccaa gagtgacaaa gccagggttc acacacagct ctggacacaa ttcatcaccc 157380
ttcatccgtc tctctctgac tctttctttt tccctctctc tctttgtctc tcttttttttt 157440 ttttttttt tttgagacag cgtctcactc tgtcacccag gctagagtgc agtggcgcaa 157500
tctcggctca ctacaacctc catctcctgg gttcaagcga ttcttgtgcc tcaacctccc 157560
aagtagctgg gattacaggt gcgtgccacc acacccagct aattttgggg ggttttgttt 157620
tgttttgaga tggagtcttg ctctgtcgcc aggctggagt acagtggcgt gatctcggct 157680
cactgcagcc tctgactccc aggttcaagt gattcccctg cctcagcctc ctgagtagct 157740
gggactacag gcatgcacca acacgcccag ctaatttttt gtattttagt aaagacgggg 157800
tttcaccatg ttggccagga tggtctcgat ctcctgagct catgattcgc ccgccttggc 157860
ctcccaaagt gccgggatta caggcgtgag ccactgtgcc tgccaatttt ttgtattttt 157920
aacagagact gggtttcaac atgttggccg ggctggtctc gagctcctga cctcaagtga 157980
tctgcctgcc ttggcctccc aaagtgctgg tattacaggc atgagccacc atgcccagcc 158040
tttgtctctt ttattcttgt gttctctctc tctcttcctt ctctttctcc acctccttct 158100
ccttctctcc cttctcctca cccttctttg tgcttttctc tgtgagtttc tcttcttctc 158160
tatttctctc ctttggtgaa tgtcaattag aaaagcagaa aaactgcgtt taatttgtga 158220
tcataaatgc atgtccctgg ccaggcgtgg tggctcacgc ctggaatccc agccctttga 158280
gaagctgagg caggaagatt gcttgagacc gggagttcaa aaccagcctg gtcaaaaagc 158340
aagaccccat ctttaaaaaa gaaaaataat taattagctg ggcatggtgg tgtgtacctg 158400
tagtcccagc tactcgggag gctgaggaag gaggattgcc tgagcccaag ggtttgaagc 158460
tgcaccgagc tgtgattaca cccctgcact ccagcctggg tgacagaacc agaccctgtc 158520
tcaaaaaaaa cctaataatt aaaaataaat aaataaataa atgcgtgtcc cctggccagt 158580
ggttgctaat gtttggaatc acctttgacc catgcccttt ttcattcata gatgtttgtc 158640
ttgaccaaaa tcaaagcatt agactttgga ctataaatca ctggttcatt caacaaccat 158700
cattgaatgc ctactgtatg cagacactct tctggacaca gaggagttga cgtgttggtg 158760
gggaaagcca gtgatcagtt gggataaaaa gggcagacag cagacattaa atagtttagg 158820
ctttgtgggc cagatggtct ccatcgcaac gactcaatct gctcctgtag cgtgaaagta 158880
acgacagata aagcgcgtaa gtgaatgagc atggctgtgg gccaattaaa cgttaaccta 158940
taaaaacagg tggctggccc gcgggctgta gtttgtggat cactgcctta gagatagtgt 159000
tagagggtgg tgagaggtcc gggatagaat aaaacagtag agagtttgtg cattgtcaag 159060
atgagaggtt gcagttcttc ttatacaccc cgaatggccg ggcaccgtgg ccattatgat 159120
ctataattct aacactttgg gaggctgagg caggaggatc ccttgagccc tagagtttaa 159180
gaccagccta ggcacatagt gagaccccat ctctacaaaa aaaaaaattt aaaaattagc 159240
tggacatggt ggagcatgcc tgtaggccca gctacttgag aggctgagat gggaggactg 159300
cttgagcctg ggaggttggg gctgcagtga gccgatcatg ccactgcact ccagcccgga 159360
tgacagagca agaactgtct caaaaaaaaa aaacaaaaaa acaaaaaaaa cagacctgaa 159420
ggaacaaatc atatgaatgc attaaagtat cacatgtatc caaaaaatat atacatctat 159480
cagcctggca cggtggctca tgcctgtaat cctagcacat tgggaggcca aggcaggcag 159540
attgcctgag ctcaggagtg caagaccacc ctaggctaca tggtgaaacc ccgtctctac 159600
taaaatacaa aaaattagct gggcatggtg gcaggcgcct gtagtcccag ctacttggga 159660
ggctgaggca caagaattgc ttgaacccag gagacagagg ttacagttag ccgagatcgt 159720
gccactgcac tccagcctgg acaacagagc aagactctgt ctcaaaaaaa aaaaaaaaaa 159780
aaaaaaaaaa aaaatatata tatatatata tatatatata tatatatata tatatatata 159840
tataatcaat taaaaatttt ccttaataaa taaacatttc tctccttctc tcccttggtg 159900
aatgtcaatt aataaagcaa caaaactatg tttagttagt gatcattaat gtatgtccct 159960
ggctgggtgt gatggctcac acttgtaatc ccagcacttt gggaggctga ggcaggagag 160020
gatagtttga ggccagcaat tgcttgaggc tttttgaaag acatgaagga gatgaaggga 160080
gccatggaga tatctcaggg aacagcagcc gaggtagatg gaacagccag tgcaaaggtc 160140
ctgaggcagg atgttcctgg catttgtgag gacatgtagc tgcccagatg tccagtgggg 160200
agtgagtgag gatgaaggaa ggagctgatg aaggaagatg ataaaatact tcatggatca 160260
gccaggcatg gtggctcccg cctgtaatcc cagcactttg ggaggccaag gcgggtggat 160320
cacaaggtca agagttccag accagcctgg ccaacatggc gaaaccccgt ctctactaaa 160380
aaatacaaaa aagttagcca ggcgtggtca tgcacgcgtg tactctcagc tacttgggag 160440
actgagactc gagaatcgct tgaacccagg agatggaggt tgcagtgagt tgagatcacc 160500
ccactgcact ccagcctagg tgacagagcg agactctgtc tcaaaaaaaa aaaaaaaaaa 160560
aaaaagactt cgtgaacaga cagcctatat aatttatgat ccaaaccagg acagttttga 160620
gagtgaaagg ggaaaaagag cactgaaaaa ataattagca ggcctggcat gatctataac 160680
gggtataaag tgggacacac agcctctctc acggtcactg tcagacttca gctttttcac 160740
actcaaatcc acccccatgt ttatcccata tactggagaa acgggtgttc tcctgagctg 160800
agttttgggg ttttttcctt ttgttttgtt ttgtttttgt ttttttaaca tcctgtatac 160860

```
tttttctcaa tgaaccatgc tcaaaaaaat tagaggaaaa taaaccataa aacagaaggc 160920
actgaaggat tttgctggga ctcagccatt agtttgtttg atgagtattt atggagcgct 160980
ttctaagcac caggcaccac cagcgatact gggatgaatc agtaacatcc ctcacccttg 161040
aagctctctt gggcccattg ttatttactt aaaatactat gcaagtacgg agaaggggtg 161100
aagtgggaaa aaatcagttg gttgtaaagg ccagaatgac gggtctagtc ccacccatgc 161160
catctgcacc ctgtgtgatc caggcacatc atgttgcctc tctcagcttc agtttctcca 161220
tccaccaggc acagagatgg cgggaatcga ggaagatgtg gggagtattt catcagccca 161280
aaaagacttg gctaatgcga ccataattct gccttctgcc tctcctttcc cagaaaaata 161340
gcttaatcat ttggatttgg gataaacaca tttcctgtgt ttattattta aatgatccac 161400
caagctgggc atggtggctc accccctgtaa tcccaactct ttgggaggct gaggagggcg 161460
gattgcttga gcccaggagt tcaagaccag cctggccaac atggcgaaac cccatcttta 161520
ctaaaaaaat acaaaaaaat tagctgagcg tggtggtgcg tgcctgtaat cccagctact 161580
tgggaggccg aggcacaaga atcacttgaa cctgggaggc agaggttgca gtgagcctag 161640
atcgtgccat cacactccag tctgggcgac agagtgagat tctgtcccta aataaataaa 161700
taaataaata aataaataaa taaaataaat gatccaccaa caggaacccc aggaacattt 161760
gtattgacta tgcaactaat gcttagtgag cacctactat gtccctggtg ctgatctgga 161820
cactgggatt tagacaggaa aaatctctac cctggaggag ctgatgatca agatgacaat 161880
cttgaaatgc ataagttgac aagatgattc agacagtgga acgtgctggg aagagaatga 161940
gatgtctggc tgagctgcag gaaggggcaa gtccttttga ttgagaggtc caagaaggct 162000
tctctgatgg gggcacaatg gatctaaggt tgagtgataa gaagaaattg gccaagccaa 162060
gacctaaagg cagagttgct ccaggcatag gttcagagaa tggaaataat tggctgattg 162120
tgatcttgaa cttgaccttt cttttcttct gctaactttg ggtttggttt gttcttgctt 162180
ttctggctcc ttgaggtacg tgttgggttc ttaatttgta attttttttt ttttttttg 162240
ctttttgag acagagtctc actgtggtgc ccaggctgga gtacagcagc atgatcttga 162300
ctcactgcaa cctctgcctc ctaggctcaa gtgaacctcc cacttcagca tccccagtag 162360
ctgggactac tggtgcacag caccacaccc agctaatttt tttattttta ttttttagag 162420
atggggtctc actgtgttgc ccaggctggt ctcaaacccc tagctcaagc gatcctcctg 162480
ccttagcccc ccaaagtgct gggatgagag gcgtgagcca ccacatctgg cctctgtttt 162540
ttgtgatgta ggtatttgat gctataaact tccctcttag ttgcttcttg gccctttagc 162600
taaggtcaag tgtaaacttc cctcagcact gcttctgctg catctcacag gtgttggtgt 162660
gttgtgtctc tattttcatt catttccaaa attttttaag tctccatctt aatttctgca 162720
ttgacccaat ggttgttcag gagcatgttg cgtaatatcc atatatttgc atcatttctg 162780
aaattcttct tggtattgat ttctagtttt atcccacggt agtctgagaa gatgcttgac 162840
agaattccag tattttaaaa tttgttgaga gttgttttgt ggcctaacat gtggtctgtc 162900
ttggagaatg tccatgtgct gatgagaaga atgtatgttc tccatcagac atgcaagaga 162960
cagacacttt ctcacctgcc tcatgggatc cataaaagag tcaatcagaa gttggcattt 163020
aagaaagacc agaaggaggc tgggtgcagt ggctcatgcc tgtaatccca gcactttggg 163080
aggctgaagt gggtggatca cctgaggtca ggagttcaag accagcctga ccaacaaggt 163140
gaaatcttgt ctctatttta aaaaatacaa aaattagcta ggtgtggtgg cgggcacctg 163200
taatcccagc tactctggag gctgaggcag agaatcactt ggacccagga ggtggaggtt 163260
```

gcagtgagct gagatcacac cattgcactc cagcctgggc aacagagcaa gaccccatct 163320
caaaaaaaaa aagaaagaaa aaaaagaaag aaagaccaga aagaggtgaa ggagcaagct 163380
acagagatat caaactgtat caatctggct gggcgtggtg gctcatgcct gaaatcccag 163440
cactttggga ggctgaagca ggaggatcac ttgagcccag gagttcgaga ccagcctggg 163500
caacagagac cccctctcta caaaatataa aaatttaatt aaaaagatgt attggtcagg 163560
gcagccaagt tatgctgcag taacaaacat ccccaaagcc tccatgactt ttgacaacag 163620
atgtatttcc tgctcatgct acatgtccag tgcaggttgg cagtggggaa gaagggggct 163680
ctgttcagtg cagtcacttg agacctagct aatcacctag aacattgcca cttgctattc 163740
cagaaggaaa aaaggaatgc tagaaggtcc cacactgaaa gttcaatgct ctggctccaa 163800
aatgacagct atttccactc actcctcatt ggccagcact tagcatgtgg tcctcagcca 163860
accccaaagg gactcaggaa ggaccatccc accatattgc tggaaatatt tgatggcagc 163920
attaatgggg aacagtgttc caggcagtgg aagtctttga gcccttggaa gaaagacaag 163980
gcgatctcta gagcacatcc ttcccaatat taatgaattt aacaaatgag caagccatcc 164040
tcccccactc tccttcccga attcagactt gtgcatatcc ctcccttaac ttgaactgcc 164100
aaagaagaga tgagaaccag gagaagagat ctgtgacccc atctttgctg atgaactacc 164160
acagaacagc catggcatct ccagtccttg tgcttgtaaa atgtactttt cattttgctc 164220
ctgaacgaaa tccacccacc cccaccccca aaccagggaa agctcatctc ctaatccaaa 164280
actgcaccca gccttccacc accttcttcc ctgggaattg ttgattccag agtatggaat 164340
tgaataattg gatgagtttg gaagagaaaa agtgtctcta aaatcaggca gcagaagccc 164400
actccccaga gaggatggtg cagatgagag ttcaggaggg agcttggctt ggggttgacg 164460
atctgagcta tgcagggaac ttggacacac ctctcaatca gtcattcaac agacaccact 164520
tattgagcac cgactgtgtg ccagatgttg tcctaggggg ctgggaatac aggaatacag 164580
cagggaacaa aaaggacaaa gcccctccct cttgtcgaat ggacattcca gccaggaaga 164640
cgagagaaca agagaaataa gtaaagtata taggcggtga aatgcaaatg ggaaaaaaga 164700
aacaatgggg accagaaatg aggggtgcaa ttgtaaaggg ccatcagggg aggcctccct 164760
cagaaggtgg catttgagta aaaaacctga aggaggtgag gggaaaccat gtagcaatct 164820
caggaaagag cattccaggc agggagggac agcctgtgca agggccgagg taggactgtg 164880
cttggcgtgg ttgagaaact gcaaggaagc caggtggctg gaaccgaatg agcgagggaa 164940
aaggggagga gataaaagca aggagatggg agggttggag gccccctctg ccattcagta 165000
actgagtaac ttcatttatt tcctgtagct tgaaccacaa agaaccacaa atagagtagc 165060
tgaaaacaac agaaatttat ttattctctc gcagttcagg aggccaggag tccacagacc 165120
atcaaggtca gctgggccac agaccatcaa gatgtcagct gggccatggt gcctcctgag 165180
acttggtctg aaatcccttc ttgcctccct cctagcttct ggtggtttgc caacagtgct 165240
tggtggtcct tgtcttgtag acgtatcacc ctgatcccgc cttcatctcc atttcacatg 165300
gccttctccc tctgtgcaag gttgtctctg tgcccaggtt tctccttttc ttattattta 165360
cttatttgtt tgtttgtttc tttattttag acacagggtc ttgctctgtc tcccaggctg 165420
gagtgcagtg gtgcgatcat agctcactac agcctcaaac tcctggcctc aagcaatcct 165480
cctacctcag cctcctgagt agctgggact gcagatgtga gccactgtgc tctgcccaga 165540
tgtcctcttt ttataaggaa acccgtcatt taggatgagg ttccacccta atgacctgat 165600
cttaacttga ttccatctgc aaagacccta tttccaattc ataggtacca gggattagga 165660
cttcttcaat gcatcttttt ggagagaccc actgcaaccc acaacagaac tgtgggcatg 165720
taacttgacc tctcggccag gcgtgatggc tcacacctgt aatcccagca ctttgggagg 165780
ccgaggtgag tggatcgcct gaggtcggga gttcgagacc agcctggcca acatggtcaa 165840
accccgcctc tactaaaaat agaaaaatta gctgggcatg gtagcaagca cctgtaatcc 165900
caactacttg ggagggtgag gcaggagaat tgcttgaacc caggatgtag aggttgcagt 165960
gagccaagat agtgccattg cactccagcc tgggtgacag agtgagactc catctcaaaa 166020
aaaaaaaaaa aaaaaataga cctctctgtg cctcagcttt ctcacccggg aggatgggga 166080
taattatata cccactcctg gggttcatga gaggattaaa tgagctcaaa cagtccaagc 166140
ctccacgtgt gtctgttgtg gtgctgggta gcatgtcctg tggccagagg ttcccaagct 166200
tgtcgaggac ccaggcaagg gcagattcgg gtcttgttgg cagcacctga gatggacggg 166260
ctgccttggt atggaagggc ctcggctgtt tttccctttc agtcctgtcc ctctccccca 166320
tcctccaccc tgtccctgtc atctgagcct gctcctcgtg atggctcaga gtctccctac 166380
tggcggccgg tgcagagttt cgttccctgg gctatattta gccctgagaa atgggaacga 166440
gaaccctcag ccgccaaagt gatggagaga ggagcacaaa gccagtgctg ccttctgtcc 166500
agcaatgttc cgctgactcg gttctttctt ccagaacctt ccagaagcaa agcattggca 166560
tttctgagct cgttaaaaca aggatgtggg ctggtggctg gcacattcat tgtccccaga 166620
acctgtctgt gtccatgatt aaagctgact ttgttagttt tattttcagt gctttttttt 166680
ttttttaatc catggcaaaa cacacatgac ataaaattta ccatcctaat attttttta 166740
actttgtaac atttttaat tgacaagtaa ttgtacttat tcatggggta catagtgacg 166800
tttcaatgca tataatgcgt agtgctcaga tcagggtaat tagcatatcc atcttctcag 166860
acctttattg tttctttctg ttaggaacat tcaagctcct ccttctagct atttgaaacc 166920
attaatatat tgttgtcatc ctaaccattt ttaaggatac agtttcgtga aattaagtat 166980
aatacattca cattgttgtg caactgtcac caccatccat ctcccaaact tttccatctt 167040
ccaaatgtaa ctctgtcccc actaaacgcg aactccctgt tccccctccc ccagcccttg 167100
gcacccacca tgctactttc tgtttttata aatctgacga ctctagggac ctcctataaa 167160
tggaatcata caggattttc ccttttatga ctggtttatt tcacatagca taatgccctc 167220
aaggttcacc catgttgcag cacgtatcag cattttcttt ctttttaagg taaagttgac 167280
tattaaaaaa aaacttctgc cgggctcagt ggctcacgcc tgtaattaca gcactttggg 167340
aggccaaggc aggcagatca ggaggtgagg agttcaagac cagcctgacc aacatggtga 167400
aaccccatct ctactaaaaa tacaaaaatt agccaggcat ggtggcgggc gcctgtaatc 167460
ccaactactc aggaggctga ggcaagagaa ttgcttgaac ccgggaggca gaggttgcag 167520
tgagctgaga tcatgccact gcactccagc ctcggcaaca gagtaagact ccgtctcaaa 167580
aaaaaacaac tttttaagaa ttgaagtaga ataaacatac agaaaaatcc gcggattata 167640
agtgaagagc ttgattaatt gtcacaaact aaacacatcc atgtaaccag cacacaaatg 167700
aggaaacaga aacttctcag ccccagaagc ccccctcata tcctgttcct agtcactacc 167760
tccccgcaag ggtaccccta ccaggacttt gagcatcatt caccagttta gcctgttttg 167820
tattttgcat aaatgaagtc tggcttcttt tgcttgacgt taactttttta agatctcatg 167880
tgacctgtgg cattgttcat tgcatgtatc ctctctctcc tattgataac agtgtggatt 167940
gtttgcaatt tggagctatg atgaatacca ttgctatgaa tgttcttgtg tgtgctttct 168000
gttgtgtaat tattcagaat tactatttcg gaattactat ctaattgtag tgatcttgga 168060
tcagtaacta tccaagaatt actgggtgtt ggcaaaggta catacagtta tacactgcac 168120
aatggcattt tggtcaacaa cagatcaaat atgtaacagt ggtcccataa tggaccgaat 168180
acataacagt gattatcata cagtattttt actatagctt ttctgttttt agattctttt 168240
tttttgaga cgaagtctcg ctctgttgcc caggctggag tgcagtggtg tgatctccgc 168300
tcactgcaag ctccgccttc tgggttcacg ccattctcct gcctcagcct cccaggtagc 168360
tacaggcgcc cgtcaccagg cccggctaat ttttttgta tttttagtag agacggggtt 168420
tcaccatgtt agccaggatg gcctcgatct cctgacctca tgatctgccc gcctcggcct 168480
cccaaagtgc tgggattgca ggcgtgagcc accgcacccg gcctgttttt agatattttt 168540
agatacacta tagagttaca attgcctaca gtattccata gaataacatg ctgtatgggt 168600
ttgtagccta ggagcaatag gcgagaccat gcagcctagg tgtgtagtag gctataccat 168660
ctaggtttgt gtaagtacac tccatgatgt ttgcacaaca aaatgaccta gtgacacatt 168720
tttcagaatg tatgcccatt gttaagcatg acttaatttt agcatagaaa ctctcaacca 168780
atttttcaag tagttgtacc atgtgttatg ggttttattg tctcacccca aaattcatat 168840
gttgaagtcc taaccccag tacctcagaa tgtgacctta tttggaaata gattcattgc 168900
acatgtaaag gttttgccat tggcaaaact gccgttattt ttgcaccaac catagcagtt 168960
aagatgagat cattagggtg ggtcctaatc taatacgatg gtgtccatat aaaaagggga 169020
gattttggca cagagacagg cacactcaca ggaagaatgc catgtttaaa caaaggcaga 169080
gctcaggatg atgcctctac aagccaagaa tcagcaaaga ttgccagcaa accgccagaa 169140
gctaggagag aggcataaaa cagattctgt ctcacagctc tcagaaggaa ccagcccttc 169200
tgacaccttg agcttggatt tttggcctct ataactgtaa gacaataaat ctttgttgtt 169260
taagccacct aggttgtggt tccttgttac agcagccaca ggagatgaat acagcatggt 169320
gccctcccat tggcagatta tgagggttcc agttgctcca cagcttcaca gacacctggt 169380
agtaatgacc tcatcttaac ttctttctca ttttagcctt tcttccaggc agcagcagtg 169440
tcatacatgc ttttaaaggt gggcttttaa agccacactt gagagccctg cattctgcag 169500
gtgtcacagg gtgatcaact attcaaaggc taccccctgcc ctgacagctg gaggcaaggc 169560
ttcccagcac agaggttaag cccatggact ctggggccag gtggttagtg caaatcccat 169620
gtccactagt gaataactct gtgatcttgg gctgatgatt ttgtctttct aagcctcagt 169680
ttcctcaata gtaacatggg cattataaca tagaggcatc atgaggatta aatgactaag 169740
tgagctaaca tacataatgt gcttaggaag gtgccagcac accataaata ctctgtaagt 169800
gctggctttt atcattcttt tctctctctc tctctctctc tctctctctc tctctctctc 169860
tctctccctc tctctctctg tctctctttc tctctccacc ccccaacctc ctctccttga 169920
ttttcttccc ctcatcttac ttccttcttg ctatagtgtt ctattttctg tttcagagag 169980
tattctattt gtggactttt ttcctcttga aaattgagct gaaacttctg agaatttttt 170040
gtgattggca ttaaggctgc agggaatgga gcagggagac acttgaggaa agggctcatg 170100
gaccatctgt ctggcttggt gatttcacca ggccatcaga ctctgtggtc atgcatctcc 170160
tctaagggga gtctatgact gtgttgggag aagagaagga accagggatt aattaatcca 170220
tttcaatagg ttttgtgttt tgtttggttt actttttcct tctccttctg gactgtggtc 170280
tgggaagtcc tcttgtgttt cttactccat tcccaggtca attatgttat gtgaggagaa 170340
cataattaag agagagcttt accctttgga tgttttcttc agaaaacgtt cctccatttc 170400
cccctctggg atgccagagc cccagaactc cacaagccaa gaacatttaa gacagagcca 170460
caagagaacc gagcttcccc ttccctcacc tgtcaggttc tatctgagtc ccagtcaact 170520
ctcacctgct ttccctcctc acaccctaca gagcaacgat gcctcaggga acacttggaa 170580
ctggttgtac ttcatccccc tcatcatcat cggctccttt tttatgctga accttgtgct 170640
gggtgtgctg tcagggtaag tttctgctac tccccacccc atcccactca ctcctctttg 170700
ctaacttctt tccaagtaga ggccattgaa gctttgtttt cattcactag acagagaaaa 170760
ggcttcttcc cttgtttggg ttaccagact gttattagca agccatgcac aggtgcagag 170820
gttgtgtact gctaggggta cccagtgaga gggttcatat gggctttact ttctttacat 170880 ttttttaaa aaccaatagt ttgggtttac ttctccccca ttttccaaat ataaaatcat 170940
agcatatgct ctaacggtgt attttcctga cccatattgt cctctatccc caagattttt 171000
ttggcttaat cataaatggg cttcattttt cttaccataa gaagtctggg cacttgtatg 171060
gtggctctat ggcaccatca gcaaccccag attcttccag ctttccattc tgacatcttt 171120
accagaggct tccaatctcg tggatacctc atggtcttaa gatggctgcc tcacgccctc 171180
cggatggcca cttcatgttc caaacaggaa aaggaagaag ggaaacagga agaggtggga 171240
cctatggcag agaagccaac ctgctgcaga aatctttcat tcatggctta ttggtctaac 171300
ttaaaagagg gctgaaataa ttattagcca aaagtatgaa gagaatgaga atgaggtatg 171360
cagccagtgg tggttggcat ggcatggttt tatcctttcg gttttttct tttttattgt 171420 ttttttttga gacggtgtct agctttatta cccagactgg agtgtagggg gcgatcatag 171480
ctcactgtaa cctagaactc ctaggcacaa gcgatcctcc tgcctcagcc tcctgagtag 171540
ctaaggcaac aagtgtatgc caccatgccc agctacattt tttatttttc atagagatgg 171600
ggcccactgt gttgtccagg ctggtctcaa attcctggcc ttaaatgata ctcccatctc 171660
agcctcacaa agtgctggga ttacagacat gagccactgt gcctggcctt tttctttacc 171720
taggcacagt tgtcgggaaa tgtgtgaagc tggcagaagc acccatcact ataatatccc 171780
agtcttttcc cagaagtcct gactcctcct gttgaaaact cctgacctcc agggacttct 171840
gaatccccaa acacacacac acacacaaac acacacacac acacacacac acacacacaa 171900
acacacacac aaacgtttcc taacattttc aaaacagcca tactctggct tttctatgct 171960
tctccaggga gtttgccaaa gaaagggaac gggtggagaa ccggcgggct tttctgaagc 172020
tgaggcggca acaacagatt gaacgtgagc tcaatgggta catggagtgg atctcaaaag 172080
caggtgaggc cctttcatcc tggggcccag ggatggagat cccaggccac ggagtacaaa 172140
gagagtcatg cagtttggag aaggctaagc tgggagggtt atgatgggag gagaaagaga 172200
acctgaattg gtagtcccaa attttatcaa caagaatcca gagtctgata tgaagaagtc 172260
taagatgaag ccaggatctg acatcacgta acttgaattc tgaaatcaga cgctggttta 172320
catcccggcc ctgccacttt ttacccatgc accacacatc cctgtacctc cgtttcctca 172380
gctgttacat ggaggcgatg gtagtgccta agtcatagta ctattggagt atttagtaaa 172440
ataatctcag ctgagtcact tggggagaga agtgcctgat acacggtagg cacatattta 172500
tttgttcagc catttaacaa acatttaggg agcacctgct gtgtgccagg cactgatcta 172560
agcactgagg atatgggagt aaacaataca caccaaatcc ctgccctcag agctctgata 172620
ttctaatgag agagataaag caaacaaata catgtcatgt tgggaactcc caaattcaga 172680
gaaggaagat aaaacagact aggaagataa aacagagtag gaagttggcc gggcgcggtg 172740
gctcacgcct gtaatcccag cactttggga ggctaaggcg ggcagatttc ctgaggtcag 172800
gcattcgaga ccagcctggc caacatggtg aaaccctgtc tctactaaaa atacaaaaat 172860
tagccaggca tggtggcgca cgcctgtaat cccagctact cgggaggctg aggcaggaga 172920
attgcttgaa cccaggaggc agaggttaca gtgagctgag gtcgcaccac tgcactccag 172980
cctgggcaac agagtgagac tctgtgtcag agaaaaaaaa aagagtagga agttagaggc 173040
agggtggtca gggaaggctt ctctaaggaa gtaccctctg agcagagaga cctgaaggac 173100
gtgaagaagg aagctgtggg gatgtcaagg gaaggggcat tccaggcaga gacagcaagt 173160
gcaaaggccc tgagctagga acgtatttga gacacagcaa ggaagccagt gcagctgaaa 173220
cagagtgaga ggtggggaca gctggaggag aggaagacag gaaggtgatg gagatcagat 173280
caagcagggg cttataggct gtggtgtgga cattggtttt tattttgcgc gaggtgggga 173340
gaatgttggc tattgctact gttgcggagg tggggcttga agtcacaaac cacccagcag 173400
catgtttttt ggtcggttga gctgtcacca tcagtcagca gagaatgggg gtggccgggc 173460
agacccttct tcctggtcca agggagaact catcctccaa atgcaggagc ttaactctgt 173520
gctcttcctc ttcagaagag gtgatcctcg ccgaggatga aactgacggg gagcagaggc 173580
atccctttga tggtaactgc tctaaaccca cctcaggggt gggtcccagg ggagaaggga 173640
gaagctgtgg tggggagtcg ggggagagca ggtgactggt tctaaggatc ttgcagaggg 173700
tagacgttcc tcttggagga attttaggac ttccatgcag agtttcccta ttctggcctc 173760
cacttttttg ttttaaccat ggacctggtt ttttctgctt tgtgccttgg tttttctcat 173820
ctgcaaaatg ggtatgatat aaacaatacc ctagctcacg agattgtttc tcagaatgat 173880
attcgttatg gcaaatagaa cacctgggat agtgcctggc atggggtcag cacgtttctg 173940
tttgctaaat aagtaataat tccaccaata atccagttta ctgtgaacgg ctgctgtctc 174000
ccatgttaga aacttaacga gacagaacca tgactttctt tcttttcttt tttttttaat 174060
tgagacagag tctcgctctg tcacccaggc tggagtgcag tcacacgatc tcacctcact 174120
gcaacctctg gctcccaggt tcaagcaatt ctctgcctca gcctcatgag aagctgagat 174180
tacaagcatg agccaccatg cctggctaat ttttatattg ttgatagaga tggggtttcg 174240
ccatgttggc cgggctggtc ttgaactcct tgcctcaaat gatctgcaca ccttggcctc 174300
ccaaaatgct gggagtgtag atgtcaattc atggtcccct ggaaacctga atatgaaagg 174360
agggaccatt aaaaaggtgt ccaaaagccc aacctcccca gcatagctgg gagtcagggg 174420
acagactgta agagtcactg tgtatccaac ctgaggcttc atgaaagtaa agtttcctag 174480
aatttagaga tagggttgga tgcggtctgt ctgtggctca catctgtaat cccaacactt 174540
tgggaggcca agacaggagg aacacttgag cctgggagtt caagaccagc ctgggcaaca 174600
taatgaggtt ccgtctctac aaaaaataaa cttagccaga tgtgggggca cacgcaccta 174660
tggtcccagc tactcaggag gctgaggtgg gaggatcact tgagcccaag aggtcgaggt 174720
tgcagtgggc accactccac tccagcctgg gtgacagagt gagaccctgt ttcaaaagaa 174780
aaaaaaagaa tttagagata ggccagaata atatgtctgc aatataataa taacagcaat 174840
aagaaaaata atagtactcc ctgaaaaatg caacttcttg cttgagattt atcttctcat 174900
actttagaaa actggttaga caggggctgg gcgtggtggc tcatgcctgt aatcccagca 174960
ctttgggagg ccaaggcggg tggatcactt gaggccagga gttcaagacc ggcctggcca 175020
tcatggcgaa accccatctc tactaaaaat acaaaaatta gctaggtgtc atggcacacg 175080
cctgtaatcc cagctactca ggaggctaaa ctacgagaat tgcttgaacc tgggagacgg 175140
aagttgcggt gagccgagat cacaccactg cactccagcc taggcgacag agcaagactc 175200
tgtctcaaaa aaaagaaaga aagctggtta gacagggtga tgacttttga ttaaaaatct 175260
gagagatttg agggaaataa aagaactggc actgcgtccc agaaggttat aaaatgaatt 175320
ttattatctt agttggggag gggagattac ctaactcccc taaatgagtt aggtaatcta 175380
actcatttag ggtacctaaa tctttttatt ggaagtctac acctgaactt gtctgctgtg 175440
gagcccctgg ggtgtatagc ttgaatatgg gggcagaatc ccaaaattgc agcctgccta 175500
gcgagtatgc tacaggtcaa ggggtggact gttttcataa gaaagtgagg tttcttagaa 175560
tttaaaaata gaggctgagt ggggcggctc acgcctgtaa tcctagcact tttggaggcc 175620
aaggcaggca aatcacttga ggtcaagagt ttgaccagcc tggccaacat ggcaaaaccc 175680
catctctact aataatacaa aaattagcca ggcgtggtgg tgcatgcctg tagtctcagc 175740
tactcaggag gctgagggag gagaatcgct tgaactcagg aggcagaggt tgcagtaagc 175800
caagatcaca ccactctctg ggtgacagag caagattctg tctcaaaata aataaacaaa 175860
taaataaata aaccagaagg aaaatagtgg ctgagggccc agacctggag tcggactgaa 175920
cccgacttga ttcttgtctt taccccttta agcaaagtga tagtgccacc ttgaacctca 175980
gtttacacat ctgaaaaatg ggtatactat tagttcccgt gagaacagtt gccgtgagag 176040
ttaaatccaa ggacacactg tgtccatatg gtctgtgttg caaaaagggt aacgtctttt 176100
tctcttgcca tgtttccatt gttggagctc tgcggagaac caccataaag aaaagcaaga 176160
cagatttgct caaccccgaa gaggctgagg atcagctggc tgatatagcc tctgtgggtg 176220
agtcccttcc tctgccacct atcagttgtt catcacctat cgcccaagag acatggtggg 176280
gtgggggcag agggcttgca aaccgtgctg cctggatttg ggtctcagct ccaccctttc 176340
ccacctgtgc gtgtgtcctg ggcagattac atcattatgg gaataacatc cgtgcctagc 176400
ttctcattat tttgtgggaa ttcaactaaa tgatccccat gaagcatggc aaaccagcac 176460
ctggcaggga cgaagctccc agtcaagttg gtgaatgttt gtgactcatt cgggaagtat 176520
tcatggggga cctgcttata ttaggtgctt ggttgcaaac aagacaaggc agtcacgagg 176580
ctgagctggg aggatcactt gagcctggga agtggaggct gcaataagcc attattgtgt 176640
tactgcactc cagcctgggc acagaaaaaa aaaaaaaagac acaaactgag ccaggcacag 176700
tggctcacgc ctgtaatccc aacactttgg gaagctgaga tgagcggatc acctgatgtc 176760
gggagttcga gaccagcctg gccaacatgg tgaaaccctg gctctactaa aaatacgaaa 176820
aaaattagcc tgtagttcca gctactctgg aggctgaggc gggagcatca cttgaacctg 176880
ggaagcagag gttgcagtga gctgagatct catcactgcc ctccagcctg ggcaacagag 176940
caagatcctg tctcaaaaaa aaaaaaaaaa aaaagacaca aaccaaatcc ctacctacat 177000
ggagctcaca gtccagtgca ggaaatagaa attaaacaga gaattacaca aataaacctg 177060
taatggtaat ggcacttcag ggagaggctc tgggcttagc ttgctctaga aggatgggga 177120
gcagtcaggg aaggctacct ggaggaagtg acggttaagc tgggaactga aggatgggta 177180
ggagatcact gtggtggtga tagcagaagg aacagtgtga gaggcagggc tcagaccttt 177240
gccaccacaa gggccagagt tcgagggagg agggaacatt tattctttcc cttctcactc 177300
ctctgtccta ttgattcatt ggctgtgatg atgttgattt tgaccttcta aagtgagaat 177360
gtattgttat tgttgttgtt gttctttaat gggtttttgt ttttaatgga aggaagagca 177420
tccaggcaga ggaaataaga ctggaataag attgagggga gaaggaattt aggctgcttg 177480
ggaaactgtg tggccgcagt ttagaggaag aaaggatggc aagagaaaga ggaagggagg 177540
aagagaagga gggagagaag tgaaggaagg agggaagtta gtacatccat gtgtttctga 177600
tccatagttt ctgatccact atttcgtatt cccctttat cgctcgcccc tagtttataa 177660
ccttattgct gagtttaggc ataatttcca ttgcgatcac atatctcgta gggtggatac 177720
actatggttt gtttagccat agctctatta tagggtgttt gagttgtttc caataatttc 177780
tcttacgaag aacactgctg tgcacattta cgtacaatga ctccccccac cctttgggcg 177840
tatttccttg gggataatta taggatcaaa gatattaaca gcttttcaac tcattattca 177900
aagagccatt ctgagtttca aaaacatgga acccatttat aaacctgcca agtatgcata 177960
tgttcatgga ttccccaccc aggccatcga atattaccaa tttaatttcc tttcccagtt 178020
aagtgggttt gtaatgaaac cttaaagctt gttttcattt gcatttttaa tttccagcca 178080
aaacacgctt ttctttgtaa tggagaactc attctgcttc cactcgtgtg tgcatctgtt 178140
taatttcctg taagcaaatg tcaagaattg gagcgctcag taggtgtctt gagtatttga 178200
tcaattatgt ctgtctcacg tgttacgtta cctccattgt ttaaaatctg ttttatgacg 178260
aggtacagtg gttcacgcct gtaatcccac tgctttggga ggccagtgca ggaggatctc 178320
ctaagatcag ccgttcaaga ccagcctggg caacataaca aggctccatc tctgaaaaac 178380
aaaatgttga aaaacttagc caggcattat ggcacacacc tatagtccca tctatttagg 178440
aagctaaggc aggaggattt cttgaaccca ggaattcaag gttgcagtga gctatgattg 178500
tgccactgca ctgcaacgtg ggcaacagag tgagaacctg tctcttaaaa aaataaaata 178560
acatacattc ttaaaaatct actttgctgg ccgggcgcgg tggctcacgc ctgtaatccc 178620
agcactttgg gaggctgagg cgggtagatc gcttaaggtc aggagtagga gaccagcctg 178680
gccaacatgg tgaaaccgtg tctgtactaa aaattcaaca attagctggg tgtggtggcg 178740
tgagcctgta atcccagcta ctcaggaggc tgaggcacaa aatcacttga acccgggagg 178800
cggaggctgc agtgagctga gatggcgcca ttgccctcca gcctgggcat caagagtgaa 178860
actccatcaa aaaaataaaa aatctgcata tacatatata tgtatatata tttttaattt 178920
ttttaatttt tttttttttt tctgagatgg agtcttgctc tagcacccag gctggagagc 178980
aatggtgcca tctcggctca ctgcagcctc cgcctctgtt aacaaggcag gtgacattgc 179040
agctttctaa acagacccaa aacccaggcc agtggcttgt tctttcatag ccacgtttgc 179100
tacaggcaaa tccaccaaaa cccacctcat cagcctgatt actcaaaaag acaaagaaag 179160
gagcccccaa tctagccagt ggttttctag accaccccaa aagagatctc tggaattcca 179220
ggattctggc aaggaatcac atttagcttt atttatttat gtaaagaatg caacaataca 179280
ggctgggtgt ggtggctcac gcctgtaatc ccaacatttt gggaagctga ggtgggagga 179340
tcgtttgagg tcaggagttt cagaccagcc taggcaacat agtgagaccc tgtctctatc 179400
aaatattagc tgggcattgt ggcacacgcc agtagtccca gctactcgtg aggctgaggt 179460
ggatcacctg agcccaggag gtcaaggctg cggtgagcca cagcatgccc ctgcactcca 179520
gcctgcgtga cagagacttc atctcaaaaa aaaaaacaaa aaaaagtaat aatacagtaa 179580
tgcatatttc aaagtaaggt gggagctatg tggtatttgc gttcacgttc acattatacc 179640
acagtatgca cagtcctttt tttttttttt ttgagacagt gtcttgctct gatgttcagg 179700
ctggagtgca gtggtgcagg catagctcac tgcagcctca aacccctgga ctcaagtgat 179760
cctcccacct cagcctccca agtagctggg actataggtg tacactgcta cactcagcta 179820

```
agttttttat atttttttact agagatggga tctcaatatg ttgcctaggc tggtctcaaa 179880
ctcctggcct caaacaatcc tcctacctcc acctcccaaa gcagtgggat tacaggcgtg 179940
agccaccaca cctggcccac atgcagtctt atataattgg tgattctact gcgctgttga 180000
atcagttgat aaacgcacta taaagcaggt tcattcctaa ttgatgaact tactgctgaa 180060
ataaggaact tgaatcattt acatgaaaag ttgagccatg ttgctgaaag gatatcaatt 180120
tttttttctt tttttctttt ttttttgaga tggagtctta ctctgtcgcc caggtgggag 180180
tgcagtggtg cgatctcggc tcactgcaac ctccaccttc caggttcaag cgattctccc 180240
acctcagcct ccaagtagct gggactacag gtgcacacca ccacgccctg ccaatttttg 180300
tactgttagt agagatgggg tttcaccatg ttggccaggc tggtctcaaa ctcctgacct 180360
caagtgatct gcccacctca gcctccgaaa gtgctgggat tacaggtgtt agccaccgcg 180420
cctgacagga tatcaaattt catttagact gcaggaatac gttcaagaga tctattttgt 180480
acagcctggc gactgtatta ataacaatgt attatatact tgaaaattgc tcagagagta 180540
ggttttaagc attctcaccg tgagaaaagt gataagcata tgtaataatg catatgttaa 180600
ctagctcaac tgagccactc catagtgtat acatatggtc aaaatatcat gttatgcact 180660
ataaatagat acagcctgta tctgtcaatt taaaataaat gaataataac tttaaaaaga 180720
aaaataacag tatggctggg cacggtggct cacacctgta atcccagcac tttgggatgc 180780
caagacaggc ttgaggccag gagtttgaga ccagcctggc caacatggcg aaactttgtc 180840
tctaataaat atacaaaaat cggctgggca tggaggcggg cgcctgtaat cccaactact 180900
tgggaggcag aggcatcact taacctggga gatggaggtt gcagtgagcc aagatctgca 180960
ctccagcctg ggtgatagag tgagccttta tttatttctg taaagaatgc aataatacag 181020
gcctggtgcg gtggctcatg cctataatcc caatgttttg gaaggccaag gtgagaggat 181080
catttgaggc tacaggcgca tgccacagtg cccagctaat acttgataga gacacggtct 181140
cgctatgttg cccaggctgg tctcaaaacc ctggcttcaa atgagcctcc caccttggcc 181200
tcccagagtg ttgtgattac aggtgtgaga cactgtacct ggcctgtatt aaaaaaaaaa 181260
aaaagaagaa gaagaagaag aggaggaaag aagaagaagg aagaaggaag aagaagaaga 181320
ggaggaggag gaggaatggg aaggggaagg ggaagaagaa gaggaggaag gggaagggga 181380
agaagaagag gaggaggaag gggaagggga agaggaagaa gaagaggaag aagaagacga 181440
agaagaagca caatgataaa taagtaaaat gtggagcata tgaaaacaaa acaaaaaaaa 181500
gttgatccat tatgaatgga agctgccatt gtaactctgc ttttttagga aaaccagacc 181560
ccatttagat gattttattt gtttttaaag gcaggttctt gctctgtcac tcaggctgga 181620
gtgcagtgat atgatcatag ctctctgcag cctggagctc ctgggctcag gcgatcctcc 181680
cagcttagcc tcccaagtag ctgggactac aggcaccacc acacccagct aatttgttgt 181740
tgttgttgat gttgttgttg agatggggtc tggctatgtt gcccaggctg gtctcaaact 181800
cctggcctca agtgatcctc ctgccctggc ttcccaaagt tctgggatta caggcatgat 181860
tttttattaa tttatttgca gctgacaaat ggtaattgtg tatgtttatg gagtgcagtg 181920
tgatgtttta atctatgtat acatcataga atgattcagt catgctaatt aacacatcca 181980
tcgcctcacc acctcaccgt tttttgtgtg tggggaaggc attaaaaatc tcttagcaat 182040
tttgaaatat gcaacacatt actatttatt aataatgcaa tataaataca caataatgta 182100
ttaatgcatc actaaatgcg atgcaatgca atgcaatgca atagatcact aaaacttact 182160
cctccagtct aactgcaact tataccettt gatcaacatc ttctccttct caatccctcc 182220
```

tcctcccctg cagcctccag gaaccacctt cctgctcttt ctatgagatc aatttttttt 182280
agttttaagc tcccacatgt gagatcatac tgtaattgtc tttctgtgcc agcttatttt 182340
actcagtata atgtcctcca gttctgtccc tgttgtcaca cattacagaa tttctttctt 182400
ttagggctgt atagtattct atttgtatac ataccacatt ttctttatcc attcatccat 182460
tgtgggacac ttagtttgct tccatatttt ggctattgtg aataatgctg aagtgaacgt 182520
gggagtgcag atgttctgaa aagacttaaa tgtcagacct gaaatggtaa agatgctcca 182580
agaaaacata aggagaaagc tccatggcat tggtctcggg aatgattttt tggacaggac 182640
ctcaaaagca caggcaacag aagccaaaat ggacaaatgg gatcgtatca aactaaaaaa 182700
tttgtgcaca gcaaaggaag cgttcagcag aggaaagaga caacctaagg aatgtgagaa 182760
aacgtttgca aacaatacat ctgataagga gctaatatcc aaaatatata aggaactcaa 182820
acaactcaac agcaagaaaa caacccaatt aaaaatgggc aaagacagct actcgggagg 182880
ctaagatgtg acgatccctt gagcccggga ggaggaggtt gcagtgagct gacattgcat 182940
cactgcactc caccctgggc gacagaagga gaccgagacc ctgtctcaaa ataaaaaata 183000
aaaatgtgca aaggatctga acatacatat cccaaaagaa aagacataca agtggccaac 183060
aggtatatga ataaaatgct gaacatcact catcatcagg gaaatgcaaa tcaaaaccac 183120
cattagctat cacctcacac ctgttagagt agctattatc tttttgtttg tttgtttgtt 183180
ttttgttttt tgttttgttt ttgagaggga gtctcactct gtcacccaag ctggagcgca 183240
gtgttgtgat ctcagctcac tgcaacctct gcctcctggg ttcaagggat tctcctgcct 183300
cagcctcccg agtaactgaa attacaggca cacgccacca tgcccagcta acttttgtat 183360
ttagtttcac tatgttggtc aggctggtct tgaattcctg acctcaaatg atctgccctc 183420
cttggcctcc caaagtgctg ggattacagg tgtgagacac tgtgcccagc ctagagtagc 183480
tattatcaaa aagacaaatg aggtttgttg aagttctaac ccctggtacc tgcaaatgtg 183540
gccttacatg aaaatagggt ctttgcaggt ggtaatcaag ttaagatgag atcaaactta 183600
attagggtgg gtcctaaatc caatgactgc tgtctttata agaggagaag caggctgacc 183660
aacatggtga aaccccatct ctactaaaaa tacaaaaatt agctgggtgc agtagtgcac 183720
acctgtagtc ccagctactc aggaggctga ggcaggagaa ttgcttaaac ccaggaggtg 183780
gaggttgcag tgagcagacg tcatgccact gcactccagc ctgggtgaca gagtgagact 183840
ccatcttaca agaaaaaaaa aaaagacaaa tcataacaag tgctggcaag gatgtgggga 183900
aacggggatc catttacatc attttaataa cacaggctct atatgggtgg tattgagttc 183960
ccagagttgc cattacaaaa tgtcacaaac ccagtggctt aaaacaacag aaatttcttc 184020
tctcacagtt ctagaggcca gaagtccaaa ctgaaatcaa ggtgtcagca gagccaccac 184080
gttccctcag aaggttttag gggagaatct gttccatggt attttcttag tttctggtgc 184140
tgccagcgat acttggtgtt cctcagttca tagatgcata attccagtct ctgcctctgt 184200
tgtcatatgg tcttctttct gtgtttctgt atgcgatttc tttttttttt ttttttttct 184260
gagacaagtc tcactccatc acccaggctg gagtgcaatg gcacgatcac agctcactac 184320
aaccccaacc tcacaggctc atgccgtcct cccacctcag cctcccgagt agctgggatt 184380
acaggcgtgt gccaccatgc ccggctaatt tttgtatttt tagtagatac ggggtttcac 184440
catgttggcc aggctggtct cgaactcctg accttacgat ctgcccatct cggcctccca 184500
aagtgttggg attacgggca cgagcccacc gcacctggcc ctaattactt tattttttg 184560 taaatttttt tttgtaaatt tcatgtagcc tgagcataca gtgtttataa tatatacagg 184620
agtgtacaat aatatcctag gccttcacat tcactcacca ctcaactcac tccctcacca 184680
agagcaactt ccagtcctgc aagctccatt catgccaagt accctatgca gctgaaccac 184740
cttttctctt ttatactgtg tttttactgt accttttcta tgtttagata tgttcagaca 184800
cacaaatact atgatgttac agttgcctac agtattaagt acagtaacat gctgggcagg 184860
tttgtagccg aggagctaca aaccacgtag cctgggtgtg gagtaggcta caacatctag 184920
gtttatgtaa gttcacttta agatgctcac acaaggacaa aattgcctaa caatgcattt 184980
ctcagaacac gtctccctca ttaagccaca catggctgta ttacaattta catataattt 185040
taagcgtata taaattgcca gaaatcacca gatgaatcct tggcggtgac ataccccttc 185100
ccccaccata gaacattgca gactggcccg gacgcccagt atctcatgcc tgtaatgcca 185160
gcactttggg aggctgcagc gggcagatca cttgaggtta ggagttcgag accagcctga 185220
ccaacatggc aaaacaccat ctttactaaa aatacaaaaa ttattcggac gtggtagtgg 185280
gcacctgtag ttccagctac ttgggaggct gaggcaggag agtcacttga acttgggagg 185340
cagaggttgc aatgagccaa gatcgtgcca ctgcactcca gcccgggtga cagaatgaga 185400
ctctatctca aaaaaaaaag aaaaaaaaaa aaaaaggaaa agaacatttc agactggtac 185460
cagttacacc ggctcttgat cccttgaatg tggctgaccc tgaactagga tgtacttcat 185520
aataacacgt ccggctggga atacttagta caaaagaaag agtataaaat atcttttgaa 185580
tccaccttga tattgattcc atgttgaaat ggtaatattt tggatgtatt gggttgaata 185640
aaacatctca tgaaagtgat ttttaaaaat ctagaaattg tctgcaatta taattccaga 185700
ccacagagaa aaacgagaga caggaatgta tagaaaaagg gaacgtggga caaagtgagt 185760
atgaaattca actaacagaa gtgacagtgc ctagcatggg gtccagcact tagtaggtgt 185820
tcaattaata ttcatttccc tctcccttac cagtgaaggg tatgcctgtc gtggggaatg 185880
tgtcttcagg ctgagtgatc aggaaggact ttctcaatgg ctggcacgtg aacctagtca 185940
tgatttcagc tcttgaggtt gtactagaag atttatatcc aataatcgta aggtaccact 186000
tagcatcacg ctaagatgta ttaattcatt tatgcctttg gatggccctt tgaggtagga 186060
agtgtggttg tctccagttt accaaggtgg cttgcccaag gtcatctgct ggttggtgat 186120
taagccaggt tttcagtgtg gctccagcag gagtgggggc tggggacctt ctacctgctg 186180
tggtttctct ctctctctct ctctctctct ctctctctct ctcgatctgt ggaacatccc 186240
ccctgtcccc caaggtccca agggtcttat ttcttttggc caagcccttt ggagacctgc 186300
agatctggac acatctttga gagtttcagg aactagggcc agaaatgctg ggcagggtca 186360
tgaggagctg ccactggggt tgagaaggtg atggacatga ggggaagggt ctttgcagaa 186420
aggagaggcg tccctgtaag caggtcacag ccactgggcc tggccaactg cagccgagtg 186480
gaatgtgccc ctgccccatg accatatgcc ccaggtgtgc aatgtggcgg cccagagcac 186540
acactctgaa ccatcttgac acatcttcac tggttactag acccccctca gcctgtttcc 186600
ttggctgtaa aatggggatg acgctggtcc ctacttccta gggctctgag caggagtaag 186660
tagcttgtcg tataaaacat gttccctgca gtgcctggtg cctgctaaat gttccataaa 186720
cgtcagctgt tattttcatt caggggaagc tgaaatccat attttcatgg aaaatctccc 186780
agtttttaaa tgtggaccaa taatttcagc tttcacaaac ccagtatgag tcggtatggc 186840
ccctagggtg ccaactcaaa atctctgttg agaattttgc tgataggaag tggcctcctt 186900
ggaggtgttt gctgtgtcct gtgtctggca agtggggtgg ttttgataaa cgtgctggat 186960
ggatgtatgg gtgaatggat aaatggagga atgaatggag aaacaaatga gcaaatgaat 187020
aatgaatgga tggatgaatg gatgagcgaa tggatggatg aatggatgag caaatgaatg 187080
atgtacacac aaaggaatgg ataaatgatg aatgtgctaa tgaatttaag aatgatgaaa 187140
gaatgaatga ataaatgaac aaatggatgg atgaaagaat gaatgaatgt actaatgaat 187200
gaatcaatca atgaagaacc atttaaaaat gaatgcaact gagggtttat aagaaaaggt 187260
atcttaagcc tgggcatggt aattcatgct ggaatcccaa tgcttaggga cgctgaggcg 187320
ggaggatcgc ttgaacccag gagttcaaga ccagcctggg caacacaggg agacctcatt 187380
gctaccaaaa acaaaattgt tttaattaag cgggcatggt ggtacgtgcc tgtagtcata 187440
gctacttggg aggctgaggt gggaggatcg cttgaaccca ggagttcaag gctgcagtga 187500
gctaggatca agccactgca ttccagcctg ggcaacaaag caagatcctg tctcaaaaaa 187560
aaaaaaaaaa gatgtatttt agaaggtaaa ttcaatctgt ccaaaactga gctctgacct 187620
tcccctaaac ctgtgcccat tcagtggatg agagctccat cccttaaggg gttcaccaat 187680
tcatccattc ctttgtatgt acatcattca ttcaccttgg ctcatccctc tctcttacat 187740
ccacaccgtt ccatcagcaa atgttgaatc tgtcttaaat gattcatccc aaatcctccc 187800
cgcttaacta ccacccaact ccagccccca tccatcatca tcatcacttg cctggatggg 187860
ttcagtcacc tccagcctgg tctcccagct cccgtcctca cctctcactg tctactctcc 187920
cactcggcag ccagagggtg cctgtgaaca cccaaatcag gttccatccc tcctctactc 187980
agaaccctcc acggctcccc cctcactcag ggtaaaagcc aaagtcctcc ttgtggtcca 188040
ccaggccatg catgatctgc ctgtcacctc cctgccttca ccaccttcct cttttcccct 188100
caaccactcc actccagcca cactgacttc cttgtgctct tccccaaaaa tgtcgggcag 188160
acacattcat gcttcaggac cttaaatttg ctgtttcctc tacctaagat actaaagtga 188220
caagtcaaca cactcacctt gaccatgcaa tttaatgttg cagcctaccc tgtggactct 188280
ccaagggctc ccagtccctc tgtgatgctt tactttttct cttaaaaaaa aaattgttat 188340
ttaaaagaac ttgtctcgct gtgttgccca ggctggtgtc aaactcctgg cctcatacag 188400
tcctcccatt ccagcttccc aaagtactgg gattagaggc atgtgccact gcacccatcc 188460
caactttttt tttcccatag cacttttcat tttccatccc actgttaatt tacttattac 188520
gtccactgtc tgtctcctcc ccttagaggg tcagaccccg gaagtccagg ctctgttgcc 188580
taatgtatcc tgagcccctg gaacagagcc tggcacaaaa taggtactca ataaatgcat 188640
aagagcaaaa ctatatgtag gcagaggaca cacccagctt attcctcagt gatcacttct 188700
aaagttaaat gtccatggaa aacagtctca tccacatctc tttctggagg ccttccaagc 188760
gtgctccatg cagctctgtt gcctgcccct gcatcaggga atggaggctc tgctttatcc 188820
tgccctgtgg tgtgactccc agaggcatca gatgtggctg ggagtgggag acatggaaaa 188880
ttggctcctg caacagagaa ctatcagcct tcccatcaat tggttacttc taattctgtt 188940
atttttcagg ggcactgtct tctcataagc tccatctatg caaaactaag cccatgggtc 189000
atgatggttc cctcaggcca gaggcttgct ggagagacta atggatcccc tggctaaaat 189060
ctgtgcttgg gctgcacatt ggttaatttc ttctgaagga acagcctgag cctgacattc 189120
tccatctttt ccctggcagg ttctcccttc gcccgagcca gcattaaaag tgccaagctg 189180
gagaactcga cctttttttca caaaaaggag aggaggatgc gtttctacat ccgccgcatg 189240
gtcaaaactc aggccttcta ctggactgta ctcagtttgg tagctctcaa cacgctgtgt 189300
gttgctattg ttcactacaa ccagcccgag tggctctccg acttcctttg tgagtatcac 189360
ccagccccac ccctgccaac tccctgatcc ctccctcaca cccttttttcc acttctcttt 189420 ctctggtagt atgtgtatct tctttggtcc tcattgaatc tgccctttcc tttagccatt 189480
tctataactg tcactggggc caatgttact gttgctatga caatggaacc catctccctt 189540
agacctgaga gctggaagct ggaattcaga ccaacaaatg ctcctgtgat tcctttctaa 189600
gagagaggga cagaggggtg ctggtgaagg ggatgttgga agagagacag agaaagacgg 189660
agctcataag atagacagat agaaacagaa acatacatgt attaataatt tttatgtaca 189720
tctctggaaa tgttcataac ttatggttaa gagaggatgc cttagaaata aggagtggct 189780
tatatgttgc cctcattttc tctacttatt tctgactcta cttctctctt ctttcaaacc 189840
ttctgcttct ttcctgttag gttggtgcaa aattaattgc gttttttgcc tttttttttt 189900
ttttttttaa ccacagttac ttttgcacca acctaatact tcctcccctg cccttttttgg 189960 cttccttatt cattcataga acatcccctc cagtatctgc gagagcgttt tgctccctca 190020
aggtacaagg cccactaagg ctttgccctc tgggcctatt cccagattct atgtgagtta 190080
gcatgagata gtatcaaaat tgagggccaa gtgagggtga ggaaaagcag caaaagatgg 190140
ggagatgtct gagcaggatt taaaaagtaa agagctcgag gaatcaacaa gagcagcgac 190200
tggggccagg catggtggct cacacctgta atcccagcat tttgggaggc tgaggtgggt 190260
ggatcacttg aggccaggag ttcaagacca gcctggccaa tatggtgaaa ccctgtcttt 190320
acaaaaaata caaaaattag ccagatgtga tggtgcacac ctgtaatccc agctactcag 190380
gaggctgagg cactagaact gcttgaatcc aggaggcaga ggttgcagtg agccaagatc 190440
atgccactgc actccagcct gagcaacaga gagagtgtct gtctcaaaaa ataaagtaaa 190500
ataaaataaa ataaaataaa gagtagtgat tgggcagtga ggggggcagg tggatgccct 190560
ggctttggct cacaggcccc aagtaaggac ttctcaaaac gtcttttgcc tactggctgt 190620
ctaatttatt cactgacctt ctgacctggt tcagaattga cttaggacag caagaagaga 190680
cagtctagtc tttgacctag aaaggcccgt gagcctagtc caggccattg tcttcttata 190740
accctccttg ttcccagtca cgttggctga ccccccagga cacccctcag gaaccagttc 190800
tccttcccag ggccctgacc tagtttcaaa cttagtaatt gtttttagtc cctctggagt 190860
ctcttataaa tgaggactct acttcgtgtt ttaacttcct ctaatactct atttttaatc 190920
tcctatattc tctctactaa tcatcttgta cagtctgtcc tggttcagga acaagggact 190980
gagacttcct gcctgggtcc tcagtgtcta taaaggtcct ttactcattc ccactttccc 191040
tttgagaaaa ctgagacaca gagaggttaa gtagattgcc caggatcaca cattagcttg 191100
gcatgatggc gggcgcctgt aatcccagct acttgggagg ctgaggcagg agaatcgctt 191160
gaacctggga ggcagaggtt gcagtgagcc cagatcatgc cactgcactc tagcctgggc 191220
aacagagcta gacgccatct caaaaaaaaa aaaaaaaaaa aaaagataca cattaatttc 191280
agagatgtca aaatataaac aaaaatgtat atcttggcat cagtgaagtg tagttgtttc 191340
tctggatctc agactccaca tctatgtggt agaaaccgga tttgatggtc ctgaaagttc 191400
ttccagatgc aacaatgcta aggataagta attctttcaa gtcttgtgca tcacctgcta 191460
tcatgtttcc atggtaactg aggaacaaga tctcagaaac tcttcagtcc tcccagagtt 191520
acttctggtg ggtctaggaa tgtgtcagat gttacaaaca gacttcctct gctgatattt 191580
tggtcctagg aaccctagag ttcccctcag acactaagat ctccttagcg tcctataaat 191640
aaggagaaat tttggtgata aatactgtga aggactttga cggtcagttc aaaacacctc 191700
ttaaaagcat gacatagcaa acacccttgg caaatatctt agttcatttg tactgctata 191760
acaaattacc cgagactggg taatttgata agaacagaaa tttattttct cacagttctg 191820
gaggctggga agcccaagat caaggcattg gcaggtttcc ctgtctggcg aaagctactc 191880
tctgcttcca agattgcacc ttgaacactg tatcctctgg aagggaggaa cactgggtcc 191940
ttacatggca gaaggtggag gagcaagagg gacaaacttc ctctgtcaac ctcttttata 192000
agggcaccta atcccattca tgagagctct accgtaatga cttaatcacc tcctgaaggc 192060
cccacctctt aatactgtta cattggcaat taagtttcaa cgtgaatttt ggagggggaca 192120 caaacattta aaccatcaca accaccaaac acaattagct ttgtggcctt aattagctat 192180
atgaaattca tggaagttag tttcagtcct ctgtctcttt cctttctgta tgctttctgc 192240
tcctcagaaa ccctcctcat ctctcctttc tatccattaa gtacccacgc ccttcctaac 192300
tcctcatctt cctaccctac caagaaagcc ctctcagaaa aggatctgat gtcagccatt 192360
tatttgctgg agcaaatgca tatccatgtt ttacccctcc ctgaggcatt tgcaatttta 192420
tgcttgctca tcaaagaaca aaaggctttg tcttactcaa gactttttag gtcactcaca 192480
acacaggatt tctaggggac ataagacaag ttttctgagt taggagaaaa gccatacctt 192540
aggtgggttg cctgtgtcgc tccaactaag tacttaactt caggattaca aataggatat 192600
cattatgatt tctatttcct tttatccttt ggagctcagt cacgtagaag tagattaaat 192660
ataattgtta gatcacagca ccctggcatt atggggccgt tatggtccat tgttattatg 192720
tgaattattc agttaattag tttatttttt aaatgtgata aacacccagg aacccaccag 192780
tcaacacaaa agtccttggc aataatctat atccgatcct tctcatcgaa ccagggcaaa 192840
aactacaaga tggagaccca ctgatatttt tctcattcct tttaaaatcg gcctaaggtt 192900
ggttagcttg ttggttggag ggtagggcat aattgttgct tttttttttt tttttttttt 192960
ttagacaagg tcttgctctg tcacccaggc tacagtaggg tggcccaatc ttggctcact 193020
gcaacctcca cctcccaggt ttaagtgatt ctcatgcctc agcctcccaa gtagctgggt 193080
ttacaggcat gtgtcaccac actggctaat ttttgtattt ttagtagagg cggggtttgc 193140
catgttagcc aggctggtct caaactcctg acctcagttg atctgaccgc ctaggcctcc 193200
caaagtgctg ggattacaga cgtgagccac catgcccagc cagctcttcc tttttaacag 193260
aggggaaact gaggcccatg ggaaggacac cttggacagg gcgtggccac agtgggtcat 193320
gtatataatc ccagcacttt gggaggctgt gctgggagga tcacttgagg ccaggagttc 193380
aagaccagcc agggcaacat agtgagaccc ccatctccac ataaaaattt taaaaagaaa 193440
aaagataagt cagaagttgg gtgtggtgac acatgcctgt agttctagca tgttggaggc 193500
caaatcaggg aaactgtttg aggccaggag tttgaaacca gcctaacagc atagcaagac 193560
ctcatctcta caaaaaataa aaagtttaaa aatgataata aaaggaaagt cagagccacc 193620
tggaacccct accctcagca agcctaacct cctctctgtt tcctccttct cccttctaga 193680
ctatgcagaa ttcattttct taggactctt tatgtccgaa atgtttataa aaatgtacgg 193740
gcttgggacg cggccttact tccactcttc cttcaactgc tttgactgtg gggtaagtgc 193800
tcttgtttct aagagttcat ttctccagct cttgcctgga atgacagata cctggacaca 193860
ttaaagggag aaaggtaaag tcacccctga atatgagaga ctcagatgga tgcagaagga 193920
atgagaaaac aatcccaaac actggcaagg atacagtgta cccagaaccc tcaaccaccg 193980
ccagtgggag gaaaacgtat agaccccctt tggaaagcta agtgggggac ataagacaag 194040

```
ttttccaagt tgggagaaaa gccatgcctt aggtgggttg cctgtgtcgc tccaactaag 194100
tacccaactt caggattaca aacaggacat caatatgatt tctatttctt cttttccttt 194160
gtagctcagt catgtggagg tagatgaagt ataattgtta gattacaaca ccctggcatt 194220
atggagccat tatggtcctt tgttattttg tgaattactc agttaattaa tttatttttt 194280
aaatgtgatt aacacccagt aacccactag tccacacaaa acctaagtcc tggagaataa 194340
tctacgtcca atccttctca tcgaaccagg gcaaaaacta caagatggag atatgaccca 194400
gcattccatt gctaggaatt catcctagaa aatctcaccc agatacctag gagacacagg 194460
ccagaatgtc cctgcagctg gaagtgaaat taaggttgtt cgcaaataag tggagaatgc 194520
ctggcccagg gcagccctaa tcatttacca tagtcctgtt ggtctcagaa aggcttaata 194580
atttatttat ttttttttat tttttgtttt tattttttgt ttttgagatg gagtctcgtt 194640
ctgtcaccca ggctggagtg cggtggcgcc atctcggctc actgcaagct ccgcctccca 194700
ggttcactcc attctcctgc ctcagcctcc cgagtagctg ggactacagg tgcccgccat 194760
catacctggc taattttttg tatttttagt agagatgggg tttcaccgtg ttagccagga 194820
tggtcttgat ctcctgacct cgtgatccac ccgccttggc ctcccaaagt gctgggatta 194880
caggcgtgag ccaccacacc cagccagctt aataatttat aataactgaa tgttgtactg 194940
ttttctgcca ttatagaaaa ttatgttgtt ggagaaaaca aaatacatac aaacaagcaa 195000
accttcccta cataaatgac ccaagtagtt aaagaataaa accaatttct ttccattaaa 195060
aagaaaagaa agccgggtgt gatgcctcat gcctatagcc tcagctattc aggaggctga 195120
ggcagcagaa ttgcttgagc ccaggagttg aaaaccagcc caggcaacat agcaagaccc 195180
tgtctctaca aaaattaata ataattagcc aggtgtggtg gtgcacacct gtagccccag 195240
ctactcagaa ggctaaggtg ggaggattgc ttgagcccag cagtttgagg ctgcagtgag 195300
ctatgatcac accactgccc tccagcctgg acaagagagt gagaccccat ctctaagaaa 195360
taaaagtagg ccaggcacag tggctcacac ctataatccc agcactttga gaggcggagg 195420
caggtggatc acctgaagtc aggagttcaa gaccagcctg gccaacatgg cgaaaccccg 195480
tctatactaa aaaaatacaa aaattagcca ggcgtcgtgg cacatgcctg taatcccagc 195540
tacttgggag gctgaggaag gagaatcact tgaactgggg aggcagaggt tgcagtaagc 195600
tgagattgca ccactgcact ccagcctggg tgacagaatg agactccgtc tcaaaaaaaa 195660
aaaaagaaaa attttaaaat gtcctgagca accttgtttg taatagttcc aagtctcaat 195720
atccgtgtat ccctttgctg tagaacagat aaatattttg tggcatatct atataatgaa 195780
atactctgtg acaatcaaag tccaccaaca gcagccacat gcccaacaac aggaatgaat 195840
ctcacccatg taacatggca cagaaggagg caggagctag caacgtaagt ccatacagtt 195900
catgcaaagt tcaagtggac aaaattaaac tctctctctc tctctacata tatatatata 195960
tatatatata tttttttttt tttttttttt tttttttttt ttttttgaga cagagtctca 196020
ctctattgcc caggctggag tgcagtggcg caatcttggc tcactacaac ctccacctcc 196080
cgggttcaag ccattctccc gcctcagcct cccaagtagc tgggattaga ggcatgcacc 196140
accacccccg gctaattttg tatttttgt agagaccggg attcagcaat ttgcccaggc 196200
tggtctcgaa atcctgatct caggtgatcc acctgccctg gcctcccaaa gtgctgggat 196260
tacaagcgtg agccaccacg ccccgcctta aactgtattt tttaaggatg atacttgaat 196320
acgttaaaaa ggcgaggacc ttgaaaacac aacgctcggt aaaagaaacc aaacacaaaa 196380
ggtcaagtat tgcataattc catttgtatg aaatgtccag agcaggcaaa tccatagaga 196440
```

cagaaagtag attagtggtt gctagggtct gggtgaggga gagtggggag taactgctca 196500
tggggacagg gcctcctttg ggggtgatga aaatgttttg gaacttgata gaggtgatag 196560
ttgcagaata ttgtgcatgt acctaaaggc actgaattgt gtaattcaaa gtgtgaattt 196620
tatgttatgt gaatttcacc tcagtttttt ttaaggtaag aaaatggtta ttacaaaatt 196680
caggatggta gttatatcac agtgtctctg gaaacttcca gggtatccac atgtcccttt 196740
ttattttatt ttattttta ttttatttga gatagggtct tgctctgttg cccaggctag 196800
agtgcagtgg caggatcatg accctctcct gtctcaaatt cctaggctca agctatcctc 196860
cctcctcagc ctcctaagta gctgggacta taggcacatg ccaccatgct tgactaattt 196920
ttttttttt tgtaaagtca gggtttccct gtgttaccca ggctggtctt gaactcctgg 196980
gctcaagtga tctgcccacc tcggcctccc aaagttccag aattacaggc atgagccact 197040
gccctagcct tctcctaatt gttgacatag gtagtagttg catgacattc actttgtaat 197100
tatgtgtttc aggaattctc aggcctgtgg gagctcttaa taaataaaaa agaggccagg 197160
tgtggtggct cacgcctgta atcccagcac tttgggaggc cgaggcaggc ggatcacgag 197220
gtcaggagtt cgagactagc ctggccaaca cagtgaaacc ccgtctctac taaaaataca 197280
aaaaattagc cgggcgtggt ggcgggtgcc tgtaatccca gttacttggg aggctgaggc 197340
aggagaatcg cttgaacctg ggaggcggag gttgcagtaa gctgagatcg cgccactgca 197400
caccagcctg ggtgataaga gcaagactcc atctcaaaat aaatgaataa ataaaaataa 197460
ataaataaat aagaggccgg gtgcagtggc tcaatgcttt ggaaagtgga ggccaacagt 197520
tggagagacc aaagcaggag gatggcttca gcccagaagt ttgaggccag cctgggcaat 197580
actagcgaga cactatctct ataaaaatgt tttaaaatta gccagatgtg gtggggcaca 197640
cctgtaatcc cagctactca agaggctgag gtgggaggat cacttaagcc caggaggaca 197700
gtgctgcagt gagctatgat tgcgccactg cactccagcc tgggtgacac agtgagaccc 197760
ggtctctata gataaatgaa tggatgaatg agggggtcaa ggatcctcac ccggcttcca 197820
tttggaggga ggagtttggt tgagttcttg caaggttggt acctaggaaa tgcttgccag 197880
ttctggagcc cagacactgt ccctggacat gagaccaggt tctctgccct aggttatcat 197940
tgggagcatc ttcgaggtca tctgggctgt cataaaacct ggcacatcct ttggaatcag 198000
cgtgttacga gccctcaggt tattgcgtat tttcaaagtc acaaagtaag tctttggggt 198060
tcctggacat ttgtacaggg ggtggggatg ggggacatgg tggggccgcc tccagaaagt 198120
tgggaaagtg agcctcgtgt ttcgagggct gactccgggg ccctgcctcc cccgcctggc 198180
ctgagtcctc gcctggcctc tgtcggcagg tactgggcat ctctcagaaa cctggtcgtc 198240
tctctcctca actccatgaa gtccatcatc agcctgttgt ttctcctttt cctgttcatt 198300
gtcgtcttcg ccccttttggg aatgcaactc ttcggcggcc agtaagtcct tcacaggaat 198360
tccaactcct ggttccctgg ggtcaggctc agggaacaca cagtcccctc caccgtgcag 198420
gctgccttcc tcgtagccca gacacccatt gcggtcaccc aaatgggcag ggccctgggt 198480
accactcagg gtttcctggg gacagagatg atggagacgt tcgtttcctt ggagatgaga 198540
tactgagcca caccctcaga gcaccccggg tggggccaac gtgaaatgtc tgtgtcctcc 198600
ctgcaggttt aatttcgatg aagggactcc tcccaccaac ttcgatactt ttccagcagc 198660
aataatgacg gtgtttcagg tacagcctcc acctggcccc acgggccaac acctctcagt 198720
gtcacagatg aaagtgcctg ctccacatcc aaggggcttc cctgaactcc tccttctcta 198780

```
cctggccttt tcacaccact ttgaaacaca gattttatgg ttatcattat tcaattatgg 198840
tgaggccaac agatcaggag atgaatgtca ttggaaagat agtttgtggc tgggcacggt 198900
ggctcacacc cataatccca gcactttggc caggtacggt ggctcacacc tgtaatccca 198960
acgctttggg aagcccaggt gggcggatca cttgagatca ggaattcgag accagcctgg 199020
ccaacatggt gaaaccccat ctctactaaa aatacaaaaa ttagccgggc gtggtagcac 199080
atgcctgtaa tcccagctac tcgggagatg aggcacaaga attgcttgaa cctgggaggc 199140
agaggttgca gtgagccaag atcgcgccac tgcactccag cctgggcaac agagtgagac 199200
tccatctcaa aaaagaaaaa gaaaaaaaaa accactttgg gaggtcaaga tgggaggact 199260
acttgaggcc aggagtttga gacaagtctg ggcaacatag tgagactccg tctctgcaaa 199320
aaaataataa taataattag ctgggcatgg tgatacatac ctcctagcta ctagggcagc 199380
tgaagtggaa ggattgcttg agcccaggag gttgaggctg cagtaagcta caatcacacc 199440
actatactcc agcctgggcg agagagcaaa gccctgtctc aaaaacgaaa agaaagtttg 199500
ttatactcac agatcctcag agaaggagca caccatgcag gaccaagcag agaagcaaca 199560
gggtcaagca ggaagagaag gaaaatgtgg gcaagaggct tgattgtggt ttccatggga 199620
cggaatgggt gaggcagagt aaacagctcg agactggcta gtttggatca tttcagtggg 199680
ctctggggca gaggagctgt tcctacttgt ctaggacctg gccttggggt gattagggca 199740
ggtggatagt gctgggaaga taaaggaggt ggttgggata tgggctggtt gggatattgt 199800
ttggtttgct tttaaaaagc ctgctcaggg ctaaattgtt tactacctct agggactggc 199860
tagtgctgga ccgggcagtc cctccagagt cagcaagacc ccagatgcat cagaataaag 199920
aaaataaaat gcgtggccag gccaatgagg tggttcatgc ctgtaatctc agcactttgg 199980
gagaccaagg cgggaggatt gcttgagccc aggagttcaa ggctgccgtg agctccagcc 200040
tgcaccacag agcaaggccc tgtctcttaa aaaaaaggca gagaaaaaaa atggctaata 200100
cacccatcaa atctgaagat accttggtct catattccag ggtgatcaac ccaaagcaac 200160
ttctgcaccc atgtgggcgc attccctgag gcttgggact ggcccagccg ggaccttcag 200220
agcatctttg gtggattctt tctctttgag ggactgagag tgtatagaaa atgtgacttc 200280
actctctcct tctcctgggg aggtagtttc taaatgagac cccaagacag ggagttgaag 200340
aggaaacctt ccatgaaggg aagttctgag cccccacata agcgattttt tttttttttt 200400
tgagatggag tctcgctctg ttgcccaggc tggagtgcga cggcacgttc ttggctcact 200460
acaacctctg cctcctgggt tcaagcgatt ctcctgcctc agcctcccga gtagctgaga 200520
ctacaggtgc atactaccat gcctggctaa tttttgtatt tttagtagag acagggtttc 200580
actatgttgg ccaggctggt ctcgaactcc tggcctcgtg atctgcctgc ctcggcctcc 200640
caaagtgctg ggattacagg catgagccac cacacctggc ccataagcga ttattaatag 200700
cactgatcgc tagtcatgta tctttagctc agaggttctc acccaaggac aagtctgtcc 200760
tccaaggaca tgtagcaatg tctgcaagca ttgttggttg tcacagctag ggagagggtg 200820
ctactggcat ctggtgggtg gagactagga atgctgctca atatcctaca atgcacagga 200880
cagccccaaa tagaataatc tggccccaaa tatcagcagt gctgaggctt agaaaccctg 200940
ttttagcaga ttcatgtttt tggagttctt taacatttac tttatcctca tggggatatg 201000
gatagaagga aggaagttgg atcttttttta aaggagcatg taggtgctgt ttgaatatcc 201060
ccttggttct ttcagtatgc atcagcacaa cttgcgtctg tcaacaccta atcctttgcc 201120
ttggtctttc tctggtcccc tgctctgccc ccaaggaact gcagtccagc agtactgtga 201180
```

atttttgtg ccacacctta aaaggagcag ccgttggtgg ataaataccc cagctccctc 201240
accctcaggt gggatgaccc ctagagctcc ccagcaagac caagccccgg ttacctacag 201300
tggaaactcg cttgatcaca tactgtttac gttccaccct cttttccctt ttctcacttc 201360
tcctctcccc tactggtgct tcctgagatc acctcccaga caaaccactt gcacccgaac 201420
ccttgttcca gggtctgcct caggcagggg gaccccaaac gtgtccttgt gctacatttg 201480
tgctatccac gtagtagctt gtttaatcat caccatgacc acatgaggaa cacaggtaaa 201540
tattaaaatc ctgtcttagt ctgctcaggc agccataaca aaataccaca cactgggtgg 201600
cttatacagg aaacatttat tctctcatag ttctggaggc cgggaagtcc aagatcaaag 201660
tgttagcagg gttagttagt tcctggtgag ggccctcttc ctagcttgca gatagccacc 201720
ttcttgctgt gtcctcatat gtcaaagaga gagagagaga gttgtgatgt ttcttcctgt 201780
tctttttttt tttttttttt tgagacaaaa atctcaaaaa aaaatctatt ttttttttag 201840
gcaaatcaca tttttttgtc acccagcctg gagtgcagtg gcacaatcat agctcactgc 201900
agcctcaaac tcctaggttc aaacgatcct cccacctcag ccccttgagt agctgggact 201960
acagatgggc accagctaat ttttttaaat tttttgtaaa gatggggtct tgctatattg 202020
cccaggctaa tcttgaactc ctgggctcaa gtgatcctcc caccttggcc tcccaaagtg 202080
ctgggattac aggcatgagc catggcatgc ggtctcttcc tgttcttata agggcactaa 202140
taccatcatg aagtccccca tgacctcatc taaccctagt tacctcttaa aggccccatc 202200
tccaaatacc atcccatcat aggttagggc ttcaactcat gaatttggag gcgggcacaa 202260
tttagtccat aacaaatccc cttaatcaca tcaagtaaga cagagttaca ggagggtctg 202320
tgactcctcc agggtcccat tttcctagaa gccaggctaa gagccccacg acgcaggaac 202380
ggccctttct actcgcaaac aaagagaaaa gccaaggaga agccaacacg gagtctggct 202440
ctgcaaaccg ggcaggattg ttaaagacct cctgggctcg gggatggggt gggcggattc 202500
cggctccaca gctgcatctc caaggggccc gtggctgaga ggggggttgg ctgtgtgttt 202560
cttcctcccc tttcagatcc tgacgggcga agactggaac gaggtcatgt acgacgggat 202620
caagtctcag gggggcgtgc agggcggcat ggtgttctcc atctatttca ttgtactgac 202680
gctctttggg aactgtatcc ttcatggaga gagagaaggg gacaggcctg gacctctggc 202740
agaggagagg ttgcaggggc tcaagggagg gtactgagag acccagatac ccagggccca 202800
agtggtgtcc caccagtggt tgcttttcct gactcagaca tttgcagaca ccctcctgaa 202860
tgtgttcttg gccatcgctg tggacaatct ggccaacgcc caggagctca ccaaggtgga 202920
ggcggtggga gaatgtttct ctggcaaagt taccacctgc ccatggcaga tcaggacggg 202980
ggtgggggtg ggggtggggg tgggggtggg ggcatgggaa cagggttaga acttttgccg 203040
gggatgcacc atgcaaagag aaggcgcctc tccccccact cccagaaaca gactgtccct 203100
catcaagcaa attctacagc caagagggtg ggaaggggga aggcagtgag gtcgctgcag 203160
gaaacggatg gcaaactcaa ccaaaaggcc gtttacaggg agtaagcagg gtttccaagg 203220
aatggtgtag cccccaggct agtggatggg agagggagtg ctgttatggg gacccagtca 203280
gagctggggc caaggaaaaa gggctgccac cagccctggg accttagaga acccagaacc 203340
atggcaaggc acagatggag tggccaataa atgtccccac cttctctctt cctctggctt 203400
cccgctggag cctcccctta gccaaacgca gcatgttaag agctagcctc cgtccagcct 203460
aagcctctcc ccaaggaccc tattaagtta agattacatg taacaggtac agggtcttcc 203520
tctcagccct ggggtctccc tcagcattgc agccccacct ccagtgcctc gaggtattca 203580
ggacatgttt gtgaaattga accaaaccaa gcagacgttg ccaacgctcc atctgccggc 203640
cctggcagga gggagagaga gtttcccggc cccagctccc agtggaggga agcggaagtc 203700
tctgccatcc caagcacacg gccacaagcc tggccactgt ggagctggct ggcatggctg 203760
agccgagggc tgatccagcc atgagctcat ccaagttcca agagtccatc cttaggggct 203820
ggtgcaggag ggtagcagaa ggggagggag aaaggccagt tcgtttatct cctgggaggt 203880
gtggacattc ctctccagat ccacattctt tctttcattg atcctacaag catttcttgg 203940
tcatttaata cgtgttttta atcctattca gtcctcatgg aaaccttagg agccaagttc 204000
tctgagcccc attttacaga tttcatcatt cagtaagcac ttaatgagca cctactgtgt 204060
gaccaaggcc ctggtctagg acttagggat taagcagtga acaaaaaaag gcaaaaatcc 204120
ctgcctccgt ggagcaggga ttcaagaggg gagacagaca agaaacaaga taaatttgta 204180
aacatacgta gcttgtcagt tggtgataaa cacaacagag aaaaattcag tagggaaagt 204240
cagggagagt tggaatttta gatgagatgt gtgtcgcaca gagaggttga gagacttgcc 204300
caaggccaca cagcagtaag ttgtggagct gggatttgaa cccaggccgt ctgggtctgc 204360
agcttgtgct cttaactgct gtgtaccagt tgcttgaatt tggcatgtt ttatgctcac 204420
ttgggaacct gtgggaaatg cagattccag ggcccagcac tggttctata gattatttgg 204480
ggagcctgag gatctgcatt ttaggtgttt ctgaggcaga tggtccagag acctagctct 204540
gaaaaatgct gggaatggtg ccaggagggg tgggggtggc cctatgagag cagggtggcc 204600
agccagatcc catctccatg ttgtctctga cagtgtcctg atctgaccat ttccaaggtg 204660
gtaaggttgc tccccgttcc agtgattcgg agcacagcgg gagagctgcc tgcaatggca 204720
tgacttttct tatgggcggg ttcatttctg gccatttctt tctcgttgcc ttttctttgc 204780
tttttctttg ttggcttttc tgttttacga atgaggccct gcatgaaggc tgaagaagga 204840
tttaaagtcc aaaaacgtct ttttctgtat gtatttttaa aacctcttcc cccattctcc 204900
tcctctctga acctaaccac cagtgagcag cagcaccctg ggcagttggc tgtagcccaa 204960
gtgccctgct ctcctctccc caccgccttc ctgtcatggg ggctgggaat ataaattcct 205020
ctcctcattc tccttctggg ggctgttgac agtgcatggc aggggccatc ggatgccagg 205080
ctcttctgtg tgtgagggta gttggtgttt tttgaaagtt ggttcagaga gttcacatgg 205140
ctcagaaagc ctagtgagag gaaaatcttt gcactgcttt ccagctcatt aagacaggat 205200
gcaggggcca ggcatggtgg cacatgcctg gaatcccagc actttgggag gccgaaatgg 205260
gaggatcatt tgaggccaga agttcaagac cagcctgggc aacatagtga gaccctgtct 205320
ctacaaaaaa aaaaaaaaaa ttaaatgtat acaggcatag tggcatgcac ctgtagtccc 205380
agttgcttgg gaggctgagg tgggaggatt gcttgagccc aggagttcaa ggttacagtg 205440
agctatgatt gtgccactgc actccaggct gggcaaccaa gggagactct gtctctgaaa 205500
acaaacaaaa gaaaaaaaaa taggctgcag gaaagtcttc attgtaggaa gagaagggac 205560
atttttattt tttgttatct ggctgtgtgt taaaataggc ttcataatga gttagatgtc 205620
aaacttatac acagagggga tagcaataca cttaaccaat agcaggtacc cattccaatt 205680
ggggagcctt ggttctgatt ggtcgaaata tttcaaatgt tgcccctggt cagcaacagg 205740
gtcagaagtg agtccccaag gcctagttca tgttttgtga acaaagattc cacgtgcctt 205800
ttaggacgag caagaggaag aagaagcagc gaaccagaaa cttgccctac agaaagccaa 205860
ggaggtggca gaagtgagtc ctctgtccgc ggccaacatg tctatagctg tgtaagtgcc 205920

```
cctaatccct gggatgctac cctggctcct gaacgtccac actatcccag gcacagattt 205980
gggaagcagt gggggtggtc cttgacagaa ctgagcttta ggaagagaca cttcttgtcc 206040
ttccacccac tttcactcaa taaatatttg gttagcagct gttatgtacc cagcactgtt 206100
ctaacttctg ggatacagc attaacaagg aggaaaaaaa aaatcccacc tgtgtgtagc 206160
cattctagca agggaaggag tcaataaatt agataaataa gtaaattata tattgtgtta 206220
gaaggcgatg gaactacaga gaaagtaggg gagggaaata gcaaatgctg ggagtgaaga 206280
gagttgtgat tttaaacgaa gttgtcaggg aaggcatcac ctagaatagg ggtccccagt 206340
cccggggctg tggactggta ccaggccgag gcctattagg aacggggctg cacagcagga 206400
ggtgaacagt gagcaagcaa gcattaccgc ctgagctcca cctgccgtca gatcagcagg 206460
cagcattaga ttctcatagg aacacaaaca ctattgtgaa cggtgcatct gagggatcta 206520
ggttgcgtgc tccttttaag aatcgaatgc ctgatgatct caggtgaaac agtttcatcc 206580
caaaaccacc ccccacacct aggtctgtgg aaaaactgtc ttccacaaaa ctggcccctg 206640
gtgccaaaaa ggttggggac tgctcaccta gaaggttaca tggcctgaag gaggtgaggg 206700
aggagccact ggggggcctg gggaagggca tcccaggcag agggaacagc ataggcaatg 206760
gccctgaggc aggaacatgc ctgatgtgaa ggaggcctgt gtgactagaa tcgaatagta 206820
agtgtgagga ggtgaaggca aggaggtgac aagcagatta cacagggcct tctgggtcag 206880
gggggaggac ttgggctttt gcccctagcc aggtgggagc catggagggt tcttgagcag 206940
aggaggctgg gacctgactc agatgctcac agactcctag cattcagtgg ggagtagagg 207000
gtggagagca ggagtgggag gctgagatgt gggttggttc gcctgggtca tccatccaag 207060
ctacagtgcc tagcaatgct ctaagtcctg tgaccatgcc actgcaggaa agagcaacag 207120
aagaatcaaa agccagccaa gtccgtgtgg gagcagcgga ccagtgagat gcgaaagcag 207180
aacttgctgg ccagccggga ggccctgtat aacgaaatgg acccggacga gcgctggaag 207240
gctgcctaca cgcggcacct gcggccagac atgaagacgc acttggaccg gccgctggtg 207300
gtggacccgc aggagaaccg caacaacaac accaacaaga gccgggcggc cgagcccacc 207360
gtggaccagc gcctcggcca gcagcgcgcc gaggacttcc tcaggaaaca ggcccgctac 207420
cacgatcggg cccgggaccc cagcggctcg gcgggcctgg acgcacggag gccctgggcg 207480
ggaagccagg aggccgagct gagccgggag ggaccctacg gccgcgagtc ggaccaccac 207540
gcccgggagg gcagcctgga gcaacccggg ttctgggagg gcgaggccga gcgaggcaag 207600
gccggggacc cccaccggag gcacgtgcac cggcaggggg gcagcaggga gagccgcagc 207660
gggtccccgc gcacgggcgc ggacggggag catcgacgtc atcgcgcgca ccgcaggccc 207720
ggggaggagg gtccggagga caaggcggag cggagggcgc ggcaccgcga gggcagccgg 207780
ccggcccggg gcggcgaggg cgagggcgag ggccccgacg ggggcgagcg caggagaagg 207840
caccggcatg gcgctccagc cacgtacgag gggacgcgc ggagggagga caaggagcgg 207900
aggcatcgga ggaggaagta agtggaggtg acctcgaatc cgcagaatga cggtaacatt 207960
aataatgaca acagccaaag tagcacgtgc tgtgtatttg tttataaaaa tatattataa 208020
aatgctgtat ttggccaggc gcagtggctc acgcctgtaa tcccagcact ttgggaggcc 208080
gaggcggatg gatcacgagg tcaggagttc aagaccagcc tggccaagat ggtgaaaccc 208140
cacctctaat aaaaatacaa aaattagccg ggcacggtgg caggcgcctg tagccccagc 208200
tactcaggag gctgaggcag gagaatcgcc tgaaaacagg gggcggaggt tgcaatgagc 208260
```

```
cgagatcaca ccaccgcact ccagcctggg cgacagagtg agactctgtc tcaaaaaaaa 208320
aaaaaaagtg ctgtatttgg ccaggagcag tggctcatgc ctgtaatccc agcactttga 208380
gaggccgagg cgggcggatc acttgaggtc aggagttgga gaacaggctg gccaacatag 208440
tgaaaccccg tctctactaa aaatacaaaa attagtggtg gtgcccacct gtattcccac 208500
tactcaggag gctgaggcgg gagaatcagt tgaacctggg aggtggaggt aggttgcagt 208560
gagctgagat cgtgccatca cactccagcc tgggcaacag agcaagactc tgtctcaaaa 208620
aaaaaaaaat gctgtatgtt tttgtttttt tgacacaggg tctcgcctgt tgcccaggct 208680
ggagtgcagt ggcagtcata gctcagtgca gcctctacct cccgggctca agccatccgc 208740
ctcagcctca caagtagctg ggaccacaga catgtgccac atgcctggct aatttttgta 208800
gagacagtgt tttgtagaga cagggtttca ctgtgtttcc caggctggtc tcaaactcct 208860
gaactcaagc attccgcctg ccttagcctc cctaaagtgc tgggactaca gggttgagcc 208920
accacactca gcctaatttt tttaccttta gtagaaatga ggcctggctc tgttgcccag 208980
gctggtcccc aactcctggc ctcaagcaat catcccacct cagtctccca aagtgttcgg 209040
attagaggct tcacagatgg ggaaactgag agattgagtg agctcctcaa ggtcattcct 209100
ctaaccagtg tccttgaacc caggctctct ggcaccagag gccttgagca tttcagggaa 209160
actattaaga gaagccccac tgtcgtccag aattatatag tcttctgtgt tcttgctgtg 209220
tgacttttgc aaagtgactt catatctctg ggcctcacac aatggaaata gtgggatcta 209280
attgggtcat tgccaggatt gaatgaggta atgtatgcaa agggcctgga agagcagctg 209340
acacataata agtgctcggt aaatttagag cctttttggc catttttcagc caactctatt 209400
tacctaatgc tattctttgg aagtttgaaa agccactctg ttgggaggcc aaggtgggag 209460
gatcacttga taccaggagt tggagaccag tctgggcaat agaggcagac cccatctcta 209520
taaaatataa aaaattaaac agatgtggtg gcatgcacct gcagtcccaa ctacttggga 209580
ggctgaggca ggagggtcac tggagcccag gatgtctagg ctatgatgag ctatgattgc 209640
accactgcac ttcagcctgg gcgacagagc aaggctttgt ctcaaaaaat aaaataaaaa 209700
ataaagaaaa agaaaaggca ctttgggccg ttagaattga agggagagca gagtttcaaa 209760
gctttggatg cagcgggatg tggtggctca tgcctgtagt cccagcactt tgggaggcca 209820
aggtgggagg atccacttga gccccggagt tcaagaccag cctgcgcaac atagtgagac 209880
ctcacctttt aaaaataaat aaaaatgtta gaaagctttt gaggcatctt ccaggccagc 209940
aacttatcca ttcagaacca gcatcctctt tttcataacg acattttgta atactttcta 210000
gcagatgcta tagtgattct gcatataggg actcaacaac ttacccatta aaatagacat 210060
cgtagacatt gtcctattac aaattaacct gctcttagtc ctcttttata ttaccatcag 210120
ggcataatat tgattttttt aatgatgggt ttaagtgatc ctgttgtatg acatatgagg 210180
taggccagca cttctcaaaa tctaatgtgt atgtgaatcc ccagggatct tgttaaaaca 210240
caaattgtaa ttccgtaggg ctaaggactc agtggagcct gagattctgc atttgcaacg 210300
agctcccaga tgaggctgat actactggtc cagggaccac attttgagta atgagactct 210360
ggaggacata gtgaagtaat tctgatatgt acaccataca caaaatcacc atgaagtgac 210420
aggcacaaat gatggctaac tctgggttgt gtggacaatt caaaccacat gaggggagtt 210480
gccagcagtg tcaagatgtt ccacaatgtt gaacacctct tggcaaagtt ccatatacaa 210540
aagagtctag tctttcttcc atttatttaa tagttgcatt gcaggaaaat gcaatgtata 210600
ttaaaaacat acaaaaaata tgttgtgttc ttatgtaaaa gagttaggtt taaactaaaa 210660
```

gcacaggatc aggtgcagtg gctcccacct gtaatcccag tgcattggga ggctgaggaa 210720
ggagaatcgc ttgaggccag gagttcgaga ccaacctggg cgacataagg agacctcgat 210780
ctctacaaaa gaagtttttt aattagccag gtgtggcggc aggtgcctgt agttctagct 210840
acttggaagg ctgaagcagg aggattgctt gagcccagga gttcaagatt acagtgagct 210900
atgattatgc cattgcattc caacctgggc aacagaacaa gtccttgtct caaaaaaaaa 210960
aaaaagaaag aaagaaagaa aaaacccaaa caaacaagca aactaaaagc acaggtaatt 211020
acaagcaaga tttttcacct ctttgaggga cattagaaag tcatgaagag gaaaagataa 211080
gtctttccca tatgggactg tcatgtacat ggtagggtat ttagtataac tgcctaccat 211140
tctctaagtg cctgcagtgc ccctcaatca ttatgttatt aggtttccac gtagttctac 211200
aacagttttc tgaaaaccat tgttctaggt cattctttcg cttcaatctt ctcctatggg 211260
tttatgcatt cattcagtta gtatttacta agtgcctact atattctaag ctcatgctgt 211320
gagttcagtc acacaactgc aagtgaagtg gtctgagaca ttctgagaaa tacgaccaag 211380
aaactgctcc cagggtctca gggcaggttt ccagaggagc aatctgagaa gggagtagag 211440
tgtttcagtc taacaacagc atgtgcaaag gccctggggt ggaccagaag gaggccagtt 211500
tgcaggacat gactagtgac gagaaagtga caaagaaatt gaaggtgcat tgatgagact 211560
ctggggctgt cagtcactca ggggaatgag agatcaaaac gggagtttag gtggaataaa 211620
gtgtttacca cagcactctc tgtatagtaa agaccaatga agagccaggt acaggccagt 211680
gtgatggttc acgcctgtaa tcccagcact ttgggaggca gagacaggtg gatcacctga 211740
ggtcaggggt tcagaaccag cttggccaac atggcaaaac cctgtctcta ctaaaaatac 211800
aaaaaattag ccaggcgtgg tggtggacgc ctataatccc agctactcag gaggctgagg 211860
cacaagaatt gtcctgcgag gcagaggtta cagtgagctg agatcacacc actgcactcc 211920
agcctgggca acagaacaag actctgtctc aaaaaaaaaa aaaaaaaaaa aaagccaggt 211980
acagtggtat gcacctgtaa tcccagctac tcaggaggct gaggcaaagg attgcttgag 212040
cccaggagtt cgagaccagc ctgagcattt agagaatggg aggccagtat actaaatacc 212100
ctaccatgta caagacagtc tcatatggaa aagaattatc ctttcctctt catgactttc 212160
tagtgctcct cacacaggtg aaaaatcttg cttataatta tctgtgcctt tagtttgttg 212220
gtttatttag ggttttgttt gttttttttt tttttttgag gcagggtctt gctctgttgc 212280
ccaggttgga ttgcagtagc attgctcatt ttagagatga gcaagacctc atgtctaaaa 212340
aaaaaagaaa gaccaatgat tattaattac tcttgctatt attactaata ttactgttat 212400
tatcagcctt attaacagat ctactgttat tgaaggaggc agagtgacag ggacaaaatg 212460
tctctcccta acaatatgcc aggaagagtt tttgaaagac aacagtaaac attggaaact 212520
acaagagcag caaagcctgg ttgtgaaagg caaggacttt ggggcaggca gtcacattcc 212580
tgccctatca cttccaggct gtgtgacttt cagaatttca ctcctctctg ggcctccatt 212640
tcctcatcta taaaatgaag ataagaatag tagctacctc cttctctggg tataagattt 212700
aactgagccg ggcgcggtgg ctcatgcctg taatcccagc actttgggag gccgaggtga 212760
gcggatcaca aggtcatgag ttcaagacca tcctggctaa tatggtgaaa ccccatctct 212820
actaaaaata ccaaaaaaaa aaaaaattag ccgggcgtag gtggtgcacg cctgtagtcc 212880
cagctactcg ggaggctgag gtaggagaat ggtgtaaaac ccgggaggcg gagcttgcag 212940
tgagccgaga tcgcaccact gcactccagc cggggagaca gagcgagact ccatctcaaa 213000
aaaaaaaaaa aaaaaaaaaa agatttaact gagttagtac gtgtaaaatg ctttgagtgg 213060
ttcctggctt ataccaagag ctcaataaat gttagcaatt ttttgtagca ttttggggtc 213120
tcactatgtt gcccaggctg gtgtcaaact cctggcctca agaaattctc ccactttggc 213180
ctcccaaagt gctggattta cagacatgag acaccatgcc tggccatgtt agctattatt 213240
aatatgaata ttattaagta ctcaatgaat gctattttta gcagtaatag taagcactca 213300
ggaagtgtca gctaatactg ttagtaatac tctcatcaat aaacataaaa agcaataagg 213360
acccagcttg cccaaatccc acagatggtt cctgctccct ctcttcttca gaggaagaaa 213420
ctatctcccc actttcaccc ccatagcctc agctggccag acccccattc tgaaccaggg 213480
gagtactgct aattccatta ttaatagaca catcaaacaa tctggccggg agagacatta 213540
ttcatttggc tgataaagag gttctaaggc tctttggaaa taaaagttca tgaagattca 213600
tgcactttaa gagaaaaaaa ttcaagatca gtcattcatc tgctttaaaa aaagtggcaa 213660
agataaaact ttatttgaga atataaaata ataaaaagac attttcgttc tctgttgtga 213720
caaagccagt ggccttcgga ggtctgcctt gtacattttt cctcttcttc agtcattcct 213780
tgaggctttt tgcaaacgta ccctgtgttt ttcattctcc agcatattga taattttttt 213840
tttttgagac atggtctcgc tttgtcatcc aggccccgga gtacagtggt acaatcatgg 213900
ctcactgcag ccttgacttc ctgagctcag gtgattctcc cacctcagcc tcccgagcag 213960
ctgggactac aggtgtgcat gaccatgcct agctaatctt ttgtattttt tgtagacaca 214020
gggttttgcc acattgccaa ggctggtctc caactcctgg gttcaagcga tcctcccacc 214080
tcagcctccc aaagtgctgg gattacagga gcgagctacc ttgccaggcc gatcatattt 214140
ttttcctttt tattcacttt gtcttctcct cattcctacc ttcatctgtc tttcagtggc 214200
tcactccagt gaaaagtgga ctgacgcaca ttctatttca tataattcaa tggctgctgg 214260
ccccagatcc cccataccag gtggccgagc ccagtggccc tgcagggtgg acaaaatgag 214320
ggtggaactt tcccagactg tcagtaaaaa tctatggagg acagagcttc tgcctctccc 214380
ttgcaaccag gcagtgcctt ctcccaggcc tatctgcttg caaagggaac ttttgccaag 214440
acctgctcca ctctagaatt cttatctctg ctgttcgcat cctaattcca cctgcatctg 214500
tcaccatgac aacctgctcc ccaaaaggaa caggaagaga gatgctggac ttttgagctc 214560
cacagtttat cctgcatggg ggtagggagt ggttaattac ttagcactct aattcttacg 214620
gtacccccaa tgggcccaag ttggtttttt taaaaaaaaa cagtcttgct ctgttaccca 214680
ggctggagtg cagtggcaca atcatagctc actgtagcct caaactcctg gactcaaatg 214740
atcttcccac ctcagcctcc caagtaactg gaacaacagt ctcgtgcaac tacgcccagc 214800
taattttttt tttttttttt tttttttaga gatggggtct cactatgttc cccagactga 214860
tctcaaactc ctgggctcaa gcgatcttcc ttcctcagcc tcccaaagtg ctaggattac 214920
aggcgtaagc cactgtacca agctgcccca ttaaagcttt gaacaccaga gagcccagct 214980
cagctgtttt ccagctgggt aactctgggt aactttgcct ctctgaacct cagtctcctc 215040
ctgtgtgaaa tggggctgat cactataccc atctcggatg gtggtagttg cagggattaa 215100
atgagttaat acgtgaggtc cttaggacag ggggtgggga cacgagataa gcaataaaca 215160
ggaactgctg ttattatcac ccccacataa tccgatctca gggtctgagt gtgccccagg 215220
caaggtgtcc acagccctct gcagaaggat gcccaagtga tcagctggca caagaacgcc 215280
acgcacagca ggtgttatgc aactggccac ctattccagg cagaggatgc cagatcccca 215340
gggagaaggg ggtaggggtg cagcttcaaa gttttctgcc ccttttgagt tctccttgga 215400
gacactttgg aaatgaaacc tcccggaaat tgatattagg cctctgcagg ctgagcttgt 215460
taaaatttcc caacaaacag agccaacaga cgctctacaa ggaagcaaaa acaagacaaa 215520
acacattggc agaccctttt ccatctgctc ttggtagatg gtattcctct aagaaaatgc 215580
cgccacgagt ttctccatgg cttcttgagc tggtggccaa aggatttagg ttctctttga 215640
aattataact taactgggcc tgctttatgg cagggatatc actctctgaa atgtgtatat 215700
atatgtgtat gtatatatat acacatatat acacatatac atacacaggg ccaggcgtgg 215760
tggctcacac ctgtaatccc agcactttgg gcggccaagg caggtggatc tcttgagccc 215820
caggagttca ataccagcct gaacaacata gtgagaccct gtctctacaa aaattaataa 215880
aaataaccag gcatggcagt gtgtgcctgc aatcccagct acccagggtg ggaagatcgc 215940
ttgagcccag gagttaaaag ttgcagtgag ctatggtcat accactgcac ttcagcctgg 216000
gcaacagagc aagaccctgt ctcttaaaaa tatattatta ttattataca cacacagaca 216060
cacacagaca cacacacaca ttacagatga tgagaaaata ctctcagcca ggttttcatg 216120
atacacaact tctcaaaaag catcacaagc aggttagaat tagggatttc tttgtggact 216180
gtccaagatg ttgaggaaat attggtttag aatttacctc atttaggcca gaaatggtgg 216240
ctcacgcctg taatcctaac actttgggag gccaaggcca atggatctct tgaagccagg 216300
agttttagcc tggccaacat ggcaaaatcc tgtctctact aaaactacag aaaaaaaaaa 216360
aaaaattagc cgggtgtggt ggcacaggcc tgtagtccca gctactctgg aggctgaggc 216420
aggagaatca cttgaacctg ggaggcagag gttgcagtga gccgagatcg tgcattacac 216480
ttcagcctgg gtgacagagc aagactccat ctcaaaaaat aagatagata agataaatat 216540
atataatata tatgttatat atataatata gaaactacag aacaagtgat ctttgtatgt 216600
ttccagaata taacagcggg acaggcatag gatagacgtt cccattgcaa aagggagaaa 216660
ttggaaggga taaagaggtc accagtccta agcaagtgct aaatccagca agacaaatcc 216720
cattaggttt caaggcctga gaataatcct cggtgactct cagctcatta acatacttag 216780
ttctcagagc cagactcaat gaggttacgg cccgcatgtt atgggtcagg aactgaggct 216840
aagtaactca ctggagatta tgtggtaaag aaggtccagg atcattgctt cagtctccag 216900
gatatgggga aggttctact cctgttatcc caaattttaa aatgtgggaa ctaaggctca 216960
gagaggttaa gcaaatcaca cagggttgca cagctagtga tgttgctgag atttccctgt 217020
gtgtagtggc tcatgcctat aatcccagca ttttgggagg ctgaggcaag agggtcgctt 217080
gatcccagga gtttgagacc agcctgggca atatagtgag acctcatctc tacaaaaaga 217140
aaaattaaaa agttagccag gcgtggtggc aggcacctga agtcccagct actgggaagg 217200
ctgaggtggg aggattgcct gagcctggga ggtggcgatt acagtgagct gagatcgcgc 217260
cactgcacta caacctgggc gacagagtga gaccctgtct caaaaaaaaa aaaaaaaaaa 217320
gacattgccg agattcaaac ccaggtcagc ctgtcttctg aaatgtccct ctatgaccca 217380
ctcacaaaac tgagaaggca gaaagttgct tggacctgtc tatttcccct gtgcagtctc 217440
agagaaacag tggaactgcc tcggtttctc cttccgggaa gtattcatag aagcatccca 217500
cttacctact ttggtctgaa aataaattag cttgtctctc ttccacttac taaaaacacc 217560
gtgggttttt gcaagttaaa atgcaaaaat aaaatgagga gaatggtgct ggtagtttag 217620
ccagtgggaa gccctctggg gaaagccagc cttttattta ttacttattt atttatttat 217680
tctttctaga tagatttatg ggaaaccagg gctgtgttgt ccaggggtct gtagtccaga 217740
aggcatcaga tgggctacta agtgagtctt tgtccacctg tagatggcaa gaggcagggc 217800
ccaggtgtcc atggcttgga gaggcagggg ttgatgggag gtttgaggct gtgggatctc 217860
tcctggggcc tcagtatcct catctggata atggggacat tctggccagg cacggtggct 217920
ctatatatcc agcacttagg gaggcctata atcccagcac tttgggaggc tgaggtgggt 217980
ggatcactgt aggccacgag ttcaagcagc ctgggcaaca tggcgaagcc ctgtctctac 218040
tgaaaataga aaaactagct gggtattgtg gtgcacgctg gtaatcccag ctattcggga 218100
ggctgaggca cgaggatcac ttgaatccac gaggcagagg ttgcagtgag ccaagatcct 218160
gccactgcac tccagcctgg gcaacagagt gaggctctgt ctcagttaaa aaaaaaaaga 218220
aaaaagaaaa agaaagaaag aaaaagaaaa tgggggtatt catttatcat ttgacagtaa 218280
gtttacccag cattgactgt gtgagaggcc ctgtactagg cagtgaaaac tcagctaaga 218340
ataagaaagt taaaaacaag ctgggcattg tggtttacgc ctgtaatccc aacattttag 218400
gaggccgagg aggaagaatc acttgaggcc aggagtttga gaccaccctg ggcaacatag 218460
tgagacgcca gtctctacaa aaaattgtaa aattagccag acatggtggc gtgagcctgt 218520
agcctcagct acctggaggc tgagatggga ggatcactgg agcccagaag ttcaaggctg 218580
cagtaagcta tgatcctgcc actgctctcc agcctgggca acagagtaag accctgtctg 218640
aaaaaaaaaa aaaaaaagag gccaggtgca gtggctcaca cctgtaatct cagcactttg 218700
ggaggctgag gtgggtggat cacttgaggt caggaattcg agaccagcct ggccaaaatg 218760
gtgaaacccc atctctactg aaatacaaaa aattagccgg tcgtagtggt gggcacctgt 218820
aatcccagct actcaggagg ctgaggcaag agaatcgctt gaacctggga gccagaggtt 218880
gcagtgagcc gagatcacgc cactgtacga cagagcaaga aaaaagaaag aaagaaagaa 218940
aagaaataag atgatgggga gttgtggaaa cctgtccatg ggcacgtgaa ggtcttgacc 219000
tctgaccaag aagtgaacag gctcctctca attccaggca ctgcagggat ctgggacatg 219060
acttctccat gaccaaactg taccctttcc ttttcttttt tgttttttttg gtgacagggt 219120
ctcactctgt cacccagact ggagtgcagt ggggcgatca cggctcactg cagcctcaac 219180
ctcccaggct caagcaatcc tcccacttcg gcctcccaag tagctagaac tacaggcaca 219240
cagcgccacg cccgtcaatt tacacatttt ttgtagaaat agggtctcac tatgttgccc 219300
aagctggtct tgaactcctg gccttaagca atcctcctgc ctccgcttcc caaagtgctg 219360
ggattacagg cgtgagccac tgcgcccagc ccaaattgta ctcttgaaag atggaatctt 219420
agctaggatc ctgaactgtt gccttttatc ctaaatcagt tgttggttct ttttcattca 219480
cttgccttcc tcagagagaa ccagggctcc ggggtccctg tgtcgggccc caacctgtca 219540
accacccggc caatccagca ggacctgggc cgccaagacc cacccctggc agaggatatt 219600
gacaacatga agaacaacaa gctggccacc gcggagtcgg ccgctcccca cggcagcctt 219660
ggccacgccg gcctgcccca gagcccagcc aagatgggaa acagcaccga ccccggcccc 219720
atgctggcca tccctgccat ggccaccaac ccccagaacg ccgccagccg ccggacgccc 219780
aacaacccgg ggaacccatc caatcccggc ccccccaaga cccccgagaa tagccttatc 219840
gtcaccaacc ccagcggcac ccagaccaat tcagctaaga ctgccaggaa acccgaccac 219900
accacagtgg acatcccccc agcctgccca cccccccctca accacaccgt cgtacaaggt 219960
gagaccctct gctctcacat cactgggcag gggacctggc gtccctggag ccagaggctc 220020
tgctgagtga ccctggactg tgaccccatc tctctggcct cagtctcctc ccctggaaaa 220080
tgggcatagg cgtagtttcc taccccacag ggctgtggag ggttcagtga gataatttgt 220140
gcacagtgcc tggcacgggg ttgtgttcag tcgggttagc aatatcttct acgtccttcc 220200
ttcccaaggg gagccaggaa gccaccccat ttgaggagca atagggtcct ctgatggaag 220260
cttgaggggg tcagatgatt gattctctcg gcccagcact gtccaaaaga aatgtaacac 220320
aggccacatg caaatgtcag tttaaactct ctagtcgcca cattaaaaaa ggggccagat 220380
gtactggctc atgcctgtaa tcccagtact tcaggaggcc gaggtagagt gagccaagat 220440
ggcacctctg tactgcagcc tgggtgacaa agcgagactg tctcaaaaaa aaaaaaaaaa 220500
aaaaaaaatg gtgaactgct gggtggatta tgtcttaagt tcatctagtg tcagttctat 220560
gtgagagatt ttcatgagtt tgctggataa aggctttcca tggtcctgag acctaagatc 220620
ctaaggtctt gtcactgtgc ccattttata gatgtaggga ctgaggctca gagaggctca 220680
gcctgcccgt gggcacataa gcaggctggg ctgcagaatg gaagctccag aggctgatgg 220740
ctcctccccc tgagtcaaga gaggggtgct aatgggggca tgccatgcag tttatgggag 220800
gtctcagtat ttctatctgt tcagtgggtc tcttggcact ctccctacct gcctgcaagt 220860
gagggtgtga aggtccaacg aggatagggg caggtctgtg ttaatatccc atgagggccc 220920
caccgcactc aaggctatag agtggttgag agcaggctct cgggggccag gccgcctggg 220980
ttccaaatgc cagctctgcc acttcctgct gtgtgacctt agacaagtca ctttacttct 221040
ctgtgcctca atttcctcat ctgtaaacag gagatcagaa tatatcaacc tcagggctat 221100
acaagggttc agtgatgtca taagatgcct ggtatataca gcaggcactt tagaaatgtc 221160
agccgcttct tgcctgccct gggagtacac aggagttccc agagacttgt gggaaattgt 221220
ggagggagcc ctgtgttggt tcttgtccca acagtgaaca aaaacgccaa cccagaccca 221280
ctgccaaaaa aagaggaaga gaagaaggag gaggaggaag acgaccgtgg ggaagacggc 221340
cctaagccaa tgcctcccta tagctccatg ttcatcctgt ccacgaccaa cccgtgagta 221400
tggcccccag caagggcagg gggggcctgg ggctcccacc agggtggcgg aagtcaggcc 221460
agatagaggg caatgagtga gtgttgacca ccatgagtcc agggatacct ttgaacaagt 221520
tgaaaatgga tgctccttcc gtaagtcagg taagatgatt tgtcacaata tactttgttg 221580
gaagagaccc ctgtcctgcc atccactaga aaatcattgt tatttatgac aataaataaa 221640
caaatttgtc ataaataaac aaataaattt gtcctaaaca acaaataaat ttgtcataaa 221700
taaacaaatc ttcactgtga tgtaagaggc accccccttag aaatggctgc cttgtgcagt 221760
acacagcctg aacaactgca cgtggcagcc ctaggacctg aactctgttt ctaacctaga 221820
ctctgtaagg gtttagattc tgggcggata gtgtctgagt tccatggcct tctgtcttgg 221880
gcatctttga aatggataga ctatttaggg gagaaattta tcccatgaat gtcgtagtgg 221940
ctcggaggtt gttttagaat tgaatgtctc ccagggatat ttcttgaaag cctgaccgct 222000
caaaatgctt cttgacaatg aaggatcatg tcagataaga tgggggagaa gctgctttct 222060
ataatctgcc tcttggcaac tcaccctggg tagtaataaa taaaagtacc tttaaagtac 222120
ttttttattt agttgactta tcgattttac taaggaaaca cttatgtggt atctactcag 222180
tgccaggcac tgttctgagt gccttaaaat tttttttaat ttctctgagg ttgttactat 222240
gcttagctcc atttgacaga tgaaaaaact gaggtccaga gacgtgaatt cacctgccca 222300
aggtcacaca gcaagccagt gggagagctg gagtttgagc ccagacactg gctctagcct 222360
ccttgttctt aaccactcag ctctgctgcc attcacacaa ccttatgaac tatttattat 222420
tggctccact tattaagagg ttaactggca catcccattg gcacattcaa ggctctgata 222480

-continued aggcctgcaa ttcataattt caataactaa ctttttggag cccctatcat gagccaggca 222540
taaattaagt cttgggtctc atgattttgt gaagtaagca ctagtattac ggctatttta 222600
cagatgaggg caccaaggca cagaggggac aagtaacttg cccaaggtca cacagctaat 222660
ttttaaaaag aaagaaagaa atctacttaa cccatagatt cacaatattg tttggccctg 222720
ggacatttaa tatcgaaaag ccttttttatc tcctacagaa ttaaggaccg tatttcttca 222780
acctagcttg gggatcaaga tacttcaaga gggtcgtttg ggagtgatag gaactttgct 222840
aaacagggca tgtgaatgtc ttctctcacc gaggtcccct ctgccttctt ggggttccag 222900
gacccagaga gggcccccac ctggaggagt ttaatagttt gttgtgtagg aggccttggg 222960
ggttggagat ctcagtagtg gtaggtaaca tgagattatg gaagaaaagg gtttgtgagc 223020
ctgtggtctg agtggacctc tgcacgccca tctgtctcca acagccttcg ccgcctgtgc 223080
cattacatcc tgaacctgcg ctactttgag atgtgcatcc tcatggtcat tgccatgagc 223140
agcatcgccc tggccgccga ggaccctgtg cagcccaacg cacctcggaa caacgtgagt 223200
cccacagagc acaccccttc ctagcctggc tgctctgcct caggccactt tctcctgcat 223260
ccaaaatgct cataggtagg gtgggatgtt ggggtcaccc ctaggcatag cccttatggc 223320
tgctggttga gaggggaagc tctgattcct tggggatgct cttgggagca agacattcct 223380
tgaggcagtt tctctgtgag cctggtgggg tggaggtggc ccagagtgac tggggctgaa 223440
aattgctgga ttctctaatg gaggcgtgag actagcagga tatggatgtt gcacattctc 223500
tacatggaat agggggggtta ctggggcagg ggcggtgctc agaggtggtc ccctccgcag 223560
tagacatttc cctttgtaca cgaagctttg aaagaaacaa ctatttggct cagaaacaca 223620
gcctaagctt ttggttttta tgaaagcaag cccctttgcg gatggtgggt ctgttgacaa 223680
cccctgttaa ttgagcactt gctgtgtccc aggaagaaac tcagcatgca gtatctcatt 223740
taatcctcac aatgcgcccc cccaaccccc cgcccaggca tccccatttg acagatggga 223800
aaactgaggc tcaggggaat gagagagtgg taagtggcct gtccagggtc acacagcaga 223860
attccaactc tgcatccccc aaagctccca ctgcttcccc caactgtctg catttactaa 223920
tcacctactg tatgctacgg atgggtgtgc atagcccctt tgagtcctga caagcaggaa 223980
tgagtgcatg cttgtggttg agatggggaa accgaggcac caacaggcaa gggcgtgcct 224040
cagtcatggg ctgcgggcag aggcttgacc ccagggcctg gtagagggtg gactggtggc 224100
tcctgtttcc ctccccagct ccctccccca acccttccct cccaacccag agccaaaaaa 224160
gtgtgttttc tgctggtcca aggctctgct gccctggcta agtaggttag gacccaggca 224220
aagctggcga gccccatccc tcaagcccgc ccacagctta ccatgcactt tcccttcctt 224280
cccaggcctg gcaggccccc ctggggacct gatgggggag atggaaggaa ataattagaa 224340
cgcagctcct ggaggaagct agagccagtg ctcagcctcc tcacagtccg cttagttgct 224400
tcccgcagcc tggtttcccc caggggcctc caggagccag gcgtggggag gaggtgtccc 224460
tggaggggtc cacaaacccc ctgctgacgc gaggatgctg aagaaggcgt tgccttcggc 224520
agggagggca caggcatgga tgatccaggg ggcacggcag ctcccagggc tgaagggaat 224580
ctaggcagtg ctcagaccag gccccaggga ctgtttgcaa agagcgttca gctccccggc 224640
cccctccctc gtccatctcg cagtcgaaac ttctctacaa gaacactgtg gccccataac 224700
gttcacacca cgtaaccacc atccagggca agaaatagaa caaaaacgcc ccacgcggca 224760
tgtgcctcct cgatccccca cccccaccgc cttctttccc tctagagctg ctggggacac 224820
tgtctggaga catttttggt tgtcacgaca ggagggggga ggtgctcctg gcatctggtg 224880
ggtggaggcc agggatgttg ctcagcaccc gccgatgccc aggacagccc ccactctaga 224940
ggatgatcca gacccaaatg tccacagagc ccagcttgag aaaccctgcc ttaccggtaa 225000
ccacgacccc agcttctgga atgagcgttt ttggcttctc tctttttccc acctgcacag 225060
gctttttttt tttttttttt taagagacaa tgtctctctc tgtcgcccag gttggggtgc 225120
agtaacgtga tcatggctca ctgcagcctc aacgtcccgg gctcaagtga tcctcccacc 225180
tcagcccccc aggtagctag gaccacaggc atgcaccacc acacccagct aatttttaaa 225240
tgcttgtaga aacgggcctc gctatgttgc caggctggtc tcgaactctt gacctcaagc 225300
aatcctccct cctcagattc ccagagctct ggaattacag gcatgtaatt ccaattctta 225360
catgcctgta attggccaac actggccaat tcttaaaaac tgaatttatg tttgctcttc 225420
tgtaacattc aataaatgag acacttctat gcttcgcatt aaatgagtac atgttgcttt 225480
tgcaggattg atgggcattc tttttttttt tttttttttt gagatggagt cttgctctgt 225540
cacccaggct ggagtgcagt ggtgcaatct tggctcactg caacctccgc ctcccgggtt 225600
taagcgattc tcctgcctca gcctccagag tagctgggac tacaggcagg cgccaccaca 225660
cccggctaat ttttgtattt ttagtagaga cggggtttca cactatcagc cagactggtc 225720
tcaaactcct gacctcaagt gatccgcccg ccttggcctc ccaaagtgct gggattacag 225780
gcgtgagcca ccacgcccgg tcaatgagca ttctttatga tgctgttttg agatttactg 225840
tgtggcatgg gatgtgttat ccatcccctg ttgacagatg tttgggttgt ttctaagtgt 225900
gaatactgtc cccatgccac gcccctcaac atgtttcctg agtcacctgg acagtaattt 225960
ctccaggagg ccagatgcag tggctcacgc ctataatccc agcacttcga gaggccaagg 226020
tgggagcaat gcttgaggcc aggagttcaa gaccagcttg ggcaacatag tgagaccccc 226080
acctctacca aaaaaaaaaa aaattttttt ttttttaatt aaccgagcgt ggtggtgcac 226140
acctgtggtc ccagccactt gggaggctga ggtgggagga tcacttgggt ctggaaggtc 226200
aaggctgtag tgatccatgt tcataccact gcactccaac ctgggtgaca gagcgagacc 226260
ctgtctcaat aaataagaat tcctccaggg tataaaccaa aagcgaagtt tctagagcat 226320
ataatttgca agtggttggc ctcagtaaat gcagcttgaa tgtttattgg acaataaaca 226380
cagtgaccct ttgggaggcc aaggcgggtg gatcacctga ggtcaggagt ttgagaccag 226440
cctggccaac atggtgaaac cccgtctcta ccaaaaatac aaaaattatc tgggcgtggt 226500
aacacacaac tgtaatccca gctactcggg aggctgaagc acaagaatca cttgaaccca 226560
ggaggtggag gttgcagtga gccaagatgg cgtcactgca ctctagcctt ggcgacagag 226620
cgagaccctg tctccaaaat atatataaat aaataaaaat aaacacagtg ggccgggcac 226680
agtgggccgg gctcgcacct gtaatcccag cactttggga ggccaaggtg ggtagatcac 226740
gtgaggtcag gagttcgaga ccagactggc caatatggta aaacctggtc tctactaaaa 226800
atacaaaaat tagccgggcg tggtagcatg cgcctgtaat cccagacact tggaggctga 226860
ggcagaagaa ttgcttgaac ccgggaggca gaggttccag tgagccaaga ttgtgccact 226920
gcactccagc ctgggtgaca gagtgagaca ccatctcaaa aaaaaattaa aaaataaatg 226980
aacgcagtgg cccttgcacc agtagctcat gggaactcct gttcttccac atccttgtca 227040
acacttggta ctgtcgactg tttcatttgg ccgatctgct gggtgtggag tgagatctta 227100
ttggggttgt gcttggcatt tccctgtaat gaatgagatc aagcactttt ttggattaga 227160
ctgagccaca ggaaataaca ttttcaaata gatgaaaaag atctaagtat taggaatact 227220

```
tgaacctaat ttattggtct tttgatttcc tcttgcacag cttattaaga gctccagaat 227280
tagattcacc tgacccccac ggcctgccct ttcccagctc cctctcttcc ttctttcctt 227340
ccattcattc ctttagtaag tatttgataa gcaactacta tgtgccaggt actgagcgag 227400
ccagggagga ttgacagggt atgagatggt ccctgcactc ccagagccca caaaccacca 227460
ggcctttgac caggctgtgc ccactgcctc gtgcacctga aatactctcc caccaccatc 227520
ccctctgccc acccaggtct ttcaagccaa tccccttgca ccagcccctc cctccaggaa 227580
gtcacctcac cctgacccca ggcactctgg tctctgattc ctcttcaagc accacatata 227640
acaggaatat aagttataac cacacagatc acagagccca gctcctccag gacccagtac 227700
agccccaact gttgatgcat tcattcaaca aacatttctt gagcacctac tgtattcctg 227760
accctgtatt ataagctgga gacgccatgg tgacagacag acatccctgt ccttgtgggg 227820
ctgacatttg ggtgggggag atggacaatg agattatcag taactacaac aaatgttcag 227880
ggagtgataa gtggccgggg gtgtggtggg cagagggaag gagagacttc gtaaagagga 227940
tctcaagcac caggagatgg aatttaaaca gccggtcagg ggagtcctca ctgggaaagt 228000
gttatttgag ctaagtcata aaggaggaga aagacggaat caaatgggat gtgggggaaa 228060
gcattccaga gagacagaac agcctgtgca aaggccctga ggtggaagca tcttggggaa 228120
caaaaggaag tgagcaaggg agagaatgag aggaagtgag ggcagggagc tgaatggtca 228180
gatcgtgcag gggcttgagg gcctcgggga ggactttgac ttttatccct gaatgaggtg 228240
ggagccacgg aggattgtaa gcaggggaag gatgtgcctg acttctttgg tgttcacagc 228300
gccctctggt ggccatgttc agtaatgctc agcccttgca gcttctgggt ggatctgatt 228360
ttttttttt ttttttttt agacagtctc tgtctcccag gctggagtgc agtggcacga 228420
tctcggctca ctgcaacctc cgcctcccac gttcaagtga ctgtcacgcc ttggcctccc 228480
aagtagctgg aattacaggc acacgccacc atgcccagct aattttttat atttttagta 228540
gacacggggt tttgccattt ggttaggctg gtctcgaact cctgacctca agtgatctgc 228600
ctgcctcagc ctcccaaagt gctgggatta caggctcgag ccaccgtgcc cagccggtgt 228660
ccaccccatg tctagcacca gccagacact gtgccggcgc accctcatct tcaggcctgg 228720
gtgacaccag aggtgtgcta tggtgtgtcc tggacagggg ctgggccaga ggacattgct 228780
cgtccaggca gaaacatcag gcctggggag gggcacagga aaaatcaacc taccctggca 228840
ggggcctggc cttgaagcag gaagagatgc cgtggcagga agttggcccc agtgtttaaa 228900
aaaaccacgt agcaactatt tctcgcccag gatgcccagg aaagcaaggg tactggggga 228960
ttagatccat caccaagaag gatacagtca gccctgaact tctctggggc cgcttctaat 229020
ccactacagg gcttggggca aattttaaaa ggtacccttc ccgtgggtta gcgaactggc 229080
ctagtacagt gatttttttg ttaggatttg ctgccatctg ctggacaatt tcattcacaa 229140
catacaaatc tgcagtatga aaagagatgg gaggggccct tgtgcagtgc acgccctgcg 229200
caactgtata tagcagctgt gtttcctctt ctgggtagaa actctgctcc ccagtaggcg 229260
atcgttagtt ttaccggggc tctgctggaa caggccagtg atccactgct ctcttgcttt 229320
tatcccttac aggtgctgcg atactttgac tacgttttta caggcgtctt tacctttgag 229380
atggtgatca aggtgagtgc agattataag tgagaacaca cggtaatttt ttttttaag 229440
caagtgcagg gctgggcaca gtggatcatg cctgtaatcc cagcactttg ggaggctgag 229500
gcaggcagat cacttgagat caggaggttg aggccagcct ggccaacatg gtgaaacccc 229560
atctctacta aaaatacaaa aattagccgg gcatggtggc acatgtctgt aatcccagct 229620
```

actcgggagg ctgaggcagg agaatcactt gaaccctagg ctgcaatgag ccgatgtgga 229680
ggctgcagtg agccgagatc ttgccactgc attccagcct gggtgacaca gcgagactct 229740
gtcaaaaaaa aaaaaaaaaa aaagagctgg gattccagga gatcctgagc ctccaagaat 229800 gcccccccttg agaggatgag tctcccagag gattagaaat gcctggtgtg tttgaagagc 229860
agcaaggaag ctggtgtggc tgggcggagt gagagaacag tggggaaacg aaggacagag 229920
agatgagtgg ggaggtgagg gggcaccttg tgccggggat cacagagagg gctcttcggc 229980
tcttactttg agtgaggtga gggccataga gtgttctgag cagaggaggg acttgatcca 230040
ggtgttcaca ggtgcccttt ggcatctgtg ggaagccaga ggacctgtga gcaggtgatc 230100
acactggtcc ccatgggcga tgacggggac aggatcaggc tggtgaccaa agaagaggtg 230160
agaagtggac agattcttgg aaggttctgg aaatagagcc agtgagtttt gctgatagag 230220
ccaccaatga gggatttggg acaaagaggc atcaaagagg atcccaaagt ttggatctaa 230280
gagccggcaa gccagagctg gcttccatca ggcaaagggg ggccgcctca tggggcaggg 230340
gctccccact cctccctgga gtcctctggc cactgcccat ccctgcaaga tgaggtggcc 230400
tcattggctt ccctgcctct ccccgagagg ctagagagtg ggtggcagca ccccagggtg 230460
gggatcaggt gggggttctg agcaccctct cttctccccc acagatgatt gacctggggc 230520
tcgtcctgca tcagggtgcc tacttccgtg acctctggaa tattctcgac ttcatagtgg 230580
tcagtggggc cctggtagcc tttgccttca cgtaagtctc ctcgcaaggg ttcctcttgc 230640
ctcttttccc ccaaccccca gcctgggcca cacatcggat tacaggacat gttctcaggg 230700
tctagggatg gggtgtgtgg gctccgggga cgtgggagat atcagcatgc caccaggaag 230760
agcttcgatg gctttttgca tgatgtccat ggaggaagaa ggagaaggga cccccccctcc 230820 tgccaacctt ctacctcctc acacagcaac gggcctcagc cacatcactg gccccttgct 230880
gtgcagcttc ctgtagacta gcctcgccgg aacatctcat cccccctacta ctccacaagc 230940 gccgcccaaa ccgctgtctc tttggaaagt ccctaaagag acaatcagga aacgaatgtg 231000
catgagaatt ctgacccccct ccctatgcct gaaggccccg tagttgtaga cctggtgact 231060
ccctttgtgt gtctttcact tctcctggca gtcctaggat tctctgccct ctgaaaggcc 231120
atgtgtcatc ctgcagctcc aagatggcgc cccagttgta ggcagccatt tcaggatggc 231180
acccaagctc ttagtagtca tcccaagatg gcatccaagt tctgggtggc cattccaaga 231240
tggcccctga gttctgagct atcattccaa gatggcctct gaatttgggg tggtcattct 231300
tagatggtcc ctgagttcca aggtgacctt caagttctgg gtagccattc caggatggtc 231360
cccaagctct gggtggctat tccaagatgg ccccaagttc taggcagcca ttgcaagatg 231420
gcccctgagt tccagggtgg cccccaagtt ctgggcaacc attccaaggt ggcatccaag 231480
ttctgggtgg ctattccaag atggcctctg atttctgggc taccatgcta agatggcctc 231540
tggattcttg gtggccattc ttacatggtc cctgagttcc aaggtggcct tcaagttctg 231600
ggtagccatt ccaagacggt ccccaagtct tggatggcta ctcgaaggtg acccccaagt 231660
tctgggcagc catctcaagg tggcacccta gttctgggta accattccaa aatggcaccc 231720
aagttctagg gcaaccattt caaaatggcc cccaagttct gggtgactat ttcaagatgg 231780
tacccaacag gtgagtggcc attagccctt agggccctga tagcagactt agcagtacat 231840
tcctgaagtt gtagacattt ggagcgggat gaaaaatatc taatcagtct ttaatcaaga 231900
aacaaatctt ggggaccctg gctgtgccca tcatggtgaa tgattccctg acaggttttg 231960
aaaggatctt gacacattca ctcccatcgt gagagaatca ggggcttcct cctgtgcctc 232020
tgcctctagg ctccctcctg agccaatctg gaggggccct tgaatggtct ccctcaccaa 232080
acaatgagga cttggtttgt caggagggcc aaaatagtgg cccatttcca gtagaagggc 232140
tgttaagtag gccacactta gattcttctc tgggaacaca atgaggtcaa gttgtgttag 232200
aacaaaaaat ctccagagtt tttggatgcc tcagagctgg agatgtatca tgaaggttgg 232260
gaggctgatt atacttcttt ctctttctct ttcactcctt cctcctcttt ctcctctctt 232320
tttgttcgtt tactcttttc tttttctctt ctcctctccc tccccacatc cttccctctc 232380
ctcaaagctt ttcagtgtct atttgactac tagagcaatg cacggtggct tacacctgca 232440
atcccagcac tttgggaggc tgagacaggc agattgcttg agcccaggag gccaagacca 232500
gcctgggtaa catagggaga ccccatctct aaaaaaaaaa aaaaacaatt agccaggcat 232560
ggtagtatgc ctgcactagc agctacacgg gaggctgagg tgggagaatt gcttgagccc 232620
aggaggttca aggctgcagt gagccgaaat cgcaccactg caccccagtc tggggaacac 232680
aggaagaact tgtctcaaaa aaataaaaag tttaaaaaat taaaaatcaa tgaatttgct 232740
atttagaata ttatgcttta tatggttact gaataatttt aatagtgatg agtacaaaaa 232800
aaacaggttt agcaagctgt tctgtaggtt aaaaagtaaa taaataaata attaattaaa 232860
caaaatacaa tgcacatcaa attaggggac aaagattgtg acgaataaga caaggagtcc 232920
atgtctttaa aatatgaaaa gcagttacaa atcaataaga aacactactt ctcaatggat 232980
aaatgggcaa aggacataaa cagaaatctg atagaatgct ggcaactagt aaaaatggag 233040
gtaaatcaac ccttggaatt cagagaaatg taaaataaaa acgagataca attcattccc 233100
tatcaagtta gcactgttcc cgccgcaccc ccacacacac acaaaaaatg atttttttag 233160
ctaataaaca gcatatataa gaatgtatta taataggctg ggcacagtgg ctcacgcctg 233220
taaccctagc attttgggag gccaagggag ggggatcacc tgaggtcagc agttcgagac 233280
cagcctggcc gacatgacaa aaccctgtct ctactaaaaa atacaaaaat tagccaggca 233340
tggtggcgga tgcctgtaat cccagctact caggtgggta aggcaggaga attgcttgga 233400
cccaggagat ggagactgca gtgagccgag atcatgccac tgcactccag cctgggtgag 233460
aaagcaagat tttgtctcaa aaataaaaaa aggaatgtat tataataaaa tatacttttc 233520
tccccctcta tcacctattt aagcaggtcc ttcaagttgt caggtagaca tcatgctatg 233580
agaaaattta aatcctgaaa agccagaatg ttttaccacc ctcagcctgg aatgaatcct 233640
tctcctatgg aaataaccta cgggtttctc cacccctctc tgcctttcag ccccttccct 233700
ccctctcccc tccttttctt tctccctctt tctcttcctc ctttcccctc tcttccctct 233760
ctcttcttcc ctctctctgt ctctttctgt tcgtctttct ccttttaccc cctctcagtt 233820
tctatctttt tattttcctc tttctctctc tctctccctc tctttctctc tcactccctg 233880
cactgttgat gacctatgtc cttgggtgat gtgggcctcc cctggaccgt gtagcttgga 233940
gaaagctgac cctctgtcat cggtctggca acagggactt ggccccccta ccctgcattc 234000
tgatgaggaa tggtattcag acaaaggcag atcccaggac acaggaggac atgctcaggc 234060
agggaccccc gccccttcc tctggggcaa ggtctgctca gcagcctcca agattcctag 234120
ggctcaagag gtggcaggta gctcagggca ctagggcagg cagtggggtg aatatgtcac 234180
tcatatccac ctgtccacac acaatgctta ccttggccac ctgtgcccag gggaatgggt 234240
tttatcctgt gaatcctccc agtgaccacc actgagtgtg gcacagataa atggtaccaa 234300
gcccaagctg ttcaggtctc caatgtcact ttcctctcag acctctgttg tagctgacat 234360
actgtaatgc tgaggagggc cgggcacagt ggctcatgcc tgtaatccta gctctttcgg 234420
aggccaaggc agatggatca cctggggtca ggagttcaag accagcctgg gcaacatggt 234480
gaaaccccag gcaacatggt aaaaccctgt ctctactaaa aatacaaata ttagccaagc 234540
gtgatagcag gcgcctgtaa tctcagctac tcgggaggct gaggcagaag aattgcttga 234600
acctgggaag tggaggttgc agtgagccaa gattgcacca ctgcactcca gcctgggcaa 234660
cagagcaaga ctctgtctca aaaaaaaaaa aaaatgctga ggaggtgact gtcccacctc 234720
catcctccga gttgaccatc acaatttagg gaggggaatg acctacaaag gacccagaag 234780
caagcctttc aattgttgag cttttgccat tatgggccat cgtttacaac atgctgtttc 234840
taggttctct ggaggtaaaa ttagcctcct cttttaaaca aagctaatct gcaaaagcga 234900
accaaaaatt cttttccacc agagatcaat tagcagaatg agctgggtgc gatggctcac 234960
acctgtaatc ccagcacttg gggaggccga ggcaggtgga tcacttgagg tcaggggtcc 235020
aagaccagca tggccaacat ggtgaaaccc catctctact aaaaatacaa aaactagctg 235080
ggtgtggtgg ggagggcctg tagtcccagc tactcgggag ggtgaggcag gagaattgct 235140
tgaacccagg aggtgaaggt tgcagtgagc caagattgtg ccactgcact ccagcctggg 235200
tgacggagca agactccatc tcaaaaaaaa aaaaaaaaaa aaaaaacagc agaatgattc 235260
ttttggggag ttgacttttt ttttaatttc tgagttttct ttttaaatat caagttatac 235320
aagggcattc aaattggcct acaactcaca ggaatttggc agcctgtttg cagagtcaag 235380
cttttacatt gttctcatga aattggtaca ggcataaagc caccccttcac tcttgaaaat 235440
ccattttgaa tgttgttgtt ttaattctta tgcaagaaaa ggatctggat agggatttca 235500
ggccatcctg tcaaccctgg caggcttgta gatcatgcag gaactgggag gtgtgagatt 235560
ttgccagtag gatcctggca agtgcctggg actctcccag ggttttggaa gagccgacgg 235620
acatgagtcc aacagggagc atctttatat catggccgaa gggatgagag aggagaccct 235680
caaacctcac gcctaccaca ccctccccac cccactgtca agagtccatc tggtactgct 235740
gttcctcccc cagggcaggg ctgcaggccc agcacagctg gccaggtgcc ttgatcaagc 235800
cattcctgca cacctaagag ccaaactgct agaaaaccag aataggagct actgcttttt 235860
tccctaaaaa gttttggaat cttctccccg ttacaggttt ctggcctctt ttgcctgaga 235920
aggtctctca ccctatgagg actttgctta ttgtctttcc ttgttatcgg atagttggca 235980
cattggaagg agcatggatg ctctgaggtt ctcagcctga gcgctgaact ctccacccgc 236040
cccccacccc ccaccccagg gtcctctgct tatttccttt ctggtctttt aacttgcttt 236100
gtctgtcctc tgtgcatatc ccctcataga caaggctgag agccccacaa gtattagatt 236160
gaccttattg ttttaagaaa ttgtccctcc aggtctgttt gatttctctc tagatgtgca 236220
agtcctttag cctctctgtg cctcagtttt tcccatctag atgaggaaac tgcggcccag 236280
agggactgtg gagggaagta agtccgacaa gatcactgag gttgggttca gctgtcagat 236340
gctacccatc tcccagccct gaatacggag gctcacagtg agcagaatga tgctcagcag 236400
cctggccagc ctgggttctt tgaggcctgg cagggctgcg agatccaggg gaagggaata 236460
ggggaaggga gcataaggtt attcccttcc ttgttgaaag gaaccttgcc attctggcct 236520
gttggggtca aagcaaggat tcttccccca gtgctgtgat tgtggcctcg tctccgatat 236580
gggagaaaac tatccctgtg gtcccaccaa gggatgtatt gaagctcttc tgaagatgtc 236640
cacccctcct gcacctcacc caaatatctg tgtgtgtgtg tcctgctcaa ttcactgact 236700
gtgtcccttg tatccatgcg tctaccataa acaccccatt tcatgagcca tcacacgtgg 236760
tatcacgctc tgtgcccatg catcagggcg gccaactgac atttctcagc agctggcaga 236820
tcatgatcct gccctcaccg ccaagagtcc atctggcgcg gctgttcttc ccccaaaggc 236880
aggaccgcaa ctggcagagc gccttgatca agctgctcct gcatacccag gagccaaact 236940
gtcaggaagc caaagatgga gccctcaggc tgctatctct tgatcctcat cttcaaaaca 237000
gcccccaccc ctgaaggcat tattttttctt gtgtatgatg aaatggaaag aagattagag 237060
tgcgagatac ccacacctgg gtttgaatct tagtctgtct tcccagctgt gtgcctgccc 237120
ttgggcaggt cactcttttt ctctaggcct cagcttcctc atctggaaaa tggtcataat 237180
ggtgctgtct tcccataggc aaatgcagtg atgtccagaa gactcccata ttaaacctaa 237240
agtcagcaga ttaggcaaaa atcactgtca ttgaaaactc cctcaatcat ccgtaaagaa 237300
gctgggtgtg gtgtctctca cctgtagtcc cagctacttg ggaggctgag gtgggagaat 237360
cacttgagcc agggagttca aggctgcggt aagctatgat tgtgctactg cactccagcc 237420
tgggcgacag agcaagacca cgtctctaaa aatataaaat aaagccgggt gcggtggctt 237480
acgcctgtaa tcccagcact ttggaaggct gaggcagcct ggcaacagag tgagaatcca 237540
tcaaaaaaaa aaaaaaaaaa aaaaaaagta gaatctatat gattctacgt atgcaataat 237600
tcctagatac actgaatttg agaaccccaa gtcagactac aggaaaagga gatgaggggg 237660
tgtggaggag aatccacttg gaatatttgt agacatttaa accattctgt gttttaaaaa 237720
atatcacagc cgggcgcggt ggctcacacc tgtaatccta gcactttggg aggccaaggt 237780
gggcggatca cgaggtcaag agatggagac catcctggct aacacggtga aaccccatct 237840
ctactaaaaa tacaaaaaaa attagctggg cgtggtggtg ggcgcctgta gtcccagcac 237900
tcgggaggct gaggaaggag aatggcgtga acctgggagg cggagcttgc agtgagccga 237960
gatcttgcca ctgcactcca gcctgggcga cagagcgaga ctccgtttca aaaaaaaaaa 238020
aaaaaatcac taacttccag aggggtcgtg gatggaaaat tccatagagt ccgcttggcg 238080
acagggtttc cgccattctg atggcggtca agtctttcta acctggatct ccagtcattg 238140
ttgaaggcgc ctaatgagcc ccaagcctga ttccaatgaa tcacgagagg accagctgct 238200
aggtgctgat agctttcccc aggcccgcat ttgctcagag ggcttcagag ttgcttctaa 238260
ttccatccca agtcagaact ctttgctgac cccctccttc ataaagagca aagccaaggc 238320
catagctttt gttaatcaaa catcagaatt ccacagacct gagttggttg gttgtttgtt 238380
ttaagagaca gagtcttgcc caggatgcag tggctcacac ttgtaatccc agcgctctgg 238440
gaggcctagg caggaggatc acttgagccc aggagtttga gaccagcctg agcaacataa 238500
tgagaccccc gtctctacaa aaaatggaaa aatttgcctg tatttccagc tacttgggag 238560
gctaaggtgg gagaatcacc tgagccctgg aggttgaggc tacagtgagc caagatcccg 238620
ctactgcact gcagcctggg caacagaggg agaccctgcc tcaaaaaaaa aggagagaag 238680
gagagagaca gggtctccct atgttgtcca ggctggtctc gaacttctgg cctcaagcaa 238740
tcttcccaac tcgtcctccc aaggtgctgg gattatagct gtgagccacg gcacccagtc 238800
tgggcctgtt ttgcagatga ggataacgag aggcagagtc aggattcaaa cccaggtccc 238860
ctcaacttca aagctcacaa ccttttagac attctaaaac cttgcagctc cacaacgcct 238920
ggagaagagg ggtttctccg gctcttggca gtgactttcc gtggtgaatt cacctttggt 238980
aactgacagc tttgcagctg tcctgctacc tggaaatttg gctttcttag tgctttcttg 239040
ggcagtgcca ggtgcctgcc aagggcgggg gactgaatgg aggtgggggc ggcttccaga 239100

```
tggaaggatg gacatcggcc agcgccatga gcctgaggct cccccaactg ctgcccgggc 239160
gggactcggg ggtgctcagg ggtgcgtgtg tgtacgtgcg tgttctgtgt tctttttttct 239220
gaggccactt acgatctgtc tctccctccg atgccacatc accaggagca gtacacggta 239280
aagtctctct ctatctttct ctctctctct ctttctctct ctctctctct catattctgt 239340
ctctcgtgat ctgtcccctg gtgcagcctc gttagttctg ggcctgtttc tgtggccttg 239400
tgtccttgct gccgctgtcc tgtcgcttca aatgaccaga actcactccc tgcgaaggag 239460
gcatcccaaa gggtcttgcc aatgcctccg cccatgcccc accagttctt gcagagaaca 239520
gaaggggcag aggttcagtt tcaataggca agctgggtgg agcagttatc agaagcaatg 239580
aaagtgggcc agacacggtg gctcacgcct ctaatcccag cattttggga ggccgaggcg 239640
ggtagatcac ttgaggtcag gagtttcaga ccagcctggt caacatggtg aaaccccatc 239700
tctactaaaa atgcaaaaaa ttatctgggc ttggtggtgc acacctgtaa tcccagctac 239760
ataggaagct gaggcaggag aatcacttaa acctgggagg tggaggttgc agtgagctga 239820
gattgcacca ctgcactcca ccctgggtga cagagtgaga ctctgtctca aaaaaatata 239880
taaaataaat tgaacaataa aaaaataaaa tggccatgga atcgttttca gatgaggaga 239940
tgcagaatgc ccatggagac atgctcccaa ttgtcacttg tttgggacat caagatttta 240000
gccagttcca tgtgcaacct ggatgtacag ttccttgact ttttttctat caacatgtat 240060
tctaaagttc aatttcaaaa ggaaacttta gccaggtgca gtggtgcatg cctgcagtcc 240120
cagccatttg ggaggctgag actgaaggat cacttgagcc caggagttgg aggctgcggt 240180
gagctatgat cgtgccactg cactcccccc tgagattcca tctctttaat ttaaataaaa 240240
aaaaaggaaa ctatattatc cacttacaac cagcattgct aacctaagat aaatctgcaa 240300
ctgcaaaagt aaatgtaggc cagacatggt ggctcacacc tataatccca gcactttggg 240360
aggccgaggc aggtggatca cttgaggtcg ggagttcgag accagcctga ccaacatgga 240420
gaaaccccgt ctctactaaa aatacaaaat tagccggacg tgatggcaca tgcctgtaat 240480
cccagctact cgggaggctg aggcaaaaga atttcttgaa cccgggaggc agagactgct 240540
gtgagctgag atcacgccat tcactccagc ctgggtaaca agagagaaat gccatctcaa 240600
aaaaaaaaaa aaaaagtaaa tctaacagaa accagacaat gttgttgcct tcaagctggg 240660
ctctttgtta aaaggaaaat tactaagtgt tagggaggtg ttaaaggcct attagcatct 240720
acctgaggct tcctttctcg caaaagcaga gcgtctgaaa gatacgtgga aaagaaactt 240780
aaagtataat aaaaaagaaa gaaagaaaaa gaaatgatta tgcccctctg agatccaatt 240840
atttaatctg tgcccctgtt ctgcctaaaa ttatctcagt gactgtccaa cgtgtgtctc 240900
acacttgggg gcacagcctt gagatgataa tgatgatgtt agttttaaaa agaaaaaaaa 240960
aggttcagag ttctgaatcc tggagtatat ctctgcctag caggctaaaa tacaattatc 241020
gtctttgttc cctgaaaaat gaaaaaaatg gagtccttta aaaagcaaat ggtgtgaaga 241080
atgatgtttt tgcactggat actgagaccc atcgtgatgg gggtctctgg ggcagctctg 241140
ctcatgacct gggaggtcac tgtagggaga tgttttctag gtgacctccc cacccaaata 241200
ctccaaccgg aggcattcac gtgtcctgag accacacgcc aggcgcaggc taggggctag 241260
gacaagaatc aagattaaag gggaaatggc caggtgcggt ggctcatgcc tgtaatccca 241320
gcactttggg agtcaaggcc agtggattac ttgaggtcgg gagttcgaga ccagcctggc 241380
caacacggtg aaaccctgtc tctactgaaa atacaaaaat tagccaggtg tggtgactca 241440
```

tgcctgtagt cccagctatt cgggaggctg aggtgggaga atcacttgaa cccaggaggc 241500
agaggttgca gtaagccaag atcatgccac tgcactccag cctgggcaat agagcaagac 241560
tccatctcaa aaaaaaaaaa aaagattaaa gggaaaatga acacagagaa gagtagatta 241620
cactgtaagc ctttgaagag ttttctgtct aaaaccagag accgaagaaa caaacaaaga 241680
ttaactccga aatagcacat aggagctggc aggagccaga ggtaggcagt caggaaatgc 241740
tgtcggaggg agcaacaggt aatttgggct ttgaggaccg ggtagttctg tgactggaga 241800
agtggaggaa gggcatttct agcagcggga acagtatatg cataagcaga cagaggcaaa 241860
agaatgtggc tggggcttga gatatgtagc cataaatggg aatgcaaagg tgaaggtaag 241920
ttggactaga ttttcaagag cattgaatgc catgcccaga agtttgcact tgctcttctg 241980
agaattcacg tgctccagaa gaattctgag caagagaaag agtgacaagg tcattggctt 242040
tagccactgt gtgcataaaa catggaagaa aaggcaggga atgaggagca agttgggaga 242100
cgggtgaggg gggatggcac ccaggaatgg atggcgggat gttaaggaag gtgacccact 242160
ggggatgggg atggggatag agggcaggca gttgaccatg actctcaggt ttctggtgtg 242220
gacaactgga tgggtcatga gtgccatgaa ccacaagcta ttcatggtcc cactcaatac 242280
cctcctcttg gggggcctga gtcatggttg gccaagggtg tcatggcatc tctggggtct 242340
gcattgctaa gctcagttcc aacagacctt ggactgaact tctgtgcagt cctctctggc 242400
aaagatgggc tcagagaccc ttggagcaat gcagcagaga ccatggcagc agccacatca 242460
gcatctgaaa acagcggcac ccggttattt tccctccttc agactcaggg aatatggtgg 242520
gggaggggag atttggtata agggccactt taagtatctt ccagaatccc attggaaggg 242580
ggagaaaatc ccattttttt aagagcccac tgataccacc tttaaaaaga atacacaggg 242640
ggccaggcgc agtggctcac acctgtaatc ccaacacttt gggaggccaa ggtgggtgga 242700
tcacctgagg tcaggagttc aagaccagcc tggccaacat ggtgaagccc catctctact 242760
aaaaatacaa aagttagctg ggcatggtgg cacgcacctg tagtcccagc tacttggaga 242820
ggctgaggca agagaatcac ttgaacctgg gaggtggagg ttgcagtgag ccaagatcat 242880
accattgcac tccagcctgg gcaacaagag tgaaactcca tctcaaaaaa aaaaaagaat 242940
acatagggga ccactaaact cctagaccaa gggctttttt gaaaatagct gtgaccaggt 243000
gtagtggctc acacctgtaa tcccagcact ttgagagggt gaggagggca gattgcttga 243060
gctcaggagt ttgaaaccag cctgggcaac atggtgaaac ctcatctcta caaaaagaca 243120
aaacaattag ccaggcgcag tggcgtgtgc ctgtagtccc agctacttgg gaggctgagg 243180
tgggaggatg gctttagccc aggaggcgga ggttgcagtg agccgagatc gtgccactgc 243240
actccagcct tggtgacaga gccagaccct gtctcaaaaa agaaaaaaga aaagctgtgc 243300
agaaatgggg gtggggaatc agccaacccc cttgtgctgg gtctcaggga cacccaatac 243360
agctgctcag gcccagccag atggcaaagg gccctcaacc aaccctggga ccagaaccac 243420
aaaaagccac gtacttactg gctcccgagc ccaagcttaa caggtgaaat ggaccactct 243480
tcaccaggaa gggcagggct gtgccaagct caccccagac ttctaggcct gggagggtag 243540
ggtcccatgg agctgtgggc tgccccctac ccaacctgac ctctgcttcc tctcttccct 243600
tcttcccacc taaacattcc tccacagtgg caatagcaaa ggaaaagaca tcaacacgat 243660
taaatccctc cgagtcctcc gggtgctacg acctcttaaa accatcaagc ggctgccaaa 243720
gctcaaggtg agattgggag atggtggggt gcggtggggg ggactgtcag ggttatcatg 243780
tacagctgag caggttgtac actgctcaag gacaacacat taaaggaggt gctgataaca 243840
tcctagccat cgtgtatgga tatttgtatt attacaactt cccagcagat ggcagtaaag 243900
tgagctgacc taaaataatc tgtgtattat ggcagttttt ctttagatga agtgtcttgg 243960
ggttaagatc ctttttccta attcgcatga aggcatcata tggatttaaa agggtataac 244020
cgtgatctgg gaagcaggaa ctagatttct tgttccataa aattttgact tttcatctac 244080
ctattctagg ctctagtatc tcccattcca aaatagcatg aaccagcatt tcccaaaagc 244140
ctgtcattca aaaacatata tatatattaa gggaaataaa atccagtcat tagagcaccc 244200
actttcactc tatgcttcac ctgggggtcc ccagtattat ctcttatgta atatgtttct 244260
ttaaatcaag tcacacccgt aatccctgca ttttgaaaga ccaaggcagg agtgttgctt 244320
gagcccagga gaatgagacc agcctgggca acatagttag actctgtctc tactaaaaat 244380
taaagacaga aaacagatac tgttatggaa atctaaccaa atatggctgc ctgcctaagg 244440
ctttgtgcat tgacaactgc tctttcttgg ttaaagaggg aaaatgtcaa tggtaggtgt 244500
taacatggta gcaactaagt aaaaatttct ccttcactca aaaggattga gagagttgga 244560
aaggaagtaa ctttgttacc ttgtttttct gtgttgggct cctgtatcac ttaaaagcat 244620
ctctggtatc ccatctggga gttttagatc catagaatgc caggattgag tccaactcct 244680
ccaacgctta tttctgaaag ctggggggac cttaccctag tgacttgact tatgaccttg 244740
cctgtaaaat gggaatgatc atggcagtat tttggtatga tgggccactg gaggcagaag 244800
gttgggcagg tccccagccc ctcatgctct ctgtcaactc caccccacag gctgtgtttg 244860
actgtgtggt gaactcactt aaaaacgtct tcaacatcct catcgtctac atgctattca 244920
tgttcatctt cgccgtggtg gctgtgcagc tcttcaaggg gaaattcttc cactgcactg 244980
acgagtccaa agagtttgag aaagattgtc ggtgggtctc cactttccag cacattccca 245040
ttggaaccag caggtgggca ggggggaagt ggctagaggc attggccact tgggctcaga 245100
gactggagaa gtgatgagcc ttggaagtga ctcagttgca accagcttgg atcttgggta 245160
gaaagaaaac cggttttaga atttgagtca ccacccagag ccacagaatg agtcataagc 245220
aaattgattg acctttcagc caccgccttt gtcatgtgag ggatattaat acacatccac 245280
agttccttac ttgaaatcgt tacaggcaga tgtgtttcaa agttgagaat attttgagat 245340
tcccatgtgg gacatgacac cctcagctgg gtctaaggca gccctataat caaacacaat 245400
atttctgcca taaaatgtgt aactatttac atcaaatggg gtaaataaca agtataaaga 245460
gcttcatgtc caatcagatc aggtttcatt accaaataag ttaggtaaga ggccaggtgc 245520
agtggctcac acctgtaatt ccaacacttt gggaggctga ggtgggagga tcacttgagg 245580
ccaggagttg gagaccaggt tgggcaacat aatgagagcc catcctacaa aataaatttt 245640
aaaagttagc ggggcatggt agcacacacc tgtagtccca gctacccggg aggctgaggc 245700
gggaggattg tttaaacaca ggagttcaag gctgcaatgc actatgatgg taccactgca 245760
ctccagcctg cgtgacagag tgagaccctg cctctcaaaa atatatacat ataggccggg 245820
cgcagtggct catgcttata atctcagcac tttaggaggc cgaggcgggc ggatcatgag 245880
gtcaggagat cgagaccatc ctggctaaca cggtgaaacc ctgtctctac taaaaataca 245940
aaaacctagc tgggcatggt ggcagacgcc tgtagtccca gctacttggg aggctgagac 246000
aggagaatgg cgtgaacccg ggaggcggag cttgcagtga gcccagattg ggccactgta 246060
ctccagtctg ggcaacagag ccagactcca tctcaaacaa acaaacaaac aaacaacaac 246120
aacaaaaata tatatatata tatatgtata tatatatatg tacacgcaca cacacatatg 246180
tattatatgt gtgtgtgtat atatatgtat gtgtatatat agtgatattg ttaccagtgt 246240
aaagtggcat tttgcaacac atggtagcct gttgttatct tgatggctat ttattgaaat 246300
taggaggatg ccagatgtct ggataggagt ctggaactaa cccttgtttc ctgccttgaa 246360
aaggagtagc aacctccctt agcctgatga acctctaaat gtcccctatg tctctctgcc 246420
tcctcctaaa ctccctccac cccacccccca gcaagcctga ggctctcacc ctgaggacta 246480
gaagttatca cgttggaaga gggtgctgga ccctgggtca gctctcccac caggagtaag 246540
gttgtgccat cacccatgga tttatctcaa agtagatgca cacgtcatcc cctatgaagc 246600
acaggaacac atggtggcag gatggggagt cactgcttcc caagcagtct aggctggtgg 246660
accactcttc ctttccctcc ccctgtctct gataaccaaa gacaagtgca agacagcccc 246720
tctttcccat ttactaacag tccccactct ctgtggcaga ggcaaatacc tcctctacga 246780
gaagaatgag gtgaaggcgc gagaccggga gtggaagaag tatgaattcc attacgacaa 246840
tgtgctgtgg gctctgctga ccctcttcac cgtgtccacg ggagaaggct ggccacagta 246900
agtggcccga ctggaaatct atccaggagg agccctgggg agcaggagga taaagggcct 246960
gagagcttag caataagaaa ggtcttggag gccgggcatg gtggctcacg cctgtaatcc 247020
caacacttta ggaggccaag gcagatgtat cacttgaggc caggagtttg agatcagcct 247080
ggccatcatg gcaaaactcc atttctacta aaaatcccaa aaaaaaaaaa aaaaaaaaaa 247140
aaaaaaaagc tgccaggcat ggtggctcac acctgtggtc ccggctactc aggaggctga 247200
gacacgagaa tcacttgaac ccaggaggca gaggttgcag tgagccgaga ttgcaccact 247260
gcacttcatc ctgagtgaca gagcaagact atggcctccc cgccttcaaa aaaaaaaaaa 247320
agtgaggctg aatcatggac ttagtcttta tttaaaattt tgagccactt gtggtggctc 247380
atacctgtta tcccagctac tcaggaggct gaggtgggag gatcgcttga gcccaagagt 247440
tcaaggctgc agtgagctgt gattatgcca ttgtactcca gcctagacaa cagaaggaga 247500
cccctatccc tgaaaaaaaa aaagaagaag aaattgatat ttgttcatca tggacttttt 247560
gcattaattt tgattttta aaatattgga gcaaaagatt atcttgatta ctgagatttt 247620
cagtaccccc ttaatttgca cccaaaacaa atgcctccct ccctcacctc gtccaagtaa 247680
tggtctttct ctcagaggtc ttggaaatgc caggctggaa gcttggtaga ttccagcatg 247740
tgccctcagc atcctcacct ccctccctct ctcagcaaat atgccaacct gaacatgccc 247800
tactacccac tctcagacac atccagtact cacacatgtg ggaataatgc taacccacaa 247860
ggcacctttg agcaaagttt ttttaaacac ctttctcaac agacttcatt tccatctgtc 247920
tgaaaatcat cgcaatagac ttaaatgatt ttgttcaaac aaggcactga aggaccacct 247980
gccaaaaaat tgtcatcatg aatacacaaa tctatcatgc ctatcatgtg aaggtatcgc 248040
ttagacacag agcctttgag cagtgtgcaa cctgcactac tgtacagagc tgctgtgcac 248100
ttacccactc tcatatatat ccccattgta cctcctgagc acccagcacc acctgtgctc 248160
aaatacccac tctacatgca tacacccacc tctactccct ccattgccac aacctgtctt 248220
taaatcccaa cttggccact tataagtggg tggtcttcag cacgtccctt taaattgctg 248280
aacctcaagt tcctcatgtg caaagtggag ccagtaataa cctccctggg agggttgctg 248340
agccggtggg gatgaattgt tgaatattgt ttccagcaca cagcaagccc ttcatgcaca 248400
gcagtagaaa tgactgacat tggccaggcg tggtggctca cacctgtaat ctcaacagtt 248460
tgggagaccg aggcaggtgg atcacctgag gtcaggagtt caagaccagc ctggccaaca 248520
tggtgaaacc ccgtctctac taaaaataca aaaaaattag ccaggcttgg tggcgcatgt 248580
ctgtaatccc agctacttgg gaggctgagg caggagaatc atttgaaccc gggaggcgga 248640
ggttgtagtg acccaagatc acgccgttgc actccagcct gggcaacgag agcgaaactc 248700
catctcaaaa aattaaaatt aaaattaaga aataactgac attgttgtca gcctttcaaa 248760
aaacagcgac tacttaaatt tctttttcat ttccctctgt tcctgttctg ccatctcact 248820
tccaccctct ctccaccttc ctcatcaccc cttgggtccc tgtctctctc cttcctgccc 248880
cttccctctc cctgccccat tccttgcagg gtcctcaagc attcggtgga cgccaccttt 248940
gagaaccagg gccccagccc cgggtaccgc atggagatgt ccattttcta cgtcgtctac 249000
tttgtggtgt tccccttctt ctttgtcaat atctttgtgg ccttgatcat catcaccttc 249060
caggagcaag gggacaagat gatggaggaa tacagcctgg agaaaaatga ggtgccactt 249120
ccaattccat ctgtccttta aaaactgggg acacacacaa actttaaaac acacacaaca 249180
cccaggaacc cctttctagg ggtacctggg ggagggaaca gaagcattgt cccaaccgaa 249240
tccagtcttc agggcagccc ttcatggagt ttccagagga aacacatcat atagtgtatg 249300
tatcagtcag tttagactag gttatgccgc agtaacaagc aaccccagat ttcattgcca 249360
aatatccaca aagggactta ttttttgctc acactgcatg tcaacatcag ttgtggatct 249420
tgccatcttt attctggttc ccaggctggc agagcagcag agcagcctcc ctctgagatg 249480
ctccagatga aaaagagagt atgtcagact gaggttcagt tcttcaggct tgtgctcaaa 249540
aattacacat gtcacttctg ctcacatttc atcagccaaa gcaagtcaca catccattct 249600
gacatcagtg gagtgggcaa atacaatctc ccctagcgaa gggtggtgaa tatttatgaa 249660
tgaaaagcca agccaggtgt ggtggctcac acctgtaatc ccaacatttt gggaagctga 249720
ggcaggagga tcacttgagc tcaggagttt gagaccagcc tggccaacat agcaagaccc 249780
catctctact acaaatcaaa aaaattagcc aggcaggatg gtgcacacct ttagccccag 249840
taacatggga ggctgaggtg ggaggatgct tgagcttggg agttcgaggc tgcagtgagc 249900
tatcattatg ccactgcact acagcctggg caacagagca agaccctctc tcaaaaaaag 249960
aaaaggaaag aaaatccagt cccctgtcta ccagagagta tagacatgac tctttgcctc 250020
tctggcatca tccaagctaa atagaggacc tagaatatat cctctgctcc cttgaccctt 250080
aagacttaat aaccactatt cctccttctc tctccctcaa agagaaggag aagacgcagc 250140
aaagtattca gtaagaaaga atgggctggg cgcagtggct cacgcctgta atcttaacac 250200
tttaggaggc caaggcagga ggattgcttg agcccggaag ttcaagacca gcctgagcaa 250260
catagtgaga ccccatctct atgattaaaa aaaaaaagtt ttaattagct gggtgtggtg 250320
gtgcacgcct gtagtcccag ctactcagga ggctgaagcg ggaggatcac ttgagtccag 250380
gaggtcaagg ctgcagtgag ctgtgattgc actgcactcc agcctgggtg acaaagcaag 250440
cccgtgtcaa agaaaaaaaa aaaaaaagga aggagggagg gagggaggga aggaaggaaa 250500
tgagagagag aaagaaagga gggagggaag gaaggagata gggaagaagg aatgaagaag 250560
aaagaaaggg agcgaaggaa agaaggaaga agagagaaag gaaaggagaa aggggaaagg 250620
gtggaaggaa tgaagggaag gaaggaaaaa ggaaagtgaa ggagggaggg aggaaggaag 250680
gaaaggaggg agggaaggag ggagggaagg agggagggag ggaaggaggg agggagagaa 250740
ggagggaggg agggaaggaa ggagggagga aggaaggaag gagggaggga gcgagggagg 250800
gaggaagggg aagaaggatt aggcttcaat ttgatttggc acactcggta gctgtgtcac 250860
ctcaggcaag tggtttaacc tttctaagcc tctattttgg tgatctgcaa agtgaggcca 250920

```
ttgatagtac ccacttccca tgtttgtatt agccatgcaa taatggggaa atgtcagtgc 250980
aagttttggc agttggtgac atctcaagca actgtagctg ttgggataag aaagcaatgg 251040
tgagaaggaa gagagagccc aggaatcctg gctgggggca agagaggcag agactcaagc 251100
agaagcactt gagaaccgcg acgagttaga cagagggtgc ccggtgtaca gccaccttcc 251160
tcctgcctct gccgctctca ccactggcct ctctcccgca gagggcctgc attgatttcg 251220
ccatcagcgc caagccgctg acccgacaca tgccgcagaa caagcagagc ttccagtacc 251280
gcatgtggca gttcgtggtg tctccgcctt tcgagtacac gatcatggcc atgatcgccc 251340
tcaacaccat cgtgcttatg atgaaggtaa gtgccccaca ccagccccca gcactactta 251400
acccccacct cgttcctgcc tctaccctga taaaatgaaa ccatctgcag tttcccagac 251460
agaccacact ctggatcacc tctgagattt tgttcctgct gttccctcta cctgacacac 251520
tgttcccacc actcccccgg ccagcttctt cttcccagct gtacctgcag acctcttcct 251580
ccagaaagcc ttccctgacc acccaagact gcttgaggtg cccatcttag caggcatcct 251640
atctttatgt cgcctgccac aaaaatctgc gtcaggttgc atgacagtgt cccccaccca 251700
tttatgatga cctcagccct gaattcctag aggccaacaa ggatctggct cagacggaac 251760
aagaagctct ctataaatgt ttgattaatg aaatgagggg gctgggcgcg gtggctcatg 251820
cctgtaatcc cagaactttg ggaggccgag gcgggcggat cacctgaggt cacgagttcg 251880
agaccagcct gaccaacacg gagaaaccgc atctctacta aaaatacaaa attagccagg 251940
cgtggtggtg cgcatctgta atcccagcta ctcgggaggc tgaggcagga gaattgcttg 252000
aacccgggag gcggaggttg ccatgagccg agatagcgca attgcactct agcctgggca 252060
acaagagcaa gactccatct caaaaaaaaa aagaaaagaa aaagaaagaa atgagggaga 252120
aggggtaggt gaggacccta aaatccccag ggctaaggag cggcttccaa aaaaaaactc 252180
tgaaaacctt tcaccctgtg ctttggactc caaagcgtgg attcaagccc agctcttcca 252240
tttaattcat ttacctttgt acaagcaacc agtgactttc tggggactca gtttccctgt 252300
caataaaatg ggaatgataa taagagcaca tttgcccccct ccagaggagg tgagaggatt 252360
gaatgagaaa gttcatgcaa ggaccttagc tccttctcgg cacttcaaaa acgatcaata 252420
gtggccgggc aaggtggctc acacctgtaa tcccagcact ttgggaggtc gaggcaggcg 252480
gatcacttga ggccaggtgt tcgggaccaa ctggccaaca tggtgaaatc ccgtctctac 252540
taaaaataca aaaattagct gggcgtggtg gcgcatgcct ataataccag ctgcgtgaga 252600
ggctgaggca tgagaatcgc ttgaacccag ggggcggaag ttgcagtgag ctgagatcac 252660
accactgcac tccagcctgg gtaacagagt gagactccgt ctcaaaaaaa ataaggaagc 252720
cggggacggt ggctcacgcc tgtaatccca gcactttggg aggccgagga gggcgatcac 252780
aaggttagga gatcaagacc atcctggcta acacggtgaa acgctgtctc tactaaaaat 252840
acaaaaagtt agctgggcat ggtggtgggc acctgtagtc ccagctactt gggaggctga 252900
ggcaggggaa tggcatgaac ccaggaggtg gagcttgcag tgagccgaga tcgcgccact 252960
gcactccagc ccgggtgaca gagtgagact cctcaaaaaa aaaaaaaaaa aaaaagtata 253020
attcagccaa gcacaatggc gtatgcctat agtcccgact atcaggaggc taaggtagga 253080
ttgtgagttc aagcccagcc tgggcaaaat aggaagaccc cgtctaccaa aaaaaaaaaa 253140
aaaaggttgg gggaggtttt tgttttttg gatgtgaaaa gaagagccta gtccggcgga 253200
gagcggggct ttcctgaact gtgcctccta ccagtgaggt tgctcagacc ttgcctgggg 253260
ctggagtgtt gcctggagaa cagccatgaa gctgcctccc cacttcccac ttcccacccc 253320
```

tgctcgctga cccctgctac tcctgcttct ttcccctagt tctatggggc ttctgttgct 253380
tatgaaaatg ccctgcgggt gttcaacatc gtcttcacct ccctcttctc tctggaatgt 253440
gtgctgaaag tcatggcttt tggattctg gtaagtacca ccttggggct acagctatgg 253500
gcttgggaga agcccaaggg ggaacaatgg gtcctggatg atggtctccc aacgtggccc 253560
caagaacccc aacctcaagg gtggcttcag tatcctgcca gtggccacag atcctactta 253620
ggcattcttg tgtttgccaa ggagtcccag ggagacccaa cctgtgagtg ttaccatatg 253680
gctgcttatg tatccagttc ctcaaaatga tgggagtcat catggctggg agtctttagc 253740
atccatttta gagataagaa aactgaaatc aggctgggcg aggtgtctca tggctgtaat 253800
tccagcactt tgggaggcca aggtgggcgg atcacctgag gtcgggagtt cgagaccagc 253860
ctgaccaaca tggagaaact ctgtctctac taaaaataca aaattagccg ggtgtggtgg 253920
cgcatgcctg taatcccagc tactcgggag gctgaggcag gagaatcgct tgaacctggg 253980
aggcagaggt tgtggtgagc cgagatcaca tcactgcact ccagcctggg caacaagagt 254040
gaaactctgt ctcaaaaaaa agaaagaaag aaagaaaact gaaatcaggc tgagcacagt 254100
ggctcatgcc tgtaatccta gcacttcagg aggccaaggc aggaggatcg cttgaagcta 254160
ggagttctca accagcctgg gcagcaaagc aagcccctgt ccctacaaaa aaaaaaaaaa 254220
ttttttttta attagccagg catggtaact cgtgcctgta gtgccagtta ctcaggaggc 254280
tgaggtggga agatattttg agcccaggag gtggaggttg cagtgagcta tgatcatgcc 254340
actgcacccc agcctgggca acagcaagac tccatcttta aaaaacaaac acagaggtca 254400
ggcacagtga ctcacacctg taatcccagc actttgggag gcagaggcag gcaaatcact 254460
tgagcctagg agttcgagac caccctggcc aacatggcaa aaccccatct ctactaaaac 254520
tacaaaaaat tagcctggcg tgcttgtggg tgcccatgat cccagctact caggaggctg 254580
aggcaggaga atcgcttgaa cccacaaagt ggaggttaca gtgagctgag atcacaccac 254640
tgcactccag cctgagcaac agagcaagtc tcaaaaaaat aataataata aaaataaata 254700
tgtctttatt tttcaccagc cactaactaa attttaacat ttccttccat cttaaaggga 254760
gataacaaac ccttagtatt agtattatca acccttaata ttatcaacat gacctgtgtc 254820
acttataaac atcagatatt ttcatactgc attataagag ctgcagatac cttaacattt 254880
aatttgcatt catcattgct ttaaaatgtt gcttgtgatt aaacctacag ctagaatttg 254940
ttactcagtg tttttttgtt gttgttctgt tttgttttgt ttgagacagt ctcgctgttg 255000
cccaggctgg agtgcagtgg cgcaatctcg gctcactgaa agctccaccc cctgggttca 255060
cgccattctc ctgcctcagc ctcccgagta gctgggacta caggtgcctg ccaccacacc 255120
tggctaattg tttgtatttt tagtagagat ggggtttcac catgttggcc aggatggtct 255180
tgatttcctg acctcatgat ccgcccgcct cggcctccca aagtgctggg attacaggcg 255240
ggagccaccg cacccggcct actcagtgtg ttaatggaga agtatattca ttgttagatc 255300
gccattttta aaactttttt tttttttttg agacacagtc ttgctctgtt gcccaagctg 255360
gagtaccgtg gcacaatctt ggctcactga aacctccacc tcctgggttc aagcgattct 255420
cccatctcag ccttctgagt agctgggact acagatgcac accagcatgc caggctaatt 255480
tttatatttt tagtagagac ggggtttcac catgttggcc aggctggtct cgaactcctg 255540
gcatcaagca atctgcctgc ttcagcctcc caaaatgctg ggattacagg catgagacac 255600
tgtgcctagc cttaaaaaat attttgatag ctattttatt acaaaaggta accttgaagc 255660
ccttgctatt ttgttatgca tttacaagcc tttatgcata aaataaaata gccagcacta 255720
ttctcacatg gccaaggttc atagcacaca cacaaaagta tagttggctg agtgcggtgg 255780
ctcacacctg taatcccaac actttgggag acagaggtgg gtggatcatg aggtcaagag 255840
atccagacca cccttgccaa catggtgaaa ccccatctct actaaaaagt acaaaaatta 255900
gctgggtgtg gtggcgcatg cctgtagtct cagctactcg ggaggctgag gcaggagaat 255960
catttgaacg tgggaggcgg aggttgcagt gagccgagat cttgccactg cactccagcc 256020
tgggtgacag agtgagactc catctcaata aataaataaa ttaaattaaa ttaaattaaa 256080
attatttttt aaaaaattgg gggctgagtg tgatggctca cacctgtaat cccggcagtt 256140
tgggagcttg aggagggcag atcccttgag gtcaggagtt caagaccagc ctggacaaca 256200
tggtgaaacc ccgtctctac taaaaataca aaaattagcc aggcatggtg gcgtgtgcct 256260
gtaatcccag ctactcgtga ggctgaggcc caagcatcgc ttgaacctgt gaggcggagg 256320
ttgcagtgag ccaagatggc accagtgcac tccagcctgg gtgacagagt gagactttgt 256380
ctcaaaaaaa aaaaaaaatt aaggtgaaga aggcttatac tagtgggctg ggacttgaag 256440
tgaagtgaat tcttgaaggt ccccagtgag tggccaaggt gggacttgaa ccaggacatc 256500
tgttctcttg accaccagct tagtccatcc ctttgaagag agtgacctac agtctgggtc 256560
tcagccaggg tctcaggaaa ccaggttccc accttggctc acggaggtgg ttaggggcat 256620
cagctttagc accagagttc agatcttgcc tcgtcctata taagctttgt cacctcccca 256680
tcattaaaag gagccatcct ccccctccac ctcagcagag ccctggtaaa cagcaaatgg 256740
actaacgtgc atctagaggg ttgaggatga agcctggcct ggcatgggca ctcaataaat 256800
gctaggggcc aggcacggtg gctgacacct gtaatcgcag cactttggga ggctgaggca 256860
ggtggatcgc ttgagcccag gagtctgaga ccaacctgga caacatagtg agattctgtc 256920
tctacaaaaa gtacaaaatt agcctggtgt ggtggcgtgc acctgcagtc ccatctactt 256980
aggaggctga ggtgagagga tggattcagc ccaggatgtc agggctgcag tgagtcgtga 257040
ttgagccgct gcaccccacc ctgggtgaca gagcaagacc ctgtatcaaa ataaataaat 257100
aaatgctagg aaagggatcc tactaatgga ccttttttcct ccaaaacagt ggctttcatt 257160
tggtggagat gctacttatt agaagcactt gaggccaggt gtggtggctc atgcctgtag 257220
tcccagcact ttgggacttc tgccaaggca gaagaattgc ttgaacccag gcgtttcaga 257280
ccagcctggg caacatagca agacctcatc tctagaaaac attgaaaaat tagccagcat 257340
agtggcacat gactgttgtc ctaactactt aggcgaaggc aggaggatta cttgagctca 257400
ggagttcaag gctgcagtga gctgcgatca catcactgcc ctccagcctg agcaacaaca 257460
caagacccgg actctaaaaa tcaaaaaaga agcacttagg gaaatttctt aaaattaaat 257520
gataccctga gcaaacccct agatgttctg attcatttgg tttggtgagg tgggagggaa 257580
tcactgaatc tgtaatttat tattattttt ttttttttga gatggattct cactctgttg 257640
cccaggctgg agtgcagtgg tgcaatcttg gctcactgca acctctgctt cccgggttca 257700
agcaattgtc ctgcctcagc ctcccgacta gttgggatta caggcgccca ccatcacgcc 257760
cggctaattt ttgtattttt agcagagacg gggattcacc acgtcagcca ggttggtctc 257820
caactcctga cctcaggtga tccgcctgcc tcggcctccc aaagtgctgg gattataggc 257880
atgagccacc gtacctagcc tgcagttatt ttattctgag ttgatcttct gctggtgaag 257940
tgagtcttcc actggggcct ggagctgcat ctccctcacc ctgccaatcc tgcaagagcc 258000
agcactgagc ttcccctctg ctttctcttt tttttttttt tttttttttt tgagatggga 258060
tcttactctg ttgcccagcc tgttcttgaa ctcgtggcct caagcagttc tccctccttg 258120
gcctcccaaa gtgctggaat tataggcatg agccaccacg cctggtctcc cctttcagtt 258180
ttaaatgaag ccacaagttc cctgtataac atttgggaga tagaggggag ctctctagcc 258240
taggggttga ggtctgtgac caaacgccta taaagttgtc tttgtttgga ctcccccaga 258300
agcagagcct gagacaagga ttgagtgcaa ggaatttatc tgggatgcag ggcagtaagg 258360
gagagaggaa gtgacacagg gacagaaagg caaccaggaa agagtgtatt attaagccag 258420
ttcctgctgt gaacaaatgg ggctcagttt cagtggatac ctccaggagg caacagagag 258480
cacataccac agagtcatcc cacctcacag ggagggaatt ggagtattta tcctccagtg 258540
cccatcagac ataatcacag gccactccca ggggagctat taattcccta acacttgtgc 258600
agccacagag agaccctggg caaagtagtg tacctcaggt gtgtagttga gctatgggca 258660
gggccccagc aacacctgcc aaaatgccaa aagtgccagt gggacctgaa ttcctttta 258720
tttatttatt tatttattta tttattttta tttatttatt tttgacggag tctcgctctg 258780
tggcccaggc tggagtgcag tggtgcaatc tctgctcact gcaagctctg cctcccaggt 258840
tcacgccatt ctcctgcctc agcctccgga gtagctggga ctacaggcgc gcaccaccac 258900
gcctgcctga tttttgtgtg cgtgtatttt tagtagagat ggggattcac catgttatcc 258960
aggatggtct tgatctcctg acctcgtgat ccgcccacat cggcctccca aagtgctggg 259020
attgcaggcg tgagccaccg cgcccggccc cctgaattcc ttttttaggc agttgtgaaa 259080
caacaacatc ccatctgttg ggcacctact gtatattcca tgctcagcga cgcacattca 259140
ttgtctgatt gctgtgttac cactgccttc cagagaaggg cgcagaggcc ccaggcactt 259200
cgcctaggag ggaagcacag ctctaaggtc aggctccttc tctgtaaggt agaggggcta 259260
cttcagggtc acactgaccg ccccaacccc tgacctggcc tctgcttctg cgaagatgct 259320
gagaaggccc tgtgttttgt gttttgggtc ccactgaccc cagaggggag ggccatctct 259380
ttgacccaga ctcttggatc caaactgggg tgccacccat caccatgtca gtacccggtt 259440
gaggggagtc agagatagca ggagaccttg tgggacttga ggctgtgact gttctccaaa 259500
caatgtggag tatttccata ttttaacaaa agagaggcca ggcgtggtgg ctcacgcctg 259560
taatcccagc actttgggag gccgaggcgg atggatcaca acgtcaggag atcaagatca 259620
tcctggctaa catggtgaaa ccccgtctct actaaaaaat acaaaaaatt agccaggcgt 259680
ggtggtgggc gcctgtagtc ccagctactc aggagactga agcaggagaa tggtgtgaac 259740
ccgggaggca gagcttgtag tgagccgaga acgtgccact gcactccagc ctgggcgaca 259800
gagtgagact ctgtctcaaa aaaaaaaaac aaacagagag gttatgcttg tgtttcccct 259860
tgagccagca cccagcccag gaatgcagca gtcaggatag atcaagtgaa gctgcagtaa 259920
caaacagccc ccacatctca gtgacttaaa ttgatgggaa gggtttttta cattcagcag 259980
ggaagctgtt tgcctcatag ttacccaggg acccaggctc acagagtagc tgccattcaa 260040
aatgttactg gtcgccaagc ccagggttga gaggctagag agtccaacac tgaccagaaa 260100
gtgaccacac tgcttccaca cacagcacat cactgcacct agacacacat ggccccatct 260160
aaacacaagg ggaccaggaa gtgcgtgtgc ctgaaaggcc ccaaagcccc gtccagtgcc 260220
tgttctgcac cctgttactg tccgcctcca gatcaggaaa tggaggccca gagaggttaa 260280
gccacttgcc catagccaca cagctgtggt agcagagctg ggatttgaac ccagagtctc 260340
ctttctttgc gagtatgctg ccaacctagt ggggacctga acacagactg tgggctctct 260400
gaggcctggg ttcaaatcct ggctttacat ctctgtgctg ctagcctcag gcagatgagt 260460
ggcttggtta cctcctagaa aatgggtata cctgggagtg gtggctcacg cctataatcc 260520
caacactttg gaaggccaaa gtgagcagat cacttgaggt cagaagttcg agaccagcct 260580
gaccaacatg gtgaaacccc gtctctacta aaaatacaaa aattagctgg gtgtggtggc 260640
atgcacctgt ggtcctacct acttgggagg ctgaggcagg agaatcgctt gaacccagga 260700
ggcagaggtt acagtgagcc gagatcgtgc cactgcactc cagcctggat gactgagcga 260760
gactccatct caaaaaaaaa aaaaaaaaag agaaagaaag aaaaagaaaa tgggtgataa 260820
cccttccctc caggatcttc atgaggagct cagtgatgtc atttataaag cccctggggt 260880
ctcgggagcc ctcaaaaatg ctggagagac aggccacagc tctgaagagc agccccagcc 260940
ctgtggagct gaagcagggt ctggaggccc cctctggggc caggccaatc atgggaaggc 261000
ccccaggagt tcccagggag ggagactcag cacagatgat gtcgaacagc ctttaccgca 261060
gcccttcgaa caaccataac tgtcccgggc actccgctga tgggcaactg tgcctctaac 261120
atgcacccgg ccagcctagg gggccgggaa ccaagccctc tgttggcatc tctgtcttgt 261180
gggtccccat tctagaatta tttccgcgat gcctggaaca tcttcgactt tgtgactgtt 261240
ctgggcagca tcaccgatat cctcgtgact gagtttgggg taagtctccc tccagcttct 261300
ctctgggtga ctctgggctg gacgaggcag gcggcagggg gcgggggagc ggtcccagag 261360
gcagtgtgtc ccggaagcca tagctgcttg agccagcact tggccatgac cagagaggga 261420
gaactggggc cccggggaca agggcagccc ctcaggaggg cattgtgggg agatgggggt 261480
aaccaaagct tggctgtagg gccagcactg aggggtgggc tttcctgcat cctggcctag 261540
gaattaataa tgcagatgag tacactgagg gaactgagac actcaaaagc tctgaaagct 261600
gagccggctc ccaaacacca ccctatgtca ggagcccaga aagaatgggt ttcaagtcaa 261660
ttctgtttga accaaccctc tcctagttag tgggcaggag agagccacag ccctcaggcc 261720
agtgtgggga caccactccc agggccatag aggggtcccc agggtgtctt ccctcctcta 261780
gccccgggcc tgggagactc tcaacatggg agtctctgga cctctctgtg gtggccccac 261840
aggccacatt gcccttctcc ttttctggaa gactcagggc cccagaggtc ctgtcctaga 261900
ccctctcctt ggccatctgc caatgagccc aggcttgggg tccctcagga gattgggggg 261960
agggtagaag atccttgcag ggggaagcaa tggtcaaaaa agggtgtcaa agccaagggt 262020
caagggtgat accaatgtca tcttactaac aataaaaata acaatagctc acgagaatcg 262080
cagccttgct gtgtgccagg gaactgtgcc aagtggttta cgtggattgg ctcagggtag 262140
aggtcttggt ctcagctcgt aagagaattc cctcggaggg ttcaactgaa ggcacccaaa 262200
tgcagacctc actggtggag gggaagggaa gggtacccac aagggtggca aggtgtccag 262260
cgaccaccca ccgtggggag ctgtcacctg cccaggtgct gaagtgggga gggaacctga 262320
gccggaggcc aggagaagcc accaagtggg agctgtcctg tcaatgtgga gagacagaga 262380
ccagggccca agcaggcaga gagcaatagg ggagaaacac cccaaccttt ctctcccctc 262440
atcccttatc tcctgccaga gcctcccatg gcccaaagta aaccggaagc aagctgaata 262500
tgatgctcag agcaggcagg gaagtcagga gaatagatct gggtgtggtc gggcctgagg 262560
aagagggtgt tgcctcattt cacagatggg aaaactgacc tcagctgggc acggtggctc 262620
atgcctgtaa tcccagcact ttgggaggcc gaagccggcg gatcacctga ggccaggagt 262680
tcaagaccag cctggccaac atggtgaaac cccatctcta ctgacaatac aaaaaaatta 262740
gccaggtgtg gtggtgcatg cctgtaatcc cagctactcg ggaggctgag gcaggaaaat 262800
tgcttgaacc cggaaggcgg aggttgcagt gagcgacggt cataccattg cactccagcc 262860
tgggtgacaa gagcgaaaac tccatctcaa aaaaaaaaag aaagaaagaa aactgatctt 262920
caatgcctgg ggaagtgaga gacactccca aggtcacaaa gccaggcctg ggtgactcct 262980
gagagtacac tgacagctcc tggggtgtcc cagtcagatc ccoctacaga aaaggatctg 263040 tttgcctgct cttccgtcct agaaggccag gaggggctgg ggaactacac aaaagagggg 263100
gccattcttt gatatgtcct acggcacccg cacccaagtg atacacactt atttgccttc 263160
agctccagtg agccagaatt ttccccttcc cctcacccta tccctgaaac cttcctctag 263220
agggttcttg cccacatggg ggctctctcc actggggtgc cccacctgg tcattctccc 263280 ctgtcctgag tttctagaga gggctggagc tccagctggc aatcaaaata tcttgccatc 263340
cggctacata caagacagcc ttgaaccaat gtccctttgg gtcaagaggt tagaaggatg 263400
gtccagctcc ccagaagggc aggtggggtg gaggaagtta gctgaaacct tcaatcacca 263460
gtaagagagc tgtagggaca gactccaaca gcctgttctc ctggctggca ggaagatggg 263520
gcatggggtg ttcatgggac atcaggaccc ttgcagtagc caaacagccc ccagccctcc 263580
ctaccagctg tttgatcttg gacaacttgc gctatctctt ctcatgtaga gtggggctaa 263640
ccattgcaac caacctcaga cacttgcaag actcacagtg atgcatgcac tcaaaagaca 263700
ttcattgagc acctactgtg tgcctggtgt gattataagt gctggagaca gaacgagaag 263760
gaggggtgcc aaacaaaaca gaccaagaat acagagtgtc tgctcccata gagctgacat 263820
tctaaggaga gagacgggaa ctttttacaa gtaaaagcat caacaggccg ggcatggtgg 263880
ctcacgcctg taatctcagc actttgggag accaaggcag gtggatcact tgaggtcagg 263940
agttcgagac cagcctggcc aacatggtga aactctgtcc ctactaaaaa tacaaaaatt 264000
agccgggcac ggtggcaggt gcctgtaatc ccagctactc aggaggctga ggcaagagaa 264060
tcacttgatt ctcaggaggc gagaggttgt agtaagccaa gattgtgcca ctgccctcca 264120
gcctgggcga cagagtgaaa ctctgtctca aaaagaaaag gaagaaaaag aaagaaagaa 264180
acgtgaagtg cttggcacag aacctgccag gaaaccagga gtttgaaaat ggtggttgtt 264240
aactattact gctgttgtta ttgttattgt gaatgggtgt gtagttttgt tagccagccc 264300
tgagttacag tcaatttgag ggaaagatag ggggtgggtg tttgggtcct tctgggacaa 264360
ttaactccca acctggagta gggagaggca tgtcctggca ggcaaggagg tctcagttgc 264420
ccctttctgc ctcccaggta agcccactag ttctgaggcc agggcttggc caggctgaga 264480
caggaaatgc cagatgcttg ggcgggcagg tccctggggt ttagggggca gagggcatgc 264540
ggcagtacta accagtgctg tctcagctgc tgcccccaag tggctggggt gatgtgggtt 264600
tgccctgtgt gcaatggata atgactgtgt ttcttgtctt gtctcttttc atgcctgctc 264660
ttaaaactgt atattggcgc aacgccgtct gaaaaactca tccaatcaaa atgcactatg 264720
aaattcattt gttcatccat gacatggtct gtgtgttcat acaccaatga cttatctccc 264780
aacccaccgc caccaccacc cccactcccc gcccgggaac cgaaacccat tggtttttg 264840 gcactggtta caaatcaacc taaaaaatgc tgaacacgcc tccccaactg cccccgcccg 264900
cccgctcccc ctcatcttca acatctgcat ctagaatccg gttggtctta cttctttctg 264960
aagtctaaat gccttacatt aactgtgaac gcatctcctc gcgtcggcat tgcatgccac 265020
accctgcctc tccaacgtgg gatgcctgac gctctcctca accctccgct ctcctctgtc 265080
tgtctgtcct cccgccccca gcccctgtgc ctcccacttc ctgtagactc tgtctctctg 265140

-continued

```
tttttatcgg gttctgaatg ggggttttct gtttggggtg gtttgcgtct tttgcagaga 265200
aagggatggg ttttcccagc gcagcacctc tctcttgccc catcccgcac acacatcccc 265260
tacactcaga gacaatagag gcaaatccac tcccagccac ctctcaccac tcctgtcccc 265320
cattcagctc catggacccc aggccccagg aaagctgcca actgtctcct cgcccctcca 265380
gctctctcca tcctgctgtc cccaatcctc catctcaagc ccacaagatc tttggccttg 265440
accagcagag acttgactct ccaagtctga taaaggagac ctgaaggcca ggcagtgtgc 265500
cggcaaagac tctcaggcag aggaactcag aagtgccaga cttggatctg gtagcttcat 265560
gtggggctgg cccactgagg ccctctcctg gagccttgaa ctgtacgtgc acacgcagtc 265620
acacagtcac tgcacacaga cactgcacac acagtcactg tgcacacact cagtcactgc 265680
gcacacactg tgcacacagt cactgcacac agacgctgca cgcagtcact gcagtcactg 265740
cacacagtca ctatgcacac acagtcactg cacacagaca ctgcacacac agtcactatc 265800
cacacacaca gtcactgcgc agacactgca cacacactgc acacacacaa tcactgcgca 265860
cacacagtca ctgcacgcag aaactggaca cacagtcact atgcacacac tgcacacacc 265920
actatgcaca cacactgtgc acagtcacta tgtacacaca ctggcactgc atgtagtcac 265980
tatggacaca cactgcacag tcactgtgca cacatacact gcacacactg tcactatgca 266040
aacacagtca ctgcacacag tcactatgca cacacactgc acacacagtc actgcacaca 266100
gagccactat gcatgcacac acagtctgca ttcacacatt gaacacacag tcgctataca 266160
cacacagtca ctgcacacac agtctatgca cccacacact gaacacacag tcactgcatg 266220
tacagacact gcacatagtc atgacctctt ctctttttct cactcattct ccaattctct 266280
ctctctctcg ctcttttttt tttttttttt tagacagagt ctcgctctgt cacccaggct 266340
ggcgtgcagt ggcacaatgt cagctaactg caacctctgc ctccccgttt caagcaatta 266400
tgatgcctca gcctcctgag tacctgggat tacaagcatg taccaccacg ccaggccact 266460
tcttgtattt ttagtagaga cagggtttca ccatgttggc caggctggtc tcgaactcct 266520
gacctcaagt gatgcacccg cctcagcctc ccaaagtgtt gggattacag gtgtgagcca 266580
ctacacctgg cctctaatcc tcattcactg ttcctgtctc tgtgtctctc acatacagtc 266640
atgcatgcat gcacgcatgc acacacacac acactggccc tctctgctac atctacccac 266700
cctgtacccc cactccagta catactgcac acatctctct ccctccccca cttctcagcc 266760
ccttgcacac cccttgttct gttaaatctc aactgcctct gcccctctcc tacccaccaa 266820
tgaggccctt agagggacgc cccaatggca tctttgccct ggaatcatcc cttccctgct 266880
ggcaatacac atgcattcac ccaccaaaca tttaatgagc ccctatttgg tgccacagat 266940
ggaattatgg gcagaagcag acaccattac tgtcccctct taccacatac agtcaggtgg 267000
gggaggcagg catcggtcaa ataacccctt gactccactt aaaattatac ctgcactgcg 267060
agctgaagga tgagcagcat taacaaggca gagagagatg cacagagcat tccaggccca 267120
ggacagcaca tgcaaaggcc ctgtggtggg acggaacctg tgaggggtca ggatctgcaa 267180
gcgagggaat gtggctgatg caaagacagc cgagaaaggc tggcctggag acagccgaag 267240
aaggcagaag gggacaggac ccggggctgg ggagggcggg gctatattgt ggaatatggg 267300
ctttctccta agcaccagga agggcctggg aggataggaa gcaggggagg cgcgactggt 267360
catgtgacta gacaagctcg ctctggttgc agggcaggga acagcttgac aggaggctgg 267420
gctggaggtg ggcaccagga atcgcagcaa gagatgacag tggaggagag agaacagtgg 267480
gagggttgtc ctctgcagga cccagggaaa gatcaggtct gaactgagat gaggtgcctg 267540
```

ggagcagtcg ggtctggctt aaaactggga gataggctga gcacggtgac tcaagcctct 267600
aatcccagca ctttgggagg ctgaggcagg aagatcacct gaggtcagga gttcgagacc 267660
agcctgacca acatggtgaa accccatctc tcctaaaaaa tacaaaaatt agccaggcgt 267720
ggtggcaggt gcctgtaatc ccagatcctc aggaggccga gacaggagaa tcacttaaac 267780
ctgggaggtg gaggttgcag tgagccgagg tcgtgccatt gcactccagc ctgggcaaca 267840
gagtgagact ctcttaaaaa aaaaatactg ggtgatagag gtgagcgagt gcaaggaaag 267900
gaccaggttg ggggaagaga ataggtgtgg gcatagcaag tttgaggtgc ctttaggaca 267960
tcccgaaata agtcagatag gcaggtgttg tgggggctgc agcttggagc tgaggtctac 268020
aagtagtagg acttttctgg agcccttagg tgggtggtct ccatatcctt ctgagcactt 268080
gaggaacatc tgagcacagc actggaaaag aaaagaccac aaggacgctg tcctcatgtc 268140
ttccaggggc tgtgtcccac ccccatcaca ttctagccag gaagttcagg ggaggtgttg 268200
aagagaggaa gctgcacctc ccaagccatg gattgaaatg tggaaggcag gaagagggaa 268260
cttgtcagaa gttctggggg cagtggaaag aattggtact gatgcaggaa gagatggagg 268320
gtggatgagg gcagactagt acccttcccc cactgcccca aacccttccc gtctccaccc 268380
ctacctgcct catgtgtctc ctcccccact tggctccaag aagggaagca tgttttctgc 268440
acgcatctcc ctgccagatc cctggctttt ttgcatggtt gcaagcttcc cctgctctcc 268500
tccaaacccc cctcctgagg ctgcttccag ggtccgcctg ccttcgcatg cctggccgag 268560
tccacatgtt atgatccgcc ccatgaaagg gatggcttgt actctggggt tgaacgggag 268620
ggggctgggg atacctgagc catcggcccc atccccaggt ggagctgggt ggccaggcag 268680
ggatgggggt cagggcagca gggcacagag agtgactctg ttagccaagc tgggtttggg 268740
gcttgttcga ggcactggag acattctcac agcacttgag cccagtgtgg tcagggtagg 268800
atcccccagc ccccttcccc atcctagagg cctaaggacg cactgatgtg tcccagagag 268860
catcctagac attgccatca aacccagagg cctcagaaat tccttgaact ccagtccttg 268920
cctctcagct cccaggccaa agccagcaca agacacagat ctggcagcca gaaagccctc 268980
tggaagccac caagtaggat gcccatgtca cccaaactag gacacttttg aaacaggagg 269040
gaggctgtga ctgtatggtc accctgtgcc atttgggggg tgaaggttag accaagttaa 269100
atcttgctac gtggcctgta gcaaatccta caaatcccat agaacaagtc tgattaagcc 269160
ccttccctta gtgtggagag accctctact cctcctgcct tcaccctgct gggtactggc 269220
cagcgaagga gggtttccat gtctgcctga ggctggggtc tcaaactcaa atgcctctgg 269280
gggccaggca gacaccagtc aaccaggaaa gcaagtgcca tttctaaaac gtgaggaccc 269340
tggaaaactg gagatcatgt ggcctgcttc cagggagcaa tcgcagcagg cctggggttg 269400
ccagaaagcc agattggtgg gcaaaatctc ttgattttta aacaatggca ataattttta 269460
attaaaaaca aggacaaatg aaaaaacact gctcgggccc aacaaaacag ttttattagc 269520
tagatttggc ccactcgtga cttcgagagt cccacccccc ccaccaaggt cccttgaagc 269580
cccacaatgg ccacttaact ctagctggtc tcctccctga ctctccaact ctctggcccc 269640
ctggttcttc tagcttgggt gggaggaggc agaggcagtg actagacagg gggtttttga 269700
gcagaggcag tggccaccca gggaggtcct gggggcaggg atggccccac ctcccggccc 269760
ccagcacccg ccccttggtg ggcccgggct gatttctgag ctcacccacc catgggagct 269820
gagtgcttcc tgcttcctgc aggcctggtc ccgtgctact ccacccagcc ccagaagctg 269880
agaagccatc cctgagaggg gggaaaaggg ccccaaatgc atcttctccg actcagcggg 269940
cagcgaggac tcaccctgca gccgaacagt cccagctccc tcccgtcctc cccattcccg 270000
ctcgccaagg gggtaagaaa agatgctctt ccgcttctcc caattggctc gagccgctgc 270060
tcctcttggc cgtggggtga ggtcagggcg ggcaggagcg ggtgggcagc tcggcagggc 270120
agggcagggc agggtgcccg gtgagtcccg tgacagatgc atttctggcc cggagcgtaa 270180
catgccctcg gaacccgcac atgtccacca ggcctgactg tgctggcgac ctccaccccc 270240
acccccgccc tggtgtttgt gcatcgtaca cgtatgatag attccgcaac ttgaccggct 270300
tgtgtccttt cgtctcagtg catttggttg ttgggagaaa caaaaaccat ctcgattttt 270360
ttcctgattg gatgattcgg atatattttc tttttcttgt tcttttgtta tttcttcccc 270420
atccccgttc ctttttcctc ctttcttttt cttttctttt ccccattgtg ggtggggctg 270480
gcagggaggg cttatgcttt tgagttgatg ccttttcctc cctcccaccc tctctctccc 270540
aacattattc ctttttcgag tttttcctct gcatcattgc attaatagtg ctttctctct 270600
ccctccttat ttggggtctg gcttgctttt ttcctgttgg ttggcttcat gtaggggcct 270660
ctgtgagtgg tgacagctct gagccttttg gggtgggtgg atggtcaccc ctcttcctcc 270720
atctccccag aataacttca tcaacctgag ctttctccgc ctcttccgag ctgcccggct 270780
catcaaactt ctccgtcagg gttacaccat ccgcattctt ctctggacct ttgtgcagtc 270840
cttcaaggtg agtcctcgtc cctgctgctg gcccagggct gagaagacag gtgaccctca 270900
tgctctggct gaatgtagaa gtcagattgg aagtgcctct gtgatgtagt cgtgcagaga 270960
atctgttatc tccaaggctg ttgtcaaact tcctgtccct ggtgtgtctt cagagctgta 271020
agggcctcat cctagagccc ccagagatgc ccaccagccc tggaaggact ctggcacgtg 271080
gcatatggcc acccaaccca gtggggcaga gcactgggac aagggaggaa gacagtgcgg 271140
ctgagggacc cccagcactc ttcttcattg cctttttttcc caccaggccc tgccttatgt 271200
ctgtctgctg atcgccatgc tcttcttcat ctatgccatc attgggatgc aggtgagtgt 271260
cgtgtcccta aggttcccag agcctcccaa ggagggcagc caccccttaga aaggggtggg 271320
tcagaggagc ctggttcaca gaagcagcca tggaggttga gctgggtttc ccagaagcca 271380
ctggaggaat ggcagcccct ggtcgtcacc ctccaattcc acaggtgttt ggtaacattg 271440
gcatcgacgt ggaggacgag gacagtgatg aagatgagtt ccaaatcact gagcacaata 271500
acttccggac cttcttccag gccctcatgc ttctcttccg gtgagaaggg gacctgctct 271560
gataattctg tttccgtggg gtggggtgcc tgccttcatc cttctgttcc catagaggat 271620
gtaccctcct cttccaatgc aagacgtgcc ctcctccttc tcttctggca ggggcgcgcc 271680
ctcacccttc ttttccggta gggggcgtgc ccttctcttc cggtagggga cgtgccggcc 271740
ttctcttccg ataggggggcg tgccctcctc ctccttttct ggtgtggggg tggccagatg 271800
tgctcttatc cttcttttcc cgtgaggctg gaaatgggtg tcgtgggggg cccaggaatc 271860
ctagcagggc agaagcagag ggccctggga catagtcatc aaggtcattt tccaggcatt 271920
atctctgaat cttcctgacc accctgtgag gaagggattc ttggcagccc tatccgacaa 271980
ataagaaaac aggcttacag accgtgaggc ttgattcttt ggttcatcat cttggctgca 272040
cacaaaagtt ccttcactcg ttcagtgtag gtttttggg ggggcttttt tttttttttt 272100
tttttttttt ggagatggag tctcgctctg ttccccaggc tggagtacag tggcgcgatc 272160
tcggctcact gcaagctccg cctcccgggt tcacgccatt ctcctgcctc agcctcccga 272220
gtagctggga ctacaggcgc ccgccaccac gcccagataa ttttttgta tttttagtag 272280 agtcggggtt tcaccatgtt agccaggatg gtctcgatct cctgacctcg tgatccgccc 272340
gcctcggcct cccaaagtgc tgggattaca ggcgtgagcc accgtgccca gcccttttt 272400 ttttttttt ttagatggag tctctctctg ttgcccaggc tggagtgcag tggcgccatc 272460
tcggctcact gcaagctcct cttgtggagg tgtattgagc acctacagca tgccaggcag 272520
ggctgaaaaa cgaggatgca ccaggaaata gagaaaagag acattttaag cactttggaa 272580
gctaacatcc ccatggggaa gacgaataat caggaaacaa attatagagg atgctggaaa 272640
aagataaaat tcaagaataa aggggaatag ggccaggtgc agtgactcgt gcctgtaatc 272700
ctagcatttt gggaggccga ggtgggagga tcgctttagc ccaggagttt gagaccagcc 272760
tgggcaacat agtgagaccc cgtctctaca aaaaaattgt ttttaattaa ctgggcatag 272820
tgccacacac ctgtagtccc agctacttgg gaggctgagg caggaggatt gctcgagccc 272880
aggagttcca ggctacagta agctatgatt gtgccactgc actccagcct cggcaacaga 272940
gcgagactct gtctctaaaa agaaaaatat attttttaa tttttaaaaa aagttacaga 273000
ggtagatagt ggtgatagtt gcataataat gtgagcttac ttaatgctac tgaattgtac 273060
acttcaaaat ggttaaattg ataaacttca tgctgtgtgt attttgccac agtaaaaaat 273120
aataatgttt ttaatctaac aacaaaaaaa gaatagaggg ccggcaggtt atgcctctct 273180
gaaagtgtga catttgagag aaattggcaa gggagggagt cagtgggtat atggggaagg 273240
gcaggccaag ccgaggggac tgcctgtgta aaggccctga ggcaggagta tggctggcat 273300
gtttgaggac tgtgaggagc ccagcatacc tagaacagag tgatctaggg agaatatagt 273360
atgagatgac tgtcaccttc atggagggga gcttttttt ttttttaatc tgagacagag 273420
tttcggtctt gttgcccagg ctggagtgca gtggtgcgat ctcggctcgg cgcaacttct 273480
gcctcccagg ttcaagcagt tctcctgcct cagcctcccg agtagctgag attataggtg 273540
cccgtcacca cgcccagcta atttttgtat ttttagtaga gacggggttt tgccatgttg 273600
gtcaggccgt tctcaaactc ctgacctcag gtgatccacc cgcctcagcc acccaaagtg 273660
ctgggattac aggcatgagc cactgcaccc ggcctgaagg gagctttttt tttttttgc 273720 tttttttga gacagaatct ccctctttgt cacccaggct ggagtgcagt ggcgcgatct 273780
cagctcactg caacctccgc ctcctgggtt caagcgattt tcctgcctca gcctcccaag 273840
tagctgagac tacaggtgag cgccaccaca ccgagcaaat tttggtattt tttagtagag 273900
atagggtttc accatgttag ccaggatggt ctcaatctcc tgacctcgtg atccacccac 273960
ctcagcctcc caaagtgctg ggattacagg tgtgagccac cgcgcccagc caagagggga 274020
gcttttaaag cataacagtg accagcctga gcaatgcagt gaaaccccat ctctacaaaa 274080
aaaaatagtt taaaaattag ccaggagtgg tggcgtgtgc ctgtagtccc cagctactca 274140
ggaggccgag gcgggaggat cacctgagcc tgggaagttg aggctgcagt gagcagtgat 274200
tgtgccacta cactccaacc tgggtaacag agcaagaccc tgtcaaaaaa aaaaaagaga 274260
gagagagaga aaagaaagga aaagaaagag agagagaagg aaaagaaaag aaaaaaacat 274320
atcagtgtcc tcaaatccca ccctagacca actgaatcca agtctgctgg ggtggggcac 274380
gggcattggt attttttcaa agctctctgt ggacttcagt gcacagccaa gaatgtgaat 274440
tcccttctct cagctcccag taaaaggagg tggtccacct ggggcttgcc tggccagctc 274500
cagagcccaa gtgctcaacg tgtgtgctcc acctcctggg gaggcgttgg tacccagtca 274560
gggctgggtg tccgagtctc tgatttctcc ctgtcctcag gagtgccacc ggggaagctt 274620

```
ggcacaacat catgctttcc tgcctcagcg ggaaaccgtg tgataagaac tctggcatcc 274680
tgactcgaga gtgtggcaat gaatttgctt atttttactt tgtttccttc atcttcctct 274740
gctcgtttct ggtgagtctg tggacactgt gagggccgtc tgggctccct aagcctggct 274800
tcctttcagg ggagtgggtt tctgtggaat gtggctgtgt cgaaggcttg ttccctccaa 274860
ggcttctctg aaccagcctg ggatcaggtg accctgagcg tctcaaactc agcactgttg 274920
acatttgggg gtggctgatt ctttggggtg gggccatcat gtgcactgca gtgtatggca 274980
gcatccctgt cctcccccca ccagatgctg gcagcacacg ccacccgttc ctcctgttgt 275040
gacaaccaaa aatgtctccg gacattgcca ggtgccccca gggggtgggg gtggggttgg 275100
gagtgggggc cagaattccc ccatttgaga ctcaatgaaa tatttcagct gggcgtagtg 275160
gccgatgcct gtaatcccaa cacttcggga ggctgaggtg ggagggtcac ttgagcccag 275220
gaatacaaga ccagcctgga cagcatggtg tgaaacccat ctctttaaaa aaaaaaaaaa 275280
aaattgaatt agctgcacac gtggtgctgt gcacctgcag tcccagctac tcaggaggct 275340
gaggtgggag gatcacttga gccttggagg tcgaggctgc agtgagccat gatcacacca 275400
ctgcacccca gccagggcga cagaatgaga tcctgtctca aaaacaaaca aaaacaaaca 275460
aaaaaaaaaa aaacattgcg agggaagaaa tacctcactt tggccttgtt gggggcagat 275520
gtgggaggat ttggggtcac agtggttctc ttggtgttgg tccctgtttc agaagcctcc 275580
cctccctctc actgactctg tttctttcca tcattcttgg tctttgtctc tctctctctt 275640
ttttttttt ctttgaaatg gagtctcact ctgttgccca ggctaaagtg cagtggcgag 275700
acctcagctc actgcagcct ccacctccca ggttcaaccg attcttcagc ttcaacctcc 275760
caagtagctg ggattacagg tgcacatgcc accacaccca gctaattttt gtatttttag 275820
tagagacagt gtttcaccat gttgaccagg ctggtctcaa actcctgacc tcaagtgatc 275880
tgtccacctc ggcctcccaa agtgctggga ttacaggcgt gatccaccgt gcccggccag 275940
tctttgtctc tttgtatctc tctctctcca tctctctctg tttctctctt cctcttcccc 276000
atctctccac ttgatctctc tctcactgga cctccttgtg tgagtgagca tcacctctcc 276060
attccccagt ctctttctgt ctctgtctca tttcctttcc ccatcttctc tctatccctc 276120
tctccatctg ggcctctgtg tacatgtctt tgggtctgtc tgtccgtctg tctgtctgta 276180
tccttctcac tcactcattc attccctcgg tctctgcccc cattctctct tggtccccgg 276240
ggtccccaca gatgctgaat ctctttgtcg ccgtcatcat ggacaacttt gagtacctca 276300
cccgagactc ctccatcctg ggcccccacc acctggatga gtacgtgcgt gtctgggccg 276360
agtatgaccc cgcagcttgg taagaagtca ccccgaatcc tccagccaca atactcacct 276420
ctccctggaa ctggaacacg ggctaggtca ggccccagac tctggagcac tgaactcctg 276480
gggtcctagc aggggtctca caggttcagt caggagagaa gatataagaa tcatcaccct 276540
tgcatacccc agattaaaca cgtagggtgc caaccctgcc caaaccctgg actttctggg 276600
aaatgaggga gggcgtcaac catgagatgt cctgaagagc cctctcctcc tacgagtctc 276660
tcctgtctct cactgtgaag tctccagatg gtgaggatgc attagccagg ctccagggag 276720
aaaaccaaca gcatcccagc ctcagttctc ttgagagtgt ggggaggagg gctggcctac 276780
ccttggcaga caggattggc agcaacatca gagtagcaga actcagctcc cactgggacc 276840
cgtgaacctg ggagtgagag gacatacagg ccaggggagg acgcagagcc tcaggggccc 276900
atgcatcttt gtggccacaa agggagtggg cgctcccatc tgggtagaca ccagaggggt 276960
ccctctccac tgacgggcaa tggtttcaga gggtgggttc caccttgtgc acgtgtattg 277020
```

agtgcccacc caacaccaag ccttgaagga cactcagagg ctttatctga atacctggaa 277080
cccaccagcc actaactgag gatttagttc aggctggtct tggggcctga agaagcatta 277140
ctggggggcc ctcagcagcc taagccccat cttcctctgg cctcagcacc agagaggagg 277200
ccgtcacgag gaaggtgggc aggaggtggt cttggctatt cccatagcct caaacaagta 277260
ctccatgaga ccgagaggct ggggagagcc gtgggtctgg ggctgggctt tggctggttc 277320
ctaactcttc ctcttttgat tttaggtcac agcaattgga tgctgtcccc aaggcctcta 277380
ttccacaagc cccccccac ccctgtagcc catgtagact gtggaggagg cagatgcaga 277440
gagagcccca ggggaggtgc cctgcagtcc cgaactcgac tgacatccta cacccctggg 277500
tctccccagt gtctgggaat gtactgggga ccttcacttg tccccagtct ctcccactcc 277560
ttcaagccag ggacacccca gcctcgggca tcatgacctc gctgtgtgcc cagggagccc 277620
gtgtgaaccc attgcctgca ctaacccccct ttcttctcct ttcagcggtc ggattcatta 277680
taaggatatg tacagtttat tacgagtaat atctccccct ctcggcttag gcaagaaatg 277740
tcctcatagg gttgcttgca aggtttgact tccactaaaa cctgctagca tccatggaat 277800
gagtgtggct tggggttctt caatatatat atttcatata tatatatata tatatctctc 277860
tctctctcta aaaaaacaga gccatctctc tttcttgcat taaactagaa aactctctta 277920
gccaacagaa tgcagtcatg tagactcgat aaagcatgga acatatttcc tccttccctt 277980
cagccttcag ccatctttgc ttgctcttag ctgaagctgc ccatcctggg gtctccacgg 278040
caccccaaat cagatacatc ccctgggggga ttgtaacttt gcatttctcc cccaaccatc 278100
acctccactc tctccccctc caccccctcac ctcccaaagc ccctagccct cctcccctcc 278160
ctggcactgg cccctgctcc ccacctaggc cccctcagag accagcctca gccaaaccag 278220
agaacgtgac ccaactgtag aaataacagt gatggccggg cgcagtggct catgcctgta 278280
atcccagcac tttgggaggc caaagcagga ggatcgcttg agcccaggag tttgagacca 278340
gcctgggcaa catagcaaga acccccttct ctataaaaaa ttagccaggc attgtggcgc 278400
atgcctgtag tcccagctac ttgggaggct gaggcagaag gattgcttga gcccaggagg 278460
tggaggctgc agtgagctat gatcacacca ctgcactcca acccaggcga cagagagaga 278520
ccctgtctct ttaaaaaaaa aaaaaaaaaa aaaaaaaggc aatgaacaaa agcatggctc 278580
tacgtcttcc aaagtgagaa ttctccctcc cctccgcatc cctccagaac tgtagctcag 278640
agcccacgct gaatctgact tttctctttt ctctctctct ccctgctccc gagcagtgaa 278700
gtaatctttt tttactgacc ttttcttcca ttttttttcc tcctcttttc cattgatttg 278760
aaatatctat tttatcattc tctgcatctt tctctctcta ttttttcggc tcgtgtggat 278820
ttcttttttc tttcttctgt ttctccccac ctctcttcct ttggttctct gttcccattc 278880
ccgttttgtt tttttgtttt tgtttttgtt tttttcattt tcggtgctgc caggggccgc 278940
atgccttacc tggacatgta tcagatgctg agacacatgt ctccgcccct gggtctgggg 279000
aagaagtgtc cggccagagt ggcttacaag gtagactacc cttgccgacc accgacgtcc 279060
aggcactggg tttttttttc ttcttcttct tcttttttttt tagtgctgac cagaaacacc 279120
cggccgactc tctttttcca acgtttctct tcttttttgt ttttgattct tttttttctt 279180
ttctcgagtc aactgatcat gaccatccct tgattctaag cagcacactg tgtccgtcct 279240
ttctgatgag tgtcttcgtg ttttgagact ccattatggc cgacatgccg gggggagggg 279300
gaggggagcg cccaggtccc cttgcacctg gtctcccagg taccaaattg gaaacaaaca 279360
cgcttcttca gggagtcaaa acccatgctt cccacttctg cccacccaga gcggccccca 279420
tgcccaggct ggggcaggcg ccttgcagag aggggcttta gcccccgaaa gcaggcgagg 279480
tcccgggtcc ccgcccctgc cacgcacacc tgaagctgat ctctgaccta gggccttggg 279540
gattcgagac cttccaagga gcaccaagaa cctctcttcc cctcccttcc ttcccctgga 279600
gtttcgtccc cagcccccgt ccctaatccc cccaagacac cccaacatgc ctctccattg 279660
ttccagagtg ggcaggcggc cgcagctgga cccctggacg gtggcacact gatgcaggcc 279720
atgcacgctg ccttggcggg gcctggggcg ggcaggcacc atggccgacg gggggtggtg 279780
catgctggct gagagagcga gcgtcctgcc gccaagcggc tggcccgggc cacccctcca 279840
gatccctgtc ctggaatctc ccttggtgcc caaggacaga tgctctgttc cctccattca 279900
tccacaagaa gttcagggat gacctttaaa gattctcccc acccaaaaag tattacccca 279960
tcatcctatt ctcccatcca ccttgatctt ccctgcgtcc ctatccatca atgctatttg 280020
tacctgcccc gtgttgccac ctcattcctt tccttcctct gtgcacccct cctcacctaa 280080
cctatatgtc tcccctcctt ctcaatcaaa gccggggaca aggttgtccc accagcatct 280140
cagacaatga gcctctcctg gcacctgtcg ctctgtgccc ctccctgccg cccccccccc 280200
cccccccggt tttcctcaag tcgcttctct cagtctctgc ttagatgaat gtgtgcgcat 280260
gtgcaagaga gggagggcga gcccttcctc tcctggtctt tgtgcaggac caccatgggt 280320
ccataagaca actttgtgca aatttgaaaa aggcaccctt tccacagaac atgcctgttg 280380
gaaaattgtt gcaatctacc aatgtggtga gaacaagaca ctttttttct atcacctggg 280440
aagctgttat atttaatata caaatcgggg gctgggcgtg gtggctcatg cctgtaatcc 280500
tagtgctttg ggaggctgag acgggaggat cacttgagcc cagttcgaga ctagcctggg 280560
caacatagcg agaccccatc tctacaaaaa gaaaaaatat tttaattaat aaataagtac 280620
ataaatctat catttccaag atgggagccc tttgtgcggt gtacaacctg cacaactgtg 280680
cacagtggcc cagtctatgt gtgtttctct atttcccacc tccttcccca ccctaccccc 280740
agtgtcccct ccagtgtcct gctctggatt taccataccc ctccccatct tcaactctgt 280800
gtttcctgcc cacttgtgtc tgaatcccca cccaagttgc cctcaccccc cttctctgtg 280860
ccacttcagc ctgggctggt gcacaccagc ccagcatcct ctcccatgcc accaagcatg 280920
gtggacagag cccctgcctg ggacatgggg aatctttttct tccctgggct ggaagggagt 280980
gcccctcacc ccttcccccct gccattgcac agagagccaa gatctggaca tgcccctgag 281040
atacacttcc cacggagcta tgaatgagtc tcgagattcc gtctgcatgc gcccctgtct 281100
gtgctgttct gtgtcacagc ctcgctgcat gcctgcgagg ggcctgcccc gtcagtgggg 281160
ggctgcctgc ctgctgcttc tcagaggaat gatgtggtct gtgcccatct gctctgtcct 281220
ggtctgggcc aagccaggga ttgggtgtgg ggagccagtg gcaccccccca ccagcggctg 281280
tggtcctggc cccctcagcc ttggctgttg catgcactgc tcaaatccag cttgtgctct 281340
ttttctttgg ggtcagactg aaacggggcc atccagaaga actctggggc agggcggggg 281400
tggggcaagg gttgaggcaa accctggaaa tgccagctct caggtcaagc aggtgggggga 281460
aaaaaggaga gggcagggga ccagaagtac aagagagcct tttgtgccct ccctgcgggc 281520
caccaagaga aactgagtac tgggacaggt aacctaagta agagacacct cagccgccac 281580
agctttcaga gttcttcctg ggactccctg ggtagggggcg ggcgcggctc acgggagacc 281640
caggagggat gcctgggaat gactgcgctt gccttgggtt ttctgtagcg gcttctgcgg 281700
atggacctgc ccgtcgcaga tgacaacacc gtccacttca attccaccct catggctctg 281760
atccgcacag ccctggacat caagattgcc aagggtaagg aagggacagg ggcgggcaca 281820
gacaggcgtg acagggtgga accggggatc tccctcccta ccccaaacta gaggatctgc 281880
tgtcaccacc cggatcttca ttcactcttc cattcattcg ttccacaggg tttttgggg 281940
tttggggttt tggtgttttt tttttttttt ttttgagaca gagtcttgct ctgttgccca 282000
ggcagcagtg cggtgacatg atcgcaagtc actgcagcct tgacctccca ggctcaagtg 282060
atccttccac ctcagcctcc ccagtagctg ggactacagg cacacaccac catactcggc 282120
taattttttt ttttttggtg tgacaatttc cctctgtcac ccaggctgaa gtgcagtggt 282180
gtgatcttgg ctcattgcta cctccgcctc ccgggttcaa gcgattctcc tgcctcagcc 282240
tcccaagtag ctgggattat aggtacccac cagcacaccc ggctaatttt ttatattttg 282300
ggtagagatg gggtttcacc atgttggcca ggctggtctc gaactcctga cctctggtct 282360
caaactcctg acctcaagtg atccacctgc ctcgacctct caaagtgctg gattacaggc 282420
gtgagccacc atgcccaacc taattttttta tattttttat agagatgggg tttcatcagg 282480
ttgcccaggc tggtctcaaa ctcctgggct caagcagtcc tcccaccttg gtctcccaaa 282540
atgctggtat tacaggcatg agccaccaca cccggcccat ttggcagata tttagtgcac 282600
tccttcaatg tgccagagac ccgtccaagc aggggaggac ccagcagctt acactttaga 282660
tggatgggga ggccgccact gaggaggtaa ggcagtgtct catggatccc tggggggaag 282720
gtgctccagg cagaaggact ggcaaaggcc ctgacagagg ggtgaacaca ggacacccgg 282780
ggcattgagc tgactcacct tctgagtgag ggcacgccac gcaggttcag agcagaggag 282840
gaacctgacc caactcacat ttgaacaggt tccctccggc cactgagggg atgggagacc 282900
gaaaggaggc cagtgtgggg gctgctgata tcatctgggt ggagacaggg cggcagctta 282960
gatctagggg taggctcgac gtggtggctc acgcctgtaa tctcagcact ttgggaggcc 283020
aaggtgggtg gattacttga ggtcaggatg accagcctgg ccaatgtggt gaaacccccg 283080
tctctactaa aaatacaaaa tttagccaga cgtggtggtg ggtactgtag tcccagctac 283140
tagggaggat gaggcagaag aatcgcttga acctgggagg cggaggttgc agtgagccga 283200
gatcacgcca ctgcactaca gcctgggtga cagagcaaga ctctgtctca aaaattaaat 283260
taaattaaat taactggaca tggtggcata tgcctgtggt cccagctact caggaggcag 283320
agatgagagt attgcttgaa gccaggagtt tgaggctgca gtgagtcatg atcgcaccac 283380
tgcactccag cctgggcgac agaacgagat cctagctcaa aacaacagaa agaaaaagaa 283440
aaaaacattt tttttaaagc tgagaagggg ctgggcgcag tggcttacgc ctgtaatccc 283500
agcactttgg gaggccaagg tgggtggatc acgaggtcag gagttcaaga ccagcctggc 283560
caacatggtg aaaccccatc tctaccaaaa atacaaaaag tagccgggtg tcatggtggg 283620
cgcctgtaac cccagctact ccggaggctg aggcaggaga atcacttgaa cctgggagac 283680
agaggttgca gtgagccaag atcgcgccac tgaactccag cctggatgac agagcaagac 283740
gctgtctcaa aaaaaaaaaa agctgaggcc gggcacgctg gctcacgcct gtaatagcag 283800
cactttggga ggccgaggcg ggcagatcat gaggtcaaga aatcgagacc atcctgggta 283860
acacggtgaa accccttctc tactaaaaat acaaaaaatt agctgggtgt ggtggcacgc 283920
acctgtagtc cctgctactc agaaggctga ggcaggagaa ttgcttgaac ccgagaggca 283980
gaggttgcag cgagccgagc ttgtgccact gcactccagc ctgggtgaca gagtgagact 284040
tcatctgaaa aaaaaaaaaa aaaaaagccg agaaggctgg acatggtggc tcacacctgt 284100
aatctcagca ttttgttgag gccaggcaca gtggttcacg cctgtaatct gagcacgctg 284160
ggaggccgag gtgggtggat catttgaggt caggagttcg agatcagcct ggccaacgtg 284220
gcaaaaccct gtctctacta aaaatacaaa aattagccgg gtgtcgtggc gtgtgcctgt 284280
aatcccagca ctttgggagg ctgaagcggg tggatcactt gaggtcagga gttcaagacc 284340
agcctggtca acatggcaaa accctgtctc tactaaaaat acaaaaatta gccaggtgtg 284400
gtggcgggta cctgtaatcc cagttactag ggaggctgag gcagaagaat cacttgaacc 284460
cgggaggcag agattgcagt gagccgagat cacatcactg cactttagcc tgggcgacag 284520
agcaagactc catctcaaaa ataaaaataa aaataaaaaa taccgagaaa ttcccccaaa 284580
gacctagctc agggctcact ctccatcatt agggggaaag aagaagagga ggccagggag 284640
gcgggcagag accagggcag tgtgggctcc tggaggcagc ttctatgttt aaaagggcgg 284700
cttcaggagg aaggggacca accgtgtcag gcactgccca gagaccaagg atgacaagga 284760
tcacaagtga ctggtcatca tggtcacttt gaccagtgca gctttggcgg aggggtcagg 284820
ggtcccctgt ctggagtgca tttcggaggc ccgaaagggg atgtgatgtg atttggcagc 284880
tgattaagga cagcagggca gagagacagg cgcacaattg ccagaagaaa cggggacctg 284940
aggctcacgc ctgtaatccc agcactttgg gaggctgagg aaggtggatc acttgaggcc 285000
aggaatttga gaccagcctg gccaacatgg cgaaacccca tctccactaa aaatacaaaa 285060
attagccagg catggtggtg cacacctata atcccaacaa cttgggaagc tgagcacaag 285120
aattacttga acctgggagg cagaggttgc agtgagccga gatcaaacca ttgcactcca 285180
gcctggggga cacagcaaga ctctgtctca aaaaaaaaaa aaaaaagaaa gaaagaaaga 285240
aaagaaaaaa caaatgggac cagaaaaaag gagtgggtgg gagaggagca ggtggatagt 285300
cccacacatg ggaaggtgct gagcccagct gaaaccacta gtaagtcagg aggagggaag 285360
actgagcctc gagacatatg tgccttccag ggtcttgagg gaaagaaggg aggaagagcc 285420
aaggccacgt ggcaagactc aaggaggaag tggcagggaa ggtgggggac tggaggggtg 285480
gaggacagat attgttaatg ccaggaacaa agtgaaggta aagagagcac aaggaagttg 285540
ggagcagtgg ctcacacctg taatcccagc actttgggaa gccaaggcag gaggatcact 285600
tgaggccagg agttcaagat cagcctggcc aacacagaga gaccccatct ctacagaaaa 285660
ttttaaaatt agccaggtgt ggtgatgtgc acctgtagtc ccaactactt gggaggctgg 285720
agtgggagga tcactgggga ctgggatgtc aaggctgcag tgagctatat gatgaccaca 285780
gacatagcag cttaagacac acctatttgt cagctcacag tcctgtaggt cagaagtcca 285840
aaaagctgga ctgggctgtc tgctgagggt ctcacgaggc tgaaatcaag gtgtcagcca 285900
agctgggctc ctctctggag gatctggggg agaatctact tccaggttca ttcaggtgtt 285960
ggcagaattg aagtccttgt ggctgtagga ctgaggtctt gttttatcac tggcttttta 286020
gctttttgct cctggaagtg catgtaatcc tccatgtgct ctcattctct ctgacttccc 286080
catctgccac ccagcagaga caatactgtg cttttcaagg gctcacctga ttggggcagg 286140
cctaccctga tcatctctgt attttgaggt cagctgactt gatatttttt tttttcttg 286200
agacagaatt tcactcttgt tgccaaggct ggagtataat agtgtgatct cagttcactg 286260
caatctccgc ctcccaggtt caagcaattc tcctgcctca gcctcctgag tagctgagat 286320
tacaggtgcc caccaccacg cccagctaaa tttttttgta tttttagtag agatggggtt 286380
tcacaaggtt ggccaggctg gttttgaact cctgacctca ggtgatccac ccgcctcagc 286440
ctcccaaagt gctgggatta caggagtgag ccaccatgcc cagcattttc tttcttttt 286500 tttttttttt tgaaacggag tcttgttctg tcacccaggc tggagtgcag tggcgcaatc 286560
tcggctcact gcaacctcca tctcccgggt tcaagtgatt ctgcctcagc ctcccaagta 286620
ggtgggacta cagatgcgtg ccaccacgcc cggataattt tttgtatttt tagtagaaac 286680
ggggtttcac catgatagca ggatggtctc gatctcccaa cctcgtgatc tgcccacctc 286740
ggcctcccaa agtgctggga ttacaggcgt gagccaccgc accgggcctc cggtatttta 286800
attatatctg caaagtccct tcatagcctg ggcaatggtc cctagattag tgtttgaata 286860
aacagaatct tggcagaagg gcagcttttg aattctgcct accacagttc cttcgtttgt 286920
acaacgggtc taacaacacc cccactcttt gtatgtaatg ccatcgtaac tcagcttctg 286980
tggcactctg agaatctgtg ttcaggggtc ccaaaaccac ccacaggttc agtgattccc 287040
tggaagaact cagaactgag aaaagttttt atactcacag tttattacag tgaaagaata 287100
tagattaaaa tctgcaaagg gccgggcacg gtggctcacg cctgtaatcc cagcactttg 287160
ggagggcgag gtaggcagat cacttgaggt cacgagttca agaccagcct gaccaacatg 287220
gtgaaaccct gtctctacta aaaatacaaa aattagccag gcgtggtggc tggcgccagt 287280
aatcccagct acttggaagg ctaaggtagg agaatcactt gagcccagga ggcagaggtt 287340
gcagtgagcc gagatcccgc cacttcactc caggctggac agagtgagac tctattagaa 287400
aaaaaaaaaa aaaaaaaatc tgcaaagggc ctggcatggt ggcttacgcc tgtaatcctg 287460
gcactttggg agggcaaggc gggcagatca cttgaggtca caagtttgag accagcctgg 287520
ccaacatggc gaaaccccgt ctctaccaaa aatacaaaaa ttaggcatgg tgccagaccc 287580
ctgtaatccc aactactcag gaggctgagg caggagaatc gcttgaccct gggaggcaga 287640
ggttgcagtg agctgagact gtgccattgc actccagcct gtgtgacaag atcaaaactc 287700
tgtccaaaaa gaaaattagc caggtgtggt ggcatacacc tgtagtccca gctactccag 287760
aggctgaggc acaagaatcc tttcaaccca ggagatagag ctacattaag ccaagatcac 287820
gccactgcac tccagcctgg gcaacagagc aagactctgt ctcaaacaaa caaacaaatt 287880
ccaaaaacat aaaatgcgca aaggaagggc atctggggaa gggtccagga gacaccaggt 287940
gcgagcttcc agttgtctgc ctccagtgga gttgcacaga caacgcttaa ttctccctgc 288000
agtgtgtgac aacacgcacc gtgtactgcc aaccagggaa gctcacctga gccttggtgc 288060
cccagggttt ttattgaggg tttgtcatat aggcagggct gacgtagtta ctcagtctcc 288120
agtccctcca gaggtcaaac tgataccacg tggcccaaga ccccaacgat aaatcgcatt 288180
gttagaatga actgtatgga aaattatcca ggcgtggcgg cgggcggctg taatcccagc 288240
tactggggaa gctgaggcag gagaatcact tgaaactagg aggccgaggt tgcagtgagc 288300
caagatcgca ccattgcact ccagcctggg caatagagca aaaacaccat ctcaaaataa 288360
ataaataaat agaatgaact gtattggccg ggtacagtga ctcatgccta taatcccagc 288420
actttgggag gctgaggctg gaggatcgtt tgaggccagg agttcgagac cagcctaggc 288480
aacatagtga gaccctatct cttttttttta aaaaaaaaaa aaaaaaaaaa aaagaatgaa 288540
ctatacagtg tggcccaagg ccccctgcta aataaagaca ctcttcaggc aggacatttc 288600
aaaggcttag agatcacctc ccaggagcaa gtcaatgggc cagtcctttc atcggaatgt 288660
gcagggtttg gacaacacta gcctactgag ctagtcctta ctgcttagca ccccagcttc 288720
tatgacacct actggattcc cttcctgagg gtttcaaaga ctcctggaga tgtctctgaa 288780
tttggctgtc acagttgtta cttgtacccc agatgccact cagttccctg aagacaatga 288840
tcccccagat ttctcagcca ggagcccctc cacctcttgt cctcagtggg tgccaggcct 288900
catcctggag ttccacagct gagccaggct ctcggggtta cggaaggtca agagggtgtg 288960
gggacaacaa tggaagagtg ataacagtgg cagccctttg agcagatgcg ggtctcagga 289020
gaacataacg cgctttcttt tcatagttca gctcactttc taagcacact gagcttcctt 289080
tccagcaggc taaggggctg caaagggggt acagattaac ctcattcttc agattctcaa 289140
aaatggtgtc accattcatt gctggagact gggagaaagg gggcaagtcc atctcattct 289200
ctctgtctct gtctctctct ctctcttccc tgtccatctg tttctctctc ccacccaccc 289260
ctctgttctc tctgcccaga agaatctcta ttttggtttt ggttttgttt gttttgtatt 289320
gttttgagac ggagtctcgt tctgtcgccc aggctggagt gcagtggcgc agtctcaact 289380
caccactgca gcctccacct cccaggttca agcgattctc atgcctcagc ctcccgagta 289440
gttgggatta caggcgcacg ccaccacgcc cagctaattt ttgcattttt actagagact 289500
ggtttcacca tgttgaccag gctggaccct atcctctttc aagcccccca ccccaggcat 289560
tgagggcaga gccaactacc tgcctgaacc aattagcata ttaaacgtaa acccagttag 289620
catatccaaa tagcagccca cagtgacatt ctgactgtca gaatgtggat tgcttgagcc 289680
caggagctca aggcttcggt gaacaaagat tgtgccacag cctgggcaac agagtaagtc 289740
cctgtcgatc gatagataga tgatagatag atagatagat agatagatag atagatagat 289800
agatagatag ataaattttt aaaaaaaata ataggccagg cacagtggct catgcctgta 289860
atcccagcac tttgggaggc cgaggcaggc agatcacctg aggtcaggag ttcgagacca 289920
gcctggccaa catggtgaaa ccctgtctct acaaaaatat aaaaatagcc aggcagatgt 289980
ctgtaatccc agctactcag gaggctgagg taggagaatc gcttgaactc tgaaggtgga 290040
ggttgcagtg agccgagatc atgccattgc actccagcct gagtgacaga gcgagactcc 290100
atctcaaaaa taataacaat aataaaaata ataataaatg ctctggcccc aaagtggcac 290160
attacatggt gcacacccca ttagcaagga ctcatcacat ggccctgcca accacaggag 290220
gaaccccccc atgtactcag gtaggagggc caggaaacac cgtcagagag ctttaatgac 290280
tcaccccatg actggggtga gggacgaggg actggctgca ggccaagggc atgtccgtgg 290340
cagtggagac ttgggaaagg ggaaaagacc tcctctgagc cacgcacagt ggctttcatc 290400
tgtaattcca gcactttggg aggctgaggt gggaggatct tgagcccagg aggtcgagac 290460
tgcagtgagc tatgtttgtg ccacggcact ctagcctggg cgacagagca aaaccctgtc 290520
tcaaaaatca aaataaaacc aaaaccaaaa cttcctctgt tggggatgct ccagggcgtc 290580
ccagccttga acagatgggt cactgcagta ataatcctat ggcagacact gtcccaaggc 290640
tgcacgcacg ttactttgat catcaaacaa ccaggtgata gccaggcatg gtggtgcgtg 290700
cctgtagtcc cagctactca ggaagctgaa gcgggagaat ctcttgaacc tgggaggcgg 290760
aggtaacagt gagtcgagat cacatgactg cacttcagcc tgggaacaga gagagactct 290820
gtcaaaaaaa aaaaaaaaac aggccagacg cggtggctca cgcatgtaat cgccagcact 290880
ttgggaggct gaggagggtg gatcacctga ggtcaggagt ttgagaccag cctggccaac 290940
atggtgaaac cccgtctcta ctaaaaatac aaaattagtt gggcgtggtg gtgcacacct 291000
gtaatcccag ctactcggga ggctgaggca ggagaatcgc ttgaacccag gaggcagagg 291060
ttgcagtgag ctgagattgc accattgcac tccagcctgg gcaacaagag tgaaactcca 291120
tctcaaaaaa aaaacaaaaa aaaaacaacc agccaggcgc ggtggcttac gcctgtaatc 291180
ccagcacttt gggaggccga ggcgtgtgga tcacccgagg ttaggagttc gagaccagct 291240
tgaccaacat ggtgaaactc cgtctctact aaaaatacaa aaaattagcc aggcatggtg 291300
gtgcatgtct gtaatcccag ctactcggga agctgagaca ggagaattgc ttgaacccag 291360
gagtcggagg ttgcagtgag ccaagctcgt gccactgcac tccagcctgg gcaacagagc 291420
aagactctgt ctaaaaaaaa aaaaaaaaca cacacacaca cacacaacaa ccaggtgagg 291480
caagtactct tgctatcatc tccatttcac agatggagaa actgagttac taagtggtag 291540
agtaacctaa gtcatgcagc cgataactgg gagacaagat tgggacccag gtcgcccagc 291600
tgttctccat gccgggctgt ctcctgcaca gctgctccat ggtcctggcc ccaccgaaaa 291660
ccagagccca caaggtcatt ccagcagcac tgcccagggc ctcctctggg ccaggccgtt 291720
ggggaactgg agaccccatg ggaccagaa agattggggt ctcgttctcg ggagcctatg 291780
gctttgcagc tgacccagag tccagctgac acccaggcag gcagtcaggg tctgtctaca 291840
cccccattgc aggaggagcc gacaaacagc agatggacgc tgagctgcgg aaggagatga 291900
tggcgatttg gcccaatctg tcccagaaga cgctagacct gctggtcaca cctcacaagt 291960
gtaagagctg agcccagccc tgggatccaa tccaccagga cagatggagg gggagggaaa 292020
ggggaggcct ggggagagtg ttggcctggg ctggtataca cagggaccca ggacaagggc 292080
cccaaagagg cctgcccttg gtgagctcac cgtgtgtgtg cccccagcca cggacctcac 292140
cgtggggaag atctacgcag ccatgatgat catggagtac taccggcaga gcaaggccaa 292200
gaagctgcag gccatgcgcg aggagcaggt gcgctgttcg ccgctctggg gacatctggg 292260
ctggggacag tggcttgcat gtcaccacgg gaaccaactg gaatatgagg gtggctgagc 292320
cccagggcag gtccctgaaa agtaggggct gtgcacagca gctcacacct gcaatctcag 292380
tgctttgaga ggccagggca gagggatcgt ttgagaccag gatgagacca ccctgggcaa 292440
cacagtgaga ctccatctct acaaaataaa acattagcca ggcatggtgg tgcacacctg 292500
tagtcccagc tatttaggag gccaagatgg gaggatcact tgaggccagg agtgggagac 292560
cagtctgggc aacatagaaa gacccatatc tctacaaaaa aaaaataaaa ttagctgcat 292620
gtggcgccat gcacctgtgg tcccagctac ttgggaggct gaggcaggag aatcacttga 292680
acctgggagg tggaggttgc agcaagccaa gatcaagcca ctgcactcca gcccgggtga 292740
taagagcagg actctatctc aaaaaaaaaa aaaaaaaaaa aaaaaaaagt tcttgccaag 292800
gacacatcat gtggattcat tcttcattca gctgctccac caacacttat tgagtattac 292860
tgtgtgcagg gcgctgttct cagtcctcgg ggatgcaccc atggggaaaa taggccagaa 292920
tccctgccct cagggagcag acattccaag tggggaaatg ccaatggtag caaatgactg 292980
aatcgtgcaa catccagcaa agagaaagaa agtgtcgtgg gggaaagtgg agaagaatcc 293040
agaagatagg agtatccagg ggaggagggg atgcggtggg aaatgggtag ttggggagcc 293100
tccctgagaa agtgacatgt gagcaaaggc ttgaaggaaa aggggagagg gagtgagcta 293160
agcaatacct ggaagggtgt tccaggcaga ggaaacagcc agtgcaaagg ctctgaggct 293220
ggaccgtgcc tgggttgttt gggtaacagc aaagaggcca gtgtggtgga aaagagcagg 293280
gaggagacaa gggcaaggag gtgacagggc agatccttca gggccatggg agctgcagga 293340
aggactctgg ctttttcccc aagcaagtgg gagccatgga gggttctaag caaaggaggg 293400
ataggacctg actcaagtgc tcatgggcgc cctctggtgg ctcttgtgga acagtggggt 293460
tgaaggtagg agcgggagac ctgggagaag gtgcctgcag tgagagatga ggacgtggga 293520
ccaggctggg gctatgactt gggtggagga gtgagaagtg gtccagttct gcgtggaatt 293580
ggaagggtct agatggatga gacctgagag agtgtgtgtg tgtgtgtgtg tgtatactgg 293640
ggatgtcgca atgccttctg ggtaccaccg tcccaccacc ccacccttgt ccacacactg 293700
ctctctgccc cattccccag gaccggacac ccctcatgtt ccagcgcatg gagcccccgt 293760
ccccaacgca ggaaggggga cctggccaga acgccctccc ctccacccag ctggacccag 293820
gaggagccct gtgagtgtca cccctgccag ggaggtggag tgtgggggtg ccgtggtccc 293880
cacgttctgg aagctgccca agcgcccact gctaccccgg cctctgtccc ccatgcagga 293940
tggctcacga aagcggcctc aaggagagcc cgtcctgggt gacccagcgt gcccaggaga 294000
tgttccagaa gacgggcaca tggagtccgg aacaaggccc ccctaccgac atgcccaaca 294060
gccagcctaa ctctcaggtg cctctgtccc ccaactcccc aatggctccc agggcccggg 294120
tggttcaggt ggaagggatc tggggccccc acacacacac acctgcagct ccctccctct 294180
gcagacacca gggatctgga ggtcaggccc cagagctcat ctggctttgc catctgctcc 294240
gcagtccgtg gagatgcgag agatgggcag agatggctac tccgacagcg agcactacct 294300
ccccatggaa ggccagggcc gggctgcctc catgccccgc ctccctgcag agaaccaggt 294360
gagggctttc accactgccc tggggctgga cccctcactc tgcactgggt agggccaggc 294420
ccccccacaa gcagcccagt gcatcccctc cctgccggac tcaggcctgg gtagggactc 294480
cttcagtctc tgaagcagtc tgcaggcccc acccaccacc tggtcacacc tggagcacct 294540
gcagaccctc ctccctcaca gaggacagag aggaaagtgc tccccctggg gcagagggca 294600
gtggccactg caaaatggtc tctggctgcc ctggttggag gctgcagaca ggggaggttg 294660
tggaagattt gtgggtgcag cagggttcaa cagggccagc tgagacctgc cacgaagatc 294720 accccctacac aaacacacac acacatgctc aacatacatg cacacacatg tgcagctgtg 294780
cgcctactca gatgcttgca tacacacacg tgtgtgcacg tgggcatata cacactgcac 294840
atgtactcac acatgcacac atgtacgtgc acacgtgtct gcatatggga acttggcagg 294900
tcctaggata cagtagcaga gtctggggtg ggtctggggg cagctgggct cgtattttct 294960
gtctggtctc tgtgggagtc attggggggc acaggggtgt gtgcttgatg tgtgtctgtg 295020
tgtggccgct tcacccagct gccaggccca cctgcaggtg atcccgttgc cttggactca 295080
tgggacagag ggcccagagg catagctggc tgcccacccg gcctgaacag cgggggccca 295140
tgcacgcagc ccgcctctgg aggagaacag ggcatggctg tgagagcctg gcccgggtgc 295200
gtggcatgtg tggctgtggc gagctttccg tgtgccgtgt gtggcgtctg cacggggcag 295260
gaggctgtgc tgtgcctggc tggaccaggg tcacctgagg gcctggcctc tggctgctgg 295320
gaacgtgggt tggggagcac ccagcgtgca tgctgctgct ccctcaggac cgagctgctg 295380
ggccccagga gagggttggg acaagcccag ctgacggcca ccacatggaa gctttgagca 295440
tcggccggag ccaggggttg gggtgtgcat cgcatgaggc agagcccagg gccaggggct 295500
cgaggctgcg ccgtcctgtc tttcggtccc atgcctctgc catttgtctg tctgcatctc 295560
ctgtctgtct cctctgtacc catgggaata gaggacgccc agccccgggg gcctgggaca 295620
cccacccgcc aggactttaa cttttctttt cctccctgcc ttctccctcc gatttctctt 295680
gatgccagtg ccactcccct ccttggcttc ttctccatgc accacctcct cactctccct 295740
cttgcctttt atatttattt tcttctttct gttttttctg tgtgcaccat cccatggggc 295800
tgtgacagag gagaaggggc cggccacgtg ggaataacct cagtgtatgt accgcgcctg 295860
cccagcgccc agcagggctc cggccccctc ttcctcccca cccccccctcc agggagtccc 295920 gtcatctctc accgtccccg gaccccaccc tttctttggc aatcgcaccc tctcccctcc 295980
atggagccca atccttgtgt gtggtgtcct gtgtgtgccc ctcacccata agccctggtg 296040
ggcggggcca tccccatcct cacccctacc cccttttctt cagggccccc cacgccggag 296100
gacactggct ctccaagagc ctggcccact ctgcacctct ttctgggggg cttcttctcc 296160
tgacaccacc accaacccct ggtcctgcag ctcctacctg gagcagggcc accagcgctc 296220
agctgggctg gaccctggga ggcgggcgtc tgccccatct ccctccttcc ctcctctgcc 296280
tgctgcagag aaacctgtgt gtcagggctt gacccaggga tgaagcacca gggaaaagag 296340
tgggccccca gagcctccag tgcctgggta tcccccaccc ccacccagag ctccctagct 296400
tgggcctcac cagaaggact cagacttgtg ggggcagcga gcacagcccc gttagccggg 296460
aggacccaaa gctgccatgc cgggcacctg gtcctgagcc cataggtcag ccagccacag 296520
tcggaggctt ctcaccctcc caggagagca agctggggca gggatgagtg cggcagtcca 296580
gggctcccag gtttgcaccc tggatgtgga gagggcttcc ctctggccag cctgagcctg 296640
cccaactgtg gctgggcccc caggactgga gagtgaggat cagatctttc tggtcagaac 296700
ccaggatggg ctcaaaagga gcagtcctgt ctctgaggga cagaggaatc ctcaggctcc 296760
accctcagag gcctggccac acccagagcc ctgattgatc agggggagcc aaggccccat 296820
ggcatcccct ggcccctgcc ccaggatggt cacaccgcag tcaccgaagg ccaccaccag 296880
gctgccacaa tggggcagga aggaccggga ccacttggtg ctagctgctg accccagccc 296940
accggcctgt cccctccccc agaccatctc agacaccagc cccatgaagc gttcagcctc 297000
cgtgctgggc cccaaggccc gacgcctgga cgattactcg ctggagcggg tcccgcccga 297060
ggagaaccag cggcaccacc agcggcgccg cgaccgcagc caccgcgcct ctgagcgctc 297120
cctgggccgc tacaccgatg tggacacagg tgggcagccc tgtggtgctc agggacaagc 297180
agaacagagg agaggagagg ggaggagaag gcagggcgga ggagacacta aggaagaaga 297240
aagggagagg cctccatgga gaggggacag agggggccag gcagcagctg caggaacctg 297300
ggtactaccc cctcccccca acccactgac ctgcctcggt tcaggggatc tctagggccc 297360
ccacaccttc caggtggcct cctgtgtgtg catctgcccc acctctccct cacgaccacc 297420
tgtgtgtctg tctgaccctc acccggccca ggcttgggga cagacctgag catgaccacc 297480
caatccgggg acctgccgtc gaaggagcgg gaccaggagc ggggccggcc caaggatcgg 297540
aagcatcgac agcaccacca ccaccaccac caccaccacc atcccccgcc ccccgacaag 297600
gaccgctatg cccaggaacg gccggaccac ggccgggcac gggctcggga ccagcgctgg 297660
tcccgctcgc ccagcgaggg ccgagagcac atggcgcacc ggcaggtggg tgcggctgca 297720
agtgacccca ggctgggctc ggccgggagg cggggaggag agaaggggat accccatcca 297780
acagccactc taggcaaagg tccccggatc ccggctgtga ccacctccca tcctgccccc 297840
aagccaccgg ggtgcccggc ggccggagcg gacacggatc cccaccacac cagctgccta 297900
tgctgtcccc ccagcccccct tgcccacccg ccgcccccctc cccgccgccc gcagctgctt 297960
gctcctcggt tgtggatcat atttgagttc tgggccgtgc cgcccgacct ttcactttcc 298020
tttaacccgg cttctgtttt tgtttcaatt atgatttctg tcctctggac gcctgtgagt 298080
aatttttgaa acttctgcta tttttaaccc cgaaacttac aaaactccat ttctcatttc 298140
tcttttcact ttgttgtgtt ggttttcgac tcctcccctc cctgtctcac tccccctcct 298200
cccctccctc ctccctgtgg ctgttgcttt tttccattca atgtcctgtg tcccccctct 298260
cctcctcctc ctcctcctcc ccctccccct cctccctctc ctcccggccc ctctcccttc 298320
gctcccctct cttcctccca atcccgtgtc tcctttgatt ttgttgtatc tttttttttg 298380
atttcctttg tttcaatttt cgtgtagggc agtagttccg taagtggaag cccagccccc 298440
tcaacatctg gtaccagcac tccgcggcgg ggccgccgcc agctccccca gaccccctcc 298500
accccccggc cacacgtgtc ctattcccct gtgatccgta aggccggcgg ctcggggccc 298560
ccgcagcagc agcagcagca gcagcagcag cagcagcagc aggcggtggc caggccgggc 298620
cgggcggcca ccagcggccc tcggaggtac ccaggcccca cggccgagcc tctggccgga 298680
gatcggccgc ccacgggggg ccacagcagc ggccgctcgc ccaggatgga gaggcgggtc 298740
ccaggcccgg cccggagcga gtcccccagg gcctgtcgac acggcggggc ccggtggccg 298800
gcatctggcc cgcacgtgtc cgaggggccc ccgggtcccc ggcaccatgg ctactaccgg 298860
ggctccgact acgacgaggc cgatggcccg ggcagcgggg gcggcgagga ggccatggcc 298920
ggggcctacg acgcgccacc ccccgtacga cacgcgtcct cgggcgccac cgggcgctcg 298980
cccaggactc cccgggcctc gggcccggcc tgcgcctcgc cttctcggca cggccggcga 299040
ctccccaacg gctactaccc ggcgcacgga ctggccaggc cccgcgggcc gggctccagg 299100
aagggcctgc acgaacccta cagcgagagt gacgatgatt ggtgctaagc ccgggcgagg 299160
tggcgcccgc ccggcccccc acgcacccca cgcacacacc ccacccgagg agccgcgcag 299220
aggccgcggg ggcccagcac agagggcccg ggagagggcc agccgggaga ccccagactc 299280
tggagaggcc agggctgggc cacaagggtg tcccgcagag accctcggcc aaaagagacc 299340
ctcctgggca gccacggcgc cccccaacca gccccgatcc ccccacccac gacaggggct 299400
ctcgggtggg aggcagggag cagacaaacc acacagccaa gggatttgaa ttaactcagc 299460
catttttgga gaactttggg gaacatgaaa aaaaaaaaaa aaaaaaaaaa aaaaaacatt 299520
tttaaaagaa aaaacgggga gaaaaaaata gcttctattg atgagtttta tcatctcaat 299580
tgaatctttc ctttccctga tgaagacagc tggtggccga gtgcggcaaa gaagccagaa 299640
ggaaccagaa tcccagtgcc ctacacccac caccagacac actcacaccc acacacgttc 299700
tcagacacac acaagagtgc ttgccggtta taccaaaccc tactattact gcctgcagaa 299760
atcaatttaa aaaaataata ataacaataa acaattttaa aaaggacaaa aaaattaatg 299820
attgagaaaa gaggcatttt tttctgacat ttggtcctgc ttgaaacaac aaaagaagaa 299880
gaaaaaccca ccatcaccac cgattccttt gcttcttttt tcctttttttc ctaccttgtt 299940 tgaaaaccgt gggcttggga ctgtgaatta ttgcatgaca ttcaaaaaga aaaaaaaaat 300000
aaaaaaaagt tgaatcaaa 300019

<210> SEQ ID NO 44
<211> LENGTH: 1000
<212> TYPE: DNA
<213> ORGANISM: Artificial Sequence
<220> FEATURE:
<223> OTHER INFORMATION: Construct

<400> SEQUENCE: 44
atttcattta tcaggtgttc agtgaatgct tactatgtaa cagcacagtt atcagcactg 60
gggaaataga tgagtaagat aagatttgca ctttcattag cttacatgcc ataaagaggg 120
aaataaagag aacaccagat gatgataagt ttatgctgag aattaaaatg aagtgatgaa 180
ataatgggaa tgtcaggtgg ctacttttgg tgggatggtc aggaaaggca tctctgggga 240
gataaatttt aagctcagac ctgagtgaaa agaatgagcc agccatggaa acattatgtt 300
aactcacatg gtagtttgaa atgctttatc tgatcaaagg tacttatttt tggtgacttt 360

```
caacaatatt aagggtctat aaaccaacac tcatttgcat aagaataact accagtgaat    420

ctttttgtat gataggtttt ttgtttgttg tttttttgag acagagtctc gctctgtcgc    480

ccaggctgga gtgcagtggc gcgatcttgg ctcactgcaa cctctacctc cccggttcaa    540

gtgattctcc tgcctcagcc tcccaaagta gctgggatta caggtgcctg ccaccacgcc    600

tggctaattt ttgtattttt agtagagatg gggtttcacc gtgttgtcca ggctcgtgtc    660

aaacttctga cctcaagcca tccacccgcc tcggcctccc aaagtgctgg gattacaggt    720

gtgagccacc actcctggcc atgataggtt attttgtgat gaaaatacct acctcttaat    780

ttgtctgata aatttaaatt ttatgtctag atttcctaag atcagcactt ccatatttta    840

aagtaatctg tatcagacta actgctcttg cattctttta ataccagtga ctactttgat    900

tcgtgaaaca atgtattttc cttatgaata gtttttctca tggtgtattt attcttttaa    960

gttttgtttt ttaaatatac ttcacttttg aatgtttcag                          1000
```

```
<210> SEQ ID NO 45
<211> LENGTH: 214
<212> TYPE: DNA
<213> ORGANISM: Artificial Sequence
<220> FEATURE:
<223> OTHER INFORMATION: Construct

<400> SEQUENCE: 45

acagcagcaa aagcagcaac agcagcagca gcagcagcag caggggggacc tatcaggaca     60

gagttcacat ccatgtgaaa ggccagccac cagttcagga gcacttggga gtgatctagg    120

tgatgctatg agtgaagaag acatgcttca ggcagctgtg accatgtctt tagaaactgt    180

cagaaatgat ttgaaaacag aaggaaaaaa ataa                                214
```

```
<210> SEQ ID NO 46
<211> LENGTH: 135
<212> TYPE: DNA
<213> ORGANISM: Artificial Sequence
<220> FEATURE:
<223> OTHER INFORMATION: Construct

<400> SEQUENCE: 46

aacttgttta ttgcagctta taatggttac aaataaagca atagcatcac aaatttcaca     60

aataaagcat ttttttcact gcattctagt tgtggtttgt ccaaactcat caatgtatct    120

tatcatgtct ggatc                                                     135
```

```
<210> SEQ ID NO 47
<211> LENGTH: 208
<212> TYPE: DNA
<213> ORGANISM: Artificial Sequence
<220> FEATURE:
<223> OTHER INFORMATION: Construct

<400> SEQUENCE: 47

tccccagcat gcctgctatt ctcttcccaa tcctccccct tgctgtcctg ccccacccca     60

ccccccagaa tagaatgaca cctactcaga caatgcgatg caatttcctc attttattag    120

gaaaggacag tgggagtggc accttccagg gtcaaggaag gcacgggggga ggggcaaaca    180

acagatggct ggcaactaga aggcacag                                       208
```

```
<210> SEQ ID NO 48
<211> LENGTH: 214
<212> TYPE: DNA
```

<213> ORGANISM: Artificial Sequence
<220> FEATURE:
<223> OTHER INFORMATION: Construct

<400> SEQUENCE: 48
ctacttcttg ccctcggtct tcaggtcgtt gcgcacggtc tccaggctca tggtcacggc 60
ggcctgcagc atgtcctcct cgctcatggc gtcgcccagg tcgctgccca gggcgccgct 120
gctggtggcg gggcgctcgc aggggtggct gctctggccg ctcaggtcgc cctgctgctg 180
ctgctgctgc tgctgctgct gcttctgctg ctgt 214

<210> SEQ ID NO 49
<211> LENGTH: 110
<212> TYPE: DNA
<213> ORGANISM: Artificial Sequence
<220> FEATURE:
<223> OTHER INFORMATION: Construct

<400> SEQUENCE: 49
ctgtaaatga atgagaaaac cggtttagaa agtgcacagc tgtcagggaa gtcaacactt 60
cagtgagcat gtgaccatgt ggagtcagct tcctgtttcg tgctgcaatc 110

<210> SEQ ID NO 50
<211> LENGTH: 374
<212> TYPE: DNA
<213> ORGANISM: Artificial Sequence
<220> FEATURE:
<223> OTHER INFORMATION: Construct

<400> SEQUENCE: 50
gtaaggcctg ctcaccattc atcatgttcg ctaccttcac actttatctg acatacgagc 60
tccatgtgat ttttgcttta cattattctt cattccctct ttaatcatat taagaatctt 120
aagtaaattt gtaatctact aaatttccct ggattaagga gcagttacca aaagaaaaaa 180
aaaaaaaaaa gctagatgtg gtggctcaca tctgtaatcc cagcactttg ggaaaccaag 240
gcaggagagg attgctagaa catttaatga atactttaac ataataattt aaacttcaca 300
gtaatttgta cagtctccaa aaattcctta gacatcatgg atatttttct tttttgaga 360 tggagtcttg ctct 374

<210> SEQ ID NO 51
<211> LENGTH: 136
<212> TYPE: DNA
<213> ORGANISM: Artificial Sequence
<220> FEATURE:
<223> OTHER INFORMATION: Target site

<400> SEQUENCE: 51
tttaagctca gacctgagtg aaaagaattt gagacagagt ctcgctctgt cgcctttcct 60
aagatcagca cttccatatt tggtgacttt caacaatatt aagggtctat aaaccaacac 120
tcatttgcat aagaat 136

METHODS FOR TARGETED INSERTION OF DNA IN GENES

REFERENCE TO RELATED APPLICATIONS

This application is a continuation of previously filed and application U.S. Ser. No. 16/601,144 filed Oct. 14, 2019, which claims the benefit of previously filed applications U.S. Ser. No. 62/746,497 filed Oct. 16, 2018, U.S. Ser. No. 62/830,654 filed Apr. 8, 2019, and U.S. Ser. No. 62/864,432 filed Jun. 20, 2019, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Oct. 14, 2019 is named 2019-10-14_BALTES_P12987US03_SEQUENCE_LISTING_BA2018-4WO.txt and is 517,077 bytes in size.

TECHNICAL FIELD

The present document is in the field of genome editing. More specifically, this document relates to the targeted modification of endogenous genes using rare-cutting endonucleases or transposases.

BACKGROUND

Monogenic disorders are caused by one or more mutations in a single gene, examples of which include sickle cell disease (hemoglobin-beta gene), cystic fibrosis (cystic fibrosis transmembrane conductance regulator gene), and Tay-Sachs disease (beta-hexosaminidase A gene). Monogenic disorders have been an interest for gene therapy, as replacement of the defective gene with a functional copy could provide therapeutic benefits. However, one bottleneck for generating effective therapies includes the size of the functional copy of the gene. Many delivery methods, including those that use viruses, have size limitations which hinder the delivery of large transgenes. Further, many genes have alternative splicing patterns resulting in a single gene coding for multiple proteins. Methods to correct partial regions of a defective gene may provide an alternative means to treat monogenic disorders.

SUMMARY

Gene editing holds promise for correcting mutations found in genetic disorders; however, many challenges remain for creating effective therapies for individual disorders, including those that are caused by gain-of-function mutations, or where precise repair is required. These challenges are seen with disorders such as spinocerebellar ataxia 3 and spinocerebellar ataxia 6, wherein the disorder is caused by gain-of-function mutations (expanded trinucleotide repeat) at the 3' end of the genes.

The methods described herein provide novel approaches for correcting mutations found at the 3' end of genes. The disclosure herein is based at least in part on the design of bimodule transgenes compatible with integration through multiple repair pathways. The transgenes described herein can be integrated into genes by the homologous recombination pathway, the non-homologous end joining pathway, or both the homologous recombination and non-homologous end joining pathway, or through transposition. Further, the outcome of integration in any case (HR, NHEJ forward, NHEJ reverse; transposition forward, or transposition reverse) can result in precise correction/alteration of the target gene's protein product. The transgenes described herein can be used to fix or introduce mutations in the 3' region of genes-of-interest. The methods are particularly useful in cases where precise editing of genes is necessary, or where the mutated endogenous gene being targeted cannot be 'replaced' by a synthetic copy because it exceeds the size capacity of standard vectors or viral vectors. The methods described herein can be used for applied research (e.g., gene therapy) or basic research (e.g., creation of animal models, or understanding gene function).

The methods described herein are compatible with current in vivo delivery vehicles (e.g., adeno-associated virus vectors and lipid nanoparticles), and they address several challenges with achieving precise alteration of gene products.

In one embodiment, this document features a method for integrating a transgene into an endogenous gene. The method can include delivery of a transgene, where the transgene harbors a first and second splice acceptor sequence, a first and second partial coding sequence, and a first and second terminator. In some embodiments, the first and second terminators can be replaced with a single bidirectional terminator. The method further includes administering one or more rare-cutting endonucleases targeted to a site within the endogenous gene, where the transgene is then integrated into the endogenous gene. The transgene can be targeted to a site within an intron or at an intron-exon junction. The first and second partial coding sequences can be oriented in a tail-to-tail orientation, such that integration of the transgene in either direction (i.e., forward or reverse) by NHEJ can result in precise alteration of the gene's protein product. In other embodiments, the transgene can include a left and right homology arm to enable integration by HR. These transgenes can be harbored within an adeno-associated virus vector (AAV), wherein the transgene can be integrated via HR (through the homology arms) or by NHEJ forward direction or NHEJ reverse direction (through direct integration of the AAV vector within a targeted double-strand break). In an embodiment, vectors with a first and second coding sequence and a left and right homology arm can further include a first and second site for cleavage by one or more rare-cutting endonucleases. Cleavage by the one or more rare-cutting endonucleases can result in liberation of a linear transgene with homology arms, capable of integrating into the genome through HR or NHEJ. In another embodiment, vectors with a first and second coding sequence can be flanked by a first and second site for cleavage by one or more rare-cutting endonucleases. Cleavage by the one or more rare-cutting endonucleases can result in liberation of a linear transgene, capable of integrating into the genome through NHEJ. In another embodiment, vectors with a first and second coding sequence can be flanked by a left and right transposon end. Delivery of a CRISPR-associated transposase (e.g., Cas6/7/8 along with TniQ, TnsA, TnsB, and TnsC) can result in integration of the transgene through transposition.

The methods can be used to alter the C-terminus of proteins produced by endogenous genes. In some embodiments, the endogenous gene can include the ATXN3 gene or CACNA1A gene. ATXN3 is a gene that encodes the enzyme ataxin-3. Ataxin-3 is a member in the ubiquitin-proteasome system which facilitates the destruction of excess or damaged proteins. Spinocerebellar ataxia type 3 is a genetic disorder caused by a trinucleotide repeat expansion within the 3' end of the ATXN3 gene. CACNA1A is a gene that encodes proteins involved in the formation of calcium channels. Spinocerebellar ataxia type 6 is a genetic disorder caused by mutations in the CACNA1A gene. The mutations which cause SCA6 include a trinucleotide repeat expansion in the 3' end of the CACNA1A gene. In some embodiments, the methods provided herein can be used to alter the 3' end of the endogenous ATXN3 gene or CACNA1A gene. In specific embodiments, the target for integration of the transgenes described herein can be intron 9 of the ATXN3 gene or intron 46 of the CACNA1A gene.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

The details of one or more embodiments of the invention are set forth in the description below. Other features, objects, and advantages of the invention will be apparent from the description and from the claims.

DETAILED DESCRIPTION

Figure 1:
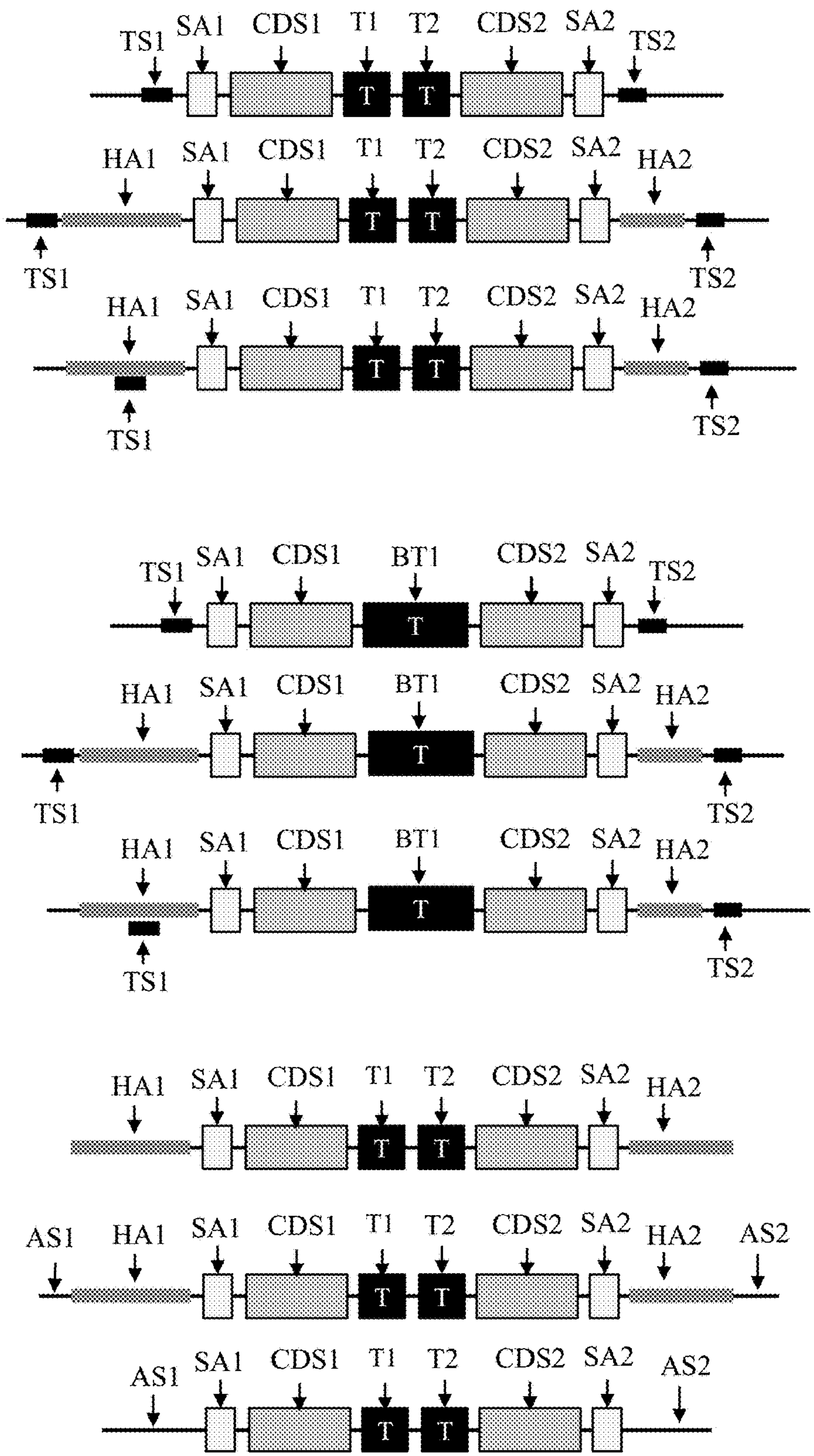
FIG. 1 is an illustration of the transgenes for the targeted insertion into endogenous genes. TS1, target site 1; SA1, splice acceptor site 1, CDS1, coding sequence 1; T1, terminator 1, TS2, target site 2; SA2, splice acceptor site 2, CDS2, coding sequence 2; T2, terminator 2; HAL homology arm 1; HA2, homology arm 2; BT1, bidirectional terminator 1; AS1, additional sequence 1; AS2, additional sequence 2.

Disclosed herein are methods and compositions for modifying the coding sequence of endogenous genes. In some embodiments, the methods include inserting a transgene into an endogenous gene, wherein the transgene provides a partial coding sequence which substitutes for the endogenous gene's coding sequence.

In one embodiment, this document features a method of integrating a transgene into an endogenous gene, the method including administering a transgene, wherein the transgene comprises a first and second splice acceptor sequence, a first and second partial coding sequence, and one bidirectional terminator or a first and second terminator, and administering one or more rare-cutting endonuclease targeted to a site within the endogenous gene, wherein the transgene is integrated within the endogenous gene. The method can include designing the transgene to have the first splice acceptor operably linked to the first partial coding sequence and the second splice acceptor operably linked to the second partial coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, transgenes with first and second splice acceptors, first and second partial coding sequences, and first and second terminators can be oriented in a tail-to-tail orientation. The transgenes with a tail-to-tail orientation of sequences can further comprise a first and second target site for one or more rare-cutting endonucleases, wherein the target sites flank the first and second splice acceptors. In another embodiment, the transgenes can comprise a left and right homology arm which flank the first and second splice acceptors. In this embodiment, the transgene can be harbored within an adeno-associated viral vector. In another embodiment, the transgene can further comprise a first and second target site for the one or more rare-cutting endonucleases, wherein the target sites flank the first and second splice acceptors. The first and second target sites can flank the first and second homology arms. In embodiments, the transgenes described herein can be integrated within an intron of the endogenous gene or at an intron-exon junction. The transgenes can be integrated within an intron, or at the intron-exon junction of the ATXN3 gene or CACNA1A gene. The transgene can comprise a first and second partial coding sequence encoding the peptide produced by exon 10 of a non-pathogenic ATXN3 gene and can be targeted to intron 9, or the intron 9 exon 10 junction, of a pathogenic ATXN3 gene. The transgene can comprise a first and second partial coding sequence encoding the peptide produced by exon 47 of a non-pathogenic CACNA1A gene and can be targeted to intron 46, or the intron 46 exon 47 junction, of a pathogenic CACNA1A gene. In certain embodiments, the rare-cutting endonuclease can be a CRISPR/Cas12a nuclease or a CRISPR/Cas9 nuclease. The first and second partial coding sequences encode the same amino acids. In an embodiment, the first and second coding sequences can differ in nucleic acid sequence but encode the same amino acids. The transgene can be harbored on a vector, wherein the vector format is selected from double-stranded linear DNA, double-stranded circular DNA, or a viral vector. The viral vector can include an adenovirus vector, an adeno-associated virus vector, or a lentivirus vector. The methods described here can be used with a transgene equal to or less than 4.7 kb. The transgene can comprise a first and second partial coding sequence that encode a partial peptide from a functional protein produced by the target endogenous gene. The target endogenous gene can be aberrant.

In another embodiment, this document provides DNA polynucleotides with a first and second splice acceptor sequence, a first and second partial coding sequence, one bidirectional terminator or a first and second terminator, optionally, a first and second homology arm, and, optionally, a first and second rare-cutting endonuclease target site. The DNA polynucleotides can include a design having the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, DNA polynucleotides with first and second splice acceptors, first and second coding sequences, and first and second terminators can be oriented in a tail-to-tail orientation. The DNA polynucleotides with a tail-to-tail orientation of sequences can further comprise a first and second target site for one or more rare-cutting endonucleases, wherein the target sites flank the first and second splice acceptors. In another embodiment, the DNA polynucleotides can comprise a left and right homology arm which flank the first and second splice acceptors. In this embodiment, the DNA polynucleotide can be harbored within an adeno-associated viral vector. In another embodiment, the DNA polynucleotides can further comprise a first and second target site for one or more rare-cutting endonucleases, wherein the target sites flank the first and second splice acceptors. The first and second target sites can flank the first and second homology arms. In embodiments, the DNA polynucleotides described herein can be integrated within an intron of the endogenous gene or at an intron-exon junction. The DNA polynucleotides can be integrated within an intron, or at the intron-exon junction of the ATXN3 gene or CACNA1A gene. The DNA polynucleotide can comprise a first and second partial coding sequence encoding the peptide produced by exon 10 of a non-pathogenic ATXN3 gene. The DNA polynucleotide can comprise a first and second partial coding sequence encoding the peptide produced by exon 47 of a non-pathogenic CACNA1A gene. The first and second partial coding sequences encode the same amino acids. In an embodiment, the first and second coding sequences can differ in nucleic acid sequence but encode the same amino acids. The DNA polynucleotides can be harbored on a vector, wherein the vector format is selected from double-stranded linear DNA, double-stranded circular DNA, or a viral vector. The viral vector can be selected from an adenovirus vector, an adeno-associated virus vector, or a lentivirus vector. The DNA polynucleotides described here can be equal to or less than 4.7 kb.

In one embodiment, this document features a method of integrating a transgene into an endogenous gene, the method including administering a transgene, wherein the transgene comprises a left and right transposon end, a first and second splice acceptor sequence, a first and second partial coding sequence, and one bidirectional terminator or a first and second terminator, and administering a transposase targeted to the endogenous gene, where the transgene is integrated in the endogenous gene. The method can include designing the transgene to have the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, transgenes with first and second splice acceptors, first and second coding sequences, and first and second terminators can be oriented in a tail-to-tail orientation. The transgenes with a tail-to-tail orientation of sequences can further comprise a left and right transposon end flanking the first and second splice acceptors. In embodiments, the transgenes described herein can be integrated within an intron of the endogenous gene or at an intron-exon junction. The transgenes can be integrated within an intron, or at the intron-exon junction of the ATXN3 gene or CACNA1A gene. The transgene can comprise a first and second partial coding sequence encoding the peptide produced by exon 10 of a non-pathogenic ATXN3 gene and can be targeted to intron 9, or the intron 9 exon 10 junction, of a pathogenic ATXN3 gene. The transgene can comprise a first and second partial coding sequence encoding the peptide produced by exon 47 of a non-pathogenic CACNA1A gene and can be targeted to intron 46, or the intron 46 exon 47 junction, of a pathogenic CACNA1A gene. The transposase can be a CRISPR transposase, where the CRISPR transposase comprises the Cas12k or Cas6 protein. The first and second partial coding sequences encode the same amino acids. In an embodiment, the first and second coding sequences can differ in nucleic acid sequence but encode the same amino acids. The transgene can be harbored on a vector, wherein the vector format is selected from double-stranded linear DNA, double-stranded circular DNA, or a viral vector. The viral vector iscan include an adenovirus vector, an adeno-associated virus vector, or a lentivirus vector. The methods described here can be used with a transgene equal to or less than 4.7 kb. The left end can comprise the sequence shown in SEQ ID NO:41, and the right end can comprise the sequence shown in SEQ ID NO:13.

In another embodiment, this document provides DNA polynucleotides with a first and second splice acceptor sequence, a first and second partial coding sequence, one bidirectional terminator or a first and second terminator, and a left and right transposon end. The DNA polynucleotides can include a design having the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. In an embodiment, DNA polynucleotides with first and second splice acceptors, first and second coding sequences, and first and second terminators can be oriented in a tail-to-tail orientation. The DNA polynucleotides with a tail-to-tail orientation of sequences can further comprise a left and right transposon end which flank the first and second splice acceptors. In embodiments, the DNA polynucleotides described herein can be integrated within an intron of the endogenous gene or at an intron-exon junction. The DNA polynucleotides can be integrated within an intron, or at the intron-exon junction of the ATXN3 gene or CACNA1A gene. The DNA polynucleotide can comprise a first and second partial coding sequence encoding the peptide produced by exon 10 of a non-pathogenic ATXN3 gene. The DNA polynucleotide can comprise a first and second partial coding sequence encoding the peptide produced by exon 47 of a non-pathogenic CACNA1A gene. The first and second partial coding sequences encode the same amino acids. In an embodiment, the first and second coding sequences can differ in nucleic acid sequence but encode the same amino acids. The DNA polynucleotides can be harbored on a vector, wherein the vector format is selected from double-stranded linear DNA, double-stranded circular DNA, or a viral vector. The viral vector can be selected from an adenovirus vector, an adeno-associated virus vector, or a lentivirus vector. The DNA polynucleotides described here can be equal to or less than 4.7 kb. The left end can comprise the sequence shown in SEQ ID NO:41, and the right end can comprise the sequence shown in SEQ ID NO:13.

In one embodiment, this document features a method of integrating a transgene into an endogenous gene, the method including administering a transgene, wherein the transgene comprises a first and second splice acceptor sequence, a first and second coding sequence, one bidirectional terminator or a first and second terminator, and a first and second homology arm, wherein the transgene is integrated within the endogenous gene. The method can include designing the transgene to have the first splice acceptor operably linked to the first partial coding sequence and the second splice acceptor operably linked to the second coding sequence. The arrangement can also include having the first partial coding sequence operably linked to the first terminator, and the second partial coding sequence operably linked to the second terminator. In an embodiment, the two terminators can be replaced with a single bidirectional terminator. The homology arms can flank the first and second splice acceptor sequence, the first and second coding sequence, the one bidirectional terminator or the first and second terminator. The coding sequence can encode a full coding sequence or a partial coding sequence. In an embodiment, transgenes with first and second splice acceptors, first and second coding sequences, and first and second terminators can be oriented in a tail-to-tail orientation. The transgenes with a tail-to-tail orientation of sequences can further comprise a first and second target site for one or more rare-cutting endonucleases, wherein the target sites flank the first and second splice acceptors. In another embodiment, the transgenes can comprise a left and right homology arm which flank the first and second splice acceptors. In this embodiment, the transgene can be harbored within an adeno-associated viral vector. In another embodiment, the transgene can further comprise a first and second target site for the one or more rare-cutting endonucleases, wherein the target sites flank the first and second splice acceptors. The first and second target sites can flank the first and second homology arms. In embodiments, the transgenes described herein can be integrated within an intron of the endogenous gene or at an intron-exon junction.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

As used herein, the terms "nucleic acid" and "polynucleotide," can be used interchangeably. Nucleic acid and polynucleotide can refer to a deoxyribonucleotide or ribonucleotide polymer, in linear or circular conformation, and in either single- or double-stranded form. These terms are not to be construed as limiting with respect to the length of a polymer. The terms can encompass known analogues of natural nucleotides, as well as nucleotides that are modified in the base, sugar and/or phosphate moieties.

The terms "polypeptide," "peptide" and "protein" can be used interchangeably to refer to amino acid residues covalently linked together. The term also applies to proteins in which one or more amino acids are chemical analogues or modified derivatives of corresponding naturally occurring amino acids.

The terms "operatively linked" or "operably linked" are used interchangeably and refer to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence but need not be directly adjacent to it. For example, an enhancer is a transcriptional regulatory sequence that is operatively linked to a coding sequence, even though they are not contiguous. Further, by way of example, a splice acceptor can be operably linked to a partial coding sequence if the splice acceptor enables delineation of an intron's 3' boundary, and if translation of the resulting mature mRNA results in incorporation of the peptide sequence encoded by the partial coding sequence into the final protein product.

As used herein, the term "cleavage" refers to the breakage of the covalent backbone of a nucleic acid molecule. Cleavage can be initiated by a variety of methods including, but not limited to, enzymatic or chemical hydrolysis of a phosphodiester bond. Cleavage can refer to both a single-stranded nick and a double-stranded break. A double-stranded break can occur as a result of two distinct single-stranded nicks. Nucleic acid cleavage can result in the production of either blunt ends or staggered ends. In certain embodiments, rare-cutting endonucleases are used for targeted double-stranded or single-stranded DNA cleavage.

An "exogenous" molecule can refer to a small molecule (e.g., sugars, lipids, amino acids, fatty acids, phenolic compounds, alkaloids), or a macromolecule (e.g., protein, nucleic acid, carbohydrate, lipid, glycoprotein, lipoprotein, polysaccharide), or any modified derivative of the above molecules, or any complex comprising one or more of the above molecules, generated or present outside of a cell, or not normally present in a cell. Exogenous molecules can be introduced into cells. Methods for the introduction or "administering" of exogenous molecules into cells can include lipid-mediated transfer, electroporation, direct injection, cell fusion, particle bombardment, calcium phosphate co-precipitation, DEAE-dextran-mediated transfer and viral vector-mediated transfer. As defined herein, "administering" can refer to the delivery, the providing, or the introduction of exogenous molecules into a cell. If a transgene or a rare-cutting endonuclease is administered to a cell, then the transgene or rare-cutting endonuclease is delivered to, provided, or introduced into the cell. The rare-cutting endonuclease can be administered as purified protein, nucleic acid, or a mixture of purified protein and nucleic acid. The nucleic acid (i.e., RNA or DNA), can encode for the rare-cutting endonuclease, or a part of a rare-cutting endonuclease (e.g., a gRNA). The administering can be achieved though methods such as lipid-mediated transfer, electroporation, direct injection, cell fusion, particle bombardment, calcium phosphate co-precipitation, DEAE-dextran-mediated transfer, viral vector-mediated transfer, or any means suitable of delivering purified protein or nucleic acids, or a mixture of purified protein and nucleic acids, to a cell.

An "endogenous" molecule is a molecule that is present in a particular cell at a particular developmental stage under particular environmental conditions. An endogenous molecule can be a nucleic acid, a chromosome, the genome of a mitochondrion, chloroplast or other organelle, or a naturally occurring episomal nucleic acid. Additional endogenous molecules can include proteins, for example, transcription factors and enzymes.

As used herein, a "gene," refers to a DNA region encoding that encodes a gene product, including all DNA regions which regulate the production of the gene product. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, a "wild type gene" refers to a form of the gene that is present at the highest frequency in a particular population.

An "endogenous gene" refers to a DNA region normally present in a particular cell that encodes a gene product as well as all DNA regions which regulate the production of the gene product.

"Gene expression" refers to the conversion of the information, contained in a gene, into a gene product. A gene product can be the direct transcriptional product of a gene. For example, the gene product can be, but not limited to, mRNA, tRNA, rRNA, antisense RNA, ribozyme, structural RNA, or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Encoding" refers to the conversion of the information contained in a nucleic acid, into a product, wherein the product can result from the direct transcriptional product of a nucleic acid sequence. For example, the product can be, but not limited to, mRNA, tRNA, rRNA, antisense RNA, ribozyme, structural RNA, or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

A "target site" or "target sequence" defines a portion of a nucleic acid to which a rare-cutting endonuclease or CRISPR-associated transposase will bind, provided sufficient conditions for binding exist.

As used herein, the term "recombination" refers to a process of exchange of genetic information between two polynucleotides. The term "homologous recombination (HR)" refers to a specialized form of recombination that can take place, for example, during the repair of double-strand breaks. Homologous recombination requires nucleotide sequence homology present on a "donor" molecule. The donor molecule can be used by the cell as a template for repair of a double-strand break. Information within the donor molecule that differs from the genomic sequence at or near the double-strand break can be stably incorporated into the cell's genomic DNA.

The term "integrating" as used herein refers to the process of adding DNA to a target region of DNA. As described herein, integration can be facilitated by several different means, including non-homologous end joining, homologous recombination, or targeted transposition. By way of example, integration of a user-supplied DNA molecule into a target gene can be facilitated by non-homologous end joining. Here, a targeted-double strand break is made within the target gene and a user-supplied DNA molecule is administered. The user-supplied DNA molecule can comprise exposed DNA ends to facilitate capture during repair of the target gene by non-homologous end joining. The exposed ends can be present on the DNA molecule upon administration (i.e., administration of a linear DNA molecule) or created upon administration to the cell (i.e., a rare-cutting endonuclease cleaves the user-supplied DNA molecule within the cell to expose the ends). Additionally, the user-supplied DNA molecule can be harbored on a viral vector, including an adeno-associated virus vector. In another example, integration occurs though homologous recombination. Here, the user-supplied DNA can harbor a left and right homology arm. In another example, integration occurs through transposition. Here, the user-supplied DNA harbors a transposon left and right end.

The term "transgene" as used herein refers to a sequence of nucleic acids that can be transferred to an organism or cell. The transgene may comprise a gene or sequence of nucleic acids not normally present in the target organism or cell. Additionally, the transgene may comprise a copy of a gene or sequence of nucleic acids that is normally present in the target organism or cell. A transgene can be an exogenous DNA sequence introduced into the cytoplasm or nucleus of a target cell. In one embodiment, the transgenes described herein contain partial coding sequences, wherein the partial coding sequences encodes a portion of a protein produced by a gene in the host cell.

As used herein, the term "pathogenic" refers to anything that can cause disease. A pathogenic mutation can refer to a modification in a gene which causes disease. A pathogenic gene refers to a gene comprising a modification which causes disease. By means of example, a pathogenic ATXN3 gene in patients with spinocerebellar ataxia 3 refers to an ATXN3 gene with an expanded CAG trinucleotide repeat, wherein the expanded CAG trinucleotide repeat causes the disease.

As used herein, the term "tail-to-tail" refers to an orientation of two units in opposite and reverse directions. The two units can be two sequences on a single nucleic acid molecule, where the 3' end of each sequence are placed adjacent to each other. For example, a first nucleic acid having the elements, in a 5' to 3' direction, [splice acceptor 1]—[partial coding sequence 1]—[terminator 1] and a second nucleic acid having the elements [splice acceptor 2]—[partial coding sequence 2]—[terminator 2] can be placed in tail-to-tail orientation resulting in [splice acceptor 1]—[partial coding sequence 1]—[terminator 1]—[terminator 2 RC]—[partial coding sequence 2 RC]—[splice acceptor 2 RC], where RC refers to reverse complement.

The term "intron-exon junction" refers to a specific location within a gene. The specific location is between the last nucleotide in an intron and the first nucleotide of the following exon. When integrating a transgene described herein, the transgene can be integrated within the "intron-exon junction." If the transgene comprises cargo, the cargo will be integrated immediately following the last nucleotide in the intron. In some cases, integrating a transgene within the intron-exon junction can result in removal of sequence within the exon (e.g., integration via HR and replacement of sequence within the exon with the cargo within the transgene).

The term "homologous" as used herein refers to a sequence of nucleic acids or amino acids having similarity to a second sequence of nucleic acids or amino acids. In some embodiments, the homologous sequences can have at least 80% sequence identity (e.g., 81%, 85%, 90%, 95%, 96%, 97%, 98%, or 99% sequence identity) to one another.

The term "partial coding sequence" as used herein refers to a sequence of nucleic acids that encodes a partial protein. The partial coding sequence can encode a protein that comprises one or less amino acids as compared to the wild type protein or functional protein. The partial coding sequence can encode a partial protein with homology to the wild type protein or functional protein. The term "partial coding sequence" when referring to ATXN3 refers to a sequence of nucleic acids that encodes a partial ATXN3 protein. The partial ATXN3 protein has one or less amino acids compared to a wild type ATXN3 protein. If modifying the 3' end of the gene, the one or less amino acids can be from the N-terminus end of the protein. If the ATXN3 gene has 11 exons, then the partial coding sequence can comprise sequence encoding the peptide produced by exons 2-11, or 3-11 or 4-11, or 5-11, or 6-11, or 7-11, or 8-11, or 9-11, or 10-11, or 11.

The methods and compositions described in this document can use transgenes having a cargo sequence. The term "cargo" can refer to elements such as the complete or partial coding sequence of a gene, a partial sequence of a gene harboring single-nucleotide polymorphisms relative to the WT or altered target, a splice acceptor, a terminator, a transcriptional regulatory element, purification tags (e.g., glutathione-S-transferase, poly(His), maltose binding protein, Strep-tag, Myc-tag, AviTag, HA-tag, or chitin binding protein) or reporter genes (e.g., GFP, RFP, lacZ, cat, luciferase, puro, neomycin). As defined herein, "cargo" can refer to the sequence within a transgene that is integrated at a target site. For example, "cargo" can refer to the sequence on a transgene between two homology arms, two rare-cutting endonuclease target sites, or a left and right transposon end.

The term "homology sequence" refers to a sequence of nucleic acids that comprises homology to a second nucleic acid. Homology sequence, for example, can be present on a donor molecule as an "arm of homology" or "homology arm." A homology arm can be a sequence of nucleic acids within a donor molecule that facilitates homologous recombination with the second nucleic acid. As defined herein, a homology arm can also be referred to as an "arm". In a donor molecule with two homology arms, the homology arms can be referred to as "arm 1" and "arm 2." In one aspect, a cargo sequence can be flanked with first and second homology arm.

The term "bidirectional terminator" refers to a terminator that can terminate RNA polymerase transcription in either the sense or antisense direction. In contrast to two unidirectional terminators in tail-to-tail orientation, a bidirectional terminator can comprise a non-chimeric sequence of DNA. Examples of bidirectional terminators include the ARO4, TRP1, TRP4, ADH1, CYC1, GAL1, GAL7, and GAL10 terminator.

A 5' or 3' end of a nucleic acid molecule references the directionality and chemical orientation of the nucleic acid. As defined herein, the "5' end of a gene" can comprise the exon with the start codon, but not the exon with the stop codon. As defined herein, the "3' end of a gene" can comprise the exon with the stop codon, but not the exon with the start codon.

The term "ATXN3" gene refers to a gene that encodes the enzyme ataxin-3. A representative sequence of the ATXN3 gene can be found with NCBI Reference Sequence: NG 008198.2 and corresponding SEQ ID NO:42. The exon and intron boundaries can be defined with the sequence provided in SEQ ID NO:42. Specifically, exon 1 includes the sequence from 1 to 54. Exon 2 includes the sequence from 9745 to 9909. Exon 3 includes the sequence from 10446 to 10490. Exon 4 includes the sequence from 12752 to 12837. Exon 5 includes the sequence from 13265 to 13331. Exon 6 includes the sequence from 17766 to 17853. Exon 7 includes the sequence from 23325 to 23457. Exon 8 includes the sequence from 24117 to 24283. Exon 9 includes the sequence from 25522 to 25618. Exon 10 includes the sequence from 35530 to 35648. Exon 11 includes the sequence from 42169 to 48031. Intron 1 includes the sequence from 55 to 9744. Intron 2 includes the sequence from 9910 to 10445. Intron 3 includes the sequence from 10491 to 12751. Intron 4 includes the sequence from 12838 to 13264. Intron 5 includes the sequence from 13332 to 17765. Intron 6 includes the sequence from 17854 to 23324. Intron 7 includes the sequence from 23458 to 24116. Intron 8 includes the sequence from 24284 to 25521. Intron 9 includes the sequence from 25619 to 35529. Intron 10 includes the sequence from 35649 to 42168.

The term "CACNA1A" gene refers to a gene that encodes the calcium voltage-gated channel subunit alpha1A protein. A representative sequence of the CACNA1A gene can be found with NCBI Reference Sequence: NG_011569.1 and corresponding SEQ ID NO:43. The exon and intron boundaries can be defined with the sequence provided in SEQ ID NO:43. Specifically, exon 1 includes the sequence from 1 to 529. Exon 2 includes the sequence from 51249 to 51354. Exon 3 includes the sequence from 53446 to 53585. Exon 4 includes the sequence from 134682 to 134773. Exon 5 includes the sequence from 140992 to 141144. Exon 6 includes the sequence from 146662 to 146855. Exon 7 includes the sequence from 170552 to 170655. Exon 8 includes the sequence from 171968 to 172083. Exon 9 includes the sequence from 173536 to 173592. Exon 10 includes the sequence from 176125 to 176217. Exon 11 includes the sequence from 189140 to 189349. Exon 12 includes the sequence from 193680 to 193792. Exon 13 includes the sequence from 197933 to 198045. Exon 14 includes the sequence from 198210 to 198341. Exon 15 includes the sequence from 198607 to 198679. Exon 16 includes the sequence from 202577 to 202694. Exon 17 includes the sequence from 202848 to 202915. Exon 18 includes the sequence from 205805 to 205911. Exon 19 includes the sequence from 207108 to 207917. Exon 20 includes the sequence from 219495 to 219958. Exon 21 includes the sequence from 221255 to 221393. Exon 22 includes the sequence from 223065 to 223194. Exon 23 includes the sequence from 229333 to 229392. Exon 24 includes the sequence from 230505 to 230611. Exon 25 includes the sequence from 243628 to 243727. Exon 26 includes the sequence from 244851 to 245011. Exon 27 includes the sequence from 246760 to 246897. Exon 28 includes the sequence from 248910 to 249111. Exon 29 includes the sequence from 251202 to 251366. Exon 30 includes the sequence from 253360 to 253470. Exon 31 includes the sequence from 261196 to 261279. Exon 32 includes the sequence from 270731 to 270847. Exon 33 includes the sequence from 271187 to 271252. Exon 34 includes the sequence from 271425 to 271540. Exon 35 includes the sequence from 274601 to 274751. Exon 36 includes the sequence from 276252 to 276379. Exon 37 includes the sequence from 277666 to 277762. Exon 38 includes the sequence from 281689 to 281794. Exon 39 includes the sequence from 291853 to 291960. Exon 40 includes the sequence from 292128 to 292228. Exon 41 includes the sequence from 293721 to 293830. Exon 42 includes the sequence from 293939 to 294077. Exon 43 includes the sequence from 294245 to 294358. Exon 44 includes the sequence from 295809 to 295844. Exon 45 includes the sequence from 296963 to 297149. Exon 46 includes the sequence from 297452 to 297705. Exon 47 includes the sequence from 298413 to 300019. Intron 1 includes the sequence from 530 to 51248. Intron 2 includes the sequence from 51355 to 53445. Intron 3 includes the sequence from 53586 to 134681. Intron 4 includes the sequence from 134774 to 140991. Intron 5 includes the sequence from 141145 to 146661. Intron 6 includes the sequence from 146856 to 170551. Intron 7 includes the sequence from 170656 to 171967. Intron 8 includes the sequence from 172084 to 173535. Intron 9 includes the sequence from 173593 to 176124. Intron 10 includes the sequence from 176218 to 189139. Intron 11 includes the sequence from 189350 to 193679. Intron 12 includes the sequence from 193793 to 197932. Intron 13 includes the sequence from 198046 to 198209. Intron 14 includes the sequence from 198342 to 198606. Intron 15 includes the sequence from 198680 to 202576. Intron 16 includes the sequence from 202695 to 202847. Intron 17 includes the sequence from 202916 to 205804. Intron 18 includes the sequence from 205912 to 207107. Intron 19 includes the sequence from 207918 to 219494. Intron 20 includes the sequence from 219959 to 221254. Intron 21 includes the sequence from 221394 to 223064. Intron 22 includes the sequence from 223195 to 229332. Intron 23 includes the sequence from 229393 to 230504. Intron 24 includes the sequence from 230612 to 243627. Intron 25 includes the sequence from 243728 to 244850. Intron 26 includes the sequence from 245012 to 246759. Intron 27 includes the sequence from 246898 to 248909. Intron 28 includes the sequence from 249112 to 251201. Intron 29 includes the sequence from 251367 to 253359. Intron 30 includes the sequence from 253471 to 261195. Intron 31 includes the sequence from 261280 to 270730. Intron 32 includes the sequence from 270848 to 271186. Intron 33 includes the sequence from 271253 to 271424. Intron 34 includes the sequence from 271541 to 274600. Intron 35 includes the sequence from 274752 to 276251. Intron 36 includes the sequence from 276380 to 277665. Intron 37 includes the sequence from 277763 to 281688. Intron 38 includes the sequence from 281795 to 291852. Intron 39 includes the sequence from 291961 to 292127. Intron 40 includes the sequence from 292229 to 293720. Intron 41 includes the sequence from 293831 to 293938. Intron 42 includes the sequence from 294078 to 294244. Intron 43 includes the sequence from 294359 to 295808. Intron 44 includes the sequence from 295845 to 296962. Intron 45 includes the sequence from 297150 to 297451. Intron 46 includes the sequence from 297706 to 298412.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -l; -r is set to 2; and all other options are left at their default setting. For example, the following command can be used to generate an output file containing a comparison between two sequences: C:\B12seq c:\seq1.txt -j c:\seq2.txt -p blastn -o c:\output.txt -q -l -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100. The percent sequence identity value is rounded to the nearest tenth.

In one embodiment, this document features methods for modifying the 3' end of endogenous genes, where endogenous genes have at least one intron between two coding exons. The intron can be any intron which is removed from precursor messenger RNA by normal messenger RNA processing machinery. The intron can be between 20 bp and >500 kb and comprise elements including a splice donor site, branch sequence, and acceptor site. The transgenes disclosed herein for the modification of the 3' end of endogenous genes can comprise multiple functional elements, including target sites for rare-cutting endonucleases, homology arms, splice acceptor sequences, coding sequences, and transcription terminators (FIG. 1).

In one embodiment, the transgene comprises two target sites for one or more rare-cutting endonucleases. The target sites can be a suitable sequence and length for cleavage by a rare-cutting endonuclease. The target site can be amenable to cleavage by CRISPR systems, TAL effector nucleases, zinc-finger nucleases or meganucleases, or a combination of CRISPR systems, TALE nucleases, zinc finger nucleases or meganucleases, or any other site-specific nuclease. The target sites can be positioned such that cleavage by the rare-cutting endonuclease results in liberation of a transgene from a vector. The vector can include viral vectors (e.g., adeno-associated vectors) or non-viral vectors (e.g., plasmids, minicircle vectors). If the transgene comprises two target sites, the target sites can be the same sequence (i.e., targeted by the same rare-cutting endonuclease) or they can be different sequences (i.e., targeted by two or more different rare-cutting endonucleases).

In one embodiment, the transgene comprises a first and second target site for one or more rare-cutting endonucleases along with a first and second homology arm. The first and second homology arms can include sequence that is homologous to a genomic sequence at or near the desired site of integration. The homology arms can be a suitable length for participating in homologous recombination with sequence at or near the desired site of integration. The length of each homology arm can be between 20 nt and 10,000 nt (e.g., 20 nt, 30 nt, 40 nt, 50 nt, 100 nt, 200 nt, 300 nt, 400 nt, 500 nt, 600 nt, 700 nt, 800 nt, 900 nt, 1,000 nt, 2,000 nt, 3,000 nt, 4,000 nt, 5,000 nt, 6,000 nt, 7,000 nt, 8,000 nt, 9,000 nt, 10,000 nt). In one embodiment, a homology arms can comprise functional elements, including a target site for a rare-cutting endonuclease and/or a splice acceptor sequence. In one embodiment, a first homology arm (e.g., a left homology arm) can comprise sequence homologous to the intron being targeted, which includes the splice acceptor site of the intron being targeted. In another embodiment, a second homology arm can comprise sequence homologous to genomic sequence downstream of the intron being targeted (e.g., exon sequence, 3' UTR sequence). However, the second homology arm must not possess splice acceptor functions in the reverse complement direction. To determine if a sequence comprises splice acceptor functions, several steps can be taken, including in silico analysis and experimental tests. To determine if there is potential for splice acceptor functions, the sequence desired for second homology arm can be searched for consensus branch sequences (e.g., YTRAC) and splice acceptor sites (e.g., Y-rich NCAGG). If branch or splice acceptor sequences are present, single nucleotide polymorphisms can be introduced to destroy function, or a different but adjacent sequence not comprising such sequences can be selected. Preferably, the window of sequence that can be used for a second homology arm extends from 1 bp to 10 kb downstream of the intron being targeted for integration. To experimentally determine if the second homology possesses splice acceptor function, a synthetic construct comprising the second homology arm within an intron within a reporter gene can be constructed. The construct can then be administered to an appropriate cell type and monitored for splicing function.

In one embodiment, the transgene comprises two splice acceptor sequences, referred to herein as the first and second splice acceptor sequence. The first and second splice acceptor sequences are positioned within the transgene in opposite directions (i.e., in tail-to-tail orientations) and flanking internal sequences (i.e., coding sequences and terminators). When the transgene is integrated into an intron in forward or reverse directions, the splice acceptor sequences facilitate the removal of the adjacent/upstream intron sequence during mRNA processing. The first and second splice acceptor sequences can be the same sequences or different sequences. One or both splice acceptor sequences can be the splice acceptor sequence of the intron where the transgene is to be integrated. One or both splice acceptor sequences can be a synthetic splice acceptor sequence or a splice acceptor sequence from an intron from a different gene.

In one embodiment, the transgene comprises a first and second coding sequence operably linked to the first and second splice acceptor sequences. The first and second coding sequences are positioned within the transgene in opposite directions (i.e., in tail-to-tail orientations). When the transgene is integrated into an endogenous gene in forward or reverse directions, the first or second coding sequence is transcribed into mRNA by the endogenous gene's promoter. The coding sequences can be designed to correct defective coding sequences, introduce mutations, or introduce novel peptide sequences. The first and second coding sequence can be the same nucleic acid sequence and code for the same protein. Alternatively, the first and second coding sequence can be different nucleic acid sequences and code for the same protein (i.e., using the degeneracy of codons). The coding sequence can encode purification tags (e.g., glutathione-S-transferase, poly(His), maltose binding protein, Strep-tag, Myc-tag, AviTag, HA-tag, or chitin binding protein) or reporter proteins (e.g., GFP, RFP, lacZ, cat, luciferase, puro, neomycin). In one embodiment, the transgene comprises a first and second partial coding sequence operably linked to a first and second splice acceptor sequence, and the transgene does not comprise a promoter.

In one embodiment, the transgene can comprise a bidirectional terminator, or a first and second terminator, operably linked to a first and second coding sequence. The bidirectional terminator, or the first and second terminators are positioned within the transgene in opposite directions (i.e., in tail-to-tail orientations). When the transgene is integrated into an endogenous gene in forward or reverse directions, the bidirectional terminator, or first and second terminators, terminate transcription from the endogenous gene's promoter. The first and second terminators can be the same terminators or different terminators.

Figure 2:
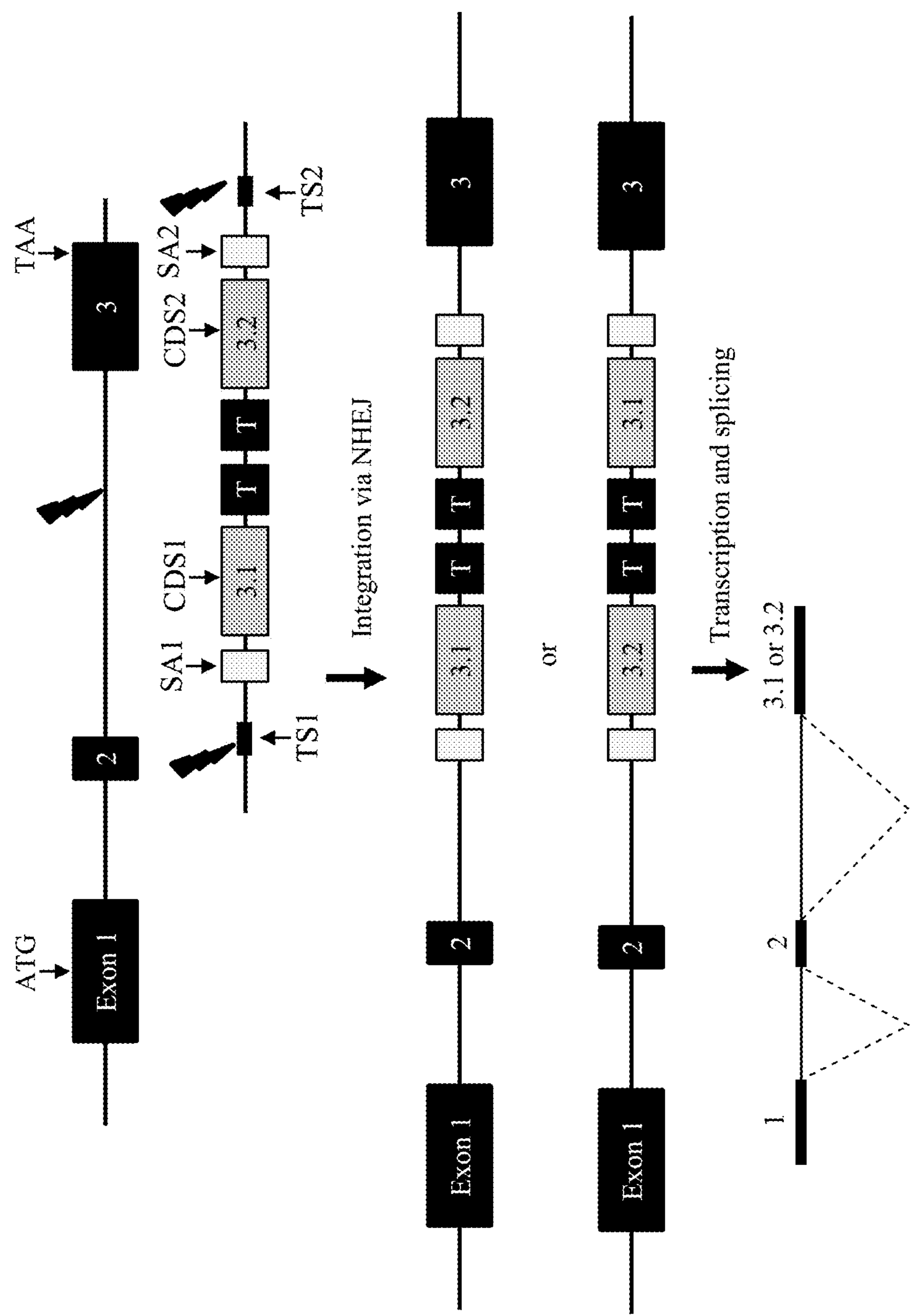
FIG. 2 is an illustration showing integration of a transgene into an exemplary gene. The transgene comprises two target sites for one or more rare-cutting endonucleases, two splice acceptor sequences, two coding sequences (3.1 and 3.2) and two terminators (T). Integration proceeds through non-homologous end joining (NHEJ).

In one embodiment, this document provides a transgene comprising a first and second rare-cutting endonuclease target site, a first and second splice acceptor sequence, a first and second coding sequence, and one bidirectional terminator or a first and second terminator. The transgene can be integrated in endogenous genes via non-homology dependent methods, including non-homologous end joining and alternative non-homologous end joining or by microhomology-mediated end joining. In one aspect, the transgene is integrated into an intron within the endogenous gene (FIG. 2).

Figure 3:
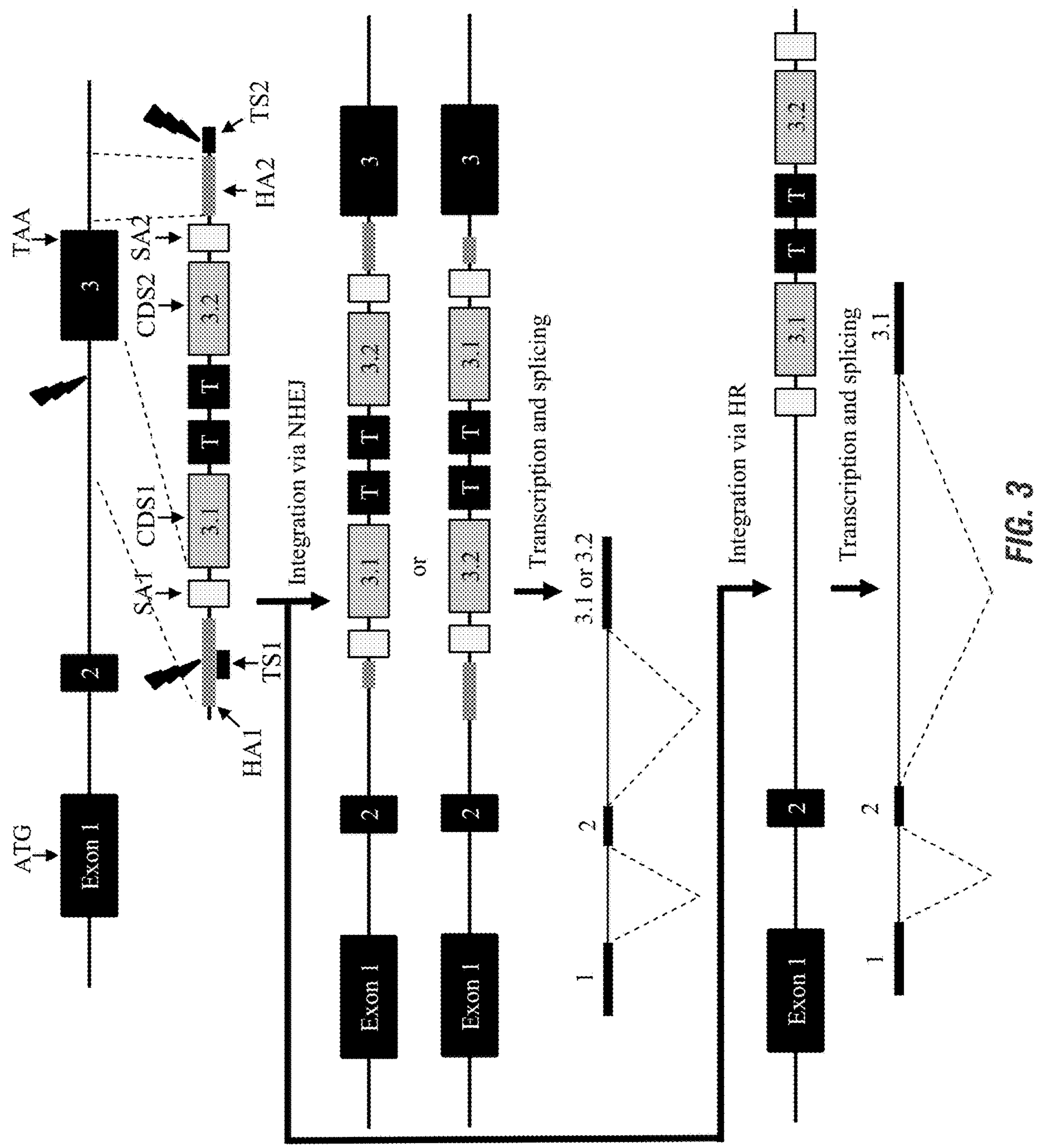
FIG. 3 is an illustration showing integration of a transgene into an exemplary gene. The transgene comprises two homology arms, two target sites for one or more rare-cutting endonucleases, two splice acceptor sequences, two coding sequences (3.1 and 3.2) and two terminators. Integration proceeds through either homologous recombination (HR) or non-homologous end joining (NHEJ).

In another embodiment, this document provides a transgene comprising a first and second homology arm, a first and second rare-cutting endonuclease target site, a first and second splice acceptor sequence, a first and second coding sequence, and one bidirectional terminator or a first and second terminator. The transgene can be integrated in endogenous genes via both homology dependent methods (e.g., synthesis dependent strand annealing and microhomology-mediated end joining) and non-homology dependent methods (e.g., non-homologous end joining and alternative non-homologous end joining). In one aspect, the transgene is integrated into an intron within the endogenous gene (FIG. 3). In another aspect, the transgene is integrated at the end of the intron or the starting of the downstream exon (FIG. 3).

In another embodiment, this document provides a transgene comprising a first and second homology arm, a first and second coding sequence, a first and second splice acceptor sequence, and one bidirectional terminator or a first and second terminator (FIG. 1). In another embodiment, this document provides a transgene comprising, a first and second coding sequence, a first and second splice acceptor sequence, and one bidirectional terminator or a first and second terminator.

In another embodiment, this document provides a transgene comprising a first and second homology arm, a first and second coding sequence, a first and second splice acceptor sequence, one bidirectional terminator or a first and second terminator, and a first and second additional sequence (FIG. 1). In certain embodiments, the additional sequence can be any additional sequence that is present on the transgene at the 5' and 3' ends, however, the additional sequence should not comprise any element that functions as a splice acceptor. The additional sequence can be, for example, inverted terminal repeats of a virus genome. The additional sequence can be present on a transgene having a linear format. The linear format permits integration by NHEJ. For example, a transgene harbored in an adeno-associated virus vector, wherein the additional sequence is the inverted terminal repeats, can be directly integrated by NHEJ at a target site after cleavage by a rare-cutting endonuclease (i.e., no processing of the transgene is required). In another example, the additional sequence is a left and right transposon end.

In another embodiment, this document provides transgenes within viral vectors, including adeno-associated viruses and adenoviruses, where the transgene comprises a first and second splice acceptor sequence, a first and second coding sequence, and one bidirectional terminator or a first and second terminator. Due to the inverted terminal repeats of the viral vectors, the transgenes also comprise a first and second additional sequence.

In another embodiment, this document provides transgenes within viral vectors, including adeno-associated viruses and adenoviruses, where the transgene comprises a first and second homology arm, a first and second splice acceptor sequence, a first and second coding sequence, and one bidirectional terminator or a first and second terminator. Due to the inverted terminal repeats of the viral vectors, the transgenes also comprise a first and second additional sequence.

In some embodiments, the transgenes provided herein can be integrated with transposases. The transposases can include CRISPR transposases (Strecker et al., *Science* 10.1126/science.aax9181, 2019; Klompe et al., *Nature,* 10.1038/s41586-019-1323-z, 2019). The transposases can be used in combination with a transgene comprising, a first and second splice acceptor sequence, a first and second coding sequence, one bidirectional terminator or a first and second terminator (FIG. 1), and a transposon left end and right end. The CRISPR transposases can include the TypeV-U5, C2C5 CRISPR protein, Cas12k, along with proteins tnsB, tnsC, and tniQ. In some embodiments, the Cas12k can be from *Scytonema hofmanni* (SEQ ID NO:30) or *Anabaena cylindrica* (SEQ ID NO:31). In one embodiment, the transgenes described herein comprising a left (SEQ ID NO:32) and right transposon end (SEQ ID NO:33) can be delivered to cells along with ShCas12k, tnsB, tnsC, TniQ and a gRNA (SEQ ID NO:14). Alternatively, the CRISPR transposase can include the Cas6 protein, along with helper proteins including Cas7, Cas8 and TniQ. In one embodiment, the transgenes described herein comprising a left (SEQ ID NO:41) and right transposon end (SEQ ID NO:13) can be delivered to eukaryotic cells along with Cas6 (SEQ ID NO:37), Cas7 (SEQ ID NO:37), Cas8 (SEQ ID NO:37), TniQ (SEQ ID NO:37), TnsA (SEQ ID NO:37), TnsB (SEQ ID NO:37), TnsC (SEQ ID NO:37) and a gRNA (SEQ ID NO:12). The proteins can be administered to cells directly as purified protein or encoded on RNA or DNA. If encoded on RNA or DNA, the sequence can be codon optimized for expression in eukaryotic cells. The gRNA (SEQ ID NO:12) can be placed downstream of an RNA polIII promoter and terminated with a poly(T) terminator.

In some embodiments, the transgenes described herein can have a combination of elements including splice acceptors, partial coding sequences, terminators, homology arms, left and right transposase ends, and sites for cleavage by rare-cutting endonucleases. In one embodiment, the combination can be, from 5' to 3', [splice acceptor 1]—[partial coding sequence 1]—[terminator 1]—[terminator 2 RC]—[partial coding sequence 2 RC]—[splice acceptor 2 RC], where RC stands for reverse complement. This combination can be harbored on a linear DNA molecule or AAV molecule and can be integrated by NHEJ through a targeted break in the target gene. In another embodiment, the combination can be, from 5' to 3', [rare-cutting endonuclease cleavage site 1]—[splice acceptor 1]—[partial coding sequence 1]—[terminator 1]—[terminator 2 RC]—[partial coding sequence 2 RC]—[splice acceptor 2 RC]—[rare-cutting endonuclease cleavage site 1]. In another embodiment, the combination can be, from 5' to 3', [rare-cutting endonuclease cleavage site 1]—[homology arm 1]—[splice acceptor 1]—[partial coding sequence 1]—[terminator 1]—[terminator 2 RC]—[partial coding sequence 2 RC]—[splice acceptor 2 RC]—[homology arm 2]—[rare-cutting endonuclease cleavage site 2]. In this combination one or more rare-cutting endonucleases can be used to facilitate HR and NHEJ. For example, a single rare-cutting nuclease can cleave the target gene (i.e., a desired intron) and the cleavage sites flanking the homology arms can be designed to be the same target sequence within the intron. In another embodiment, the combination can be, from 5' to 3', [homology arm 1+rare-cutting endonuclease cleavage site 1]—[splice acceptor 1]—[partial coding sequence 1]—[terminator 1]—[terminator 2 RC]—[partial coding sequence 2 RC]—[splice acceptor 2 RC]—[homology arm 2]—[rare-cutting endonuclease cleavage site 1]. In this combination, one or more rare-cutting endonucleases can facilitate HR and NHEJ. For example, a single-rare cutting nuclease can cleave within homology arm 1, downstream of homology arm 2, and at the genomic target site (i.e., at the site with homology to the sequence in the homology arm 1). In another embodiment, the combination can be from 5' to 3', [left end for a transposase]—[splice acceptor 1]—[partial coding sequence 1]—[terminator 1]—[terminator 2 RC]—[partial coding sequence 2 RC]—[splice acceptor 2 RC]—[right end for a transposase]. In all embodiments, the splice acceptor 1 and splice acceptor 2 can be the same or different sequences; the partial coding sequence 1 and partial coding sequence 2 can be the same or different sequences; the terminator 1 and terminator 2 can be the same or different sequences.

In embodiments, a transgene comprising the structure [rare-cutting endonuclease cleavage site 1]—[homology arm 1]—[splice acceptor 1]—[partial coding sequence 1]—[terminator 1]—[terminator 2 RC]—[partial coding sequence 2 RC]—[splice acceptor 2 RC]—[homology arm 2]—[rare-cutting endonuclease cleavage site 2] can be integrated into the DNA through delivery of one or more rare-cutting endonucleases. If one rare-cutting endonuclease is delivered, the rare-cutting endonuclease can liberate the transgene by cleavage at the rare-cutting endonuclease cleavage site 1 and 2. Further, the same rare-cutting endonuclease can create a break within the target gene, simulating insertion through HR or NHEJ.

In other embodiments, a transgene comprising the structure [homology arm 1+rare-cutting endonuclease cleavage site 1]—[splice acceptor 1]—[partial coding sequence 1]—[terminator 1]—[terminator 2 RC]—[partial coding sequence 2 RC]—[splice acceptor 2 RC]—[homology arm 2]—[rare-cutting endonuclease cleavage site 1] can be integrated into the DNA thorough delivery of one or more rare-cutting endonucleases. If one rare-cutting endonuclease is delivered, the rare-cutting endonuclease can liberate the transgene by cleavage at the rare-cutting endonuclease cleavage site 1 and 2. Further, the same rare-cutting endonuclease can create a break within the target gene, simulating insertion through HR or NHEJ. Integration by HR can occur when cleavage is upstream of the site of integration (i.e., within a homology arm).

In embodiments, the location for integration of transgenes can be an intron or an intron-exon junction. When targeting an intron, the partial coding sequence can comprise sequence encoding the peptide produced by the following exons within the endogenous gene. For example, if the transgene is designed to be integrated in intron 9 of an endogenous gene with 11 exons, then the partial coding sequence can comprise sequence encoding the peptide produced by exons 10 and 11 of the endogenous gene. When targeting an intron-exon junction, the transgene can be designed to comprise homology arms with sequence homologous to the 3' of said intron.

In some embodiments, the partial coding sequences can be full coding sequences. The full coding sequence can encode an endogenous gene (e.g., Factor VIII, Factor IX, or INS), or reporter genes (e.g., RFP, GFP, cat, lacZ, luciferase). The full coding sequences can be operably linked to splice acceptors and terminators and placed in a transgene in a tail-to-tail orientation.

The methods and compositions provided herein can be used within to modify endogenous genes within cells. The endogenous genes can include, fibrinogen, prothrombin, tissue factor, Factor V, Factor VII, Factor VIII, Factor IX, Factor X, Factor XI, Factor XII (Hageman factor), Factor XIII (fibrin-stabilizing factor), von Willebrand factor, prekallikrein, high molecular weight kininogen (Fitzgerald factor), fibronectin, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, plasminogen activator inhibitor-2, glucocerebrosidase (GBA), α-galactosidase A (GLA), iduronate sulfatase (IDS), iduronidase (IDUA), acid sphingomyelinase (SMPD1), MMAA, MMAB, MMACHC, MMADHC (C2orf25), MTRR, LMBRD1, MTR, propionyl-CoA carboxylase (PCC) (PCCA and/or PCCB subunits), a glucose-6-phosphate transporter (G6PT) protein or glucose-6-phosphatase (G6Pase), an LDL receptor (LDLR), ApoB, LDLRAP-1, a PCSK9, a mitochondrial protein such as NAGS (N-acetylglutamate synthetase), CPS1 (carbamoyl phosphate synthetase I), and OTC (ornithine transcarbamylase), ASS (argininosuccinic acid synthetase), ASL (argininosuccinase acid lyase) and/or ARG1 (arginase), and/or a solute carrier family 25 (SLC25A13, an aspartate/glutamate carrier) protein, a UGT1A1 or UDP glucuronsyltransferase polypeptide A1, a fumarylacetoacetate hydrolyase (FAH), an alanine-glyoxylate aminotransferase (AGXT) protein, a glyoxylate reductase/hydroxypyruvate reductase (GRHPR) protein, a transthyretin gene (TTR) protein, an ATP7B protein, a phenylalanine hydroxylase (PAH) protein, an USH2A protein, an ATXN protein, and a lipoprotein lyase (LPL) protein.

The transgene may include sequence for modifying the sequence encoding a polypeptide that is lacking or non-functional or having a gain-of-function mutation in the subject having a genetic disease, including but not limited to the following genetic diseases: achondroplasia, achromatopsia, acid maltase deficiency, adenosine deaminase deficiency, adrenoleukodystrophy, aicardi syndrome, alpha-1 antitrypsin deficiency, alpha-thalassemia, androgen insensitivity syndrome, pert syndrome, arrhythmogenic right ventricular dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the 6th codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency, leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Additional diseases that can be treated by targeted integration include von Willebrand disease, usher syndrome, polycystic kidney disease, spinocerebellar ataxia type 3, and spinocerebellar ataxia type 6.

In one embodiment, the genomic modification is the insertion of a transgene in the endogenous CACNA1A genomic sequence. The transgene can include a synthetic and partial coding sequence for the CACNA1A protein. The partial coding sequence can be homologous to coding sequence within a wild type CACNA1A gene, or a functional variant of the wild type CACNA1A gene, or a mutant of the wild type CACNA1A gene. In one embodiment, the transgene encoding the partial CACNA1A protein is inserted into intron 46 or the beginning of exon 47.

In another embodiment, the genomic modification is the insertion of a transgene in the endogenous ATXN3 genomic sequence. The transgene can include a synthetic and partial coding sequence for the ATXN3 protein. The partial coding sequence can be homologous to coding sequence within a wild type ATXN3 gene, or a functional variant of the wild type ATXN3 gene, or a mutant of the wild type ATXN3 gene. In one embodiment, the transgene encoding the partial ATXN3 protein is inserted into intron 9 or the beginning of exon 10.

In one embodiment, the methods and compositions described herein can be used to modify the 3' end of an endogenous gene, thereby resulting in modification of the C-terminus of the protein encoded by the endogenous gene. The modification of the 3' end of the endogenous gene's coding sequence can include the replacement of the final coding exon (i.e., the exon comprising the stop codon), up to an exon that is between the exon with the start coding and the final exon. As defined herein "replacement" refers to the insertion of DNA in a gene, wherein the inserted DNA provides the information for producing the mRNA and protein of 1 or more exons. Replacement can occur by integrating a transgene into the endogenous gene, wherein the transgene comprises one or more coding sequences operably linked to a splice acceptor. The insertion may or may not result in the deletion of sequence within the endogenous gene (e.g., deletion of introns and exons). For example, if a gene comprises 72 exons, and the start codon is within exon 1, the modification can include replacement of exons 2-72, 3-72, 4-72, 5-72, 6-72, 7-72, 8-72, 9-72, 10-72, 11-72, 12-72, 13-72, 14-72, 15-72, 16-72, 17-72, 18-72, 19-72, 20-72, 21-72, 22-72, or 23-72, or 24-72, or 25-72, or 26-72, or 27-72, or 28-72, or 29-72, or 30-72, or 31-72, or 32-72, or 33-72, or 34-72, or 35-72, or 36-72, or 37-72, or 38-72, or 39-72, or 40-72, or 41-72, or 42-72, or 43-72, or 44-72, or 45-72, or 46-72, or 47-72, or 48-72, or 49-72, or 50-72, or 51-72, or 52-72, or 53-72, or 54-72, or 55-72, or 56-72, or 57-72, or 58-72, or 59-72, or 60-72, or 61-72, or 62-72, or 63-72, or 64-72, or 65-72, or 66-72, or 67-72, or 68-72, or 69-72, or 70-72, or 71-72 or 72. In one embodiment, the endogenous gene's exons can be replaced by integrating a transgene into the endogenous gene, wherein the transgene comprises a first and second partial coding sequence, wherein the first and second partial coding sequence encodes a peptide produced by the endogenous genes exons. For example, the transgene's first and second coding sequence can encode a peptide that is produced by the endogenous gene's exons 2-72, 3-72, 4-72, 5-72, 6-72, 7-72, 8-72, 9-72, 10-72, 11-72, 12-72, 13-72, 14-72, 15-72, 16-72, 17-72, 18-72, 19-72, 20-72, 21-72, 22-72, or 23-72, or 24-72, or 25-72, or 26-72, or 27-72, or 28-72, or 29-72, or 30-72, or 31-72, or 32-72, or 33-72, or 34-72, or 35-72, or 36-72, or 37-72, or 38-72, or 39-72, or 40-72, or 41-72, or 42-72, or 43-72, or 44-72, or 45-72, or 46-72, or 47-72, or 48-72, or 49-72, or 50-72, or 51-72, or 52-72, or 53-72, or 54-72, or 55-72, or 56-72, or 57-72, or 58-72, or 59-72, or 60-72, or 61-72, or 62-72, or 63-72, or 64-72, or 65-72, or 66-72, or 67-72, or 68-72, or 69-72, or 70-72, or 71-72 or 72. The transgene can be integrated within the endogenous gene in the upstream intron or at the beginning of the exon corresponding to the first exon within the transgene's partial coding sequence (FIG. 2). The transgene can be designed to be 4.7 kb or less, and incorporated into an AAV vector and particle, and delivered in vivo to target cells.

In an embodiment, the transgene is a sequence of DNA that harbors a first and second partial coding sequence, wherein the partial coding sequences encode a partial protein, wherein the partial protein is homologous to a corresponding region in a functional protein produced from a wild type gene. The host gene or endogenous gene is one in which expression of the protein is aberrant, in other words, is not expressed, is expressed at low levels, or is expressed but the mRNA or protein product or portion thereof is non-functional, has reduced function, or has a gain-of-function, resulting in a disorder in the host.

As described herein, the donor molecule can be in a viral or non-viral vector. The vectors can be in the form of circular or linear double-stranded or single stranded DNA. The donor molecule can be conjugated or associated with a reagent that facilitates stability or cellular update. The reagent can be lipids, calcium phosphate, cationic polymers, DEAE-dextran, dendrimers, polyethylene glycol (PEG) cell penetrating peptides, gas-encapsulated microbubbles or magnetic beads. The donor molecule can be incorporated into a viral particle. The virus can be retroviral, adenoviral, adeno-associated vectors (AAV), herpes simplex, pox virus, hybrid adenoviral vector, epstein-bar virus, lentivirus, or herpes simplex virus.

In certain embodiments, the AAV vectors as described herein can be derived from any AAV. In certain embodiments, the AAV vector is derived from the defective and nonpathogenic parvovirus adeno-associated type 2 virus. All such vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., Lancet 351:9117 1702-3, 1998; Kearns et al., Gene Ther. 9:748-55, 1996). Other AAV serotypes, including AAV1, AAV2, AAV3, AAV4, AAV5, AAV6, AAV7, AAV8, AAV9 and AAVrh.10 and any novel AAV serotype can also be used in accordance with the present invention. In some embodiments, chimeric AAV is used where the viral origins of the long terminal repeat (LTR) sequences of the viral nucleic acid are heterologous to the viral origin of the capsid sequences. Non-limiting examples include chimeric virus with LTRs derived from AAV2 and capsids derived from AAV5, AAV6, AAV8 or AAV9 (i.e. AAV2/5, AAV2/6, AAV2/8 and AAV2/9, respectively).

The constructs described herein may also be incorporated into an adenoviral vector system. Adenoviral based vectors are capable of very high transduction efficiency in many cell types and do not require cell division. With such vectors, high titer and high levels of expression can been obtained.

The methods and compositions described herein are applicable to any eukaryotic organism in which it is desired to alter the organism through genomic modification. The eukaryotic organisms include plants, algae, animals, fungi and protists. The eukaryotic organisms can also include plant cells, algae cells, animal cells, fungal cells and protist cells.

Exemplary mammalian cells include, but are not limited to, oocytes, K562 cells, CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells (see, e.g., Graham et al. (1977) J. Gen. Virol. 36:59), and myeloma cells like SP2 or NS0 (see, e.g., Galfre and Milstein (1981) Meth. Enzymol. 73(B):3 46). Peripheral blood mononucleocytes (PBMCs) or T-cells can also be used, as can embryonic and adult stem cells. For example, stem cells that can be used include embryonic stem cells (ES), induced pluripotent stem cells (iPSC), mesenchymal stem cells, hematopoietic stem cells, liver stem cells, skin stem cells and neuronal stem cells.

The methods and compositions of the invention can be used in the production of modified organisms. The modified organisms can be small mammals, companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. The methods and compositions of the invention can be used in humans.

Exemplary plants and plant cells which can be modified using the methods described herein include, but are not limited to, monocotyledonous plants (e.g., wheat, maize, rice, millet, barley, sugarcane), dicotyledonous plants (e.g., soybean, potato, tomato, alfalfa), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); vegetative crops for consumption (e.g. soybean and other legumes, squash, peppers, eggplant, celery etc.), flowering plants (e.g., petunia, rose, chrysanthemum), conifers and pine trees (e.g., pine fir, spruce); poplar trees (e.g. *P. tremula*x*P. alba*); fiber crops (cotton, jute, flax, bamboo) plants used in phytoremediation (e.g., heavy metal accumulating plants); oil crops (e.g., sunflower, rape seed) and plants used for experimental purposes (e.g., *Arabidopsis*). The methods disclosed herein can be used within the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea*. The term plant cells include isolated plant cells as well as whole plants or portions of whole plants such as seeds, callus, leaves, and roots. The present disclosure also encompasses seeds of the plants described above wherein the seed has the has been modified using the compositions and/or methods described herein. The present disclosure further encompasses the progeny, clones, cell lines or cells of the transgenic plants described above wherein said progeny, clone, cell line or cell has the transgene or gene construct. Exemplary algae species include *microalgae, diatoms, Botryococcus braunii, Chlorella, Dunaliella tertiolecta, Gracileria, Pleurochrysis carterae, Sorgassum* and *Ulva*.

The methods described in this document can include the use of rare-cutting endonucleases for stimulating homologous recombination or non-homologous integration of a transgene molecule into an endogenous gene. The rare-cutting endonuclease can include CRISPR, TALENs, or zinc-finger nucleases (ZFNs). The CRISPR system can include CRISPR/Cas9 or CRISPR/Cas12a (Cpfl). The CRISPR system can include variants which display broad PAM capability (Hu et al., *Nature* 556, 57-63, 2018; Nishimasu et al., *Science* DOI: 10.1126, 2018) or higher on-target binding or cleavage activity (Kleinstiver et al., *Nature* 529:490-495, 2016). The gene editing reagent can be in the format of a nuclease (Mali et al., *Science* 339:823-826, 2013; Christian et al., *Genetics* 186:757-761, 2010), nickase (Cong et al., *Science* 339:819-823, 2013; Wu et al., *Biochemical and Biophysical Research Communications* 1:261-266, 2014), CRISPR-FokI dimers (Tsai et al., *Nature Biotechnology* 32:569-576, 2014), or paired CRISPR nickases (Ran et al., *Cell* 154:1380-1389, 2013).

The methods and compositions described in this document can be used in a circumstance where it is desired to modify the 3' end of the coding sequence of an endogenous gene. For example, patients with SCA3 or SCA6 have expanded CAG repeats in exons 10 (second to last exon) and exon 47 (last exon), respectively. Patients with SCA3 or SCA6 may benefit from replacement of exons 10-11 and exon 47, respectively. In other examples, patients with genetic disorders due to loss of function mutations within the 3' end of an endogenous gene could benefit from replacement of the final exons of said gene.

The invention will be further described in the following examples, which do not limit the scope of the invention described in the claims.

EXAMPLES

Example 1: Targeted Integration of DNA in the ATXN3 Gene

Three plasmids were constructed with transgenes designed to integrate into the ATXN3 gene in human cells. All transgenes were designed to be inserted within intron 9 or the junction of intron 9 and exon 10 of the ATXN3 gene and all transgenes were designed to insert at least one splice acceptor and at least one functional coding sequence for exons 10 and 11 of the ATXN3 gene. The first plasmid, designated pBA1135, comprised a left and right homology arm with sequence homologous to the 3' end of intron 9 and 5' end of intron 10 (i.e., successful gene targeting would result in removal of exon 10 and replacement with the cargo sequence within pBA1135). Between the homology arms, from 5' to 3', was a splice acceptor (splice acceptor from ATXN3 intron 9), coding sequence for exons 10 and 11 of ATXN3, SV40 terminator, reverse BGH terminator, reverse coding sequence for exons 10 and 11 (codon adjusted), and reverse splice acceptor. The sequence for the pBA1135 transgene is shown in SEQ ID NO:17. A corresponding Cas9 nuclease was designed to cleave i) within intron 9 of the ATXN3 gene, ii) within the left homology arm of pBA1135, and iii) at the 3' end of the right homology arm of pBA1135. Successful cleavage of the plasmid was expected to liberate the transgene, thereby enabling the sequence to be used as a template for HR or for integration via NHEJ. The Cas9 gRNA target site is shown in SEQ ID NO:18. The individual elements within pBA1135 are shown in SEQ ID NOS:44-51. SEQ ID NO:44 comprises the left homology arm, nuclease target site, and splice acceptor. SEQ ID NO:45 comprises the partial coding sequence (exon 10 and 11) of a non-pathogenic ATXN3 gene. SEQ ID NO:46 comprises the SV40 p(A) terminator sequence. SEQ ID NO:47 comprises the BGH terminator in reverse complement. SEQ ID NO:48 comprises the reverse complement, codon adjusted partial coding sequence (exon 10 and 11) of a non-pathogenic ATXN3 gene. SEQ ID NO:49 comprises the sequence for the splice acceptor. SEQ ID NO:50 comprises the sequence for the right homology arm. SEQ ID NO:51 comprises the target site sequence for the nuclease. The second plasmid, designated pBA1136, comprised the same cargo as pBA1135, however, the homology arms were removed. Nuclease target sites were kept to facilitate liberation of the transgene from the plasmid. Successful cleavage of the plasmid was expected to liberate the transgene, thereby enabling the sequence to be used for integration by NHEJ into the ATXN3 gene. The sequence of pBA1136 is shown in SEQ ID NO:19. The third plasmid, designated pBA1137, comprised the same sequence as pBA1135, except for the reverse sequences and nuclease target site (i.e., reverse terminator, reverse coding sequence and reverse splice acceptor). Plasmid pBA1137 was used as a control for conventional HR based methods. The sequence of pBA1137 is shown in SEQ ID NO:20.

Transfection was performed using HEK293T cells. HEK293T cells were maintained at 37° C. and 5% CO2 in DMEM high supplemented with 10% fetal bovine serum (FBS). HEK293T cells were transfected with 2 ug of donor, 2 ug of guide RNA (RNA format) and 2 ug of Cas9 (RNA format). Transfections were performed using electroporation. Genomic DNA was isolated 72 hours post transfection and assessed for integration events. A list of primers used to detect integration or genomic DNA is shown in Table 1.

TABLE 1

Primers for detecting integration of transgenes in ATXN3.

| Primer Name | Sequence (5' to 3') | SEQ ID NO: |
|---|---|---|
| oNJB043 | CAAAGGTGCCCTTGAGGTT | 21 |
| oNJB044 | AGGAGAAGTCTGCCGTTACT | 22 |
| oNJB113 | GGACAAACCACAACTAGAATGC | 23 |
| oNJB114 | TAGGAAAGGACAGTGGGAGT | 24 |
| oNJB116 | CCATTATGTCTCAGTTGTTCAGTG | 25 |
| oNJB156 | CCAGACCATCTCAGACACC | 26 |
| oNJB162 | GGCTGGGCTTCCACTTAC | 27 |
| oNJB167 | GTGGTTTGTCCAAACTCATCAA | 28 |
| oNJB170 | AGTAACTCTGCACTTCCCATTG | 29 |

Figure 8:
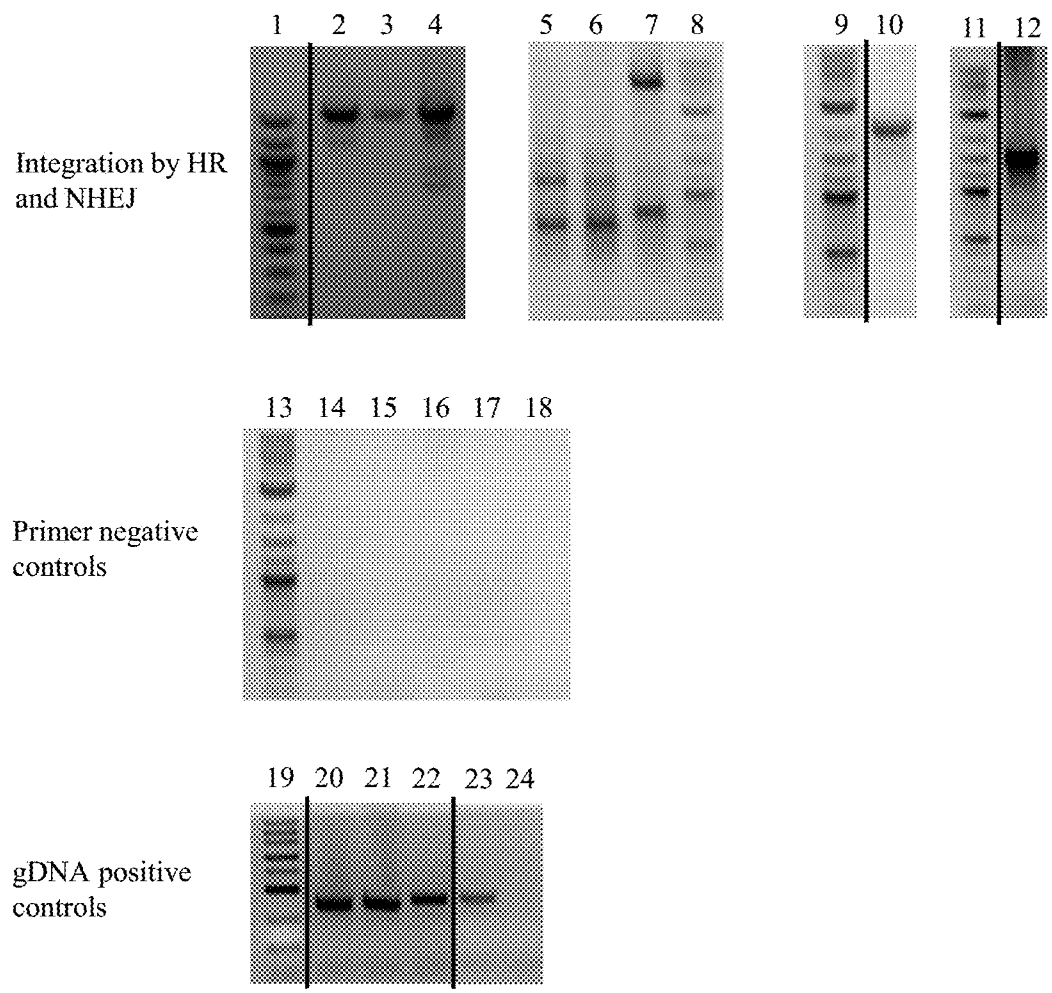
FIG. 8 are images of gels detecting integration of transgenes into the ATXN3 gene. 1, 100 bp ladder with top band running at 1,517 bp; 2, pBA1135 5' junction; 3, pBA1136 5' junction; 4, pBA1137 5' junction; 5, pBA1135 3' junction; 6, pBA1136 3' junction; 7, pBA1137 3' junction; 8, 1 kb ladder with darker bands running at 500 bp, 1,000 bp and 3,000 bp; 9, 1 kb ladder with darker bands running at 500 bp, 1,000 bp and 3,000 bp; 10, pBA1135 inverted 5' junction; 11, 1 kb ladder with darker bands running at 500 bp, 1,000 bp and 3,000 bp; 12, pBA1136 inverted 5' junction; 13, 1 kb ladder with darker bands running at 500 bp, 1,000 bp and 3,000 bp; 14; primer pair oNJB156+oNJB113; 15, primer pair 114+162; 16, primer pair oNJB116+oNJB113; 17, primer pair oNJB114+oNJB170; 18, primer pair oNJB167+oNJB170; 19, 100 bp ladder with the dark band running at 500 bp; 20, genomic DNA from transfection with pBA1135 and nuclease; 21, genomic DNA from transfection with pBA1136 and nuclease; 22, genomic DNA from transfection with pBA1137 and nuclease; 23, genomic DNA from transfection with water; 24, no DNA control.

To detect the integration of pBA1135, pBA1136 and pBA1137, PCRs were performed on the genomic DNA. Regarding pBA1137, the transgene was designed to be integrated precisely by HR. Accordingly, bands were detected in the 5' and 3' junction PCRs, which indicate precise insertion into exon 10 (FIG. 8 lanes 4 and 7). Expected band sizes were 1,520 bp for the 5' junction and 786 bp for the 3' junction. Primers oNJB113 and oNJB116 were used for the 5' junction PCR. Primers oNJB167 and oNJB170 were used for the 3' junction PCR. Regarding pBA1136, as no homology arms were present, the transgene was predicted to insert via NHEJ insertion. Appropriate size bands were observed for the transgene integrating in the forward and reverse directions. Integration in the forward direction can be seen in FIG. 8 lanes 3 (expected size approximately 1,520 bp) and 6 (expected size approximately 1,519 bp). Integrating in the reverse direction can be seen in FIG. 8 lane 12 (expected size approximately 1,520 bp). Primers oNJB113 and oNJB116 were used for the 5' junction PCR. Primers oNJB114 and oNJB170 were used for the 3' junction PCR. Primers oNJB116 and oNJB114 were used for the inverse 5' junction PCR. Regarding ppBA1135, both homology arms and nuclease cleavage sites were present on the transgene. Integration by HR was observed by detecting bands in the 5' and 3' junction PCRs (FIG. 8 lane 2 and 5). Further, integration by NHEJ was observed by detecting bands in an inverse 5' junction PCR (FIG. 8 lane 10). Expected size for the 5' junction PCR was 1,520 bp. Expected size for the 3' junction PCR was 1,157 bp. Expected size for the inverse 5' junction PCR was approximately 1,520 bp. Primers oNJB113 and oNJB116 were used for the 5' junction PCR. Primers oNJB114 and oNJB170 were used for the 3' junction PCR. Primers oNJB116 and oNJB114 were used for the inverse 5' junction PCR.

The results show that the described transgenes comprising bidirectional partial coding sequences can be integrated into genomic DNA through multiple different repair pathways.

Example 2: Targeted Integration of DNA in the CACNA1A Gene

Figure 4:
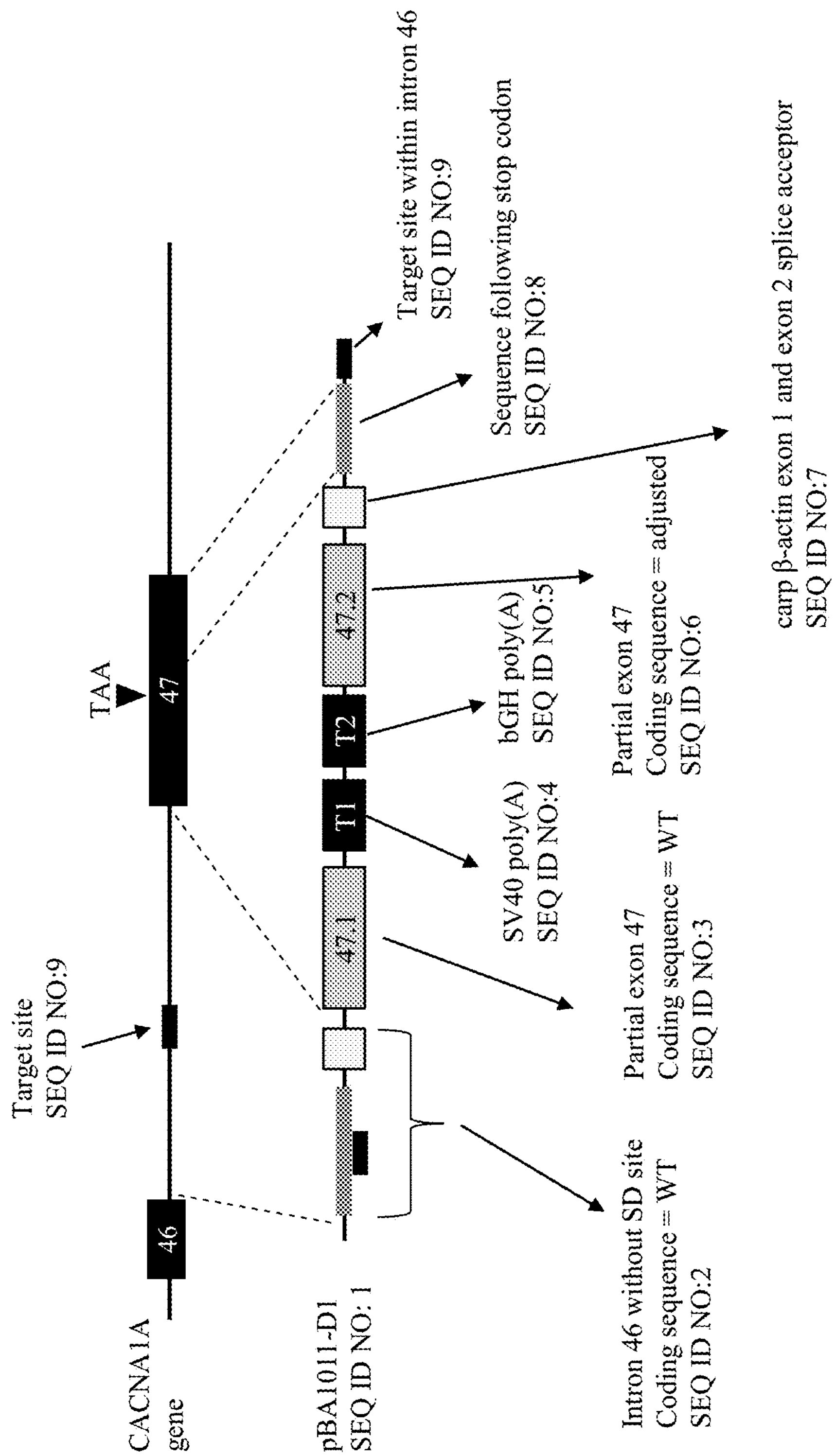
FIG. 4 is an illustration of exon 46, intron 46 and intron 47 of the CACNA1A gene. Also shown is the pB1011-D1 transgene for integration in the CACNA1A gene.

A CACNA1A-targeting transgene is designed to replace the 3' end of the CACNA1A coding sequence. A plasmid is constructed with a transgene designed to integrate WT coding sequence into intron 46 or the start of exon 47 (FIG. 4). The transgene comprises a first homology arm which is homologous to sequence immediately following the splice donor site in intron 46. The first homology arm also comprises the target site for a nuclease (SEQ ID NO:9) and a splice acceptor sequence. The first homology arm is followed by a first coding sequence comprising the CACNA1A exon 47 and a non-expanded CAG repeat sequence (SEQ ID NO:3). Following the first coding sequence is a SV40 poly(A) termination sequence (SEQ ID NO:4). In a tail-to-tail orientation, a second set of functional elements is present. The beginning of the second set of elements comprises a target site for the nuclease (SEQ ID NO:9) followed by a second homology arm. The second homology arm harbors 446 bp which is homologous to sequence immediately following the stop coding (SEQ ID NO:8). This sequence was determined to be free of consensus branch or splice acceptor sequences via in silico analysis. Following the second homology arm is a second splice acceptor from carp beta-actin intron 1 (SEQ ID NO:7). Following the splice acceptor is a codon optimized version of the CACNA1A exon 47 (SEQ ID NO:6) and a bGH poly(A) terminator (SEQ ID NO:5).

A corresponding Cas12a nuclease is designed to create three double-strand breaks following transfection of the plasmid: i) within intron 46 of the endogenous CACNA1A gene, 2) within the first homology arm in the pBA1011-D1 transgene, and 3) following the second homology arm in the pBA1011-D1 transgene. The target sequence for the Cas12a nuclease is shown in SEQ ID NO:9.

Figure 5:
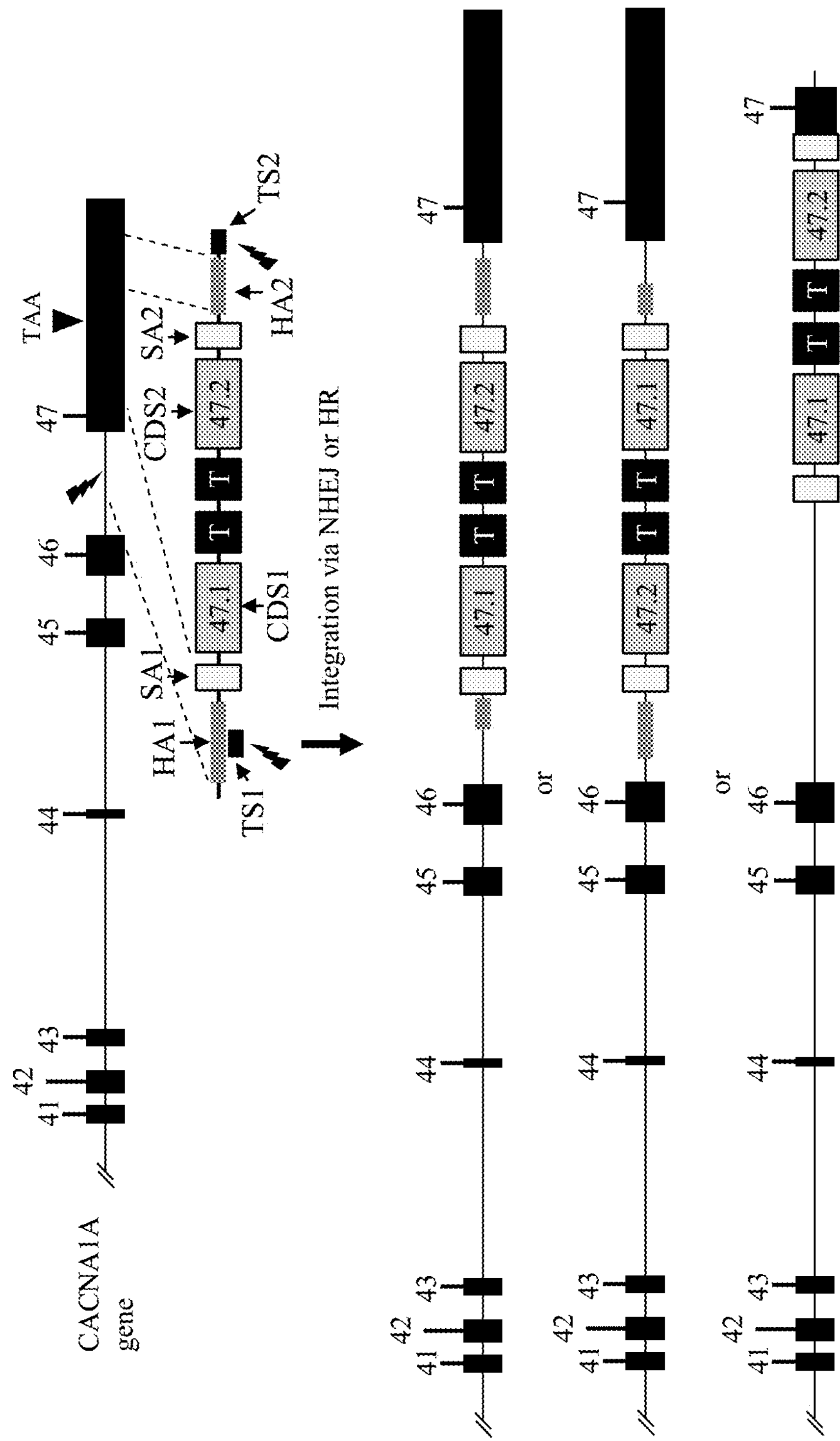
FIG. 5 is an illustration of the integration outcomes for the pB1011-D1 transgene within the CACNA1A gene.
Figure 6:
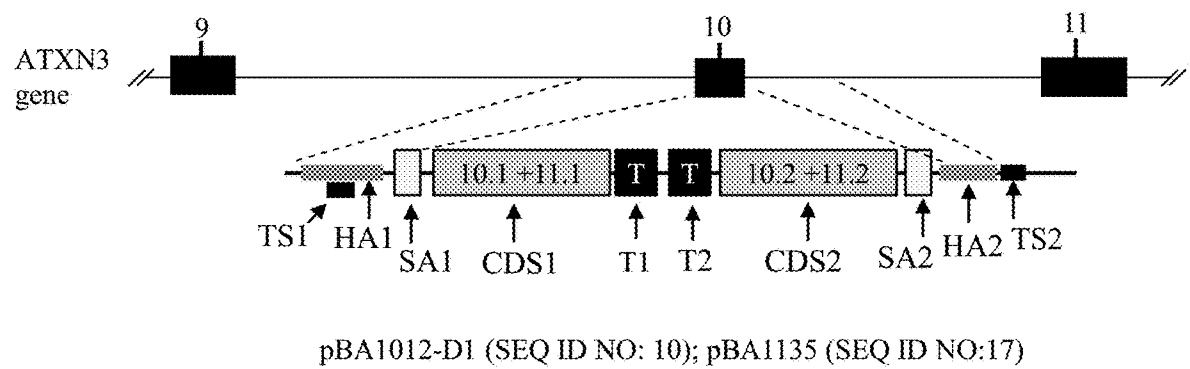
FIG. 6 is an illustration of exon 9, intron 9, exon 10, intron 10 and exon 11 of the ATXN3 gene. Also shown is the pB1012-D1 transgene for integration in the ATXN3 gene.

Confirmation of the function of the transgene and CRISPR vectors is achieved by transfection of HEK293 cells. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for mutations and targeted insertions within the CACNA1A gene. Nuclease activity is analyzed using the Cel-I assay or by deep sequencing of amplicons comprising the CRISPR/Cas12a target sequence. Successful integration of the transgene is analyzed using PCR (FIG. 5).

Example 3: Targeted Integration of DNA in the ATXN3 Gene

An ATXN3-targeting transgene is designed to replace the 3' end of the ATXN coding sequence (exons 10 and 11). A plasmid is constructed with a transgene designed to integrate WT coding sequence into intron 9 or the start of exon 10 (FIG. 5). The transgene comprises a first homology arm which is homologous to sequence intron 9 (SEQ ID NO:10). The first homology arm also comprises the target site for a Cas12a nuclease and a splice acceptor sequence. The first homology arm is followed by a first coding sequence comprising the ATXN3 exon 10 and 11 and a non-expanded CAG repeat sequence. Following the first coding sequence is a SV40 poly(A) termination sequence. In a tail-to-tail orientation, a second set of functional elements is present. The beginning of the second set of elements comprises a target site for the Cas12a nuclease followed by a second homology arm. The second homology arm harbors 379 bp which is homologous to sequence immediately following the end of exon 10 (i.e., the start of intron 10). This sequence was determined via in silico analysis to have a limited number of potential branch or splice acceptor sequences. Following the second homology arm is a second splice acceptor from carp beta-actin intron 1. Following the splice acceptor is a codon optimized version of the ATXN3 exons 10 and 11 and a bGH poly(A) terminator.

A corresponding Cas12a nuclease is designed to create three double-strand breaks following transfection of the plasmid: i) within intron 9 of the endogenous ATXN3 gene, 2) within the first homology arm in the pBA1012-D1 transgene, and 3) following the second homology arm in the pBA1012-D1 transgene. The target sequence for the Cas12a nuclease is shown in SEQ ID NO:11.

Figure 7:
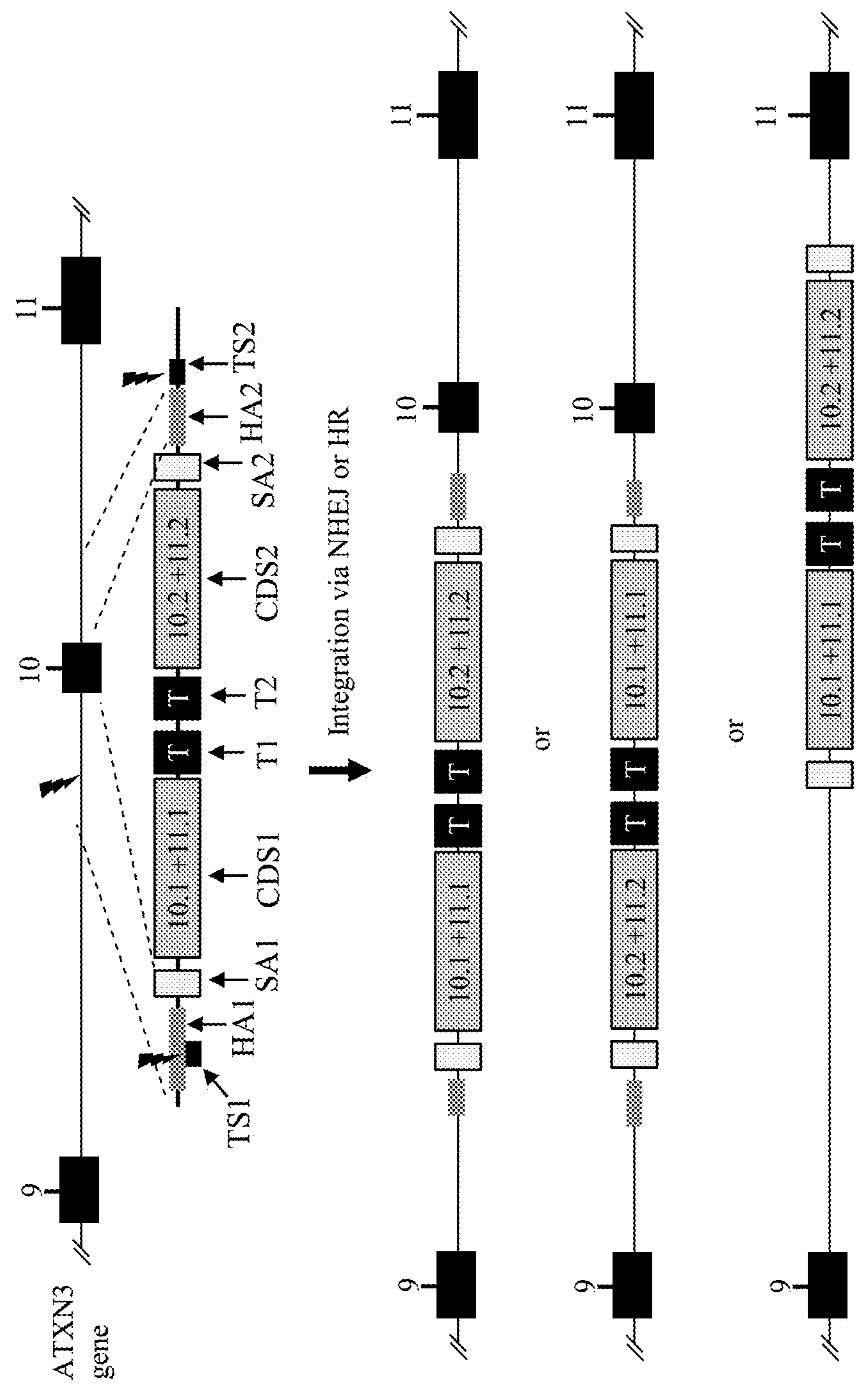
FIG. 7 is an illustration of the integration outcomes for the pB1012-D1 transgene within the ATXN3 gene.

Confirmation of the function of the transgene and CRISPR vectors is achieved by transfection of HEK293 cells. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for mutations and targeted insertions within the ATXN3 gene. Nuclease activity is analyzed using the Cel-I assay or by deep sequencing of amplicons comprising the CRISPR/Cas12a target sequence. Successful integration of the transgene is analyzed using PCR (FIG. 7).

Example 4: Targeted Integration of DNA in the ATXN3 Gene Using Cas12k Transposases An ATXN3-targeting transgene is designed to replace the 3' end of the ATXN coding sequence (exons 10 and 11). A plasmid is constructed with a transgene designed to integrate WT coding sequence into intron 9 or the start of exon 10. The transgene comprises a transposon right end and left end, a first and second splice acceptor, a first and second coding sequence (encoding amino acids from exons 10 and 11), and a first and second terminator. The sequence between the transposon right and left ends is shown in SEQ ID NO: 17.

Plasmids are engineered to express the *Scytonema hofmanni* tnsB, tnsC, tniQ and Cas12k (SEQ ID NO:30) using eukaryotic promoters. A second plasmid is engineered to express the corresponding Cas12k guide RNA (SEQ ID NO:14). The guide RNA targeted sequence CCGCCCGACCTTTCACTTTC (SEQ ID NO:15). The Cas12k transposon plasmids is cotransformed in HEK293 cells with a plasmid harboring the ATXN3-targeting transgene. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for targeted insertions within the ATXN3 gene. Integration of the transgene is analyzed using PCR.

Example 5: Targeted Integration of DNA in the CACNA1A Gene

A CACNA1A-targeting transgene is designed to replace the 3' end of the CACNA1A coding sequence. A plasmid is constructed with a transgene designed to integrate WT coding sequence into intron 46 or the start of exon 47. The transgene comprises a transposon right end and left end, a first and second splice acceptor, a first and second coding sequence (encoding amino acids from exon 47), and a first and second terminator.

Plasmids are engineered to express the *Scytonema hofmanni* tnsB, tnsC, tniQ and Cas12k (SEQ ID NO:30) using eukaryotic promoters. A second plasmid is engineered to express the corresponding Cas12k guide RNA (SEQ ID NO:14). The guide RNA is designed to target sequence CCCGGATCCCGGCTGTGACC (SEQ ID NO: 16). The Cas12k transposon plasmids are cotransformed in HEK293 cells with a plasmid harboring the ATXN3-targeting transgene. HEK293 cells are maintained at 37° C. and 5% CO2 in DMEM high glucose without L-glutamine without sodium pyruvate medium supplemented with 10% fetal bovine serum (FBS) and 1% penicillin-streptomycin (PS) solution 100×. HEK293 cells are transfected with each of the plasmid constructs and combinations thereof using Lipofectamine 3000. Two days post transfection, DNA is extracted and assessed for targeted insertions within the ATXN3 gene. Integration of the transgene is analyzed using PCR.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of integrating a transgene into an endogenous gene in the genome of a cell, comprising administering to the cell a first recombinant nucleic acid comprising a transgene comprising in 5' to 3' orientation a first splice acceptor, a first coding sequence, a first terminator, a second terminator reverse complement, a second coding sequence reverse complement, and a second splice acceptor reverse complement; or a first splice acceptor, a first coding sequence, a bidirectional terminator, a second coding sequence reverse complement, and a second splice acceptor reverse complement;

administering to the cell a second recombinant nucleic acid encoding a CRISPR/Cas9 nuclease having a target site within an intron of the endogenous gene, to thereby provide the CRISPR/Cas9 nuclease in the cell; and integrating the transgene into the endogenous gene at the CRISPR/Cas9 nuclease target site;

wherein the first coding sequence encodes an amino acid sequence heterologous to the cell and wherein the second coding sequence encodes the same heterologous amino acid sequence; and wherein following integration the first coding sequence or the second coding sequence is operatively linked to a promoter of the endogenous gene to express a fusion protein comprising the amino acid sequence at its carboxy-terminus.

2. The method of claim 1, wherein the first recombinant nucleic acid comprises a transgene comprising in 5' to 3' orientation a first splice acceptor, a first coding sequence, a first terminator, a second terminator reverse complement, a second coding sequence reverse complement, and a second splice acceptor reverse complement.

3. The method of claim 1, wherein the first recombinant nucleic acid comprises a transgene comprising in 5' to 3' orientation a first splice acceptor, a first coding sequence, a bidirectional terminator, a second coding sequence reverse complement, and a second splice acceptor reverse complement.

4. The method of claim 1, wherein the transgene is integrated into an intron of the ATXN3 gene.

5. The method of claim 4, wherein the transgene is integrated into intron 9 of the ATXN3 gene.

6. The method of claim 1, wherein the transgene is integrated into an intron of the CACNA1A gene.

7. The method of claim 6, wherein the transgene is integrated into intron 46 of the CACNA1A gene.

8. The method of claim 1, wherein the transgene is harbored on a viral vector.

9. The method of claim 8, wherein the viral vector is selected from the group consisting of an adenovirus vector, an adeno-associated virus vector, and a lentivirus vector.

10. The method of claim 8, wherein the transgene is equal to or less than 4.7 kb in length.

* * * * *